(12) United States Patent
Liu et al.

(10) Patent No.: US 12,286,427 B2
(45) Date of Patent: *Apr. 29, 2025

(54) HETEROCYCLIC COMPOUNDS AND USES THEREOF

(71) Applicant: Kumquat Biosciences Inc., San Diego, CA (US)

(72) Inventors: Yi Liu, San Diego, CA (US); Pingda Ren, San Diego, CA (US); Liansheng Li, San Diego, CA (US); Zhimin Zhu, San Diego, CA (US); Xiuwen Zhu, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/778,527

(22) Filed: Jul. 19, 2024

(65) Prior Publication Data

US 2024/0383888 A1    Nov. 21, 2024

Related U.S. Application Data

(63) Continuation of application No. 18/175,349, filed on Feb. 27, 2023, which is a continuation of application No. PCT/US2021/048101, filed on Aug. 27, 2021.

(60) Provisional application No. 63/072,056, filed on Aug. 28, 2020.

(51) Int. Cl.
  *C07D 417/14*    (2006.01)
  *A61P 35/00*     (2006.01)
  *C07D 487/04*    (2006.01)
  *C07D 519/00*    (2006.01)

(52) U.S. Cl.
  CPC .......... *C07D 417/14* (2013.01); *A61P 35/00* (2018.01); *C07D 487/04* (2013.01); *C07D 519/00* (2013.01)

(58) Field of Classification Search
  CPC .. C07D 417/14; C07D 487/04; C07D 519/00; A61P 35/00
  USPC ....................................................... 514/249
  See application file for complete search history.

(56) References Cited

U.S. PATENT DOCUMENTS

| | | | |
|---|---|---|---|
| 2009/0069300 A1 | 3/2009 | Zhou et al. | |
| 2020/0115375 A1 | 4/2020 | Barda et al. | |
| 2020/0331911 A1 | 10/2020 | Marx et al. | |
| 2023/0331717 A1 | 10/2023 | Liu et al. | |

FOREIGN PATENT DOCUMENTS

| | | |
|---|---|---|
| CN | 112300153 A | 2/2021 |
| CN | 113999226 A | 2/2022 |
| CN | 114380827 A | 4/2022 |
| CN | 115490709 A | 12/2022 |
| CN | 115611923 A | 1/2023 |
| WO | WO-2012154760 A1 | 11/2012 |
| WO | WO-2013155223 A1 | 10/2013 |
| WO | WO-2015054572 A1 | 4/2015 |
| WO | WO-2016164675 A1 | 10/2016 |
| WO | WO-2017172979 A1 | 10/2017 |
| WO | WO-2018217651 A1 | 11/2018 |
| WO | WO-2018218070 A2 * | 11/2018 ........... A61K 31/517 |
| WO | WO-2019099524 A1 | 5/2019 |
| WO | WO-2019215203 A1 | 11/2019 |
| WO | WO-2020081282 A1 | 4/2020 |
| WO | WO-2020097537 A2 | 5/2020 |
| WO | WO-2020113071 A1 | 6/2020 |
| WO | WO-2020146613 A1 | 7/2020 |
| WO | WO-2020238791 A1 | 12/2020 |
| WO | WO-2021023247 A1 | 2/2021 |
| WO | WO-2021041671 A1 | 3/2021 |
| WO | WO-2021118877 A1 | 6/2021 |
| WO | WO-2021141628 A1 | 7/2021 |
| WO | WO-2021219072 A1 | 11/2021 |
| WO | WO-2022047260 A1 | 3/2022 |
| WO | WO-2022105859 A1 | 5/2022 |
| WO | WO-2022135470 A1 | 6/2022 |
| WO | WO-2022148422 A1 | 7/2022 |
| WO | WO-2022170999 A1 | 8/2022 |
| WO | WO-2022171147 A1 | 8/2022 |
| WO | WO-2022173870 A1 | 8/2022 |
| WO | WO-2022177917 A2 | 8/2022 |
| WO | WO-2022184178 A1 | 9/2022 |
| WO | WO-2022221739 A1 | 10/2022 |
| WO | WO-2022247760 A1 | 12/2022 |
| WO | WO-2022258974 A1 | 12/2022 |
| WO | WO-2022261154 A1 | 12/2022 |
| WO | WO-2022266015 A1 | 12/2022 |
| WO | WO-2022266206 A1 | 12/2022 |
| WO | WO-2023004102 A2 | 1/2023 |
| WO | WO-2023018699 A1 | 2/2023 |
| WO | WO-2023020519 A1 | 2/2023 |

OTHER PUBLICATIONS

International search report with written opinion dated Feb. 7, 2022 for PCT/US2021/048101.
Pubchem-SID: 247483401 Deposit Date: Mar. 17, 2015 (Mar. 17, 2015) pp. 1-7.
Pubchem-SID: 374754052 Deposit Date: Jun. 23, 2018 (Jun. 23, 2018) pp. 1-8.

* cited by examiner

*Primary Examiner* — Kahsay Habte

(74) *Attorney, Agent, or Firm* — Wilson Sonsini Goodrich & Rosati

(57) ABSTRACT

The present disclosure provides compounds and pharmaceutically acceptable salt thereof, and methods of using the same. The compounds and methods have a range of utilities as therapeutics, diagnostics, and research tools. In particular, the subject compositions and methods are useful for reducing signaling output of oncogenic proteins.

20 Claims, No Drawings

Specification includes a Sequence Listing.

HETEROCYCLIC COMPOUNDS AND USES THEREOF

CROSS-REFERENCE

This application is a continuation of U.S. application Ser. No. 18/175,349, filed Feb. 27, 2023, which is a continuation of International Application No. PCT/US2021/048101, filed Aug. 27, 2021, which claims the benefit of U.S. Provisional Application No. 63/072,056, filed Aug. 28, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Jul. 19, 2024, is named 56690_716_302_SL.xml and is 1,913 bytes in size.

BACKGROUND

Cancer (e.g., tumor, neoplasm, metastases) is the second leading cause of death worldwide estimated to be responsible for about 10 million deaths each year. Many types of cancers are marked with mutations in one or more proteins involved in various signaling pathways leading to unregulated growth of cancerous cells. In some cases, about 25 to 30 percent (%) of tumors are known to harbor Rat sarcoma (Ras) mutations. In particular, mutations in the Kirsten Ras oncogene (K-Ras) gene are one of the most frequent Ras mutations detected in human cancers including lung adenocarcinomas (LUADs) and pancreatic ductal adenocarcinoma (PDAC).

Although Kras is known to be an oncogenic driver, there is no clinically approved targeted therapy for Ras mutant cancers thus far. Ras proteins have long been considered to be "undruggable," due to, in part, high affinity to their substrate Guanosine-5'-triphosphate (GTP) and/or their smooth surfaces without any obvious targeting region. Recently, a specific G12C Ras gene mutation has been identified as a potential druggable target. However, such therapeutic approach is still limiting, as the G12C mutation in Ras has a low prevalence rate (e.g., about 3% in PDAC) as compared to other known Ras mutations.

SUMMARY

In view of the foregoing, there remains a considerable need for a new design of therapeutics and diagnostics that can specifically target Ras mutants and/or associated proteins of Ras to reduce Ras pathway signaling. Such compositions and methods can be particularly useful for treating a variety of the diseases including, but not limited to, cancers and neoplasia conditions. The present disclosure addresses these needs, and provides additional advantages applicable for diagnosis, prognosis, and treatment for a wide diversity of diseases.

In one aspect, the disclosure provides a compound of Formula (I), or a pharmaceutically acceptable salt or solvate thereof:

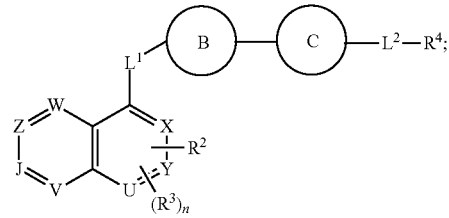

Formula (I)

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more R10;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, $N(R^{1c})$, or $C(R^{1f})(R^{1g})$;
$Q^1$ is N or $C(R^{1d})$;
$Q^2$ is S or O;
X is C or N;
Y is C, S(O), $S(O)_2$, C(O), or N;
U is C, S(O), $S(O)_2$, C(O), or N;
Z is N or $C(R^8)$;
V and J are independently selected from N, $C(R^5)$, and $C(R^{16})$, wherein one of V and J is $C(R^5)$;
W is N or $C(R^{18})$;
$L^1$ and $L^2$ are independently selected from a bond, $C_1$-$C_6$alkyl, —O—, —N($R^{26}$)—, —C(O)—, —N($R^{26}$)C(O)—, —C(O)N($R^{26}$)—, —S—, —S(O)$_2$—, —S(O)—, —S(O)$_2$N($R^{26}$), —S(O)N($R^{26}$), —N($R^{26}$)S(O)—, —N($R^{26}$)S(O)$_2$—, —OCON($R^{26}$)—, —N($R^{26}$)C(O)O—, and —N($R^{26}$)C(O)N($R^{26}$)—;
$R^1$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, and C$_{1-9}$heteroaryl are optionally substituted with one, two, or three R$^{20a}$;

R$^{1a}$, R$^{1b}$, R$^{1c}$, R$^{1d}$, R$^{1e}$, R$^{1f}$, and R$^{1g}$ are each independently selected from hydrogen, halogen, —CN, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20a}$; or R$^{1a}$ and R$^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or R$^{1b}$ and R$^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or Rif and R$^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$;

R$^2$ is selected from halogen, —CN, C$_{2-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{2-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20b}$;

each R$^3$ is independently selected from hydrogen, halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$);

R$^4$ is hydrogen, or a group other than an electrophilic moiety capable of forming a covalent bond with the cysteine residue at position 12 of a KRAS protein;

R$^5$ is

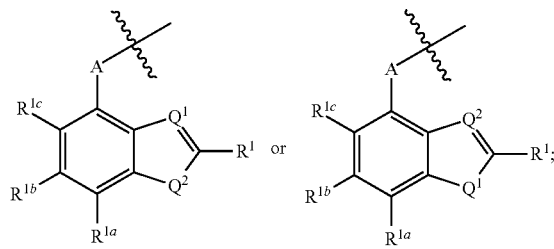

R$^8$ is selected from hydrogen, halogen, —CN, C$_{1-6}$alkyl, C$_{2-6}$alkenyl, C$_{2-6}$alkynyl, C$_{3-6}$cycloalkyl, C$_2$-heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20c}$;

each R$^{10}$ and each R$^{11}$ are independently selected from halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$)—;

each R$^{12}$ is independently selected from hydrogen, C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl, wherein C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three R$^{20d}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20e}$;

each R$^{14}$ is independently selected from hydrogen, C$_{1-6}$alkyl, and C$_{1-6}$haloalkyl;

each R$^{15}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20f}$;

R$^{16}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20g}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, and $R^{20i}$, are each independently selected from halogen, —CN, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

n is 0, 1, or 2; and

----- indicates a single or double bond such that all valences are satisfied.

In some embodiments is a compound of Formula (I) having the structure of Formula (Ia), or a pharmaceutically acceptable salt or solvate thereof:

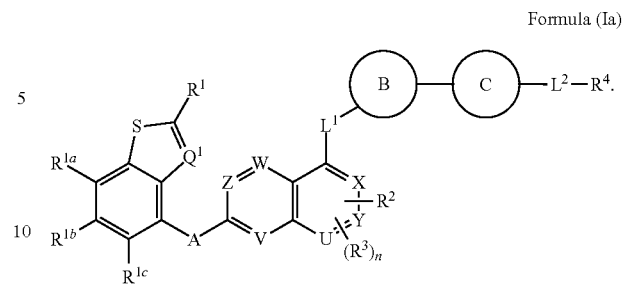

Formula (Ia)

In some embodiments is a compound of Formula (I) having the structure of Formula (Ib), or a pharmaceutically acceptable salt or solvate thereof:

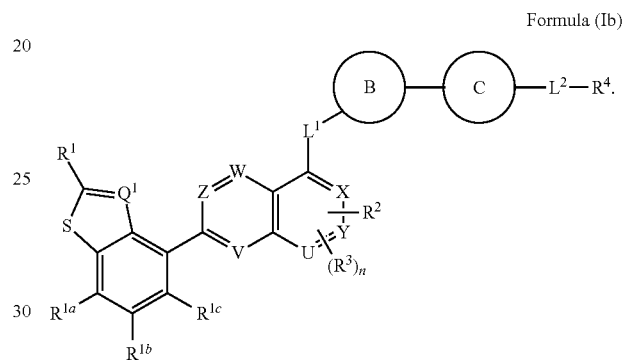

Formula (Ib)

In some embodiments is a compound of Formula (I), (Ia), or (Ib), or a pharmaceutically acceptable salt or solvate thereof, wherein V is C(R$^{16}$). In some embodiments is a compound of Formula (I), (Ia), or (Ib), or a pharmaceutically acceptable salt or solvate thereof, wherein V is C(H). In some embodiments is a compound of Formula (I), (Ia), or (Ib), or a pharmaceutically acceptable salt or solvate thereof, wherein V is N.

In some embodiments is a compound of Formula (I) having the structure of Formula (Ic), or a pharmaceutically acceptable salt or solvate thereof:

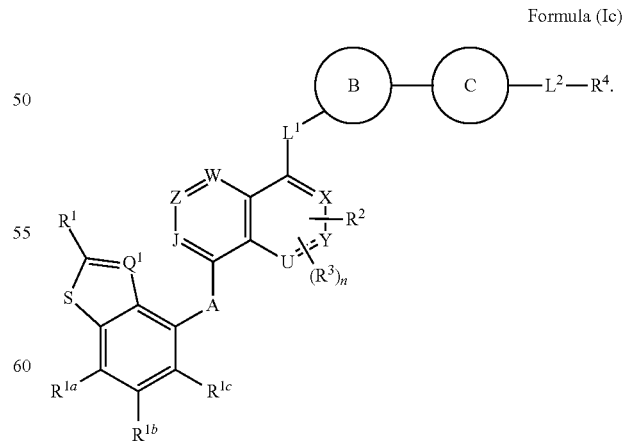

Formula (Ic)

In some embodiments is a compound of Formula (I) having the structure of Formula (Id), or a pharmaceutically acceptable salt or solvate thereof:

Formula (Id)

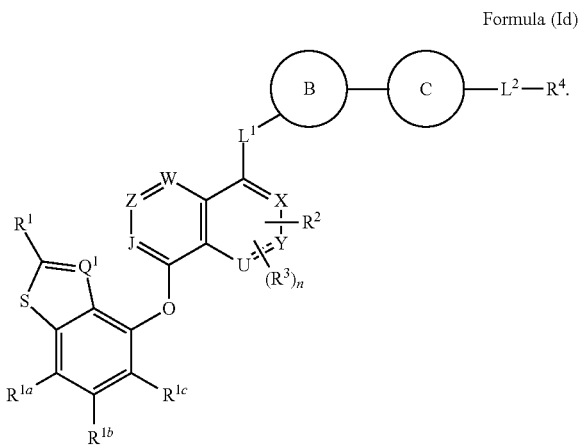

In some embodiments is a compound of Formula (Ic) or (Id), or a pharmaceutically acceptable salt or solvate thereof, wherein J is $C(R^{16})$. In some embodiments is a compound of Formula (Ic) or (Id), or a pharmaceutically acceptable salt or solvate thereof, wherein J is C(H). In some embodiments is a compound of Formula (Ic) or (Id), or a pharmaceutically acceptable salt or solvate thereof, wherein J is N.

In some embodiments is a compound of Formula (I), (Ia), (Ib), (Ic) or (Id), or a pharmaceutically acceptable salt or solvate thereof, wherein X is C. In some embodiments is a compound of Formula (I), (Ia), (Ib), (Ic) or (Id), or a pharmaceutically acceptable salt or solvate thereof, wherein X is N.

In some embodiments is a compound of Formula (I), (Ia), (Ib), (Ic) or (Id), or a pharmaceutically acceptable salt or solvate thereof, wherein U is C. In some embodiments is a compound of Formula (I), (Ia), (Ib), (Ic) or (Id), or a pharmaceutically acceptable salt or solvate thereof, wherein U is N. In some embodiments is a compound of Formula (I), (Ia), (Ib), (Ic) or (Id), or a pharmaceutically acceptable salt or solvate thereof, wherein U is C(O).

In some embodiments is a compound of Formula (I) having the structure of Formula (Ie), or a pharmaceutically acceptable salt or solvate thereof:

Formula (Ie)

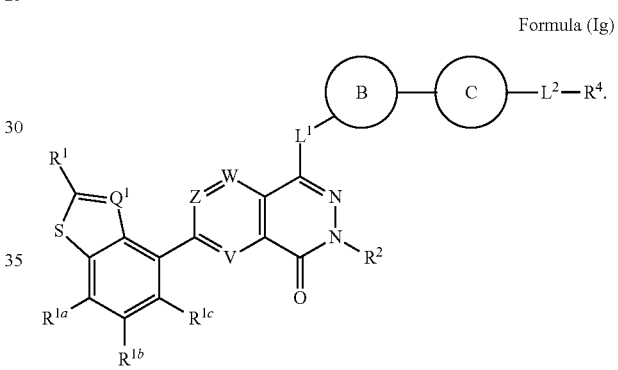

In some embodiments is a compound of Formula (I) having the structure of Formula (If), or a pharmaceutically acceptable salt or solvate thereof:

Formula (If)

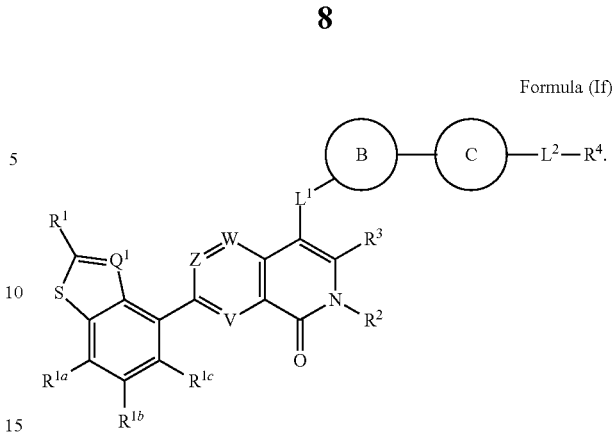

In some embodiments is a compound of Formula (I) having the structure of Formula (Ig), or a pharmaceutically acceptable salt or solvate thereof:

Formula (Ig)

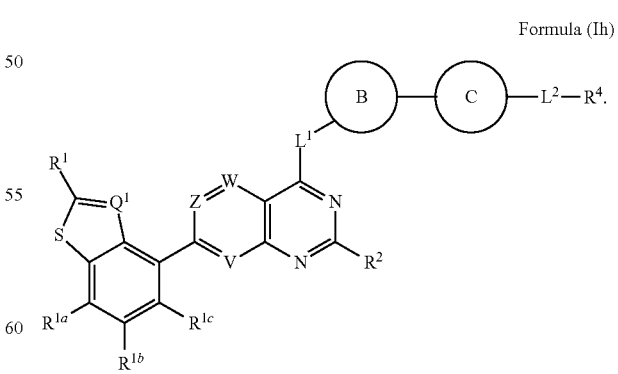

In some embodiments is a compound of Formula (I) having the structure of Formula (Ih), or a pharmaceutically acceptable salt or solvate thereof:

Formula (Ih)

In some embodiments is a compound of Formula (I) having the structure of Formula (Ii), or a pharmaceutically acceptable salt or solvate thereof:

In some embodiments is a compound of Formula (I) having the structure of Formula (Ij), or a pharmaceutically acceptable salt or solvate thereof:

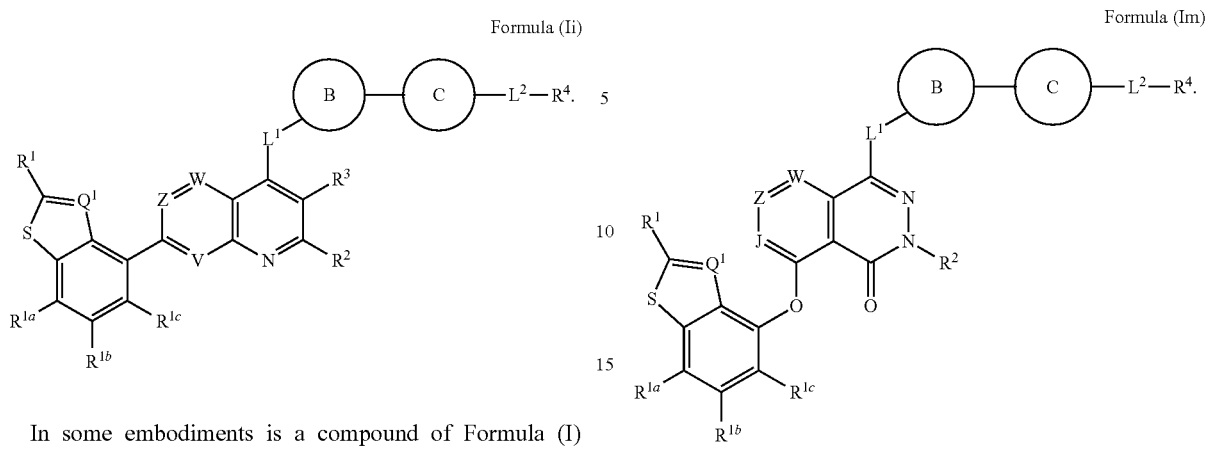

Formula (Ij)

In some embodiments is a compound of Formula (I) having the structure of Formula (Ik), or a pharmaceutically acceptable salt or solvate thereof:

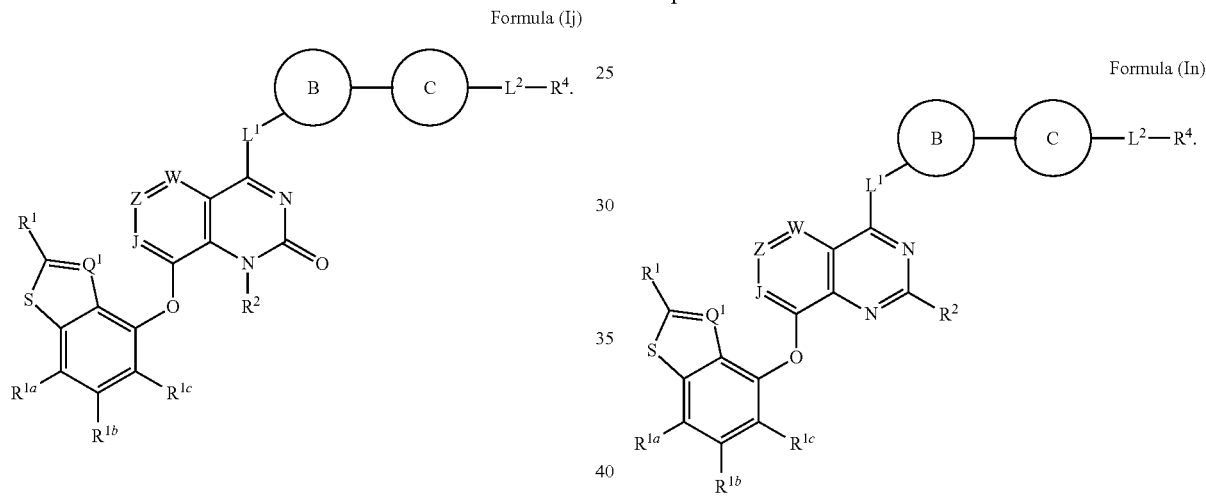

Formula (Ik)

In some embodiments is a compound of Formula (I) having the structure of Formula (Im), or a pharmaceutically acceptable salt or solvate thereof:

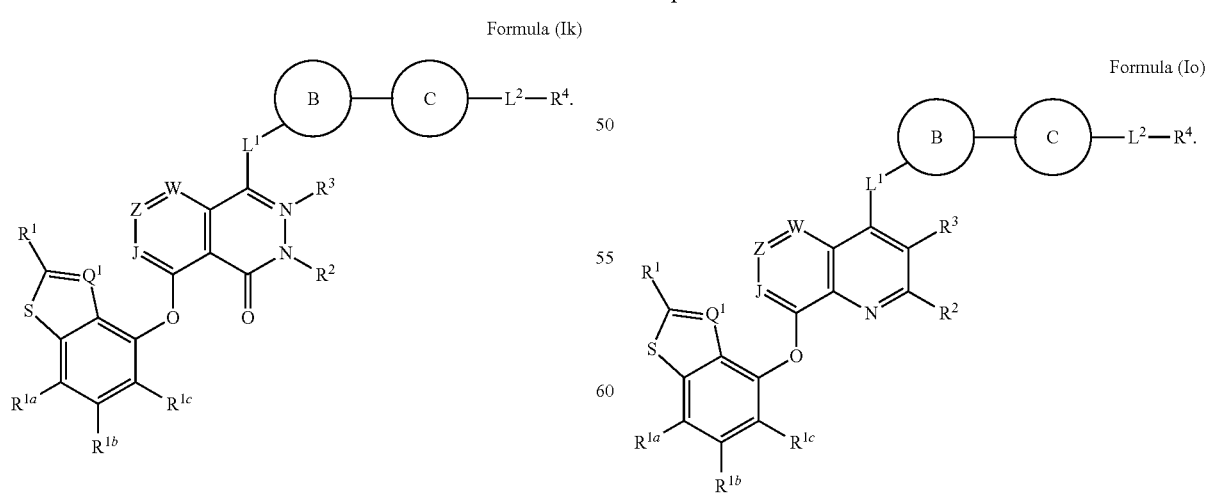

Formula (Im)

In some embodiments is a compound of Formula (I) having the structure of Formula (In), or a pharmaceutically acceptable malt or solvate thereof.

Formula (In)

In some embodiments is a compound of Formula (I) having the structure of Formula (Io), or a pharmaceutically acceptable salt or solvate thereof.

Formula (Io)

In some embodiments is a compound of Formula (I), (Ie), (If), (Ig) or (Ih), or a pharmaceutically acceptable salt or solvate thereof, wherein V is C(R$^{16}$). In some embodiments is a compound of Formula (I), (Ie), (If), (Ig) or (Ih), or a pharmaceutically acceptable salt or solvate thereof, wherein V is C(H). In some embodiments is a compound of Formula (I), (Ie), (If), (Ig) or (Ih), or a pharmaceutically acceptable salt or solvate thereof, wherein V is N.

In some embodiments is a compound of Formula (I), (Ii), (Ij), (Ik) or (Im), or a pharmaceutically acceptable salt or solvate thereof, wherein J is C(R$^{16}$). In some embodiments is a compound of Formula (I), (Ii), (Ij), (Ik) or (Im), or a pharmaceutically acceptable salt or solvate thereof, wherein J is C(H). In some embodiments is a compound of Formula (I), (Ii), (Ij), (Ik) or (Im), or a pharmaceutically acceptable salt or solvate thereof, wherein J is N.

In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein W is C(R$^{18}$). In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein W is N.

In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein Z is C(R$^8$). In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein Z is N.

In another aspect, the disclosure provides a compound of Formula (II), or a pharmaceutically acceptable salt or solvate thereof:

Formula (II)

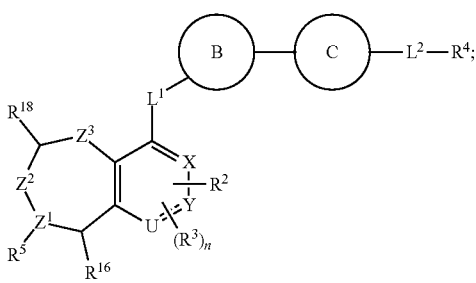

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more R$^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more R$^{11}$;

A is a bond, O, S, N(R$^{1c}$), or C(R$^{1f}$)(R$^{1g}$);
Q$^1$ is N or C(R$^{14}$);
Q$^2$ is S or O;
X is C or N;
Y is C, C(O), or N;
Z$^1$ is N or C(R$^6$);
Z$^2$ is N(R$^7$) or C(R$^8$)(R$^9$);
Z$^3$ is absent, N(R$^{17}$), or C(R$^{27}$)(R$^{28}$);
U is C, S(O), S(O)$_2$, C(O), or N;
L$^1$ and L$^2$ are independently selected from a bond, C$_1$-C$_6$alkyl, —O—, —N(R$^{26}$)—, —C(O)—, —N(R$^{26}$)C(O)—, —C(O)N(R$^{26}$)—, —S—, —S(O)$_2$—, —S(O)—, —S(O)$_2$N(R$^{26}$), —S(O)N(R$^{26}$), —N(R$^{26}$)S(O)—, —N(R$^{26}$)S(O)$_2$—, —OCON(R$^{26}$)—, —N(R$^{26}$)C(O)O—, and —N(R$^{26}$)C(O)N(R$^{26}$)—;

R$^1$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{1-9}$heteroaryl, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20a}$;

R$^{1a}$, R$^{1b}$, R$^{1c}$, R$^{1d}$, R$^{1e}$, R$^{1f}$, and R$^{1g}$ are each independently selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20a}$; or R$^{1a}$ and R$^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or R$^{1b}$ and R1G are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or R$^{1f}$ and R$^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;

$R^2$ is selected from halogen, —CN, $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$;

each $R^3$ is independently selected from hydrogen, halogen, oxo, $C_1$-$C_6$alkyl, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;

$R^4$ is hydrogen, or a group other than an electrophilic moiety capable of forming a covalent bond with the cysteine residue at position 12 of a KRAS protein;

$R^5$ is

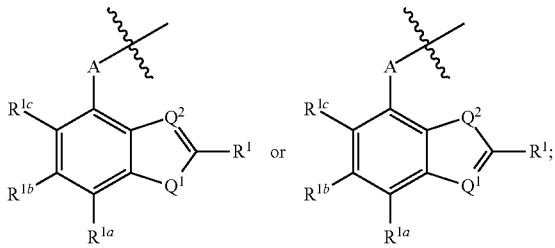

$R^6$ is selected from hydrogen and $C_{1-6}$alkyl;

$R^7$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;

$R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;

$R^9$ is selected from hydrogen and $C_{1-6}$alkyl;

each $R^{10}$ and each $R^{11}$ are independently selected from halogen, oxo, $C_1$-$C_6$alkyl, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;

each $R^{12}$ is independently selected from hydrogen, $C_{1-6}$alkyl, $C_{2-6}$alkenyl, $C_{2-6}$alkynyl, $C_{3-6}$cycloalkyl, $C_{2-9}$heterocycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20e}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20k}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, and $R^{20k}$ are each independently selected from halogen, —CN, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —CH$_2$—C$_{6-10}$aryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{23}$ is independently selected from H and C$_{1-6}$alkyl;

each R$^{24}$ is independently selected from H and C$_{1-6}$alkyl;

each R$^{25}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{26}$ is selected from hydrogen, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20i}$;

R$^{27}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20j}$;

R$^{28}$ is selected from hydrogen and C$_{1-6}$alkyl;

n is 0, 1, or 2; and

===== indicates a single or double bond such that all valences are satisfied.

In some embodiments is a compound of Formula (II) having the structure of Formula (IIa), or a pharmaceutically acceptable salt or solvate thereof:

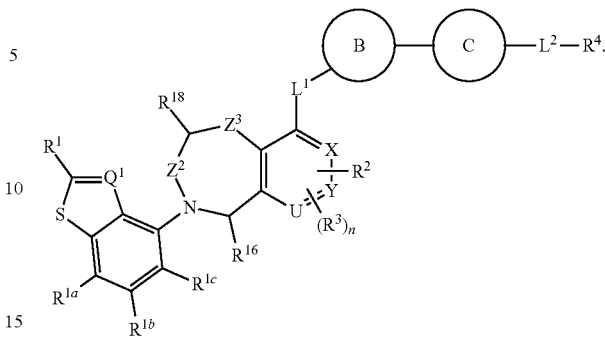

Formula (IIa)

In some embodiments is a compound of Formula (II) having the structure of Formula (IIb), or a pharmaceutically acceptable salt or solvate thereof:

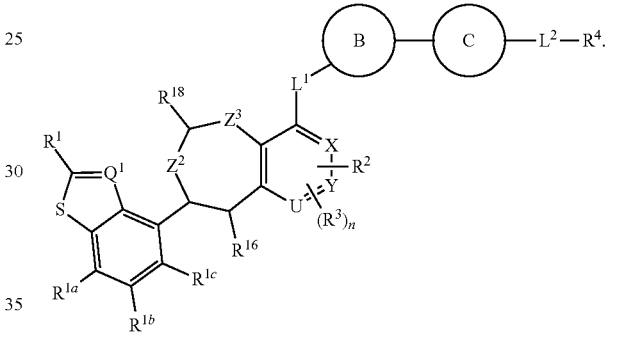

Formula (IIb)

In some embodiments is a compound of Formula (II), (IIa), or (IIb), or a pharmaceutically acceptable salt or solvate thereof, wherein Z$^2$ is C(R$^8$)(R$^9$). In some embodiments is a compound of Formula (II), (IIa), or (IIb), or a pharmaceutically acceptable salt or solvate thereof, wherein R' is hydrogen.

In some embodiments is a compound of Formula (II), (IIa), or (IIb), or a pharmaceutically acceptable salt or solvate thereof, wherein X is C. In some embodiments is a compound of Formula (II), (IIa), or (IIb), or a pharmaceutically acceptable salt or solvate thereof, wherein X is N.

In some embodiments is a compound of Formula (II), (IIa), or (IIb), or a pharmaceutically acceptable salt or solvate thereof, wherein Y is C. In some embodiments is a compound of Formula (II), (IIa), or (IIb), or a pharmaceutically acceptable salt or solvate thereof, wherein Y is N. In some embodiments is a compound of Formula (II), (IIa), or (IIb), or a pharmaceutically acceptable salt or solvate thereof, wherein Y is C(O).

In some embodiments is a compound of Formula (II), (IIa), or (IIb), or a pharmaceutically acceptable salt or solvate thereof, wherein U is C. In some embodiments is a compound of Formula (II), (IIa), or (IIb), or a pharmaceutically acceptable salt or solvate thereof, wherein U is N. In some embodiments is a compound of Formula (II), (IIa), or (IIb), or a pharmaceutically acceptable salt or solvate thereof, wherein U is C(O).

In some embodiments is a compound of Formula (II) having the structure of Formula (IIc), or a pharmaceutically acceptable salt or solvate thereof:

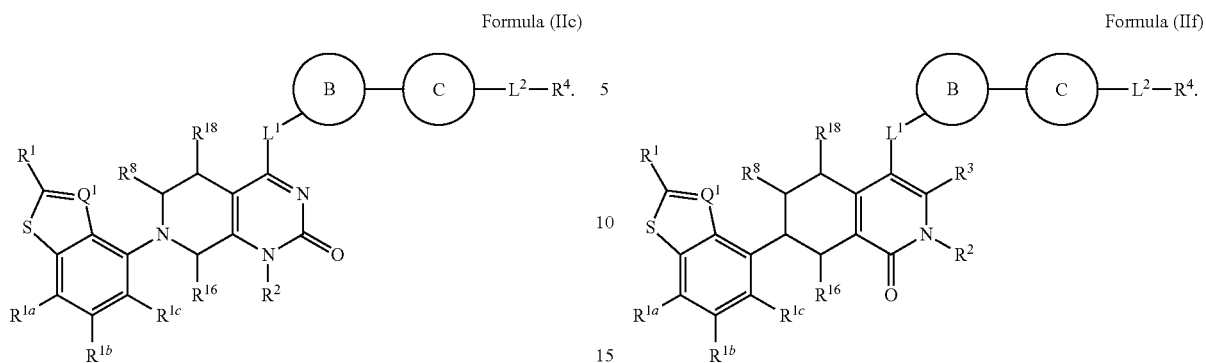

Formula (IIc)

In some embodiments is a compound of Formula (II) having the structure of Formula (Id), or a pharmaceutically acceptable salt or solvate thereof:

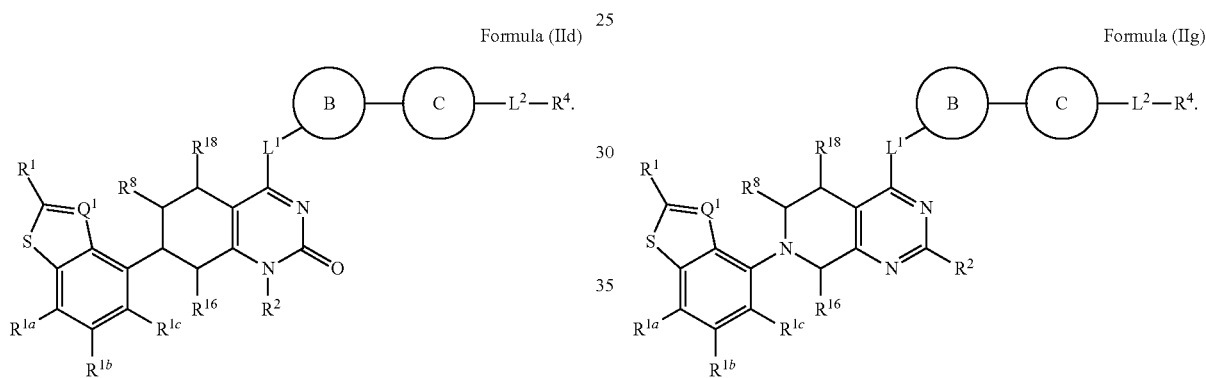

Formula (IId)

In some embodiments is a compound of Formula (II) having the structure of Formula (IIe), or a pharmaceutically acceptable salt or solvate thereof:

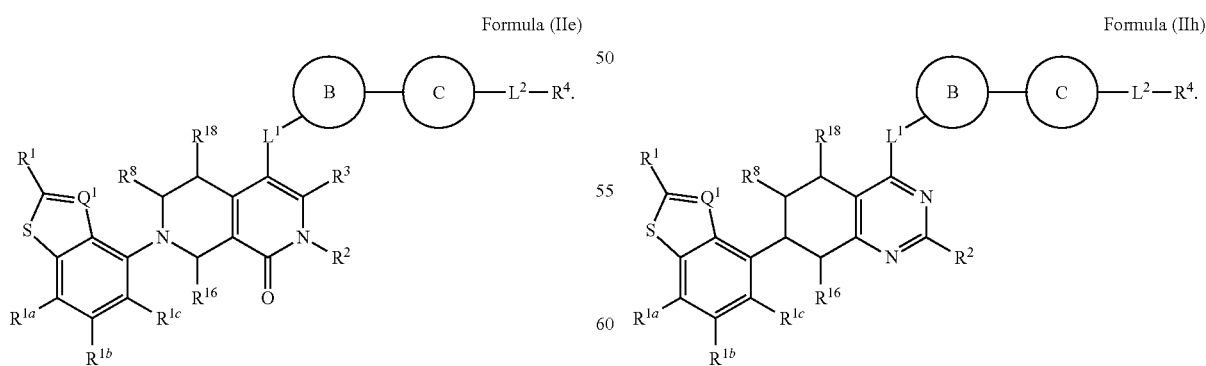

Formula (IIe)

In some embodiments is a compound of Formula (II) having the structure of Formula (IIf), or a pharmaceutically acceptable salt or solvate thereof:

Formula (IIf)

In some embodiments is a compound of Formula (II) having the structure of Formula (IIg), or a pharmaceutically acceptable salt or solvate thereof:

Formula (IIg)

In some embodiments is a compound of Formula (II) having the structure of Formula (II), or a pharmaceutically acceptable salt or solvate thereof:

Formula (IIh)

In some embodiments is a compound of Formula (II) having the structure of Formula (IIi), or a pharmaceutically acceptable salt or solvate thereof:

Formula (IIi)

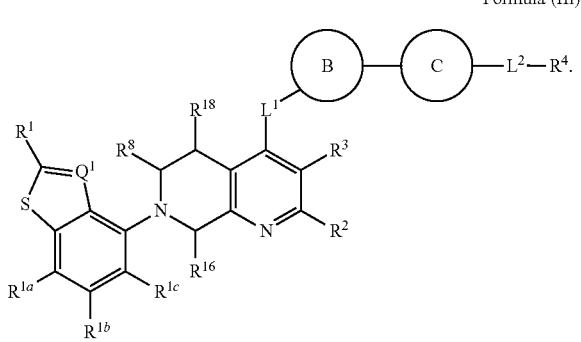

In some embodiments is a compound of Formula (II) having the structure of Formula (IIj), or a pharmaceutically acceptable salt or solvate thereof:

Formula (IIj)

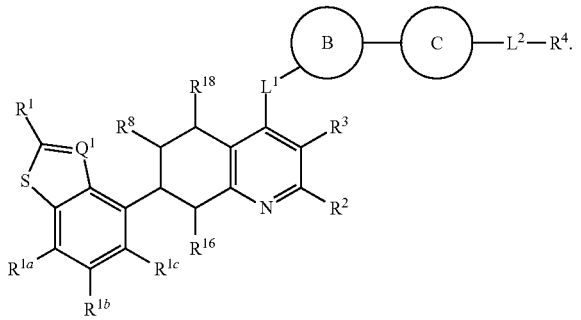

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is selected from hydrogen, —N($R^{12}$)($R^{13}$), and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —N($R^{12}$)($R^{13}$). In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —NH$_2$.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$; $R^{1b}$, and $R^{1c}$ are each independently selected from hydrogen, halogen, and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$, $R^{1b}$, and $R^{1c}$ are each hydrogen.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $Q^1$ is $C(R^{1d})$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1d}$ is selected from hydrogen and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $Q^1$ is N.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

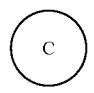

is a 3-12 membered heterocycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is selected from piperazinyl and piperidinyl, wherein piperazinyl and piperidinyl are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (C)

is a cyclohexyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (C)

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (C)

is absent.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered heterocycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is selected from piperazinyl and piperidinyl, wherein piperazinyl and piperidinyl are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is piperazinyl optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered cycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a cyclohexyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein Ⓑ is absent.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is selected from a bond, $C_1$-$C_6$alkyl, —N($R^{26}$)—, and —C(O)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a bond. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a $C_1$-$C_6$alkyl.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is selected from a bond, $C_1$-$C_6$alkyl, and —C(O)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is a bond. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is a $C_1$-$C_6$alkyl.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from hydrogen, $C_{1-6}$alkyl, $C_{3-6}$cycloalkyl, $C_{2-9}$heterocycloalkyl, $C_{6-10}$aryl, $C_{1-9}$heteroaryl, —$OR^{12}$, —$SR^{12}$, and —N($R^{12}$)($R^{13}$), wherein $C_{1-6}$alkyl, $C_{3-6}$cycloalkyl, $C_{2-9}$heterocycloalkyl, $C_{6-10}$aryl, and $C_1$-heteroaryl are optionally substituted with one, two, or three $R^{20b}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from —$OR^{12}$, —$SR^{12}$, and $C_{1-6}$alkyl, wherein $C_{1-6}$alkyl is optionally substituted with one, two, or three $R^{20b}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^2$ is —$OR^{12}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{12}$ is selected from $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{12}$ is $C_{1-6}$alkyl optionally substituted with one, two, or three $R^{20d}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{12}$ is $C_{2-9}$heterocycloalkyl optionally substituted with one, two, or three $R^{20d}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{12}$ is —$CH_2$—$C_{2-9}$heterocycloalkyl optionally substituted with one, two, or three $R^{20d}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein each $R^{20d}$ is independently selected from halogen, $C_{1-6}$alkyl, $C_{3-6}$cycloalkyl, $C_{2-9}$heterocycloalkyl, $C_{6-10}$aryl, $C_{1-9}$heteroaryl, —$OR^{21}$, —$SR^{21}$, —N($R^{22}$)($R^{23}$), —C(O)$OR^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)$OR^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), —$OCH_2$C(O)$OR^{22}$, and —OC(O)$R^{25}$, wherein $C_{1-6}$alkyl, $C_{3-6}$cycloalkyl, $C_{2-9}$heterocycloalkyl, $C_{6-10}$aryl, $C_{1-9}$heteroaryl are optionally substituted with one, two, or three groups independently selected from halogen, oxo, $C_{1-6}$alkyl, $C_{1-6}$haloalkyl, $C_{1-6}$alkoxy, $C_{1-6}$haloalkoxy, —$OR^{21}$, —$SR^{21}$, —N($R^{22}$)($R^{23}$), —C(O)$OR^{22}$, —C(O)N($R^{22}$)($R^{23}$), —S(O)$_2R^{25}$, and —S(O)$_2$N($R^{22}$)($R^{23}$). In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein each $R^{20d}$ is independently selected from halogen, $C_{1-6}$alkyl, and —$OR^{21}$, wherein $C_{1-6}$alkyl is optionally substituted with one, two, or three groups independently selected from halogen, oxo, $C_{1-6}$alkyl, —$OR^{21}$, and —N($R^{22}$)($R^{23}$). In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from

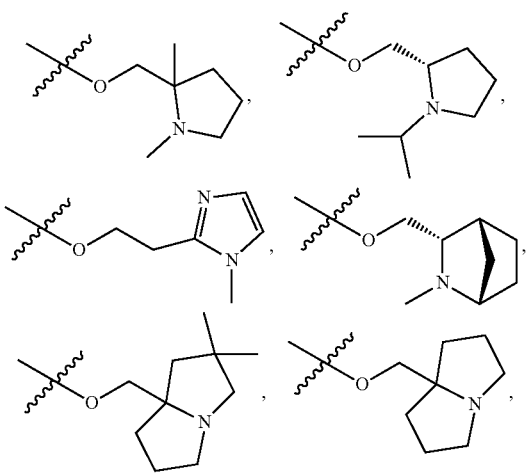

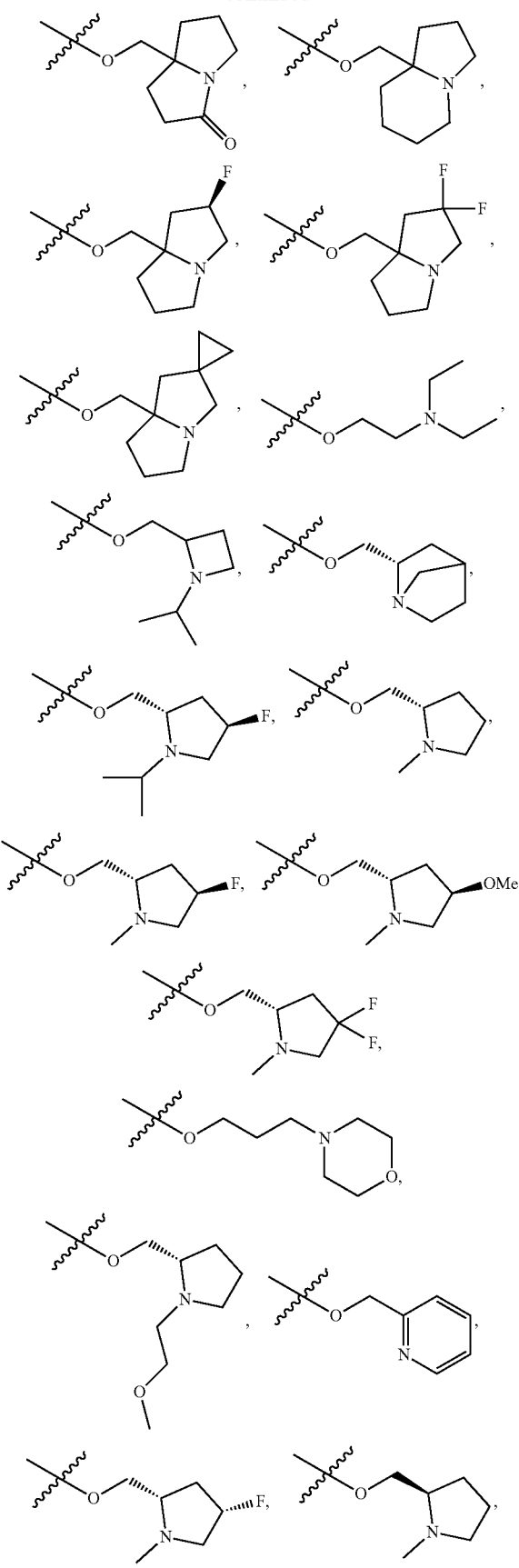
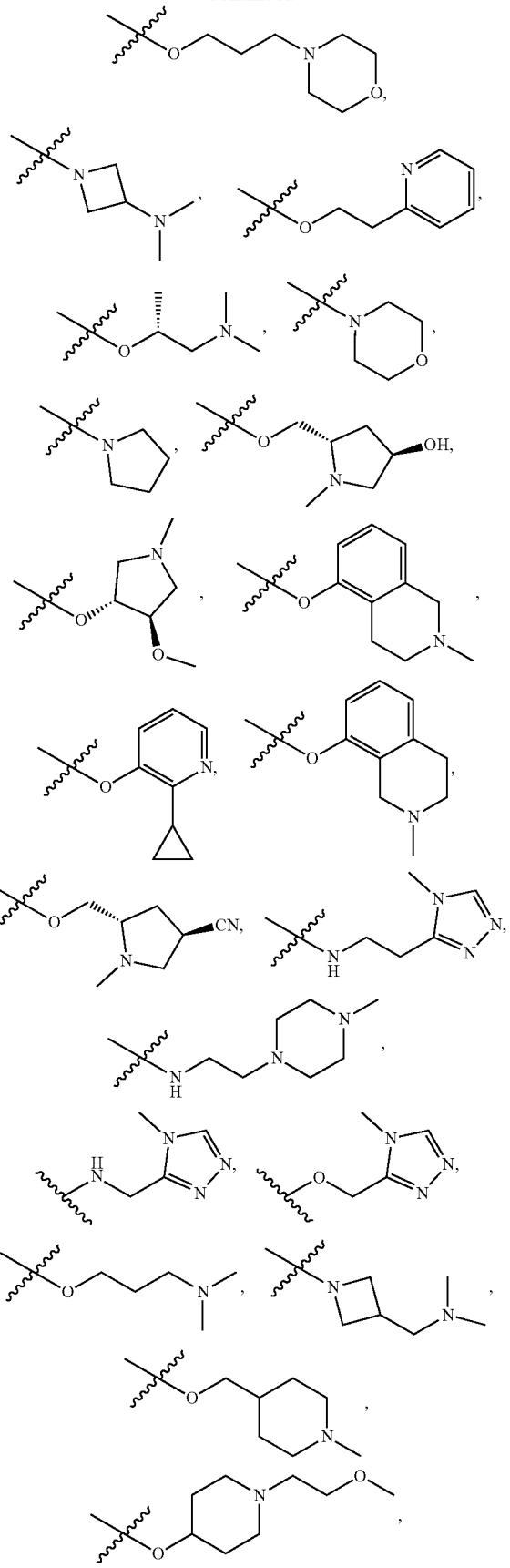

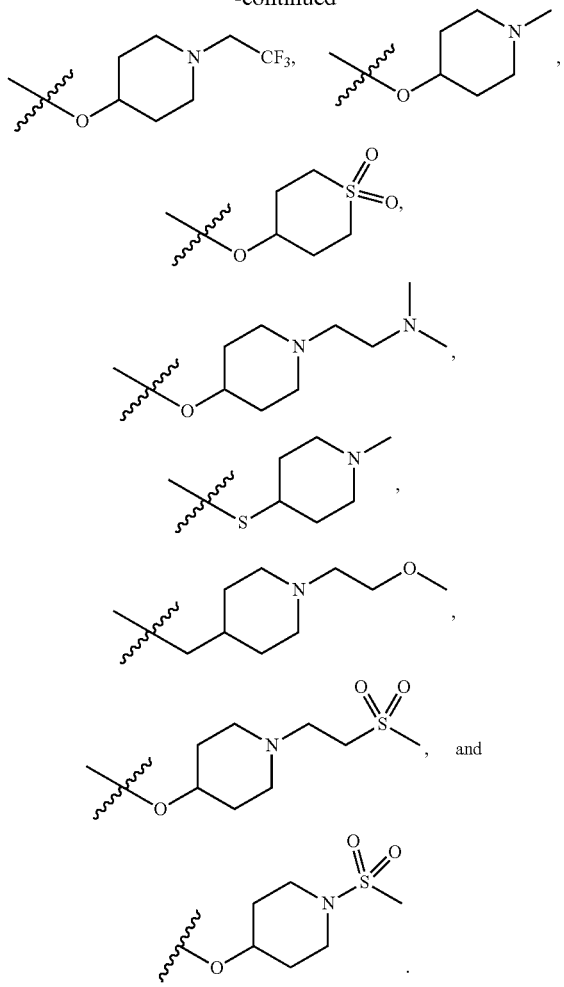

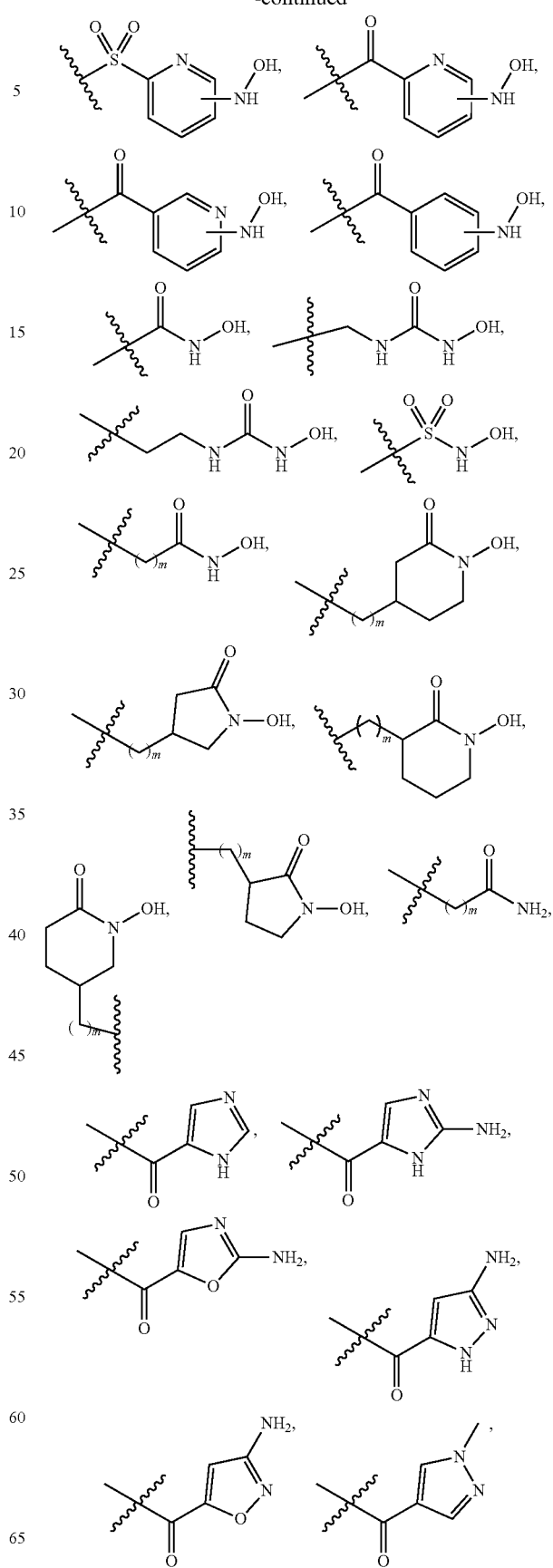

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^4$ is hydrogen. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^4$ is a group other than an electrophilic moiety capable of forming a covalent bond with the cysteine residue at position 12 of a KRAS protein.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^4$ is —H, —NH$_2$, —OH, —NH(C$_{1-6}$alkyl).

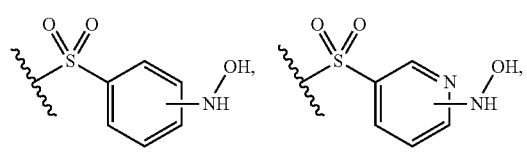

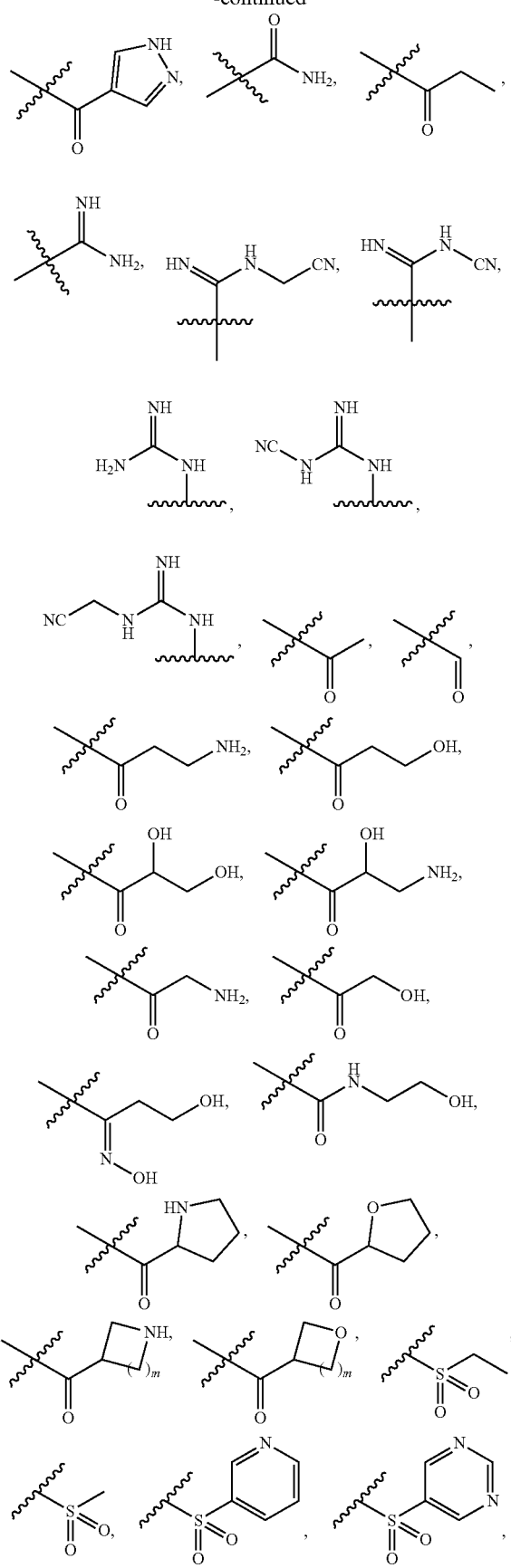
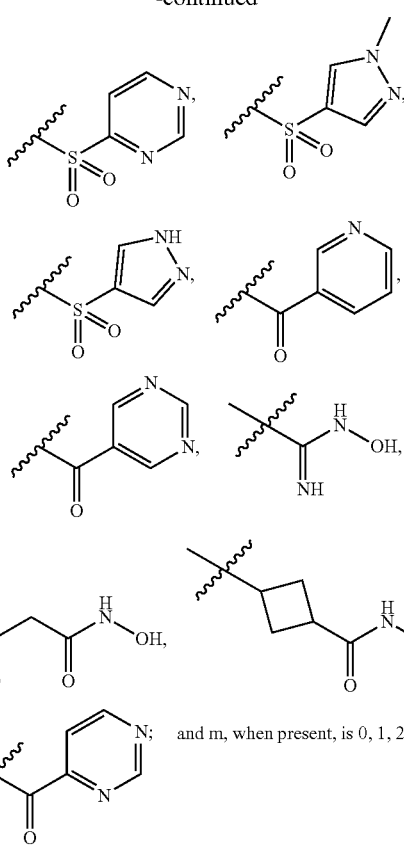
and m, when present, is 0, 1, 2, or 3.
In another aspect is a compound of Formula (If), (Ig), (Ih), or (Ii), or a pharmaceutically acceptable salt or solvate thereof:
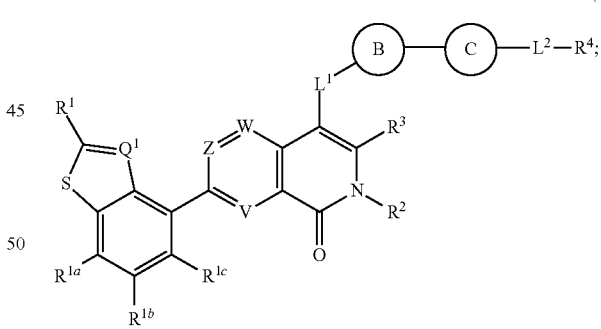
Formula (If)
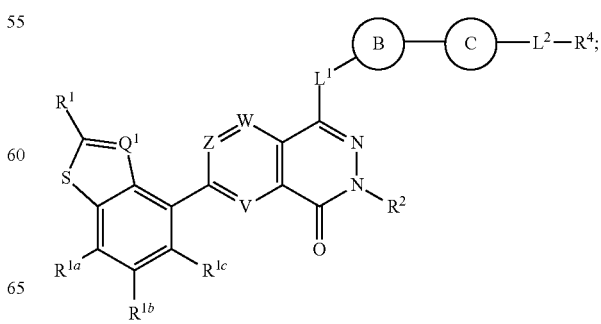
Formula (Ig)

-continued

Formula (Ih)

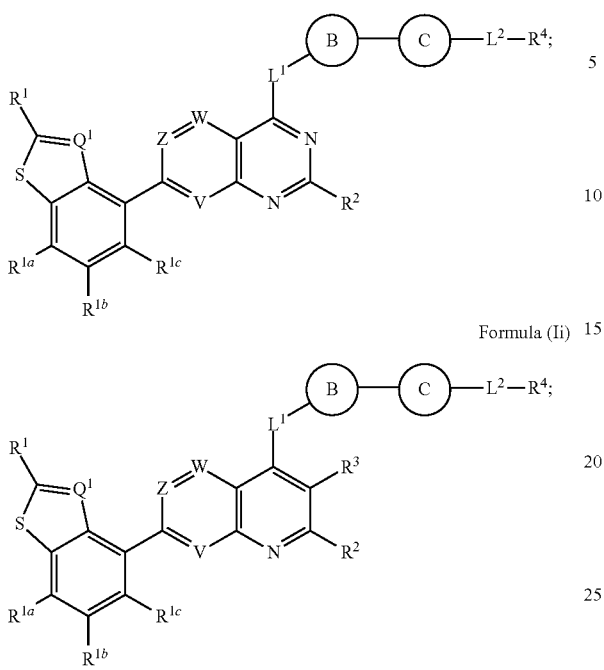

Formula (Ii)

wherein:

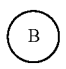

is a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

$Q^1$ is N or $C(R^{14})$;
Z is $C(R^8)$;
V is selected from N and $C(R^{16})$;
W is N or $C(R^{18})$;
$L^1$ and $L^2$ are independently selected from a bond, $C_1$-$C_6$alkyl, —O—, —N($R^{26}$)—, —C(O)—, —N($R^{26}$)C(O)—, —C(O)N($R^{26}$)—, —S—, —S(O)$_2$—, —S(O)—, —S(O)$_2$N($R^{26}$), —S(O)N($R^{26}$), —N($R^{26}$)S(O)—, —N($R^{26}$)S(O)$_2$—, —OCON($R^{26}$)—, —N($R^{26}$)C(O)O—, and —N($R^{26}$)C(O)N($R^{26}$)—;
$R^1$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, —$SR^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, and $C_{1-9}$heteroaryl are optionally substituted with one, two, or three $R^{20a}$;
$R^{1a}$, $R^{1b}$, $R^{1c}$, and $R^{1d}$ are each independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;
$R^2$ is selected from halogen, —CN, $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2$$R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2$$R^{15}$, and —CH$_2$S(O)$_2$N($R^{12}$)($R^{13}$), wherein $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$;
each $R^3$ is independently selected from hydrogen, halogen, oxo, $C_1$-$C_6$alkyl, $C_1$-$C_6$haloalkyl, —OR$^{12}$, —N($R^{12}$)($R^{13}$), —CN, —C(O)O$R^{12}$, —OC(O)N($R^{12}$)($R^{13}$), —C(O)$R^{15}$, —S(O)$_2$$R^{15}$, and —S(O)$_2$N($R^{12}$)($R^{13}$);
$R^4$ is hydrogen, or a group other than an electrophilic moiety capable of forming a covalent bond with the cysteine residue at position 12 of a KRAS protein;
$R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2$$R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20c}$;

each R$^{10}$ and each R$^{11}$ are independently selected from halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$)—;

each R$^{12}$ is independently selected from hydrogen, C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl, wherein C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl are optionally substituted with one, two, or three R$^{20d}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20c}$;

each R$^{14}$ is independently selected from hydrogen, C$_{1-6}$alkyl, and C$_{1-6}$haloalkyl;

each R$^{15}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20f}$;

R$^{16}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20g}$;

R$^{18}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20h}$;

each R$^{20a}$, R$^{20b}$, R$^{20c}$, R$^{20d}$, R$^{20e}$, R$^{20f}$, R$^{20g}$, R$^{20h}$, and R$^{20i}$, are each independently selected from halogen, —CN, C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_1$-heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{22}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{23}$ is independently selected from H and C$_{1-6}$alkyl;

each R$^{24}$ is independently selected from H and C$_{1-6}$alkyl;

each R$^{25}$ is selected from C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each R$^{26}$ is selected from hydrogen, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20i}$;

n is 0, 1, or 2; and

===== indicates a single or double bond such that all valences are satisfied.

In some embodiments is a compound of Formula (If), or a pharmaceutically acceptable salt or solvate thereof:

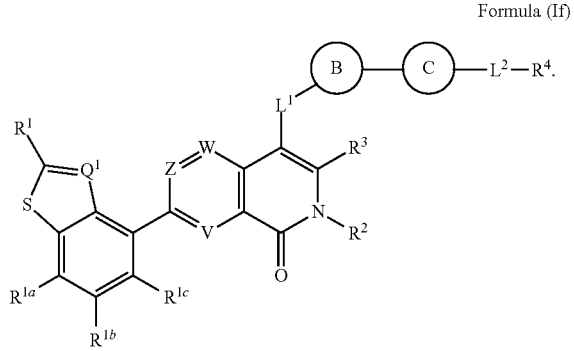

Formula (If)

In some embodiments is a compound of Formula (Ig), or a pharmaceutically acceptable salt or solvate thereof:

Formula (Ig)
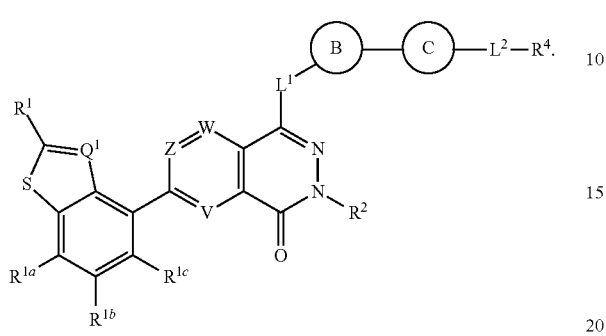

In some embodiments is a compound of Formula (Ih), or a pharmaceutically acceptable salt or solvate thereof:

Formula (Ih)
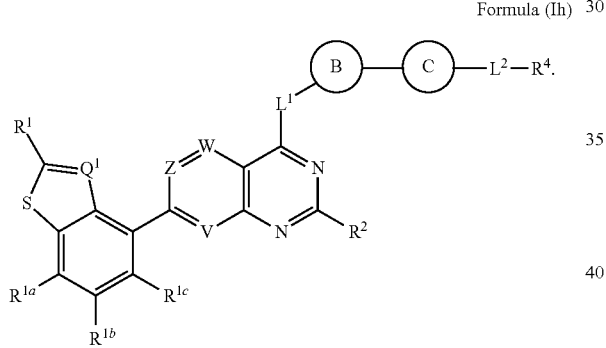

In some embodiments is a compound of Formula (Ii), or a pharmaceutically acceptable salt or solvate thereof:

Formula (Ii)
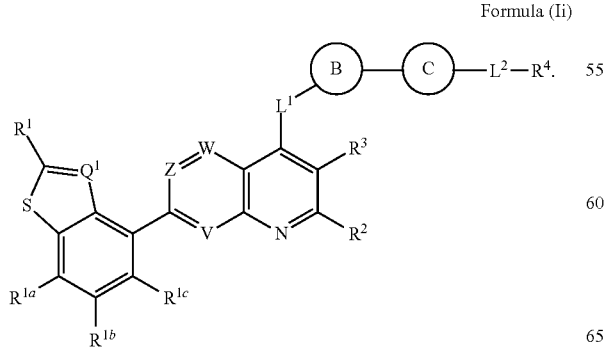

In some embodiments is a compound of Formula (Ik), (Im), (In), or (Io), or a pharmaceutically acceptable salt or solvate thereof:

Formula (Ik)
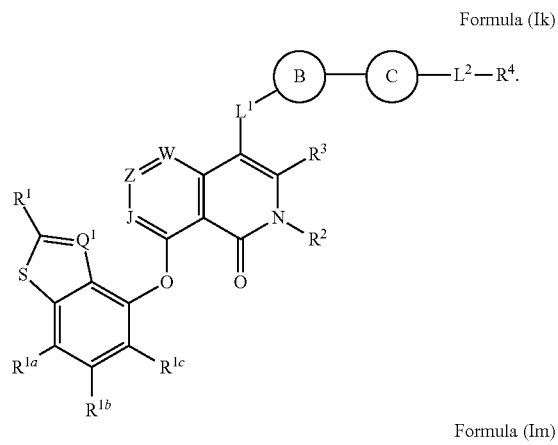

Formula (Im)
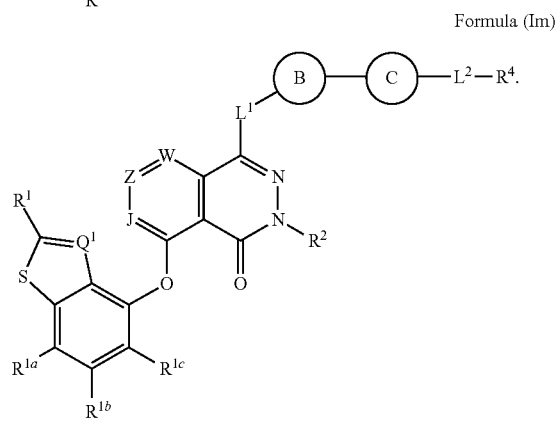

Formula (In)
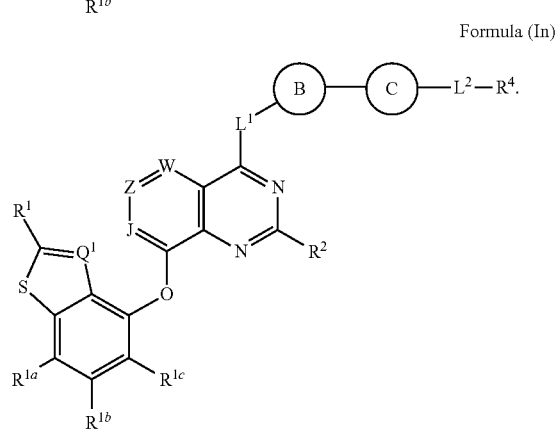

Formula (Io)
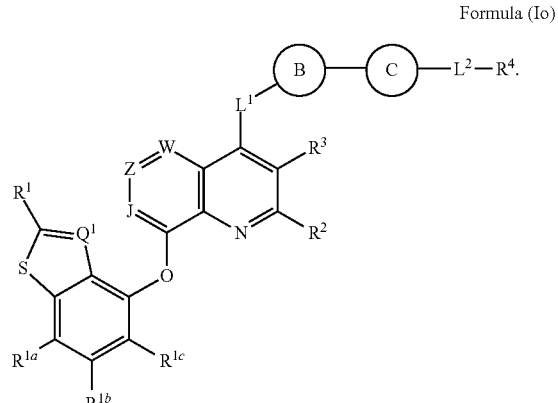

wherein:

is a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

$Q^1$ is N or $C(R^{14})$;

Z is N or $C(R^8)$;

J is selected from N and $C(R^{16})$;

W is N or $C(R^{18})$;

$L^1$ and $L^2$ are independently selected from a bond, $C_1$-$C_6$alkyl, —O—, —N($R^{26}$)—, —C(O)—, —N($R^{26}$)C(O)—, —C(O)N($R^{26}$)—, —S—, —S(O)$_2$—, —S(O)—, —S(O)$_2$N($R^{26}$), —S(O)N($R^{26}$), —N($R^{26}$)S(O)—, —N($R^{26}$)S(O)$_2$—, —OCON($R^{26}$)—, —N($R^{26}$)C(O)O—, and —N($R^{26}$)C(O)N($R^{26}$)—;

$R^1$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, —$SR^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, and $C_{1-9}$heteroaryl are optionally substituted with one, two, or three $R^{20a}$;

$R^{1a}$, $R^{1b}$, $R^{1c}$, and $R^{1d}$ are each independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;

$R^2$ is selected from halogen, —CN, $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$;

each $R^3$ is independently selected from hydrogen, halogen, oxo, $C_1$-$C_6$alkyl, $C_1$-$C_6$haloalkyl, —$OR^{12}$, —N($R^{12}$)($R^{13}$), —CN, —C(O)O$R^{12}$, —OC(O)N($R^{12}$)($R^{13}$), —C(O)$R^{15}$, —S(O)$_2R^{15}$, and —S(O)$_2$N($R^{12}$)($R^{13}$);

$R^4$ is hydrogen, or a group other than an electrophilic moiety capable of forming a covalent bond with the cysteine residue at position 12 of a KRAS protein;

$R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;

each $R^{10}$ and each $R^{11}$ are independently selected from halogen, oxo, $C_1$-$C_6$alkyl, $C_1$-$C_6$haloalkyl, —$OR^{12}$, —N($R^{12}$)($R^{13}$), —CN, —C(O)O$R^{12}$, —OC(O)N($R^{12}$)($R^{13}$), —C(O)$R^{15}$, —S(O)$_2R^{15}$, and —S(O)$_2$N($R^{12}$)($R^{13}$)—;

each $R^{12}$ is independently selected from hydrogen, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl, wherein $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three $R^{20d}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20g}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, and $R^{20i}$, are each independently selected from halogen, —CN, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

n is 0, 1, or 2; and

===== indicates a single or double bond such that all valences are satisfied.

In some embodiments is a compound of Formula (Ik), or a pharmaceutically acceptable salt or solvate thereof:

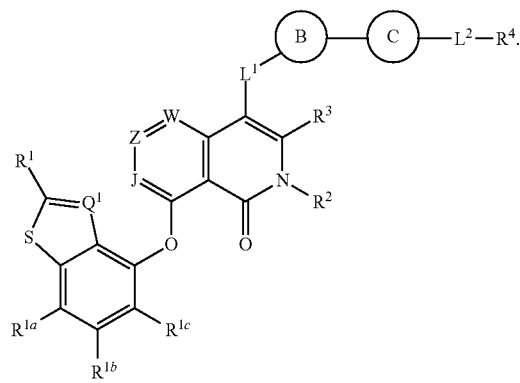

Formula (Ik)

In some embodiments is a compound of Formula (Im), or a pharmaceutically acceptable salt or solvate thereof:

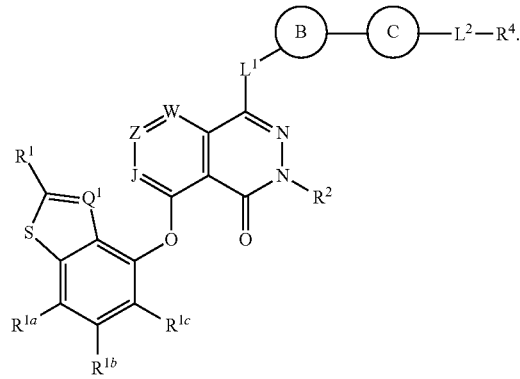

Formula (Im)

In some embodiments is a compound of Formula (In), or a pharmaceutically acceptable salt or solvate thereof:

Formula (In)

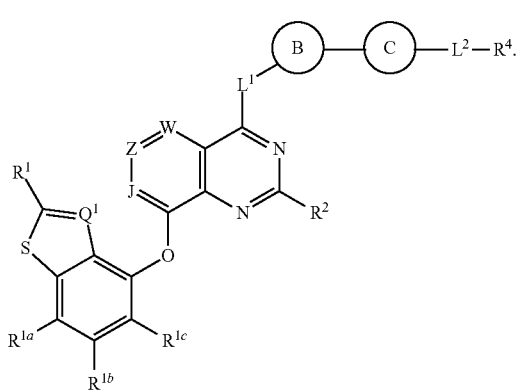

In some embodiments is a compound of Formula (Io), or a pharmaceutically acceptable salt or solvate thereof:

Formula (Io)

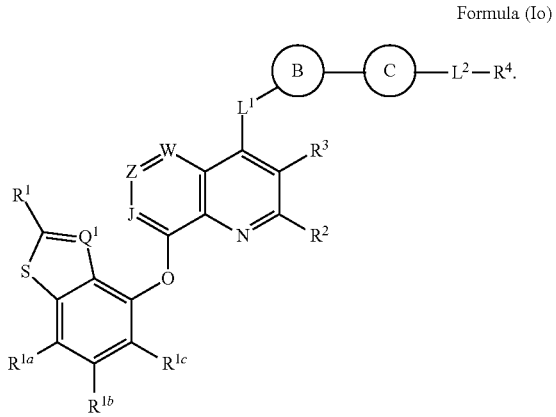

In some embodiments is a compound of Formula (If), (Ig), (Ih), or (Ii), or a pharmaceutically acceptable salt or solvate thereof, wherein V is $C(R^{16})$. In some embodiments is a compound of Formula (If), (Ig), (Ih), or (Ii), or a pharmaceutically acceptable salt or solvate thereof, wherein V is C(H). In some embodiments is a compound of Formula (If), (Ig), (Ih), or (Ii), or a pharmaceutically acceptable salt or solvate thereof, wherein V is N.

In some embodiments is a compound of Formula (Ik), (Im), (In), or (Io), or a pharmaceutically acceptable salt or solvate thereof, wherein J is $C(R^{16})$. In some embodiments is a compound of Formula (Ik), (Im), (In), or (Io), or a pharmaceutically acceptable salt or solvate thereof, wherein J is C(H). In some embodiments is a compound of Formula (Ik), (Im), (In), or (Io), or a pharmaceutically acceptable salt or solvate thereof, wherein J is N.

In some embodiments is a compound of Formula (Ik), (Im), (In), or (Io), or a pharmaceutically acceptable salt or solvate thereof, wherein Z is $C(R^8)$. In some embodiments is a compound of Formula (Ik), (Im), (In), or (Io), or a pharmaceutically acceptable salt or solvate thereof, wherein Z is N.

In some embodiments is a compound of Formula (If), (Ig), (Ih), (Ii), (Ik), (Im), (In), or (Io), or a pharmaceutically acceptable salt or solvate thereof, wherein W is $C(R^{18})$. In some embodiments is a compound of Formula (If), (Ig), (Ih), (Ii), (Ik), (Im), (In), or (Io), or a pharmaceutically acceptable salt or solvate thereof, wherein W is N.

In some embodiments is a compound of Formula (Ip), or a pharmaceutically acceptable salt or solvate thereof:

Formula (Ip)

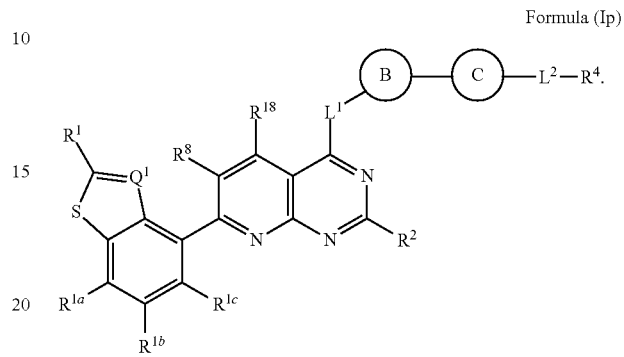

In another aspect, the disclosure provides a compound of Formula (II), or a pharmaceutically acceptable salt or solvate Formula (II)

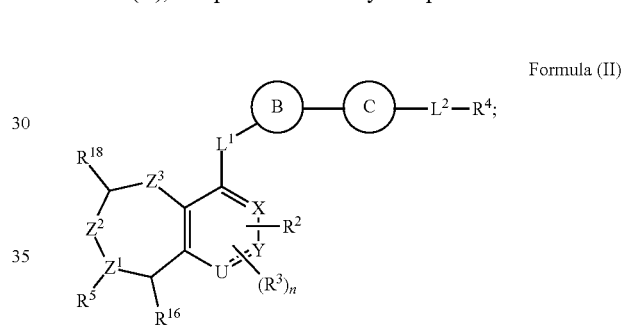

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, $N(R^{1c})$, or $C(R^{1f})(R^{1g})$;
$Q^1$ is N or $C(R^{1d})$;
$Q^2$ is S or O;
X is C or N;

Y is C, C(O), or N;
$Z^1$ is N or $C(R^6)$;
$Z^2$ is $N(R^7)$ or $C(R^8)(R^9)$;
$Z^3$ is absent, $N(R^{17})$, or $C(R^{27})(R^{28})$;
U is C, S(O), $S(O)_2$, C(O), or N;
$L^1$ and $L^2$ are independently selected from a bond, $C_1$-$C_6$alkyl, —O—, —$N(R^{26})$—, —C(O)—, —$N(R^{26})$C(O)—, —C(O)$N(R^{26})$—, —S—, —$S(O)_2$—, —S(O)—, —$S(O)_2N(R^{26})$, —$S(O)N(R^{26})$, —$N(R^{26})S(O)$—, —$N(R^{26})S(O)_2$—, —$OCON(R^{26})$—, —$N(R^{26})C(O)O$—, and —$N(R^{26})C(O)N(R^{26})$—;
$R^1$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$;
$R^{1a}$, $R^{1b}$, $R^{1c}$, $R^{1d}$, $R^{1e}$, $R^{1f}$, and $R^{1g}$ are each independently selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1f}$ and $R^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;
$R^2$ is selected from halogen, —CN, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$;
each $R^3$ is independently selected from hydrogen, halogen, oxo, $C_1$-$C_6$alkyl, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;
$R^4$ is hydrogen, or a group other than an electrophilic moiety capable of forming a covalent bond with the cysteine residue at position 12 of a KRAS protein;
$R^5$ is

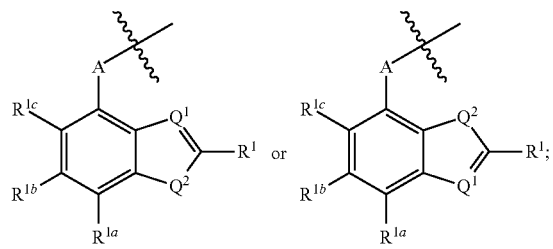

$R^6$ is selected from hydrogen and $C_{1-6}$alkyl;
$R^7$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;
$R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;
$R^9$ is selected from hydrogen and $C_{1-6}$alkyl;
each $R^{10}$ and each $R^{11}$ are independently selected from halogen, oxo, $C_1$-$C_6$alkyl, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;
each $R^{12}$ is independently selected from hydrogen, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20c}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20k}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, and $R^{20k}$ are each independently selected from halogen, —CN, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;
each $R^{24}$ is independently selected from H and $C_{1-6}$alkyl;
each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

$R^{27}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20j}$;

$R^{28}$ is selected from hydrogen and $C_{1-6}$alkyl;
n is 0, 1, or 2; and
===== indicates a single or double bond such that all valences are satisfied.

In some embodiments is a compound of Formula (II) having the structure of Formula (IIa), or a pharmaceutically acceptable salt or solvate thereof:

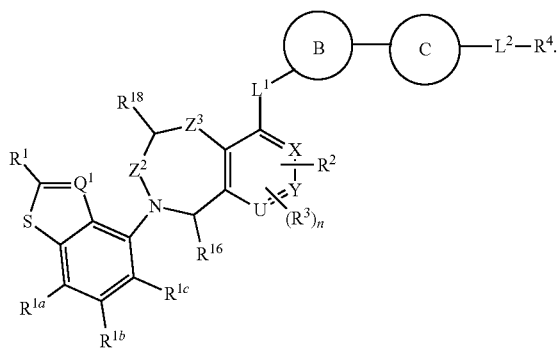

Formula (IIa)

In some embodiments is a compound of Formula (II) having the structure of Formula (IIb), or a pharmaceutically acceptable salt or solvate thereof:

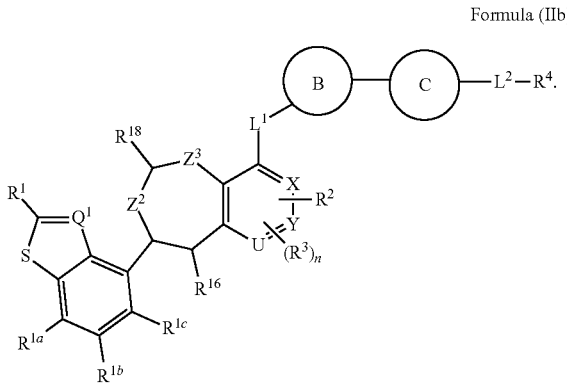

Formula (IIb)

In some embodiments is a compound of Formula (II), (IIa), or (IIb), or a pharmaceutically acceptable salt or solvate thereof, wherein $Z^2$ is $C(R^8)(R^9)$. In some embodiments is a compound of Formula (II), (IIa), or (IIb), or a pharmaceutically acceptable salt or solvate thereof, wherein $R^9$ is hydrogen.

In some embodiments is a compound of Formula (II), (IIa), or (IIb), or a pharmaceutically acceptable salt or solvate thereof, wherein X is C. In some embodiments is a compound of Formula (II), (IIa), or (IIb), or a pharmaceutically acceptable salt or solvate thereof, wherein X is N.

In some embodiments is a compound of Formula (II), (IIa), or (IIb), or a pharmaceutically acceptable salt or solvate thereof, wherein Y is C. In some embodiments is a compound of Formula (II), (IIa), or (IIb), or a pharmaceutically acceptable salt or solvate thereof, wherein Y is N. In some embodiments is a compound of Formula (II), (IIa), or (IIb), or a pharmaceutically acceptable salt or solvate thereof, wherein Y is C(O).

In some embodiments is a compound of Formula (II), (IIa), or (IIb), or a pharmaceutically acceptable salt or solvate thereof, wherein U is C. In some embodiments is a compound of Formula (II), (IIa), or (IIb), or a pharmaceutically acceptable salt or solvate thereof, wherein U is N. In some embodiments is a compound of Formula (II), (IIa), or (IIb), or a pharmaceutically acceptable salt or solvate thereof, wherein U is C(O).

In some embodiments is a compound of Formula (II) having the structure of Formula (IIc), or a pharmaceutically acceptable salt or solvate thereof:

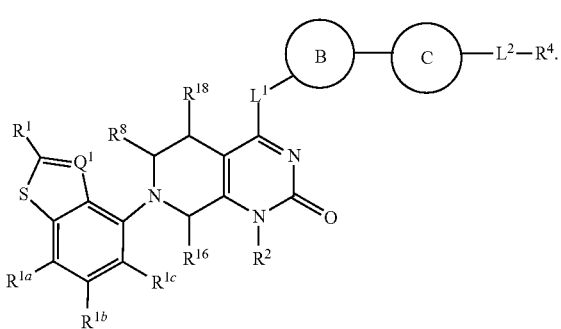

Formula (IIc)

In some embodiments is a compound of Formula (II) having the structure of Formula (IId), or a pharmaceutically acceptable salt or solvate thereof:

Formula (IId)

In some embodiments is a compound of Formula (II) having the structure of Formula (Ie), or a pharmaceutically acceptable salt or solvate thereof:

Formula (Ie)

In some embodiments is a compound of Formula (II) having the structure of Formula (IIf), or a pharmaceutically acceptable salt or solvate thereof:

Formula (IIf)

In some embodiments is a compound of Formula (II) having the structure of Formula (IIg), or a pharmaceutically acceptable salt or solvate thereof:

Formula (IIg)

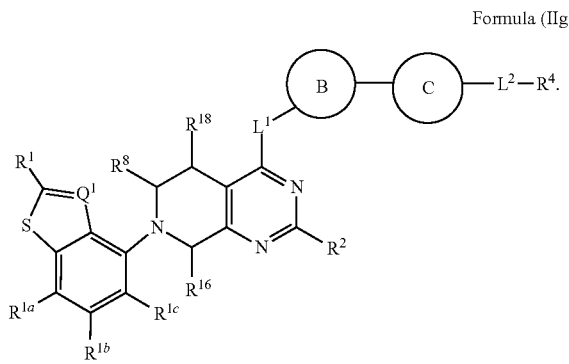

In some embodiments is a compound of Formula (II) having the structure of Formula (IIh), or a pharmaceutically acceptable salt or solvate thereof:

Formula (IIh)

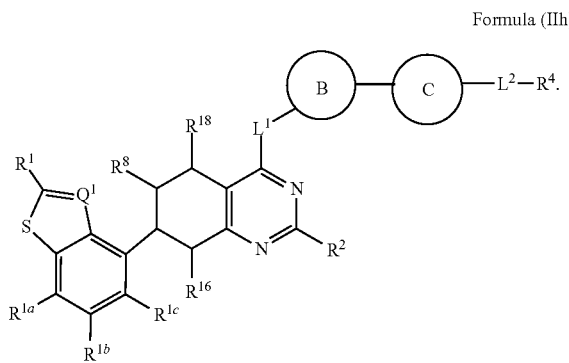

In some embodiments is a compound of Formula (II) having the structure of Formula (III), or a pharmaceutically acceptable salt or solvate thereof:

Formula (IIi)

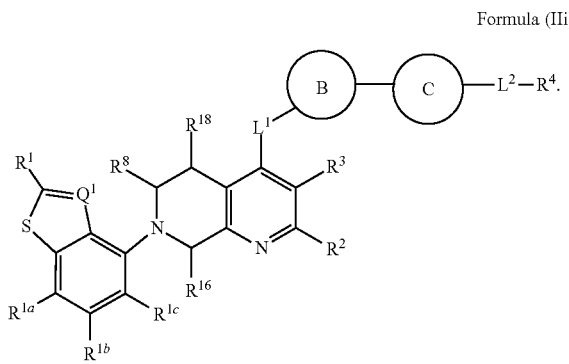

In some embodiments is a compound of Formula (II) having the structure of Formula (IIj), or a pharmaceutically acceptable salt or solvate thereof:

Formula (IIj)

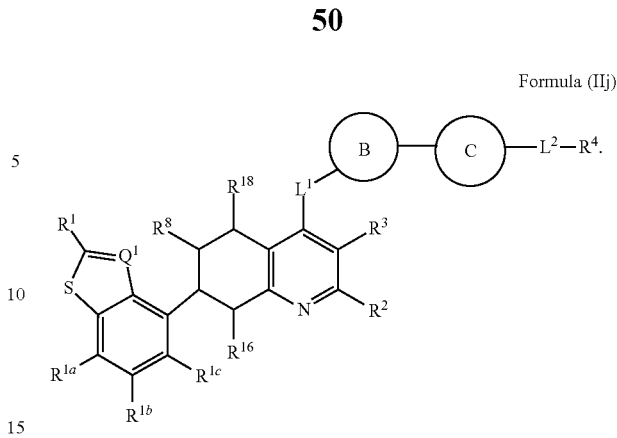

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^1$ is selected from hydrogen, $-N(R^{12})(R^{13})$, and $C_{1-6}$alkyl optionally substituted with one, two, or three $R^{20a}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^1$ is $-N(R^{12})(R^{13})$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^1$ is $-NH_2$.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{1a}$, $R^{1b}$, and $R^{1c}$ are each independently selected from hydrogen, halogen, and $C_{1-6}$alkyl optionally substituted with one, two, or three $R^{20a}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{1a}$, $R^{1b}$, and $R^{1c}$ are each hydrogen.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $Q^1$ is $C(R^{1d})$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{1d}$ is selected from hydrogen and $C_{1-6}$alkyl optionally substituted with one, two, or three $R^{20a}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $Q^1$ is N.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein is a 3-12 membered heterocycloalkyl ring optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is selected from piperazinyl and piperidinyl, wherein piperazinyl and piperidinyl are optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a cyclohexyl ring optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{11}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is absent.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is selected from piperazinyl and piperidinyl, wherein piperazinyl and piperidinyl are optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is piperazinyl optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a cyclohexyl ring optionally substituted with one or more $R^{10}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{10}$.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^1$ is selected from a bond, $C_1$-$C_6$alkyl, —N($R^{26}$)—, and —C(O)—. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^1$ is a bond. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^1$ is a $C_1$-$C_6$alkyl.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^2$ is selected from a bond, $C_1$-$C_6$alkyl, and —C(O)—. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^2$ is a bond. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $L^2$ is a $C_1$-$C_6$alkyl.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from hydrogen, $C_{1-6}$alkyl, $C_{3-6}$cycloalkyl, $C_{2-9}$heterocycloalkyl, $C_{6-10}$aryl, $C_{1-9}$heteroaryl, —$OR^{12}$, —$SR^{12}$, and —N($R^{12}$)($R^{13}$), wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from —$OR^{12}$, —$SR^{12}$, and $C_{1-6}$alkyl, wherein $C_{1-6}$alkyl is optionally substituted with one, two, or three $R^{20b}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^2$ is —$OR^{12}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{12}$ is selected from $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{12}$ is $C_{1-6}$alkyl optionally substituted with one, two, or three $R^{20d}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{12}$ is $C_{2-9}$heterocycloalkyl optionally substituted with one, two, or three $R^{20d}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{12}$ is —$CH_2$—$C_{2-9}$heterocycloalkyl optionally substituted with one, two, or three $R^{20d}$. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein each $R^{20d}$ is independently selected from halogen, $C_{1-6}$alkyl, $C_{3-6}$cycloalkyl, $C_{2-9}$heterocycloalkyl, $C_{6-10}$aryl, $C_{1-9}$heteroaryl, —$OR^{21}$, —$SR^{21}$, —N($R^{22}$)($R^{23}$), —C(O)$OR^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)$OR^{25}$, —N($R^{24}$)C(O)$R^{25}$, —N($R^{24}$)S(O)$_2R^{25}$, —C(O)$R^{25}$, —S(O)$_2R^{25}$, —S(O)$_2$N($R^{22}$)($R^{23}$), —OCH$_2$C(O)$OR^{22}$, and —OC(O)$R^{25}$, wherein $C_{1-6}$alkyl, $C_{3-6}$cycloalkyl, $C_{2-9}$heterocycloalkyl, $C_{6-10}$aryl, $C_{1-9}$heteroaryl are optionally substituted with one, two, or three groups independently selected from halogen, oxo, $C_{1-6}$alkyl, $C_{1-6}$haloalkyl, $C_{1-6}$alkoxy, $C_{1-6}$haloalkoxy, —$OR^{21}$, —$SR^{21}$, —N($R^{22}$)($R^{23}$), —C(O)$OR^{22}$, —C(O)N($R^{22}$)($R^{23}$), —S(O)$_2R^{25}$, and —S(O)$_2$N($R^{22}$)($R^{23}$). In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein each $R^{20d}$ is independently selected from halogen, $C_{1-6}$alkyl, and —$OR^{21}$, wherein $C_{1-6}$alkyl is optionally substituted with one, two, or three groups independently selected from halogen, oxo, $C_{1-6}$alkyl, —$OR^{21}$, and —N($R^{22}$)($R^{23}$). In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^2$ is selected from

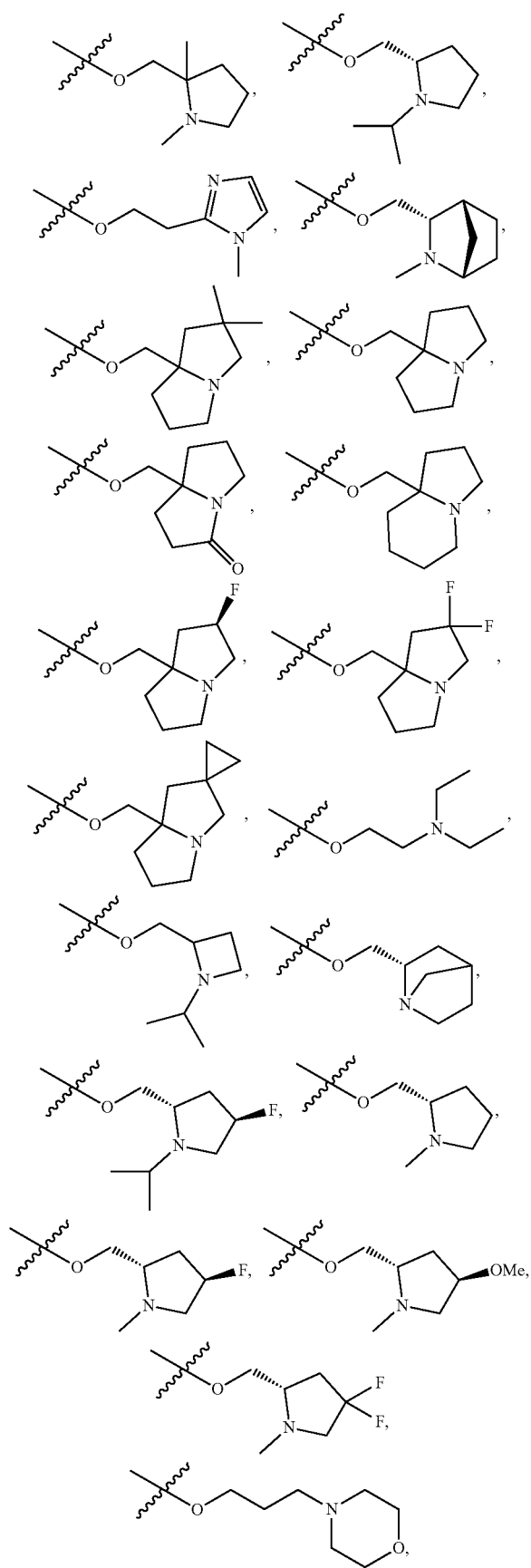
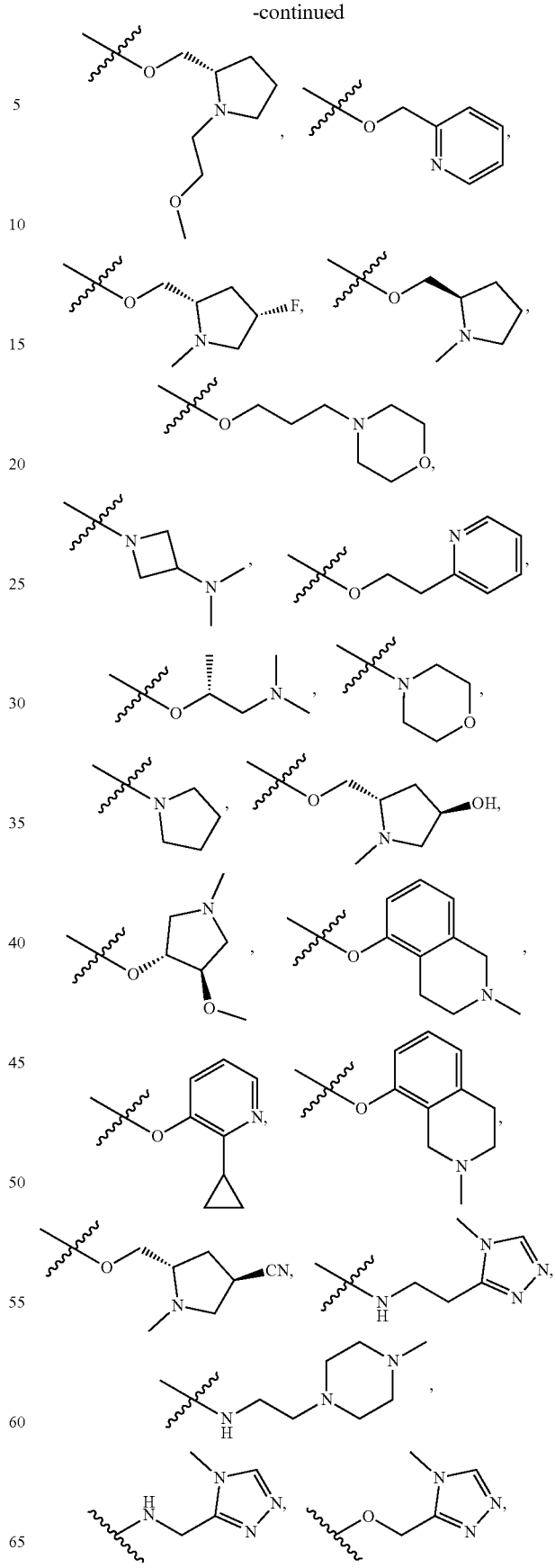

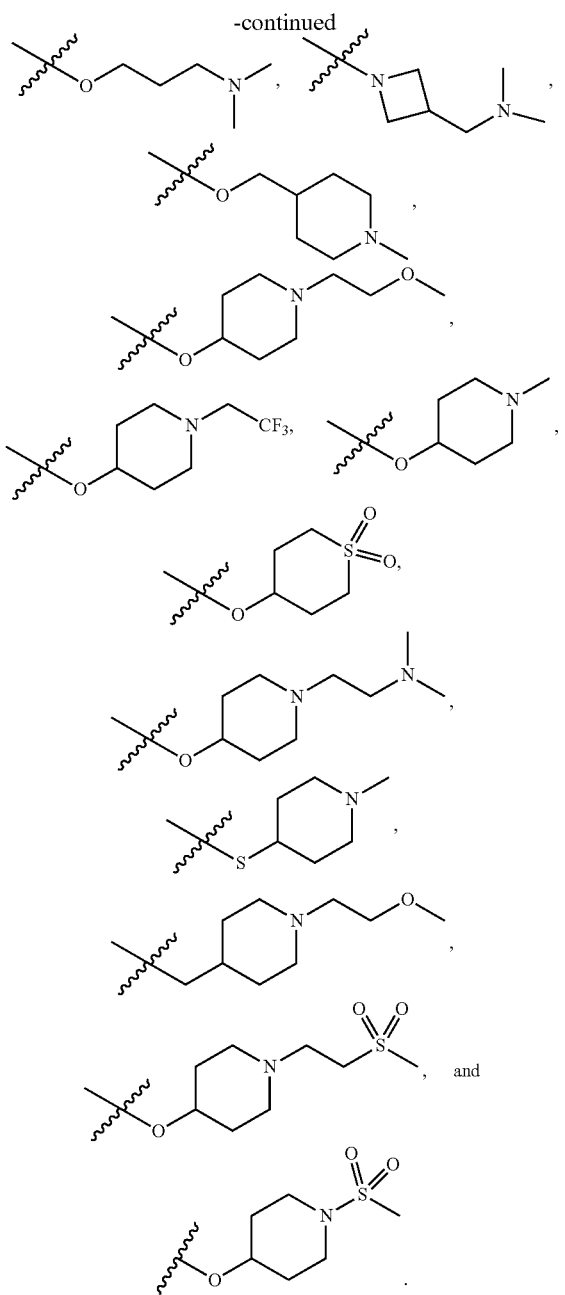

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^8$ is hydrogen, halogen, or $C_{1-6}$alkyl. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^8$ is hydrogen.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{16}$ is hydrogen, halogen, or $C_{1-6}$alkyl. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{16}$ is hydrogen.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{18}$ is hydrogen, halogen, or $C_{1-6}$alkyl. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^{18}$ is hydrogen.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^4$ is hydrogen. In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^4$ is a group other than an electrophilic moiety capable of forming a covalent bond with the cysteine residue at position 12 of a KRAS protein.

In some embodiments is a compound of Formula (If), (Ig), (Ih), (Ii), (Ik), (Im), (In), (Io), (Ip), (II), (IIa), (IIb), (IIc), (IId), (IIe), (IIf), (IIg), (IIh), (IIi), or (IIj), or a pharmaceutically acceptable salt or solvate thereof, wherein $R^4$ is —H, —NH$_2$, —OH, —NH(C$_{1-6}$alkyl).

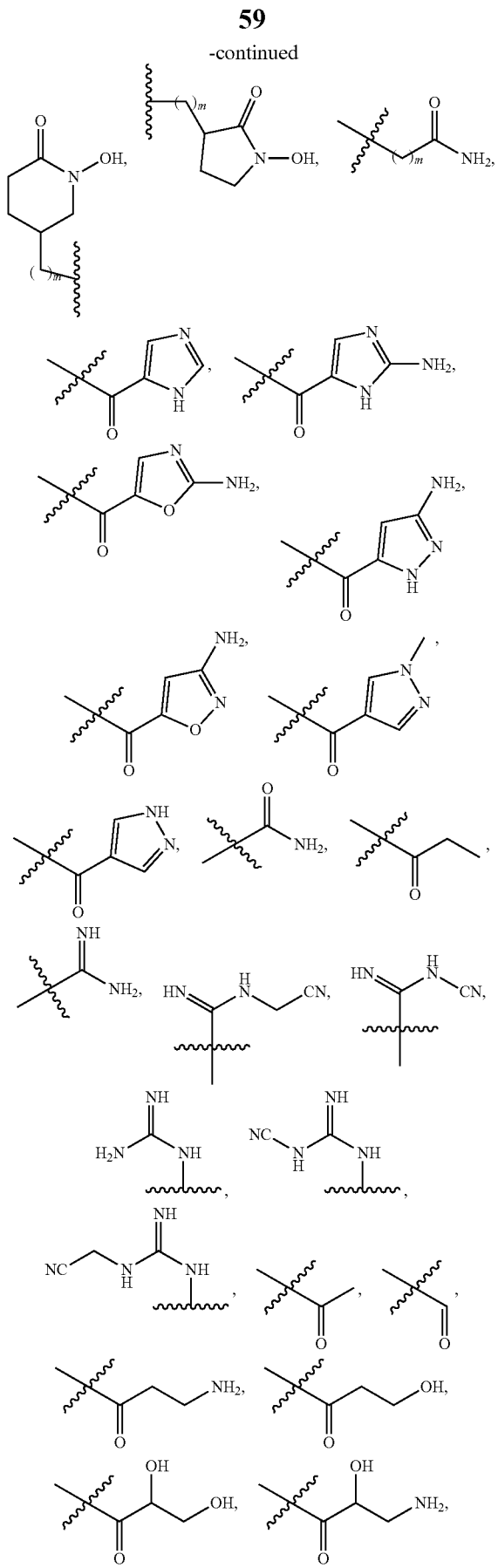
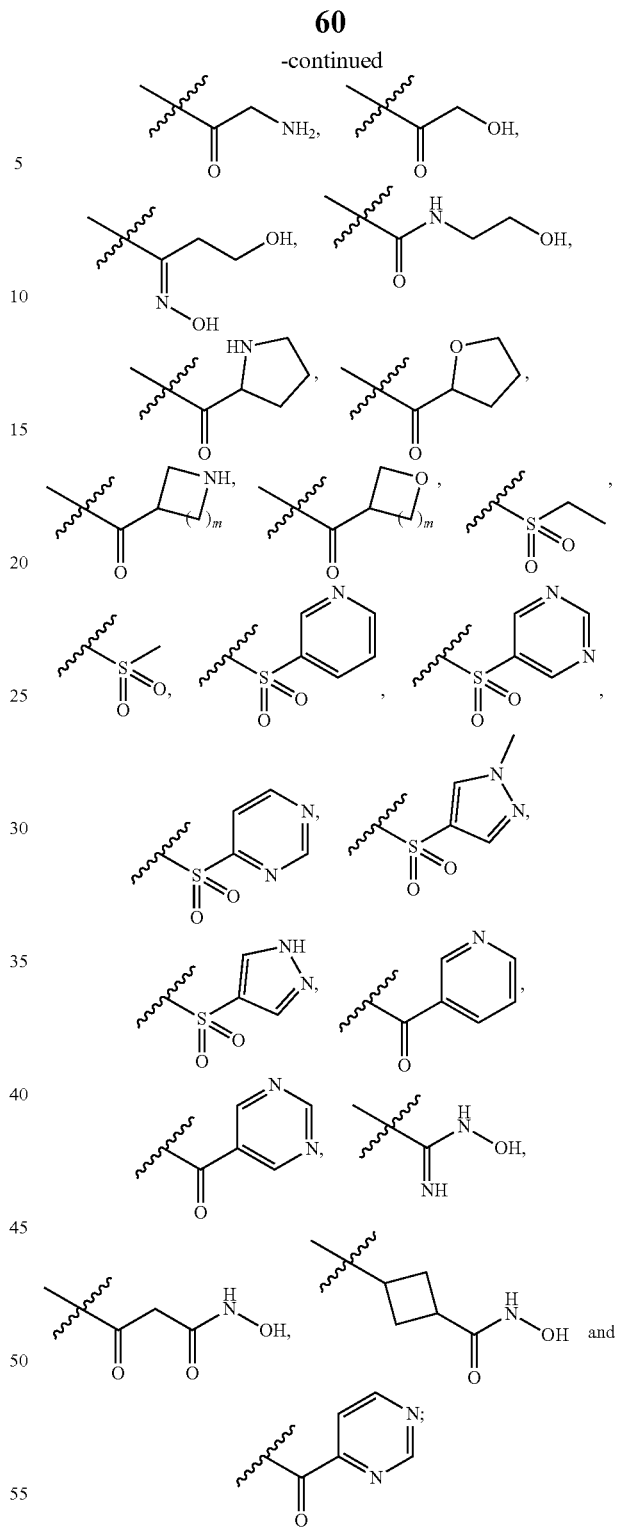

and m, when present, is 0, 1, 2, or 3.

In another aspect, the disclosure provides a pharmaceutical composition comprising a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, and a pharmaceutically acceptable excipient. In another aspect, the disclosure provides a pharmaceutical composition comprising a compound of Formula (Ip), or a pharmaceutically acceptable salt or solvate thereof, and a pharmaceutically acceptable excipient.

In another aspect, the disclosure provides a method of treating cancer in a subject in need thereof, comprising administering to the subject a therapeutically effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof. In another aspect, the disclosure provides a method of treating cancer in a subject in need thereof, comprising administering to the subject a therapeutically effective amount of a compound of Formula (Ip), or a pharmaceutically acceptable salt or solvate thereof. In some embodiments, the cancer is a solid tumor. In some embodiments, the cancer is a hematological cancer. In some embodiments, said method comprises administering an additional agent or therapy. In some embodiments, the additional agent or therapy is selected from the group consisting of a chemotherapeutic agent, a radioactive agent, and an immune modulator.

In another aspect, the disclosure provides a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, thereby modulating the activity of the Ras protein. In another aspect, the disclosure provides a method of modulating activity of a Ras protein, comprising contacting a Ras protein with an effective amount of a compound of Formula (Ip), or a pharmaceutically acceptable salt or solvate thereof, thereby modulating the activity of the Ras protein. In some embodiments, said modulating comprises inhibiting the Ras protein activity. In some embodiments, the Ras protein is a K-Ras protein. In some embodiments, the Ras protein is a G12D or G12V mutant K-Ras. In some embodiments, said method comprises administering an additional agent or therapy. In some embodiments, the additional agent or therapy is selected from the group consisting of a chemotherapeutic agent, a radioactive agent, and an immune modulator.

In another aspect, the disclosure provides a Ras protein bound by a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein activity of said Ras protein is reduced as compared to a Ras protein unbound to said compound. In another aspect, the disclosure provides a Ras protein bound by a compound of Formula (Ip), or a pharmaceutically acceptable salt or solvate thereof, wherein activity of said Ras protein is reduced as compared to a Ras protein unbound to said compound.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . . $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡CCH$_3$, —C≡CCH$_2$CH$_3$ and —C≡CCH$_2$CH$_2$CH$_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized x-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

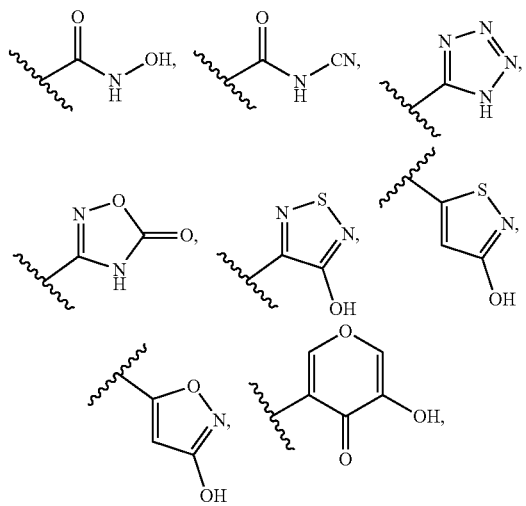

and the like.

The term "cycloalkyl" refers to a monocyclic or polycyclic non-aromatic radical, wherein each of the atoms forming the ring (i.e. skeletal atoms) is a carbon atom. Cycloalkyls may be saturated or partially unsaturated. In some embodiments, a cycloalkyl ring is fused with an aryl, heteroaryl, heterocycloalkyl, or a second cycloalkyl ring. In some embodiments, a cycloalkyl ring is a spirocyclic cycloalkyl ring. In some embodiments, cycloalkyl groups include groups having from 3 to 10 ring atoms. Depending on the structure, a cycloalkyl group can be a monoradical or a diradical (i.e., a cycloalkylene group).

The terms "heteroaryl" or, alternatively, "heteroaromatic" refers to an aryl group that includes one or more ring heteroatoms selected from nitrogen, oxygen and sulfur. As used herein, the heteroaryl radical is a monocyclic, bicyclic, or tricyclic ring system, wherein at least one of the rings in the ring system is fully unsaturated. An N-containing "heteroaromatic" or "heteroaryl" moiety refers to an aromatic group in which at least one of the skeletal atoms of the ring is a nitrogen atom. Depending on the structure, a heteroaryl group can be a monoradical or a diradical (i.e., a heteroarylene group).

A "heterocycloalkyl" group or "heteroalicyclic" group refers to a cycloalkyl group, wherein at least one skeletal ring atom is a heteroatom selected from nitrogen, oxygen and sulfur. Heterocycloalkyls may be saturated or partially unsaturated. In some embodiments, a heterocycloalkyl ring is fused with an aryl, heteroaryl, cycloalkyl, or a second heterocycloalkyl ring. The term heterocycloalkyl also includes all ring forms of the carbohydrates, including but not limited to the monosaccharides, the disaccharides and the oligosaccharides. In some embodiments, a heterocycloalkyl ring is a spirocyclic heterocycloalkyl ring. In some embodiments, a heterocycloalkyl ring is a bridged heterocycloalkyl ring. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Depending on the structure, a heterocycloalkyl group can be a monoradical or a diradical (i.e., a heterocycloalkylene group).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include $-CH_2Cl$, $-CF_3$, $-CHF_2$, $-CH_2CF_3$, $-CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include $-CF_3$, $-CHF_2$, $-CH_2F$, $-CH_2CF_3$, $-CF_2CF_3$, $-CF_2CF_2CF_3$, $-CF(CH_3)_3$, and the like. Non-limiting examples of fluoroalkoxy groups, include $-OCF_3$, $-OCHF_2$, $-OCH_2F$, $-OCH_2CF_3$, $-OCF_2CF_3$, $-OCF_2CF_2CF_3$, $-OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, $-CH_2-O-CH_3$, $-CH_2-CH_2-O-CH_3$, $-CH_2-NH-CH_3$, $-CH_2-CH_2-NH-CH_3$, $-CH_2-N(CH_3)-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH_2-NH-OCH_3$, $-CH_2-O-Si(CH_3)_3$, $-CH_2-CH=N-OCH_3$, and $-CH=CH-N(CH_3)-CH_3$. In addition, up to two heteroatoms may be consecutive, such as, by way of example, $-CH_2-NH-OCH_3$ and $-CH_2-O-Si(CH_3)_3$. Excluding the number of heteroatoms, a "heteroalkyl" may have from 1 to 6 carbon atoms.

The term "oxo" refers to the =O radical.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, $-OH$, alkoxy, aryloxy, alkylthio, arylthio, alkylsulfoxide, arylsulfoxide, alkylsulfone, arylsulfone, $-CN$, alkyne, $C_1$-$C_6$alkylalkyne, halo, acyl, acyloxy, $-CO_2H$, $-CO_2$-alkyl, nitro, haloalkyl, fluoroalkyl, and amino, including mono- and di-substituted amino groups (e.g.—$NH_2$, $-NHR$, $-N(R)_2$), and the protected derivatives thereof. By way of example, an optional substituents may be $L^sR^s$, wherein each $L^s$ is independently selected from a bond, $-O-$, $-C(=O)-$, $-S-$, $-S(=O)-$, $-S(=O)_2-$, $-NH-$, $-NHC(O)-$, $-C(O)NH-$, $S(=O)_2NH-$, $-NHS(=O)_2$, $-OC(O)NH-$, $-NHC(O)$ $O-$, $-(C_1$-$C_6$alkyl)-, or $-(C_2$-$C_6$alkenyl)-; and each $R^s$ is independently selected from among H, $(C_1$-$C_6$alkyl), $(C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

"Pharmaceutically acceptable salt" includes both acid and base addition salts. A pharmaceutically acceptable salt of any one of the heterocyclic compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and, aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), Morpholino and locked nucleic acid (LNA), glycol nucleic acid (GNA), threose nucleic acid (TNA), 2'-fluoro, 2'—OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

"Prodrug" as used herein is meant to indicate a compound that may be converted under physiological conditions or by solvolysis to a biologically active compound described herein. The term "prodrug" refers to a precursor of a biologically active compound that is pharmaceutically acceptable. A prodrug may be inactive when administered to a subject, but is converted in vivo to an active compound, for example, by hydrolysis. The prodrug compound may offer advantages of solubility, tissue compatibility and/or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. A "prodrug" can be any covalently bonded carriers, that release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

An "antigen" is a moiety or molecule that contains an epitope, and, as such, also specifically binds to an antibody.

An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or VHH), a heavy chain found in sharks (V-NAR domain), a single domain antibody (sdAb, i.e., "nanobody") that comprises a single antigen-binding domain, Fv, Fd, Fab, Fab', F(ab')$_2$, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., (VH-VL-CH$_3$)$_2$, (scFv-CH$_3$)$_2$, ((scFv)2—CH$_3$+CH$_3$), ((scFv)2—CH$_3$) or (scFv-CH$_3$-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

The term "in vivo" refers to an event that takes place in a subject's body.

The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body.

The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The term "Ras" or "RAS" refers to a protein in the Rat sarcoma (Ras) superfamily of small GTPases, such as in the Ras subfamily. The Ras superfamily includes, but is not limited to, the Ras subfamily, Rho subfamily, Rab subfamily, Rap subfamily, Arf subfamily, Ran subfamily, Rheb subfamily, RGK subfamily, Rit subfamily, Miro subfamily, and Unclassified subfamily. In some embodiments, a Ras protein is selected from the group consisting of KRAS(also used interchangeably herein as K-Ras, K-ras, Kras), HRAS (or H-Ras), NRAS(or N-Ras), MRAS(or M-Ras), ERAS(or E-Ras), RRAS2 (or R-Ras2), RALA (or RalA), RALB (or RalB), RIT1, and any combination thereof, such as from KRAS, HRAS, NRAS, RALA, RALB, and any combination thereof.

The terms "Mutant Ras" and "Ras mutant," as used interchangeably herein, refer to a Ras protein with one or more amino acid mutations, such as with respect to a common reference sequence such as a wild-type (WT) sequence. In some embodiments, a mutant Ras is selected from a mutant KRAS, mutant HRAS, mutant NRAS, mutant MRAS, mutant ERAS, mutant RRAS2, mutant RALA, mutant RALB, mutant RIT1, and any combination thereof, such as from a mutant KRAS, mutant HRAS, mutant NRAS, mutant RALA, mutant RALB, and any combination thereof. In some embodiments, a mutation can be an introduced mutation, a naturally occurring mutation, or a non-naturally occurring mutation. In some embodiments, a mutation can be a substitution (e.g., a substituted amino acid), insertion (e.g., addition of one or more amino acids), or deletion (e.g., removal of one or more amino acids). In some embodiments, two or more mutations can be consecutive, non-consecutive, or a combination thereof. In some embodiments, a mutation can be present at any position of Ras. In some embodiments, a mutation can be present at position 12, 13, 62, 92, 95, or any combination thereof of Ras relative to SEQ ID No. 1 when optimally aligned. In some embodiments, a mutant Ras may comprise about or at least about 1, 2, 3, 4, 5, 6, 7, 8, 9, 10, 11, 12, 13, 14, 15, 16, 17, 18, 19, 20, 25, 30, 35, 40, 45, 50, or more than 50 mutations. In some embodiments, a mutant Ras may comprise up to about 1, 2, 3, 4, 5, 6, 7, 8, 9, 10, 11, 12, 13, 14, 15, 16, 17, 18, 19, 20, 25, 30, 35, 40, 45, or 50 mutations. In some embodiments, the mutant Ras is about or up to about 500, 400, 300, 250, 240, 233, 230, 220, 219, 210, 208, 206, 204, 200, 195, 190, 189, 188, 187, 186, 185, 180, 175, 174, 173, 172, 171, 170, 169, 168, 167, 166, 165, 160, 155, 150, 125, 100, 90, 80, 70, 60, 50, or fewer than 50 amino acids in length. In some embodiments, an amino acid of a mutation is a proteinogenic, natural, standard, non-standard, non-canonical, essential, non-essential, or non-natural amino acid. In some embodiments, an amino acid of a mutation has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, a mutation comprises a reactive moiety. In some embodiments, a substituted amino acid comprises a reactive moiety. In some embodiments, a mutant Ras can be further modified, such as by conjugation with a detectable label. In some embodiments, a mutant Ras is a full-length or truncated polypeptide. For example, a mutant Ras can be a truncated polypeptide comprising residues 1-169 or residues 11-183 (e.g., residues 11-183 of a mutant RALA or mutant RALB).

Compounds

The compounds of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, are Ras modulators (including Ras inhibitors) and have a wide range of applications in therapeutics, diagnostics, and other biomedical research.

In some embodiments is a compound of Formula (I), or a pharmaceutically acceptable salt or solvate thereof:

Formula (I)

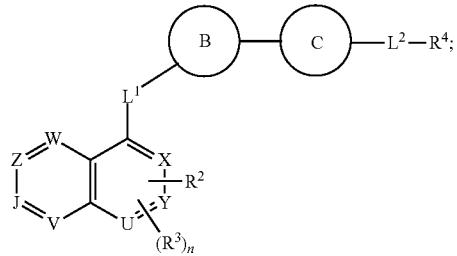

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, $N(R^{1c})$, or $C(R^{1f})(R^{1g})$;
$Q^1$ is N or $C(R^{1d})$;
$Q^2$ is S or O;
X is C or N;
Y is C, S(O), $S(O)_2$, C(O), or N;
U is C, S(O), $S(O)_2$, C(O), or N;
Z is N or $C(R^8)$;
V and J are independently selected from N, $C(R^5)$, and $C(R^{16})$, wherein one of V and J is $C(R^5)$;
W is N or $C(R^{18})$;
$L^1$ and $L^2$ are independently selected from a bond, $C_1$-$C_6$alkyl, —O—, —N($R^{26}$)—, —C(O)—, —N($R^{26}$)C(O)—, —C(O)N($R^{26}$)—, —S—, —S(O)$_2$—, —S(O)—, —S(O)$_2$N($R^{26}$), —S(O)N($R^{26}$), —N($R^{26}$)S(O)—, —N($R^{26}$)S(O)$_2$—, —OCON($R^{26}$)—, —N($R^{26}$)C(O)O—, and —N($R^{26}$)C(O)N($R^{26}$)—;
$R^1$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{1-9}$heteroaryl, —$SR^{12}$, —$N(R^{12})(R^{13})$, —C(O)$OR^{12}$, —OC(O)$N(R^{12})(R^{13})$, —$N(R^{14})C(O)N(R^{12})(R^{13})$, —$N(R^{14})C(O)OR^{15}$, —$N(R^{14})S(O)_2R^{15}$, —C(O)$R^{15}$, —S(O)$R^{15}$, —OC(O)$R^{15}$, —C(O)$N(R^{12})(R^{13})$, —C(O)C(O)$N(R^{12})(R^{13})$, —$N(R^{14})C(O)R^{15}$, —S(O)$_2R^{15}$, —S(O)$_2N(R^{12})(R^{13})$—, S(=O)(=NH)$N(R^{12})(R^{13})$, —CH$_2$C(O)$N(R^{12})(R^{13})$, —CH$_2N(R^{14})C(O)R^{15}$, —CH$_2$S(O)$_2R^{15}$, and —CH$_2$S(O)$_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, and $C_{1-9}$heteroaryl are optionally substituted with one, two, or three $R^{20a}$;

$R^{1a}$, $R^{1b}$, $R^{1c}$, $R^{1d}$, $R^{1e}$, $R^{1f}$, and $R^{1g}$ are each independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})C(O)N(R^{12})(R^{13})$, —$N(R^{14})C(O)OR^{15}$, —$N(R^{14})S(O)_2R^{15}$, —C(O)$R^{15}$, —S(O)$R^{15}$, —OC(O)$R^{15}$, —C(O)$N(R^{12})(R^{13})$, —C(O)C(O)$N(R^{12})(R^{13})$, —$N(R^{14})C(O)R^{15}$, —S(O)$_2R^{15}$, —S(O)$_2N(R^{12})(R^{13})$—, S(=O)(=NH)$N(R^{12})(R^{13})$, —CH$_2$C(O)$N(R^{12})(R^{13})$, —CH$_2N(R^{14})C(O)R^{15}$, —CH$_2$S(O)$_2R^{15}$, and —CH$_2$S(O)$_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or Rif and $R^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;

$R^2$ is selected from halogen, —CN, $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —C(O)$OR^{12}$, —OC(O)$N(R^{12})(R^{13})$, —$N(R^{14})C(O)N(R^{12})(R^{13})$, —$N(R^{14})C(O)OR^{15}$, —$N(R^{14})S(O)_2R^{15}$, —C(O)$R^{15}$, —S(O)$R^{15}$, —OC(O)$R^{15}$, —C(O)$N(R^{12})(R^{13})$, —C(O)C(O)$N(R^{12})(R^{13})$, —$N(R^{14})C(O)R^{15}$, —S(O)$_2R^{15}$, —S(O)$_2N(R^{12})(R^{13})$—, S(=O)(=NH)$N(R^{12})(R^{13})$, —CH$_2$C(O)$N(R^{12})(R^{13})$, —CH$_2N(R^{14})C(O)R^{15}$, —CH$_2$S(O)$_2R^{15}$, and —CH$_2$S(O)$_2N(R^{12})(R^{13})$, wherein $C_{2-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20d}$;

each $R^3$ is independently selected from hydrogen, halogen, oxo, $C_1$-$C_6$alkyl, $C_1$-$C_6$haloalkyl, —$OR^{12}$, —$N(R^{12})(R^{13})$, —CN, —C(O)$OR^{12}$, —OC(O)$N(R^{12})(R^{13})$, —C(O)$R^{15}$, —S(O)$_2R^{15}$, and —S(O)$_2N(R^{12})(R^{13})$;

$R^4$ is hydrogen, or a group other than an electrophilic moiety capable of forming a covalent bond with the cysteine residue at position 12 of a KRAS protein;

$R^5$ is

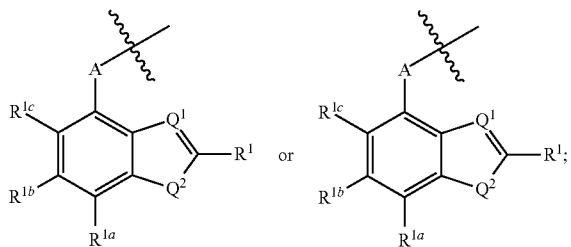

or;

- $R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{20c}$;
- each R$^{10}$ and each R$^{11}$ are independently selected from halogen, oxo, $C_1$-$C_6$alkyl, $C_1$-$C_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$)—;
- each R$^{12}$ is independently selected from hydrogen, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl, wherein $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three R$^{20d}$;
- each R$^{13}$ is independently selected from hydrogen, $C_{1-6}$alkyl, and $C_{1-6}$haloalkyl; or R$^{12}$ and R$^{13}$, together with the nitrogen to which they are attached, form a $C_{2-9}$heterocycloalkyl ring optionally substituted with one, two, or three R$^{20c}$;
- each R$^{14}$ is independently selected from hydrogen, $C_{1-6}$alkyl, and $C_{1-6}$haloalkyl;
- each R$^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{20f}$;
- R$^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{20g}$;
- R$^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{20h}$;
- each R$^{20a}$, R$^{20b}$, R$^{20c}$, R$^{20d}$, R$^{20e}$, R$^{20f}$, R$^{20g}$, R$^{20h}$, and R$^{20i}$, are each independently selected from halogen, —CN, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, $C_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;
- each R$^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
- each R$^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
- each R$^{23}$ is independently selected from H and $C_{1-6}$alkyl;
- each R$^{24}$ is independently selected from H and $C_{1-6}$alkyl;
- each R$^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;
- each R$^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three R$^{20i}$;
- n is 0, 1, or 2; and
- ----- indicates a single or double bond such that all valences are satisfied.

In some embodiments is a compound of Formula (I) having the structure of Formula (Ia), or a pharmaceutically acceptable salt or solvate thereof:

Formula (Ia)

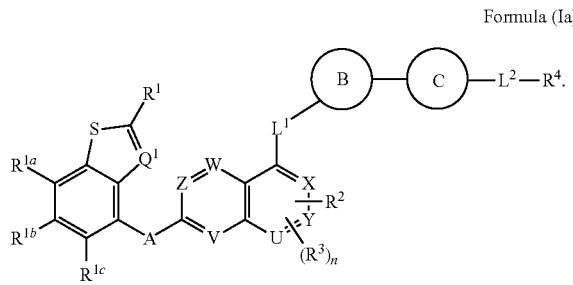

In some embodiments is a compound of Formula (I) having the structure of Formula (Ib), or a pharmaceutically acceptable salt or solvate thereof:

Formula (Ib)

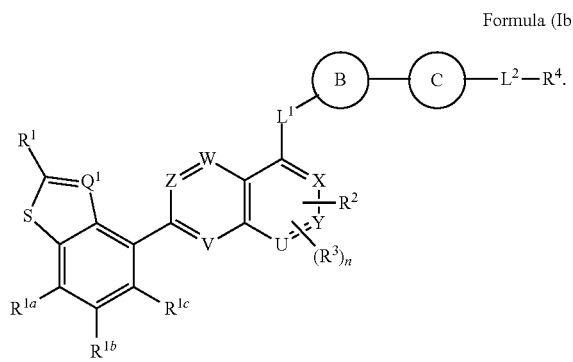

In some embodiments is a compound of Formula (I), (Ia), or (Ib), or a pharmaceutically acceptable salt or solvate thereof, wherein V is $C(R^{16})$. In some embodiments is a compound of Formula (I), (Ia), or (Ib), or a pharmaceutically acceptable salt or solvate thereof, wherein V is C(H). In some embodiments is a compound of Formula (I), (Ia), or (Ib), or a pharmaceutically acceptable salt or solvate thereof, wherein V is N.

In some embodiments is a compound of Formula (I) having the structure of Formula (Ic), or a pharmaceutically acceptable salt or solvate thereof:

Formula (Ic)

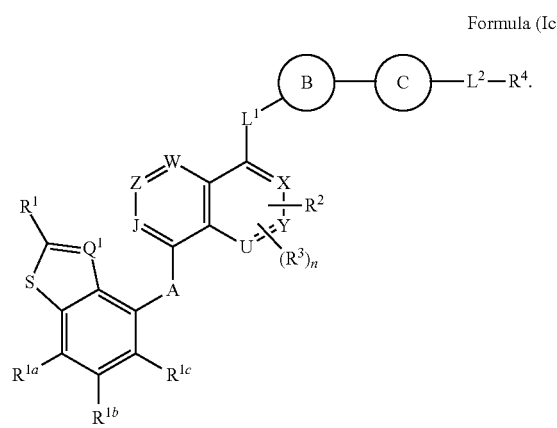

In some embodiments is a compound of Formula (I) having the structure of Formula (Id), or a pharmaceutically acceptable salt or solvate thereof:

Formula (Id)

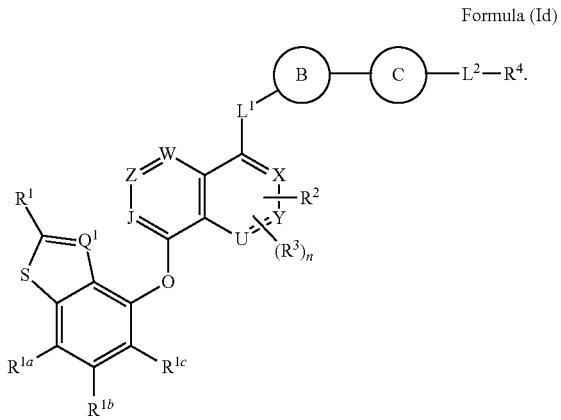

In some embodiments is a compound of Formula (Ic) or (Id), or a pharmaceutically acceptable salt or solvate thereof, wherein J is $C(R^{16})$. In some embodiments is a compound of Formula (Ic) or (Id), or a pharmaceutically acceptable salt or solvate thereof, wherein J is C(H). In some embodiments is a compound of Formula (Ic) or (Id), or a pharmaceutically acceptable salt or solvate thereof, wherein J is N.

In some embodiments is a compound of Formula (I), (Ia), (Ib), (Ic) or (Id), or a pharmaceutically acceptable salt or solvate thereof, wherein X is C. In some embodiments is a compound of Formula (I), (Ia), (Ib), (Ic) or (Id), or a pharmaceutically acceptable salt or solvate thereof, wherein X is N.

In some embodiments is a compound of Formula (I), (Ia), (Ib), (Ic) or (Id), or a pharmaceutically acceptable salt or solvate thereof, wherein U is C. In some embodiments is a compound of Formula (I), (Ia), (Ib), (Ic) or (Id), or a pharmaceutically acceptable salt or solvate thereof, wherein U is N. In some embodiments is a compound of Formula (I), (Ia), (Ib), (Ic) or (Id), or a pharmaceutically acceptable salt or solvate thereof, wherein U is C(O).

In some embodiments is a compound of Formula (I) having the structure of Formula (Ie), or a pharmaceutically acceptable salt or solvate thereof:

Formula (Ie)

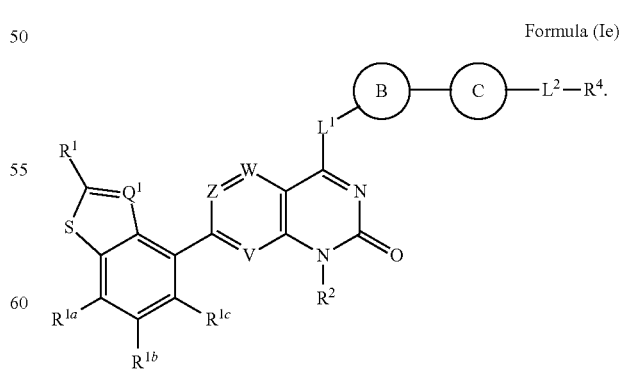

In some embodiments is a compound of Formula (I) having the structure of Formula (If), or a pharmaceutically acceptable salt or solvate thereof:

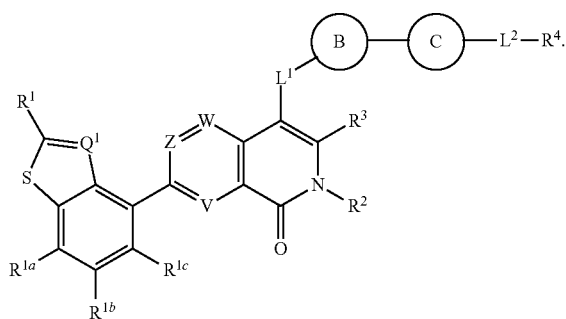

Formula (If)

In some embodiments is a compound of Formula (I) having the structure of Formula (Ig), or a pharmaceutically acceptable salt or solvate thereof:

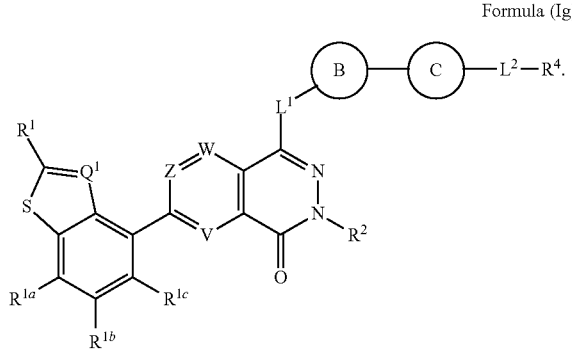

Formula (Ig)

In some embodiments is a compound of Formula (I) having the structure of Formula (Ih), or a pharmaceutically acceptable salt or solvate thereof:

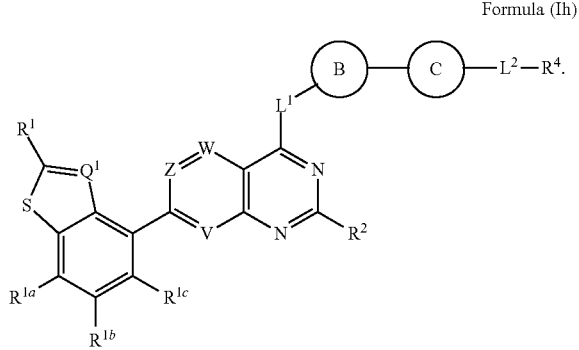

Formula (Ih)

In some embodiments is a compound of Formula (I) having the structure of Formula (Ii), or a pharmaceutically acceptable salt or solvate thereof:

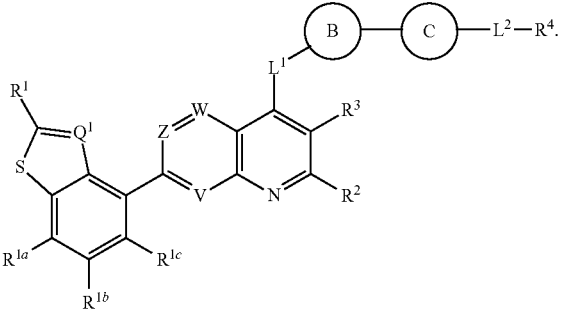

Formula (Ii)

In some embodiments is a compound of Formula (I) having the structure of Formula (Ij), or a pharmaceutically acceptable salt or solvate thereof:

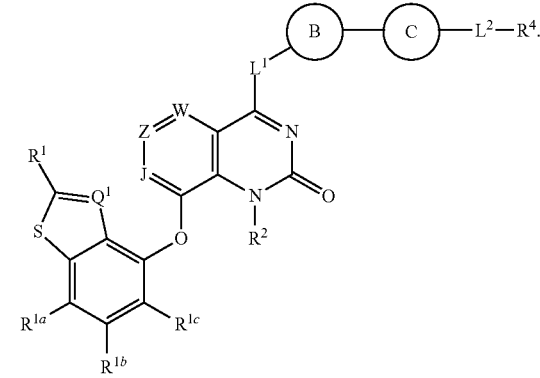

Formula (Ij)

In some embodiments is a compound of Formula (I) having the structure of Formula (Ik), or a pharmaceutically acceptable salt or solvate thereof:

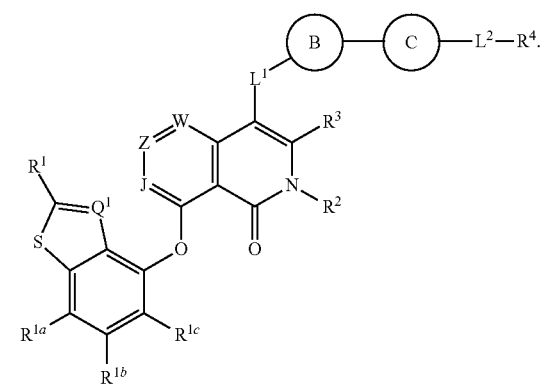

Formula (Ik)

In some embodiments is a compound of Formula (I) having the structure of Formula (Im), or a pharmaceutically acceptable salt or solvate thereof:

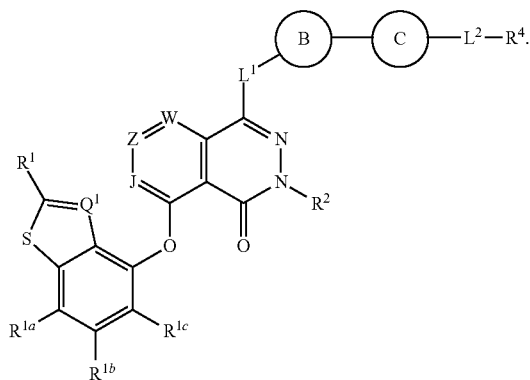

Formula (Im)

In some embodiments is a compound of Formula (I) having the structure of Formula (In), or a pharmaceutically acceptable salt or solvate thereof:

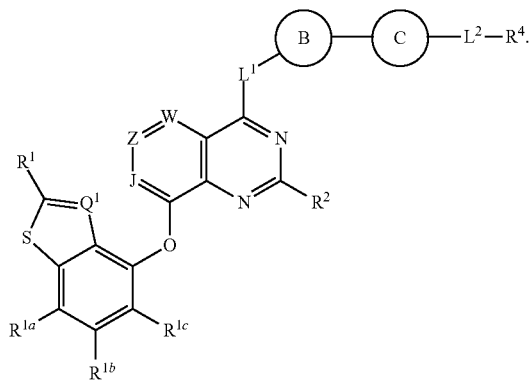

Formula (In)

In some embodiments is a compound of Formula (I) having the structure of Formula (Io), or a pharmaceutically acceptable salt or solvate thereof:

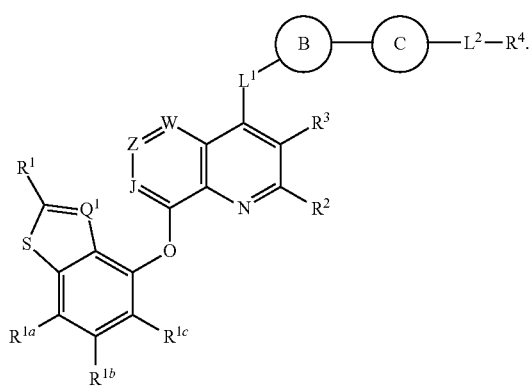

Formula (Io)

In some embodiments is a compound of Formula (I), (Ie), (If), (Ig), (Ih), or (Ii), or a pharmaceutically acceptable salt or solvate thereof, wherein V is C($R^{16}$). In some embodiments is a compound of Formula (I), (Ie), (If), (Ig), (Ih), or (Ii), or a pharmaceutically acceptable salt or solvate thereof, wherein V is C(H). In some embodiments is a compound of Formula (I), (Ie), (If), (Ig) or (Ih), or a pharmaceutically acceptable salt or solvate thereof, wherein V is N.

In some embodiments is a compound of Formula (I), (Ij), (Ik), (Im), (In), or (Io), or a pharmaceutically acceptable salt or solvate thereof, wherein J is C($R^{16}$). In some embodiments is a compound of Formula (I), (Ij), (Ik), (Im), (In), or (Io), or a pharmaceutically acceptable salt or solvate thereof, wherein J is C(H). In some embodiments is a compound of Formula (I), (Ii), (Ij), (Ik) or (Im), or a pharmaceutically acceptable salt or solvate thereof, wherein J is N.

In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein W is C($R^{18}$). In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein W is N.

In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein Z is C($R^8$). In some embodiments is a compound of Formula (I), (Ia), (Ib), (Ic), (Id), (Ie), (If), (Ig), (Ih), (Ii), (Ij), (Ik), (Im), (In), or (Io), or a pharmaceutically acceptable salt or solvate thereof, wherein Z is N.

In another aspect, the disclosure provides a compound of Formula (II), or a pharmaceutically acceptable salt or solvate thereof:

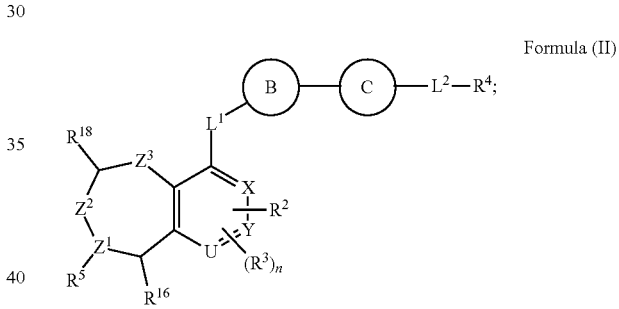

Formula (II)

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, N(R$^{1c}$), or C(R$^{1f}$)(R$^{1g}$);
Q$^1$ is N or C(R$^{1d}$);
Q$^2$ is S or O;
X is C or N;
Y is C, C(O), or N;
Z$^1$ is N or C(R$^6$);
Z$^2$ is N(R$^7$) or C(R$^8$)(R$^9$);
Z$^3$ is absent, N(R$^{17}$), or C(R$^{27}$)(R$^{28}$);
U is C, S(O), S(O)$_2$, C(O), or N;
L$^1$ and L$^2$ are independently selected from a bond, C$_1$-C$_6$alkyl, —O—, —N(R$^{26}$)—, —C(O)—, —N(R$^{26}$)C(O)—, —C(O)N(R$^{26}$)—, —S—, —S(O)$_2$—, —S(O)—, —S(O)$_2$N(R$^{26}$)—, —S(O)N(R$^{26}$)—, —N(R$^{26}$)S(O)—, —N(R$^{26}$)S(O)$_2$—, —OCON(R$^{26}$)—, —N(R$^{26}$)C(O)O—, and —N(R$^{26}$)C(O)N(R$^{26}$)—;
R$^1$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{1-9}$heteroaryl, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20a}$;
R$^{1a}$, R$^{1b}$, R$^{1c}$, R$^{1d}$, R$^{1e}$, R$^{1f}$, and R$^{1g}$ are each independently selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20a}$; or R$^{1a}$ and R$^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or R$^{1b}$ and R$^{1e}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$; or R$^{1f}$ and R$^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three R$^{20a}$;
R$^2$ is selected from halogen, —CN, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{2-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20d}$;
each R$^3$ is independently selected from hydrogen, halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$)—;
R$^4$ is hydrogen, or a group other than an electrophilic moiety capable of forming a covalent bond with the cysteine residue at position 12 of a KRAS protein;
R$^5$ is

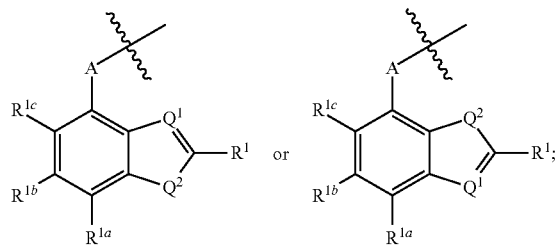

R$^6$ is selected from hydrogen and C$_{1-6}$alkyl;
R$^7$ is selected from hydrogen, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —C(O)OR$^{12}$, —C(O)R$^{15}$, —S(O)R$^{15}$, —C(O)N(R$^{12}$)(R$^{13}$), —C(O)C(O)N(R$^{12}$)(R$^{13}$), —S(O)$_2$R$^{15}$, and —S(O)$_2$N(R$^{12}$)(R$^{13}$)—, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20c}$;
R$^8$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20c}$;
R$^9$ is selected from hydrogen and C$_{1-6}$alkyl;
each R$^{10}$ and each R$^{11}$ are independently selected from halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$)—;
each R$^{12}$ is independently selected from hydrogen, C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, and C$_{1-9}$heteroaryl, wherein C$_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20c}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20k}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, and $R^{20k}$ are each independently selected from halogen, —CN, $C_{1-6}$alkyl, $C_{2-9}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

$R^{27}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20j}$;

$R^{28}$ is selected from hydrogen and $C_{1-6}$alkyl;

n is 0, 1, or 2; and

----- indicates a single or double bond such that all valences are satisfied.

In some embodiments is a compound of Formula (I) or (II), or a pharmaceutically acceptable salt or solvate thereof, wherein $Q^1$ is N and $Q^2$ is S. In some embodiments is a compound of Formula (I) or (II), or a pharmaceutically acceptable salt or solvate thereof, wherein $Q^1$ is N and $Q^2$ is O. In some embodiments is a compound of Formula (I) or (II), or a pharmaceutically acceptable salt or solvate thereof, wherein $Q^1$ is $C(R^{1d})$ and $Q^2$ is S. In some embodiments is a compound of Formula (I) or (II), or a pharmaceutically acceptable salt or solvate thereof, wherein $Q^1$ is $C(R^{1d})$ and $Q^2$ is O.

In some embodiments is a compound of Formula (II) having the structure of Formula (IIa), or a pharmaceutically acceptable salt or solvate thereof:

Formula (IIa)

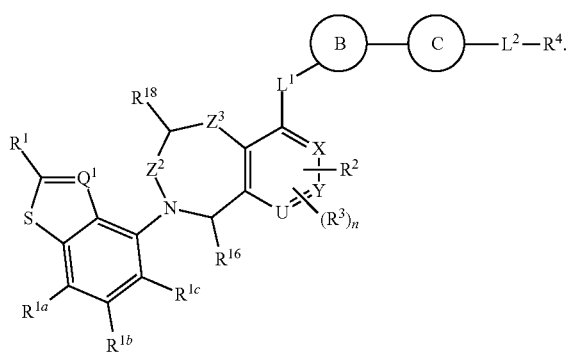

In some embodiments is a compound of Formula (II) having the structure of Formula (IIb), or a pharmaceutically acceptable salt or solvate thereof:

Formula (IIb)

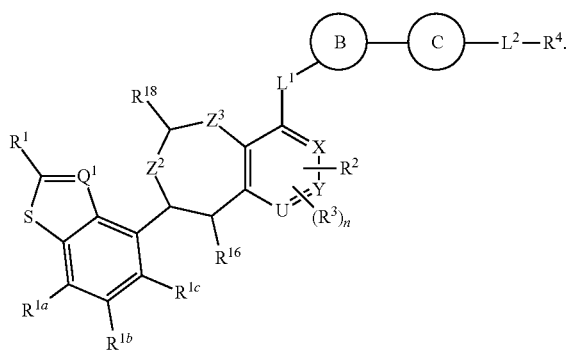

In some embodiments is a compound of Formula (II), (IIa), or (IIb), or a pharmaceutically acceptable salt or solvate thereof, wherein $Z^2$ is $C(R^8)(R^9)$. In some embodiments is a compound of Formula (II), (IIa), or (IIb), or a pharmaceutically acceptable salt or solvate thereof, wherein $R^9$ is hydrogen.

In some embodiments is a compound of Formula (II), (IIa), or (IIb), or a pharmaceutically acceptable salt or solvate thereof, wherein X is C. In some embodiments is a compound of Formula (II), (IIa), or (IIb), or a pharmaceutically acceptable salt or solvate thereof, wherein X is N.

In some embodiments is a compound of Formula (II), (IIa), or (IIb), or a pharmaceutically acceptable salt or solvate thereof, wherein Y is C. In some embodiments is a compound of Formula (II), (IIa), or (IIb), or a pharmaceutically acceptable salt or solvate thereof, wherein Y is N. In some embodiments is a compound of Formula (II), (IIa), or (IIb), or a pharmaceutically acceptable salt or solvate thereof, wherein Y is C(O).

In some embodiments is a compound of Formula (II), (IIa), or (IIb), or a pharmaceutically acceptable salt or solvate thereof, wherein U is C. In some embodiments is a compound of Formula (II), (IIa), or (IIb), or a pharmaceutically acceptable salt or solvate thereof, wherein U is N. In some embodiments is a compound of Formula (II), (IIa), or (IIb), or a pharmaceutically acceptable salt or solvate thereof, wherein U is C(O).

In some embodiments is a compound of Formula (II) having the structure of Formula (IIc), or a pharmaceutically acceptable salt or solvate thereof:

Formula (IIc)

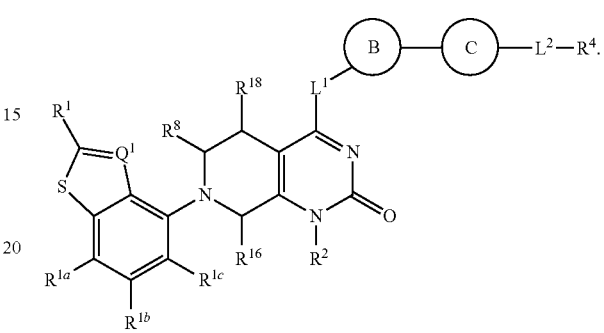

In some embodiments is a compound of Formula (II) having the structure of Formula (IId), or a pharmaceutically acceptable salt or solvate thereof:

Formula (IId)

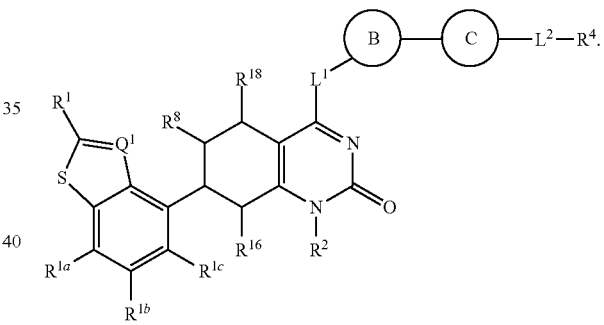

In some embodiments is a compound of Formula (II) having the structure of Formula (Ie), or a pharmaceutically acceptable salt or solvate thereof:

Formula (IIe)

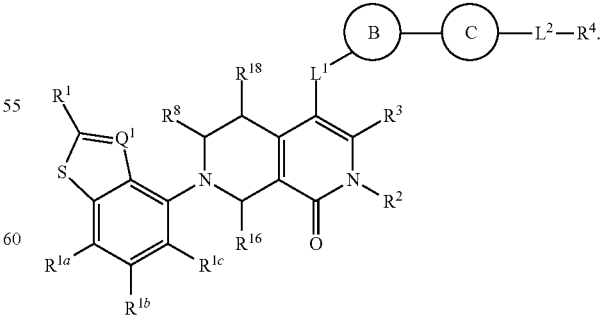

In some embodiments is a compound of Formula (II) having the structure of Formula (IIf), or a pharmaceutically acceptable salt or solvate thereof:

Formula (IIf)

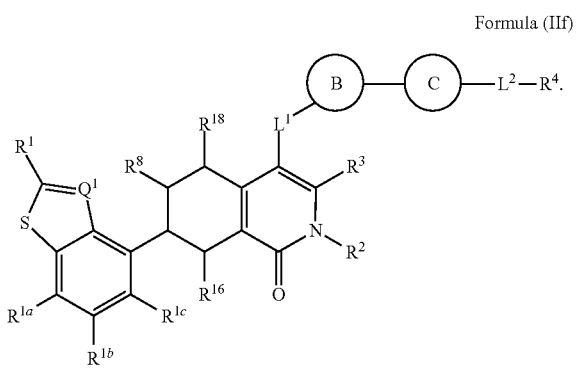

In some embodiments is a compound of Formula (II) having the structure of Formula (IIg), or a pharmaceutically acceptable salt or solvate thereof:

Formula (IIg)

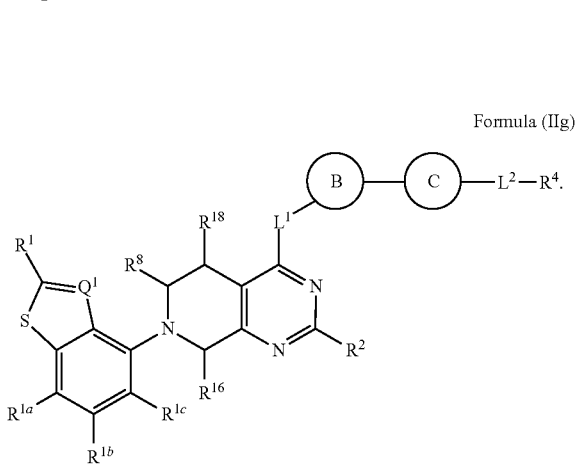

In some embodiments is a compound of Formula (II) having the structure of Formula (IIh), or a pharmaceutically acceptable salt or solvate thereof:

Formula (IIh)

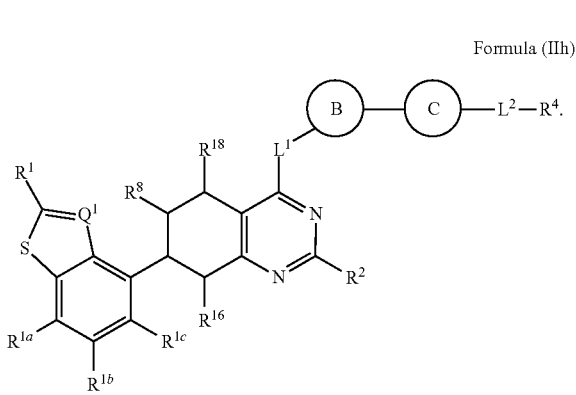

In some embodiments is a compound of Formula (II) having the structure of Formula (IIi), or a pharmaceutically acceptable salt or solvate thereof:

Formula (IIi)

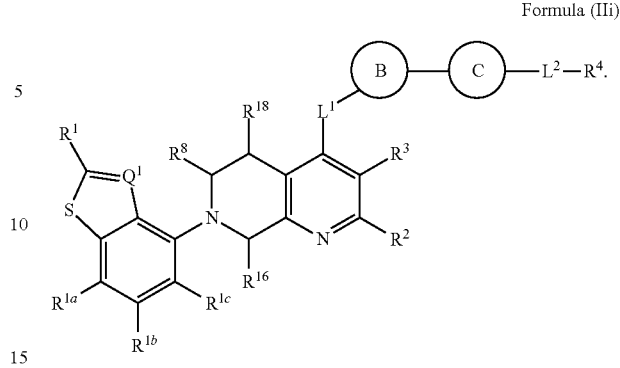

In some embodiments is a compound of Formula (II) having the structure of Formula (IIj), or a pharmaceutically acceptable salt or solvate thereof:

Formula (IIj)

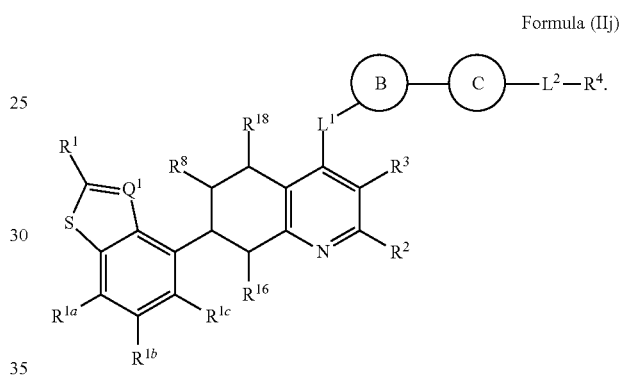

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is selected from hydrogen, —N($R^{12}$)($R^{13}$), and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —N($R^{12}$)($R^{13}$). In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —NH$_2$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is unsubstituted $C_{1-6}$alkyl. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —CH$_3$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is hydrogen In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —N($R^{14}$)C(O)$R^{15}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is —N(H)C(O)$R^{15}$ and $R^{15}$ is $C_{1-9}$heteroaryl optionally substituted with one, two, or three $R^{20f}$.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$; $R^{1b}$, $R^{1c}$, $R^{1d}$, $R^{1e}$, $R^{1f}$, and $R^{1g}$ are each independently selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$;

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$; $R^{1b}$, and $R^{1c}$ are each independently selected from hydrogen, halogen, and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$, $R^{1b}$, and $R^{1c}$ are each independently selected from hydrogen and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$, $R^{1b}$, and $R^{1c}$ are each hydrogen.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$ and $R^{1b}$ are hydrogen and $R^{1c}$ is —N(H)C(O)$R^{15}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$ and $R^{1b}$ are hydrogen, $R^{1c}$ is —N(H)C(O)$R^{15}$, and $R^{15}$ is $C_{1-9}$heteroaryl optionally substituted with one, two, or three $R^{20f}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1a}$ and $R^{1c}$ are hydrogen and $R^{1b}$ is —N(H)C(O)$R^{15}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1b}$ and $R^{1c}$ are hydrogen, $R^{1b}$ is —N(H)C(O)$R^{15}$, and $R^{15}$ is $C_{1-9}$heteroaryl optionally substituted with one, two, or three $R^{20f}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1b}$ and $R^{1c}$ are hydrogen and $R^{1a}$ is —N(H)C(O)$R^{15}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1b}$ and $R^{1c}$ are hydrogen, $R^{1a}$ is —N(H)C(O)$R^{15}$, and $R^{15}$ is $C_{1-9}$heteroaryl optionally substituted with one, two, or three $R^{20f}$.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $Q^1$ is C($R^{1d}$). In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^{1d}$ is selected from hydrogen and $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $Q^1$ is N.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein ◯ c is a 3-12 membered heterocycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein ◯ c is selected from piperazinyl and piperidinyl, wherein piperazinyl and piperidinyl are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is piperazinyl optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is piperidinyl optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered spirocyclic heterocycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered fused heterocycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a cyclohexyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered spirocyclic cycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered fused cycloalkyl ring optionally substituted with one or more $R^{11}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is absent.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein

is a 3-12 membered heterocycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is selected from piperazinyl and piperidinyl, wherein piperazinyl and piperidinyl are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is piperidinyl optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is piperazinyl optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered heterocycloalkyl ring selected from a spirocyclic heterocycloalkyl ring and fused heterocycloalkyl ring, wherein the spirocyclic heterocycloalkyl ring and fused heterocycloalkyl ring are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered spirocyclic heterocycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered fused heterocycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered cycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a cyclohexyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered cycloalkyl ring selected from a spirocyclic cycloalkyl ring and fused cycloalkyl ring, wherein the spirocyclic cycloalkyl ring and fused cycloalkyl ring are optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered spirocyclic cycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is a 3-12 membered fused cycloalkyl ring optionally substituted with one or more $R^{10}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein (B)

is absent.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is selected from a bond, $C_1$-$C_6$alkyl, —N($R^{26}$)—, and —C(O)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a bond. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a $C_1$-$C_6$alkyl.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is selected from a bond, $C_1$-$C_6$alkyl, and —C(O)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is a bond. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^2$ is a $C_1$-$C_6$alkyl.

In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is selected from hydrogen, $C_{1-6}$alkyl, $C_{3-6}$cycloalkyl, $C_{2-9}$heterocycloalkyl, $C_{6-10}$aryl, $C_{1-9}$heteroaryl, —$OR^{12}$, and —N($R^{12}$)($R^{13}$), wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three $R^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is selected from $C_{1-6}$alkyl, $C_{3-6}$cycloalkyl, $C_{2-9}$heterocycloalkyl, $C_{6-10}$aryl, $C_{1-9}$heteroaryl, —$OR^{12}$, —$SR^{12}$, and —N($R^{12}$)($R^{13}$), wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is hydrogen. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is $C_{1-6}$alkyl optionally substituted with one, two, or three $R^{20b}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is unsubstituted $C_{1-6}$alkyl. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is $C_{3-6}$cycloalkyl optionally substituted with one, two, or three $R^{20b}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is $C_{2-9}$heterocycloalkyl optionally substituted with one, two, or three $R^{20b}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is $C_{6-10}$aryl optionally substituted with one, two, or three $R^{20b}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (Ih), (IIi), or (IIj), or a pharmaceutically acceptable salt or solvate thereof, wherein $R^2$ is $C_{1-9}$heteroaryl optionally substituted with one, two, or three $R^{20b}$.

In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is selected from —$OR^{12}$, —$SR^{12}$, and —N($R^{12}$)($R^{13}$). In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is —$OR^{12}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is —$SR^{12}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^2$ is —N($R^{12}$)($R^{13}$). In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^{12}$ is selected from $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{1-6}$alkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^{12}$ is $C_{1-6}$alkyl optionally substituted with one, two, or three $R^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^{12}$ is $C_{2-9}$heterocycloalkyl optionally substituted with one, two, or three $R^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein $R^{12}$ is selected from —CH$_2$—C$_{2-9}$heterocycloalkyl optionally substituted with one, two, or three R$^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein R$^{12}$ is C$_{6-10}$aryl optionally substituted with one, two, or three R$^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein R$^{12}$ is —CH$_2$—C$_{6-10}$aryl optionally substituted with one, two, or three R$^{20d}$. In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein R$^{12}$ is C$_{1-9}$heteroaryl are optionally substituted with one, two, or three R$^{20d}$.

In some embodiments is a compound of Formula (I), (Ia), (Ib), (Ic), (Id), (If), (Ig), (Ih), (Ij), (Ik), (Im), (II), (IIa), (IIb), (IIe), (IIf), (IIg), (IIh), (IIi), or (IIj), or a pharmaceutically acceptable salt or solvate thereof, wherein R$^2$ is selected from

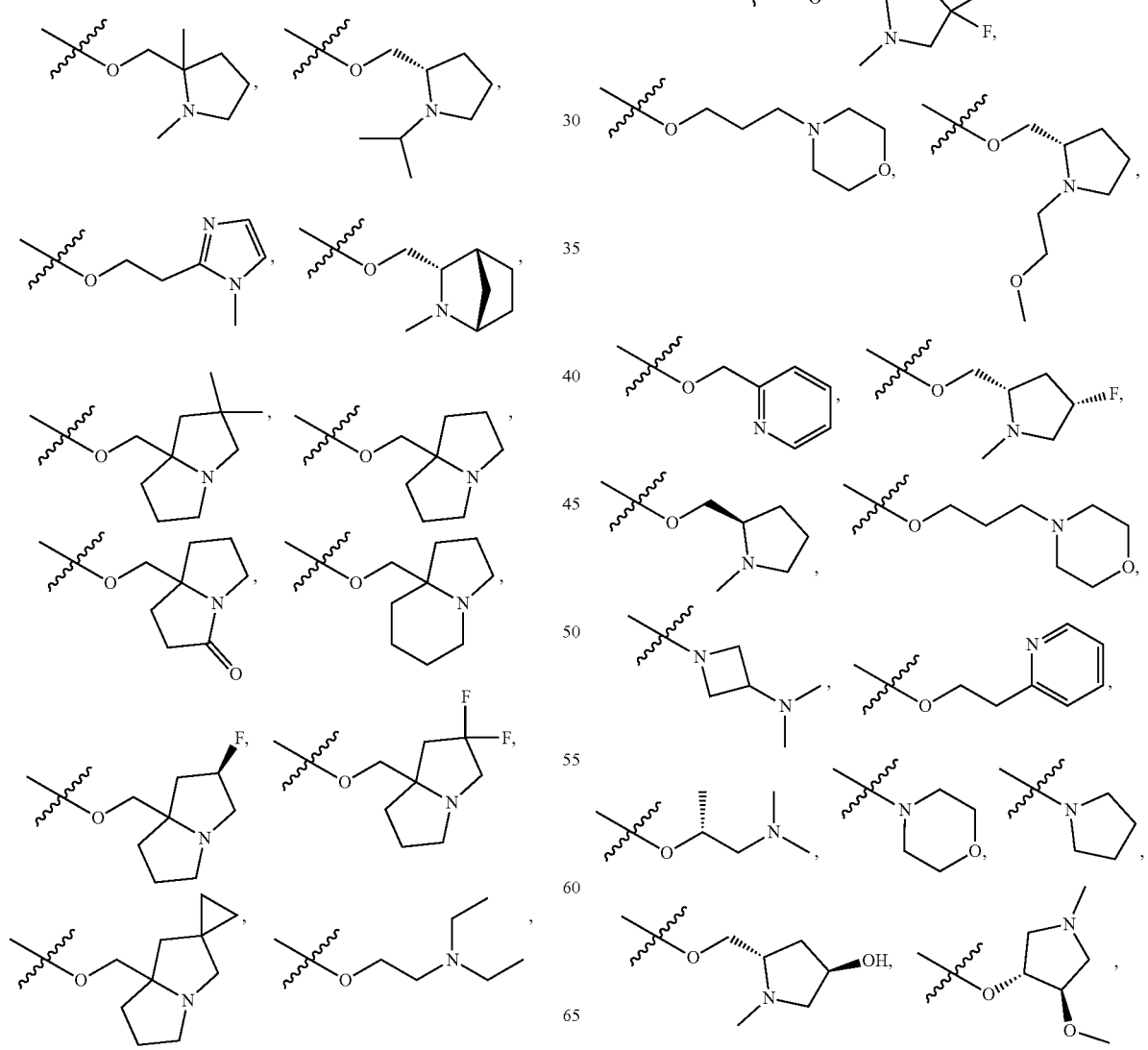

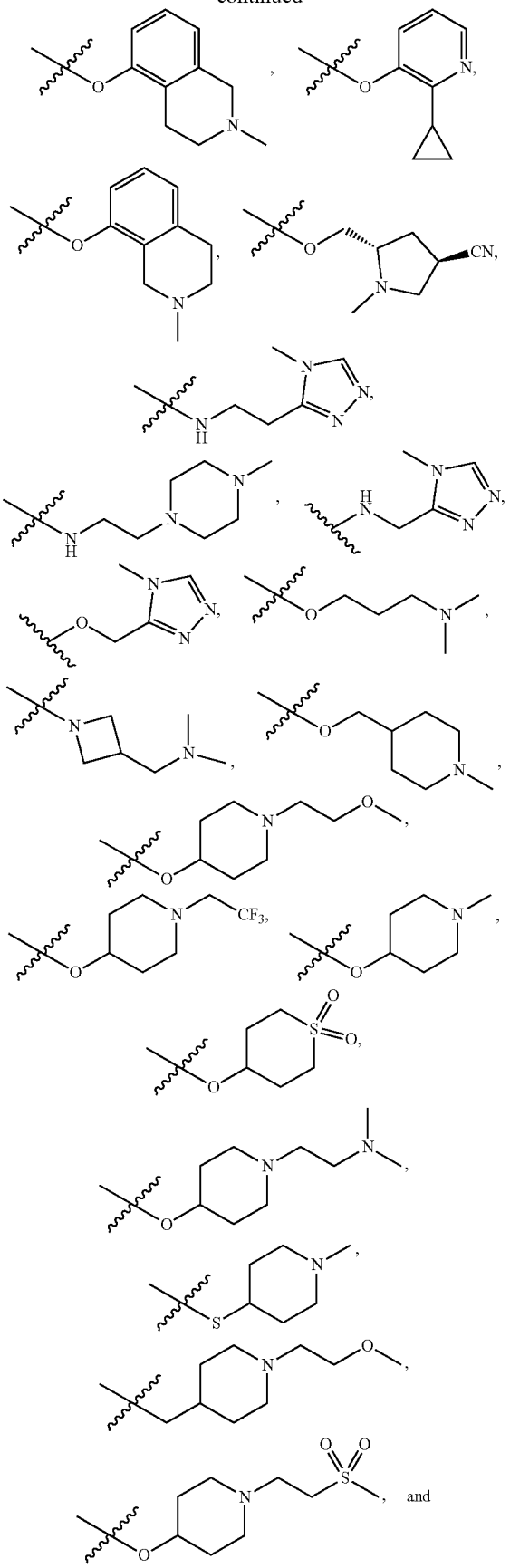

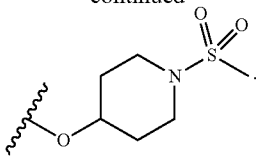

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is selected from a bond, $C_1$-$C_6$alkyl, —N($R^{26}$)—, and —C(O)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a bond. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is a $C_1$-$C_6$alkyl. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is —N($R^{26}$)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is —N(H)—. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $L^1$ is —C(O)—.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is selected from $C_{1-6}$alkyl, $C_{3-6}$cycloalkyl, $C_{2-9}$heterocycloalkyl, $C_{6-10}$aryl, $C_{1-9}$heteroaryl, —$OR^{12}$, and —N($R^{12}$)($R^{13}$), wherein $C_{1-6}$alkyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is $C_{1-6}$alkyl optionally substituted with one, two, or three $R^{20a}$. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein $R^1$ is $C_{1-6}$alkyl optionally substituted with one $R^{20a}$ and $R^{20a}$ is selected from $C_{3-6}$cycloalkyl, $C_{2-9}$heterocycloalkyl, $C_{6-10}$aryl, and $C_{1-9}$heteroaryl, wherein $C_{3-6}$cycloalkyl, $C_{2-9}$heterocycloalkyl, $C_{6-10}$aryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —N($R^{22}$)($R^{23}$), —C(O) $OR^{22}$, —C(O)N($R^{22}$)($R^{23}$), —C(O)C(O)N($R^{22}$)($R^{23}$), —OC(O)N($R^{22}$)($R^{23}$), —N($R^{24}$)C(O)N($R^{22}$)($R^{23}$), —N($R^{24}$)C(O)$OR^{25}$, —N($R^{24}$)C(O)$R^{25}$, —N($R^{24}$)S(O)$_2R^{25}$, —C(O)$R^{25}$, —S(O)₂R²⁵, —S(O)₂N(R²²)(R²³), and —OC(O)R²⁵. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹ is C₁₋₆alkyl optionally substituted with one R²⁰ᵃ and R²⁰ᵃ is selected from C₃₋₆cycloalkyl, C₂₋₉heterocycloalkyl, C₆₋₁₀aryl, and C₁₋₉heteroaryl, wherein C₃₋₆cycloalkyl, C₂₋₉heterocycloalkyl, C₆₋₁₀aryl, and C₁₋₉heteroaryl are unsubstituted. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹ is C₁₋₆alkyl substituted with one R²⁰ᵃ and R²⁰ᵃ is unsubstituted C₂₋₉heterocycloalkyl.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁸ is selected from hydrogen, halogen, —CN, C₁₋₆alkyl, —OR¹², —SR¹², —N(R¹²)(R¹³), and —C(O)OR¹². In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁸ is selected from hydrogen, halogen, —CN, CF₃, —OH, or —SH. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁸ is chloro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁸ is fluoro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁸ is hydrogen.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁶ is selected from hydrogen, halogen, —CN, C₁₋₆alkyl, —OR¹², —SR¹², —N(R¹²)(R¹³), and —C(O)OR¹². In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁶ is selected from hydrogen, halogen, —CN, CF₃, —OH, or —SH. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁶ is chloro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁶ is fluoro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁶ is hydrogen.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁸ is selected from hydrogen, halogen, —CN, C₁₋₆alkyl, —OR¹², —SR¹², —N(R¹²)(R¹³), and —C(O)OR¹². In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁸ is selected from hydrogen, halogen, —CN, CF₃, —OH, or —SH. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁸ is chloro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁸ is fluoro. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R¹⁸ is hydrogen.

In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁴ is hydrogen. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁴ is a group other than an electrophilic moiety capable of forming a covalent bond with the cysteine residue at position 12 of a KRAS protein. In some embodiments is a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein R⁴ is —H, —NH₂, —OH, —NH(C₁₋₆alkyl).

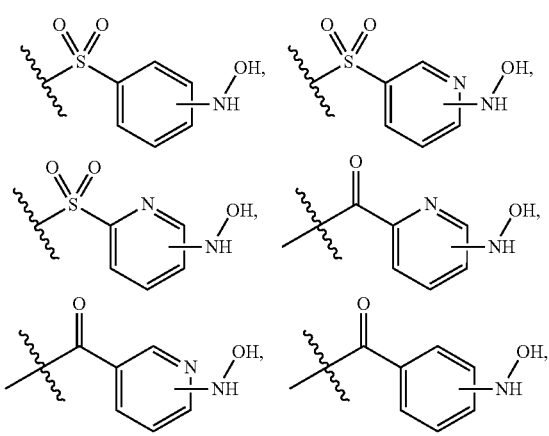

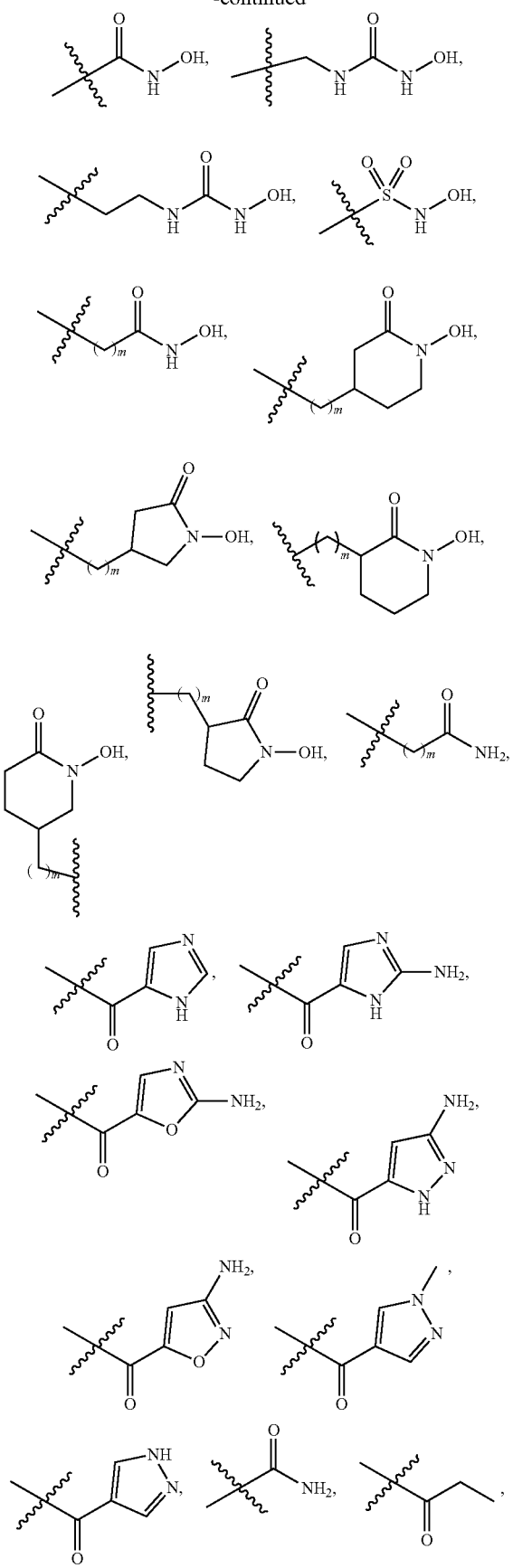
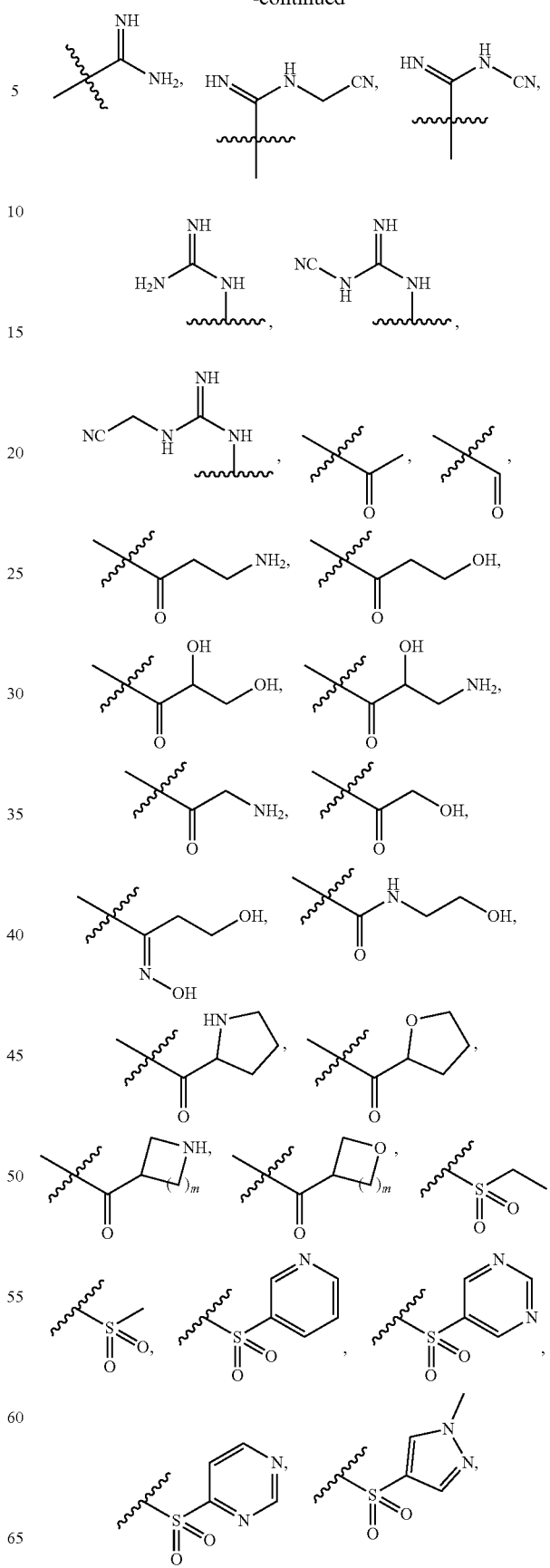

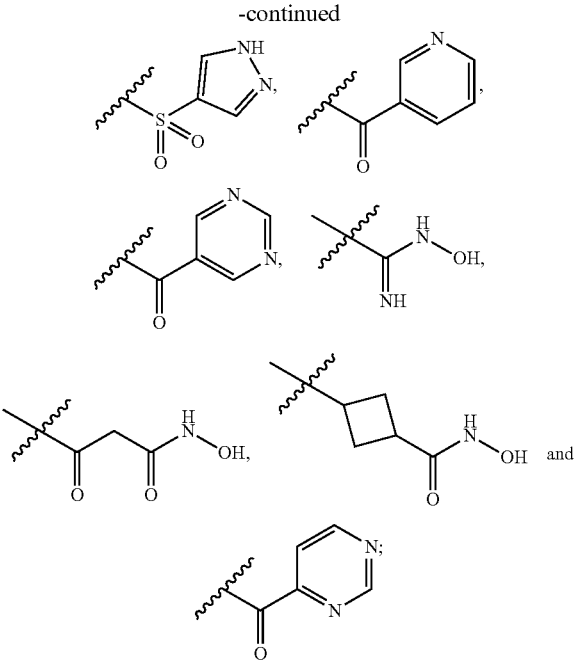
and m, when present, is 0, 1, 2, or 3.
In some embodiments is a compound selected from:
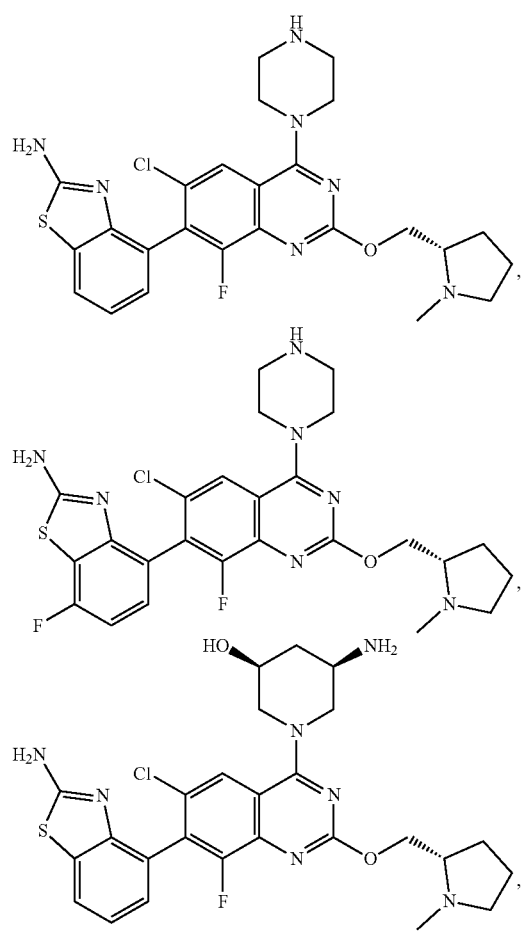
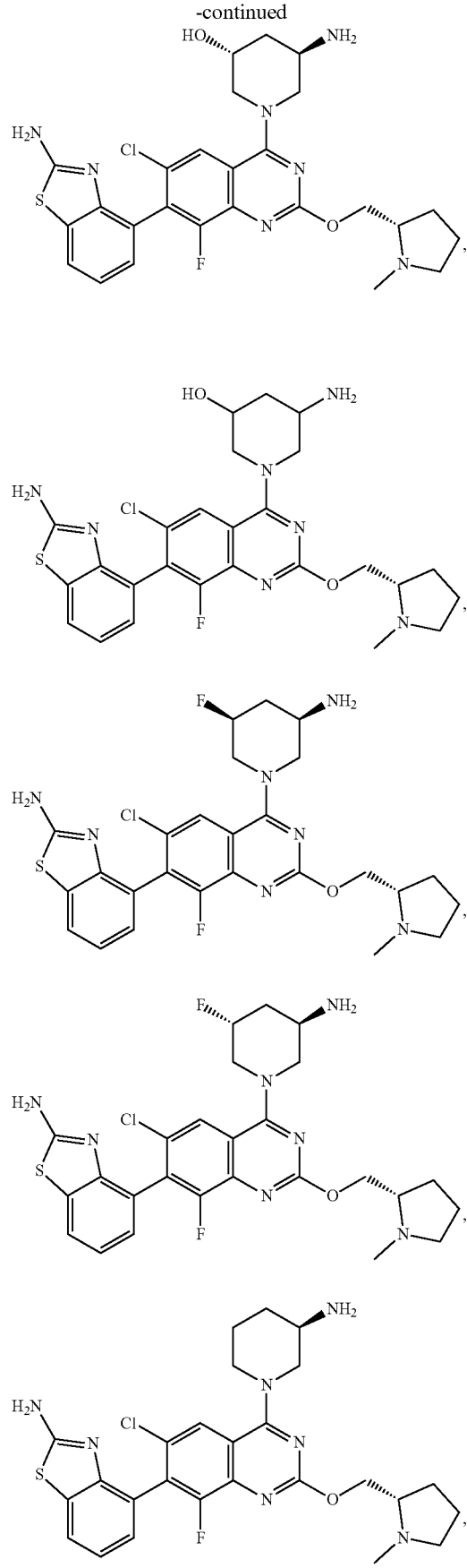

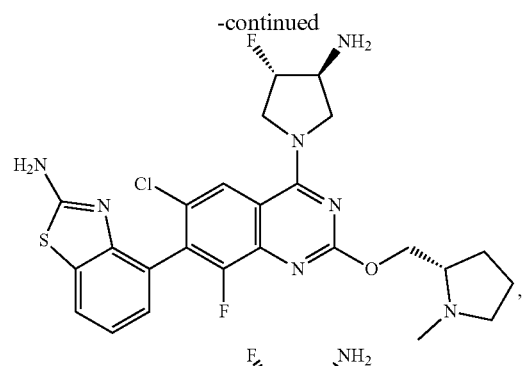
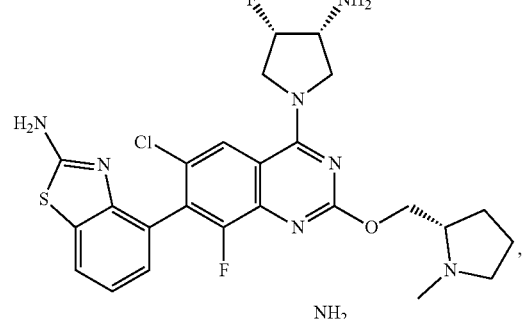
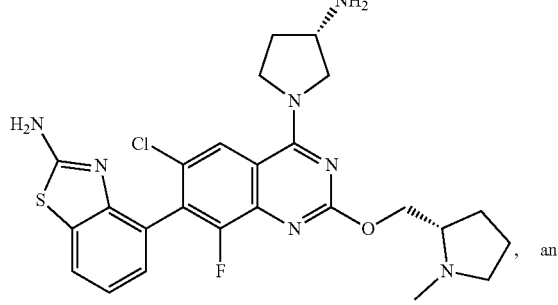
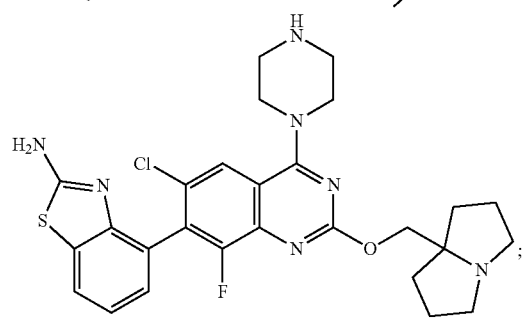
or a pharmaceutically acceptable salt or solvate thereof.
In some embodiments is a compound selected from:
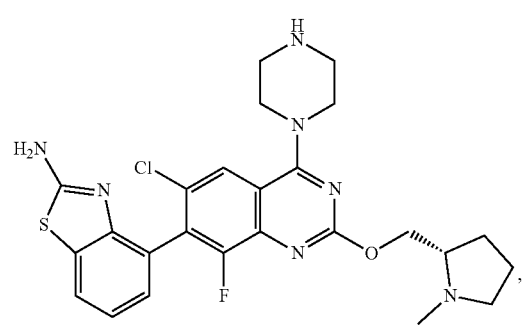
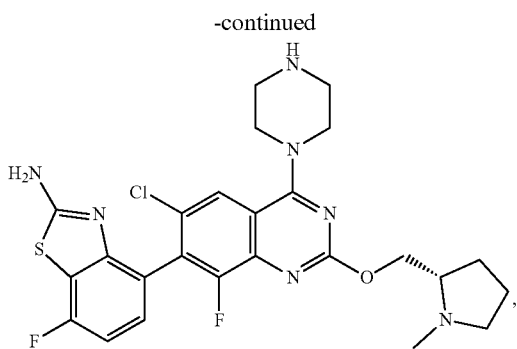
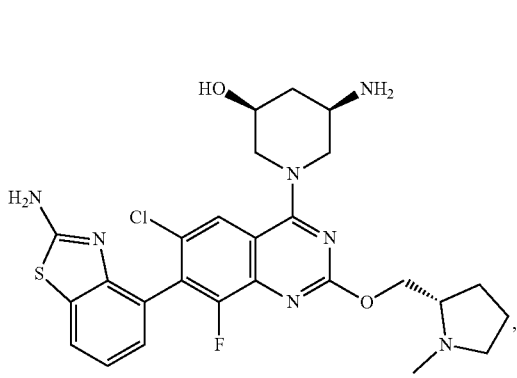
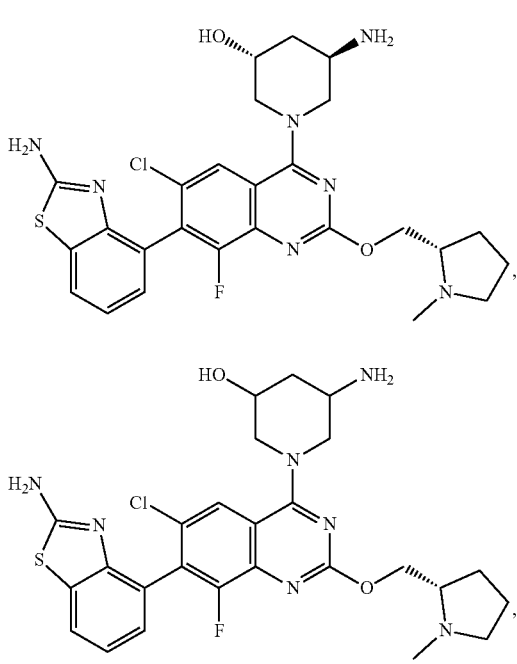
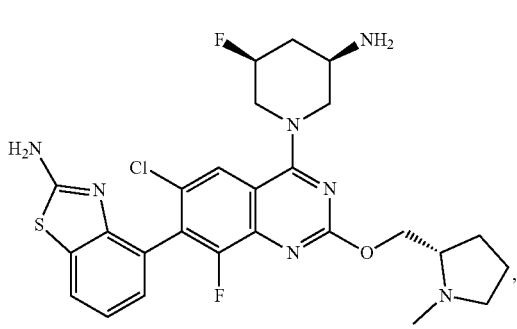

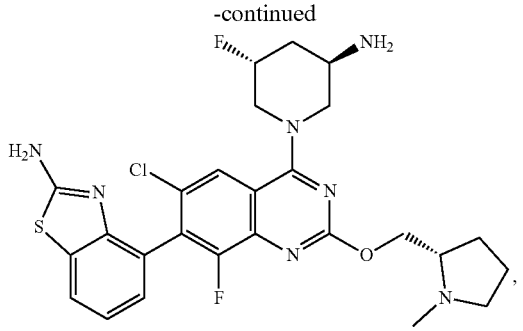
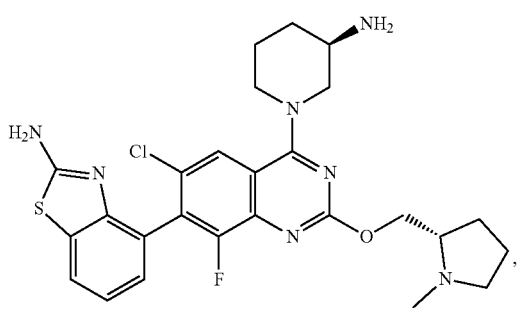
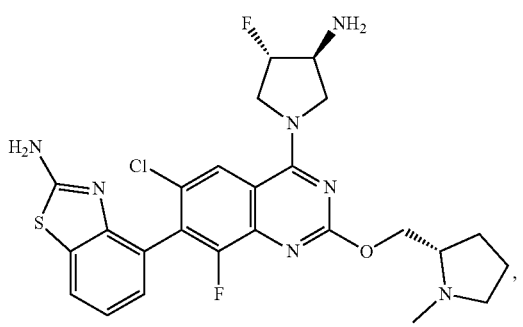
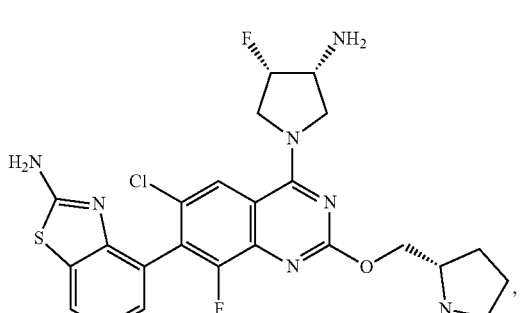
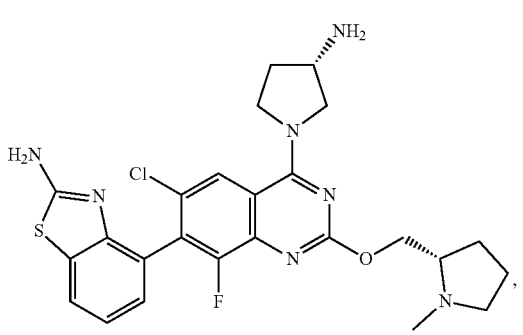
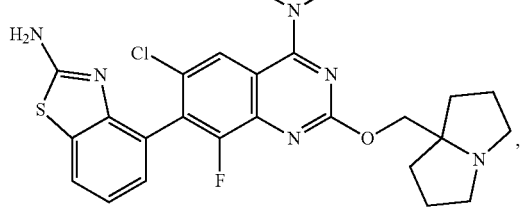
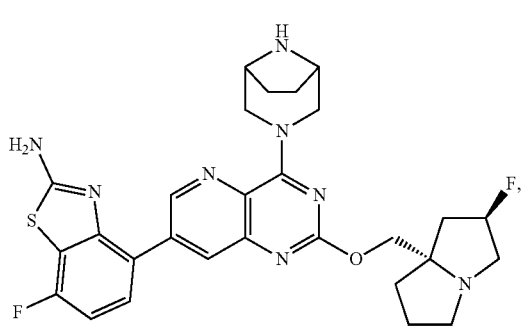
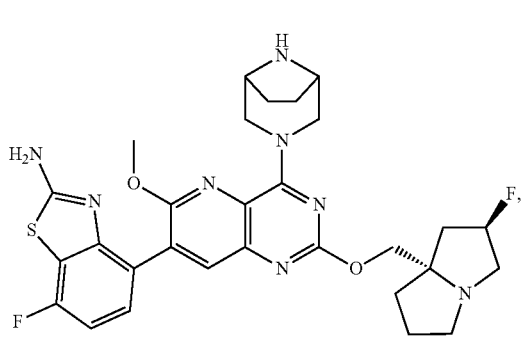
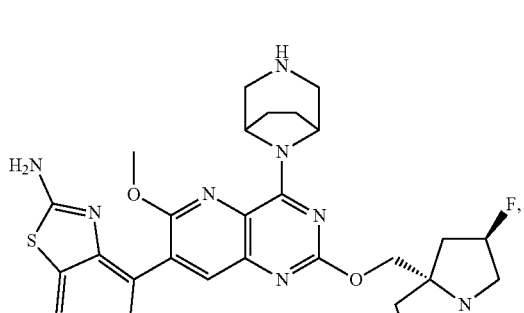
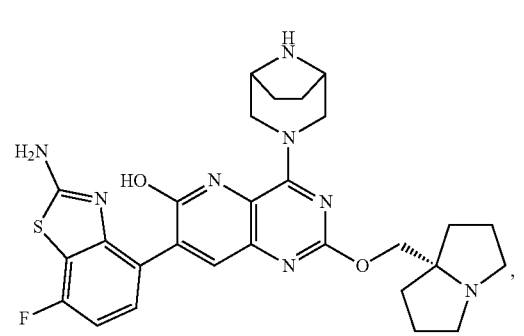

-continued

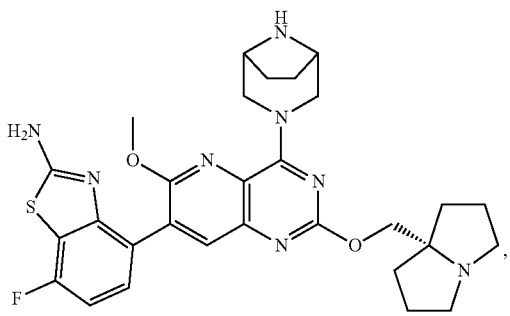

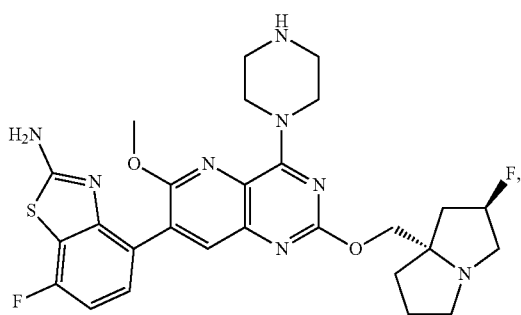

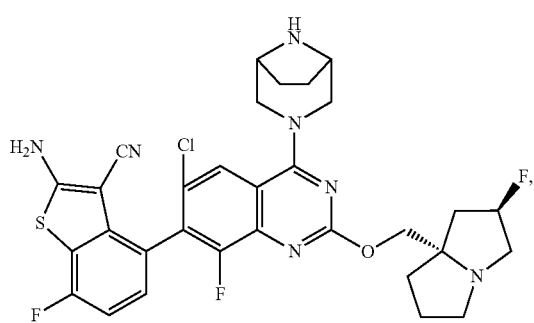

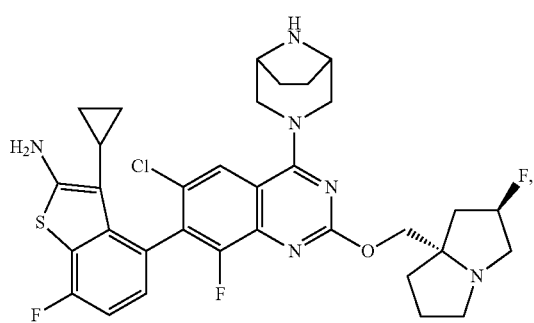

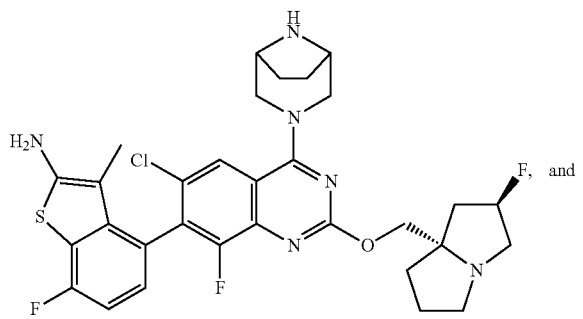

-continued

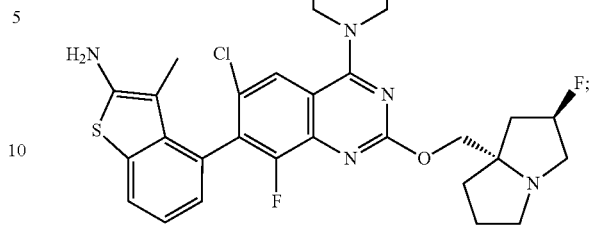

or a pharmaceutically acceptable salt or solvate thereof.

In embodiments, the compound has the formula:

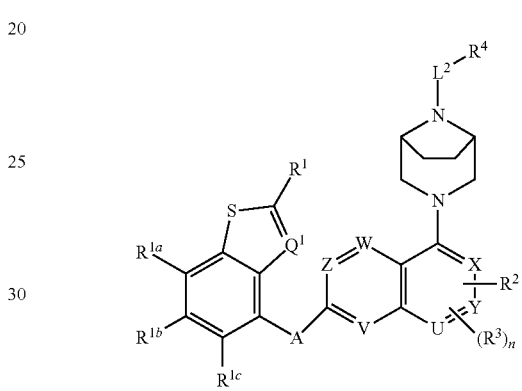

Formula (Ia') wherein $Q^1$, $R^1$, $R^{1a}$, $R^{1b}$, $R^{1c}$, A, V, Z, W, X, Y, U, $R^2$, $R^3$, n, $L^2$, and $R^4$ are as described herein, including in any embodiment. In embodiments of formula Ia', Z, X, and U are not all simultaneously N. In embodiments, the compound has the formula:

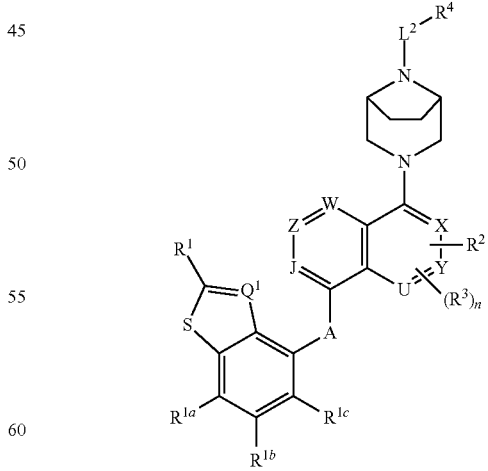

Formula (Ic') wherein $Q^1$, $R^1$, $R^{1a}$, $R^{1b}$, $R^{10}$, A, J, Z, W, X, Y, U, $R^2$, $R^3$, n, $L^2$, and $R^4$ are as described herein, including in any embodiment. In embodiments, the compound has the formula:

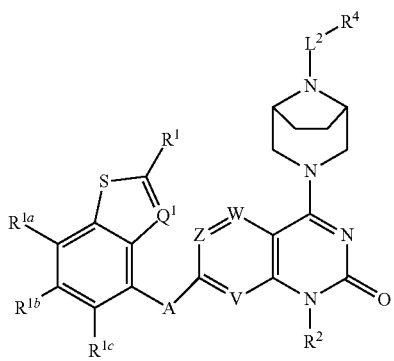

Formula (Ie') wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

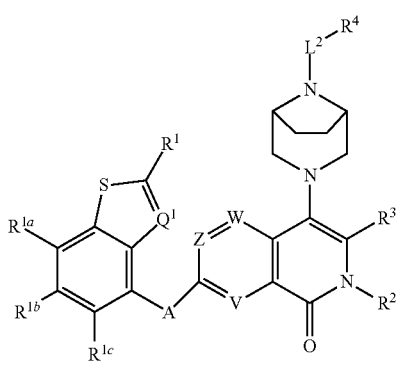

Formula (If') wherein $Q^1$, $R^1$, $R^{1a}$, $R^{1b}$, $R^{1c}$, A, V, Z, W, $R^2$, $R^3$, $L^2$, and $R^4$ are as described herein, including in any embodiment. In embodiments, the compound has the formula:

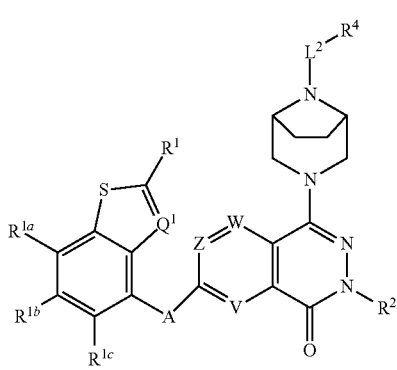

Formula (Ig') wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

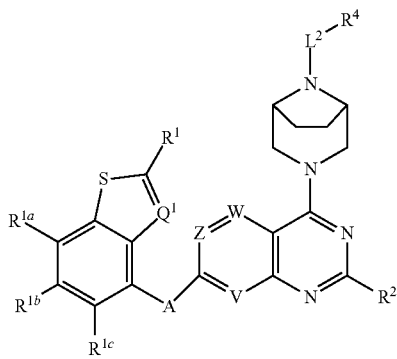

Formula (Ih') wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments of formula Ih', Z is not N. In embodiments, the compound has the formula:

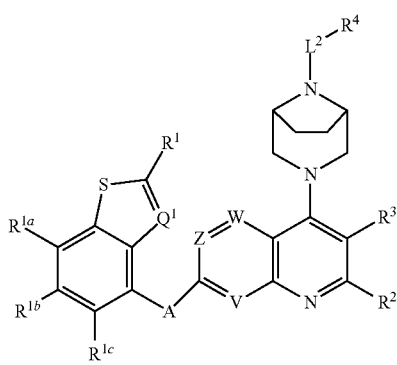

Formula (Ii') wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

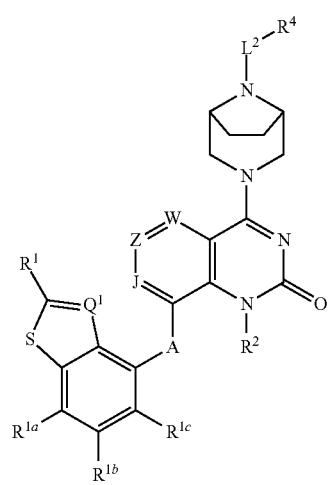

Formula (Ij') wherein $Q^1$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

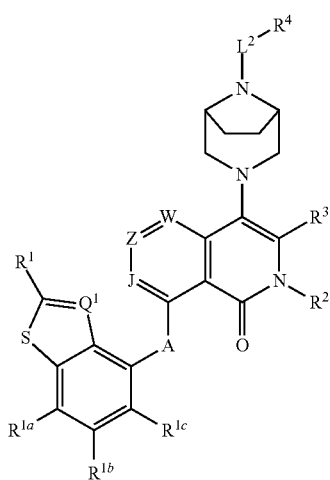

Formula (Ik') wherein $Q^1$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula:

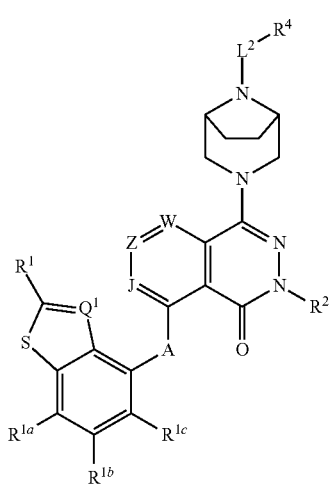

Formula (Im') wherein $Q^1$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

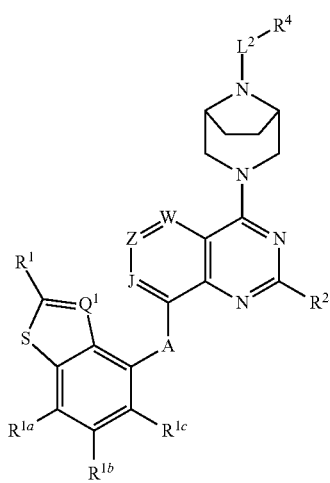

Formula (In') wherein $Q^1$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula

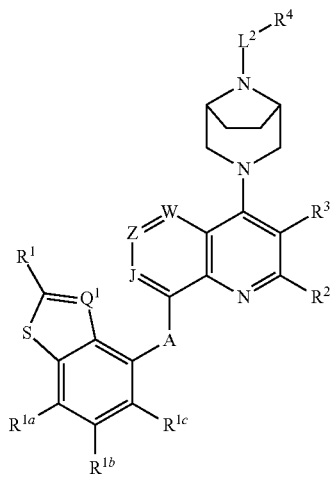

Formula (Io') wherein $Q^1$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula:

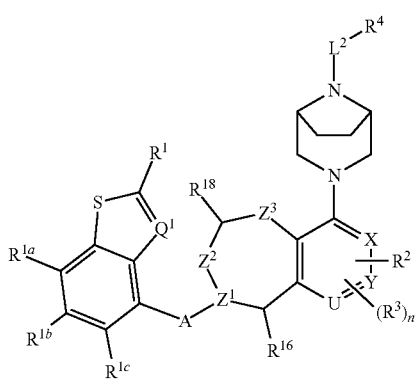

Formula (II') wherein $Q^1$, $R^1$, $R^{1a}$, $R^{1b}$, $R^{1c}$, A, $R^{16}$, $R^{18}$, $Z^1$, $Z^2$, $Z^3$, X, Y, U, $R^2$, $R^3$, n, $L^2$, and $R^4$ are as described herein, including in any embodiment. In embodiments, the compound has the formula:

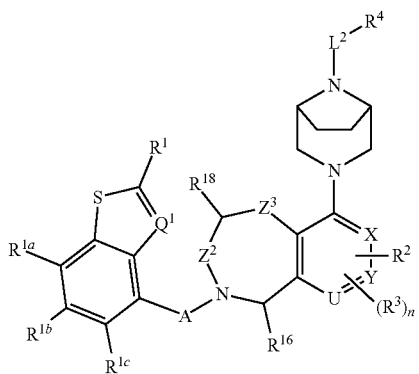

Formula (IIa') wherein $Q^1$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

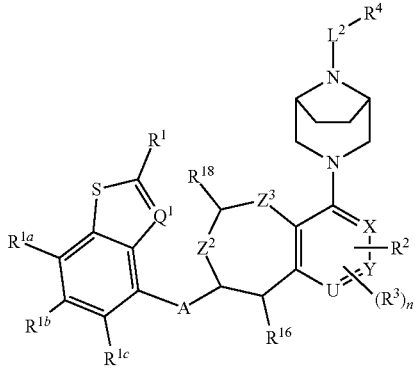

Formula (IIb') wherein $Q^1$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

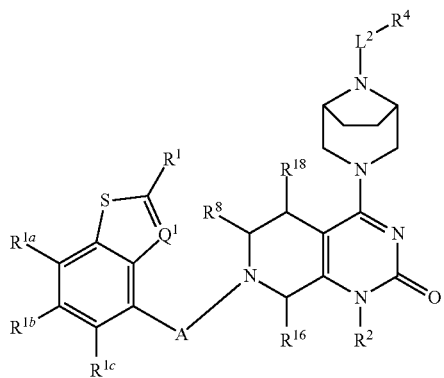

Formula (IIc') wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

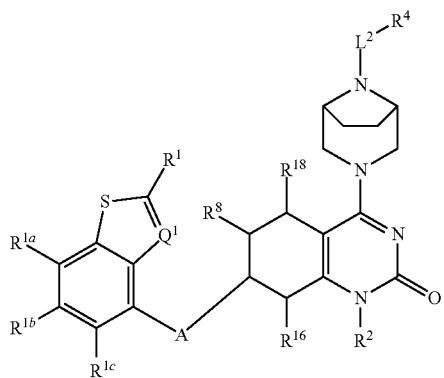

Formula (IId') wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

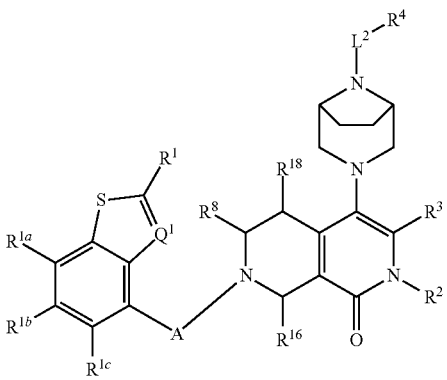

Formula (IIe') wherein $Q^1$, $R^1$, $R^{1a}$, $R^{1b}$, $R^{1c}$, A, $R^{16}$, $R^{18}$, $R^1$, $R^2$, $R^3$, $L^2$, and $R^4$ are as described herein, including in any embodiment. In embodiments, the compound has the formula:

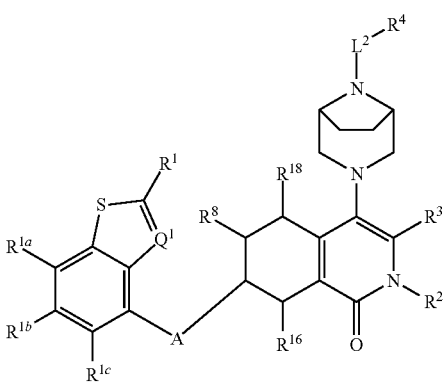

Formula (IIf') wherein $Q^1$, $R^1$, $R^{1a}$, $R^{1b}$, $R^{1c}$, A, $R^{16}$, $R^{18}$, RR, $R^2$, $R^3$, $L^2$, and $R^4$ are as described herein, including in any embodiment. In embodiments, the compound has the formula:

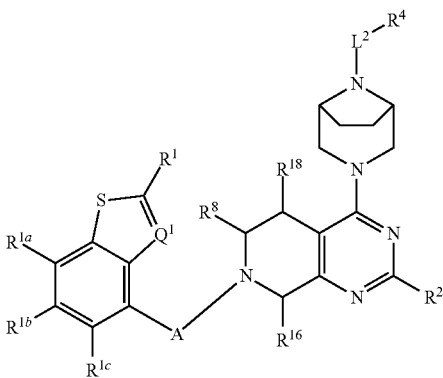

Formula (IIg') wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

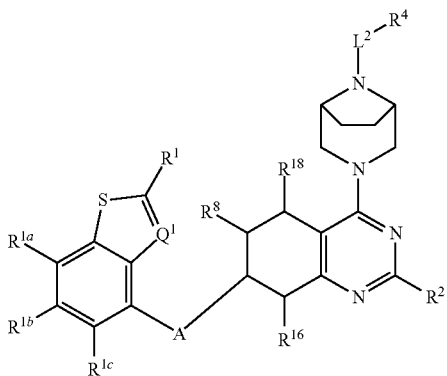

Formula (IIh') wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

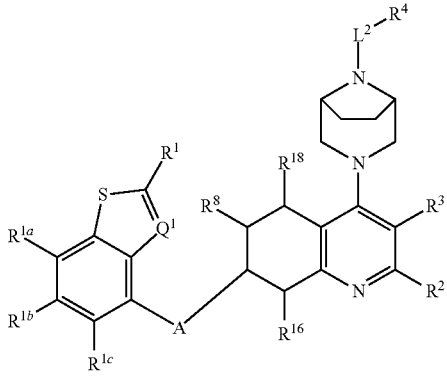

Formula (IIi') wherein $Q^1$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

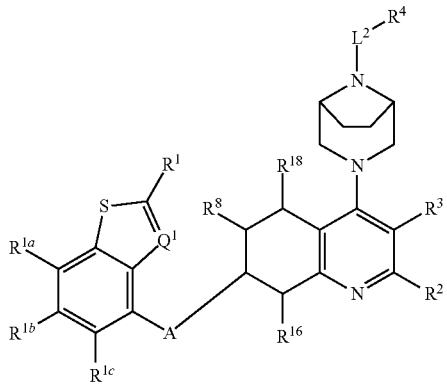

Formula (IIj') wherein $Q^1$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

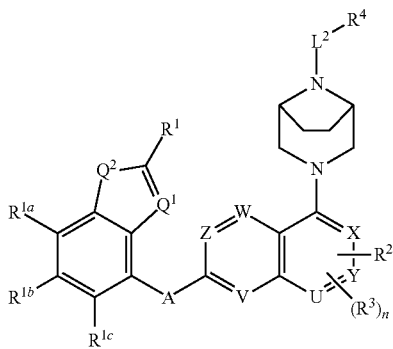

Formula (Ia") wherein $Q^1$, $Q^2$, $R^1$, $R^{1a}$, $R^{1b}$, $R^{1c}$, A, V, Z, W, X, Y, U, $R^2$, $R^3$, n, $L^2$, and $R^4$ are as described herein, including in any embodiment. In embodiments of formula Ia", Z, X, and U are not all simultaneously N. In embodiments, the compound has the formula:

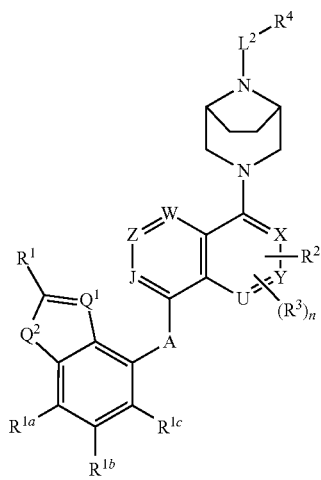

Formula (Ic") wherein $Q^1$, $Q^2$, $R^1$, $R^{1a}$, $R^{1b}$, $R^{1c}$, A, J, Z, W, X, Y, U, $R^2$, $R^3$, n, $L^2$, and $R^4$ are as described herein, including in any embodiment. In embodiments, the compound has the formula:

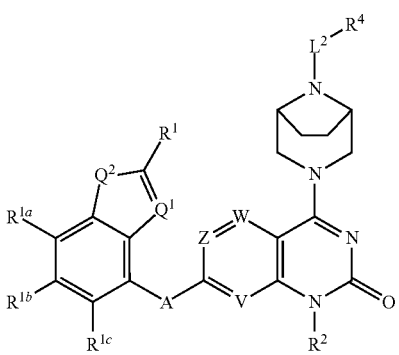

Formula (Ie″) wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

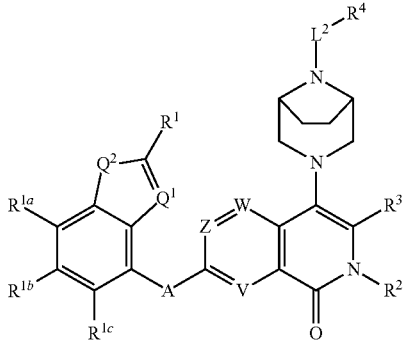

Formula (If″) wherein $Q^1$, $Q^2$, $R^1$, $R^{1a}$, $R^{1b}$, $R^{1c}$, A, V, Z, W, $R^2$, $R^3$, $L^2$, and $R^4$ are as described herein, including in any embodiment. In embodiments, the compound has the formula:

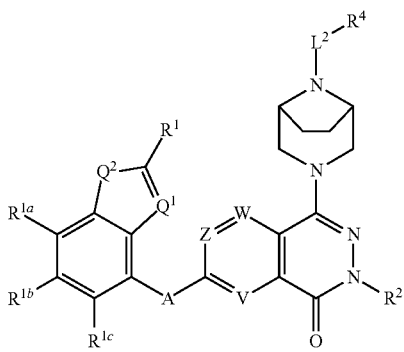

Formula (Ig″) wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

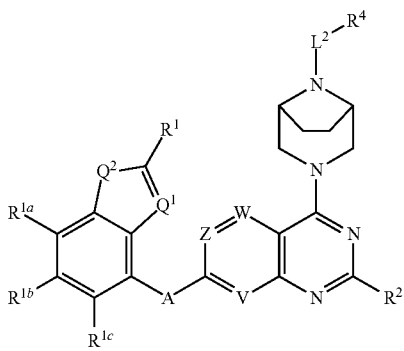

Formula (Ih″) wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments of formula Ih″, Z is not N. In embodiments, the compound has the formula:

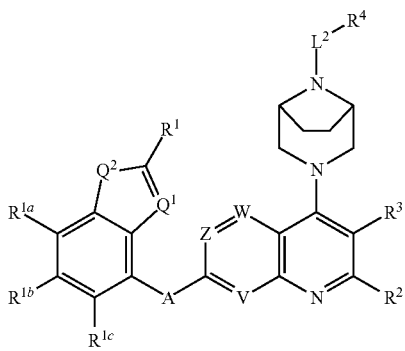

Formula (Ii″) wherein $Q^1$, $Q^2$, $R^1$, $R^{1a}$, $R^{1b}$, $R^{1c}$, A, V, Z, W, $R^2$, $R^3$, $L^2$, and $R^4$ are as described herein, including in any embodiment.

In embodiments, the compound has the formula:

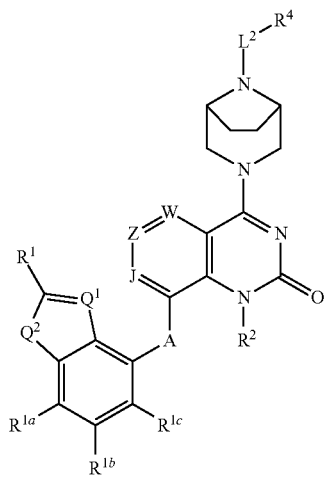

Formula (Ij″) wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

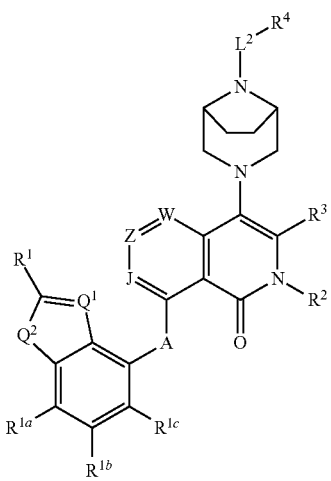

Formula (Ik″) wherein $Q^1$, $Q^2$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula

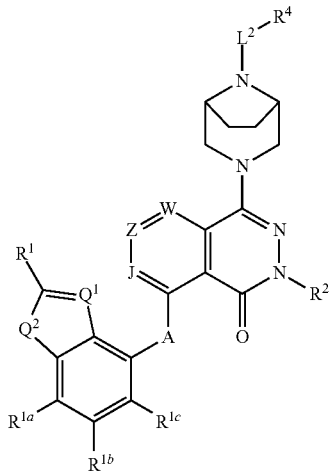

Formula (Im″) wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

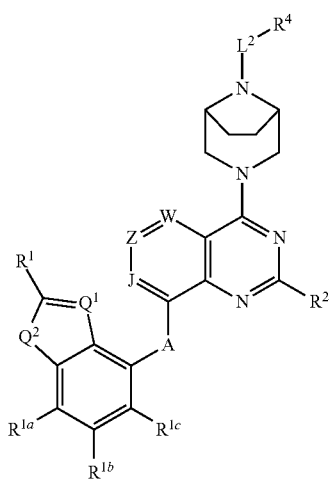

Formula (In″) wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

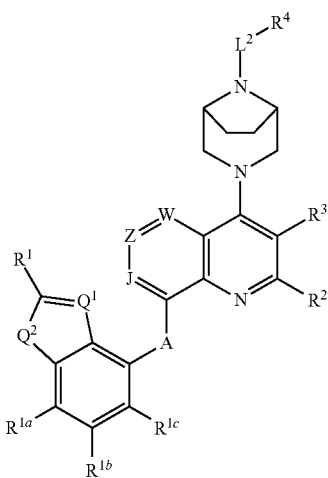

Formula (Io″) wherein $Q^1$, $Q^2$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula:

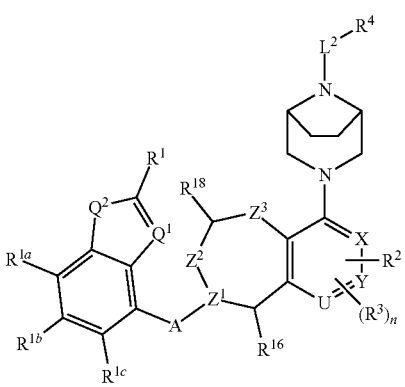

Formula (II″) wherein $Q^1$, $Q^2$, $R^1$, $R^{1a}$, $R^{1b}$, $R^{1c}$, A, $R^{16}$, $R^{18}$, $Z^1$, $Z^2$, $Z^3$, X, Y, U, $R^2$, $R^3$, n, $L^2$, and $R^4$ are as described herein, including in any embodiment. In embodiments, the compound has the formula:

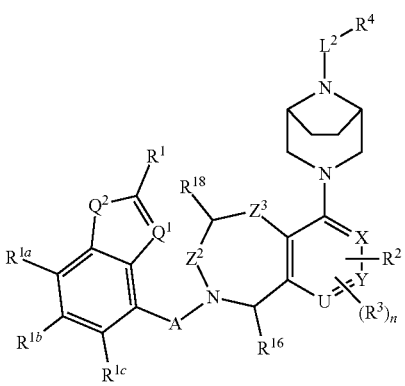

Formula (IIa″) wherein $Q^1$, $Q^2$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

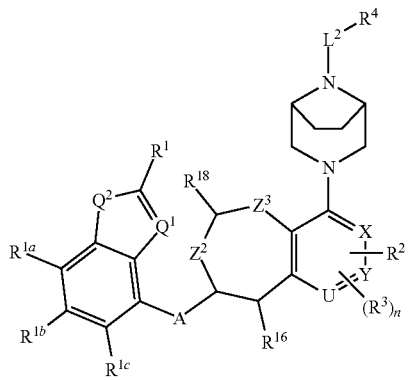

Formula (IIb") wherein $Q^1$, $Q^2$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

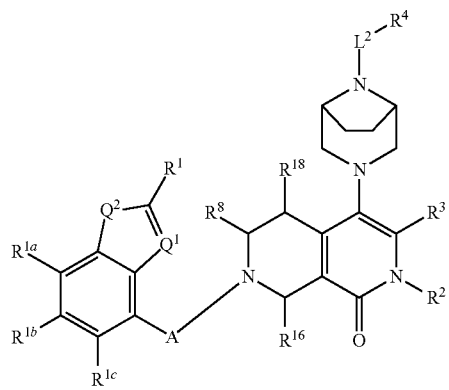

Formula (IIe") wherein $Q^1$, $Q^2$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

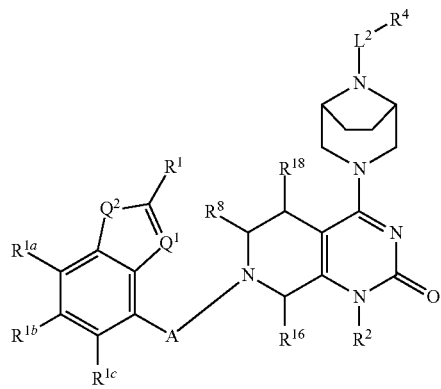

Formula (IIc") wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

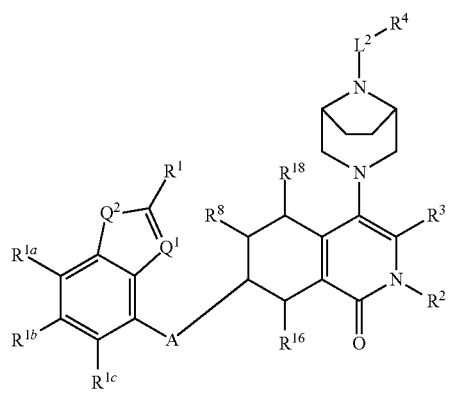

Formula (IIf") wherein $Q^1$, $Q^2$, $R^1$, $R^{1a}$, $R^{14}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

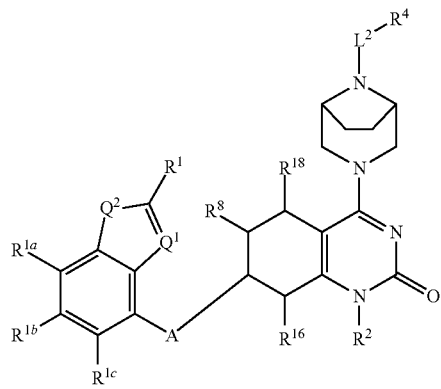

Formula (IId") wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

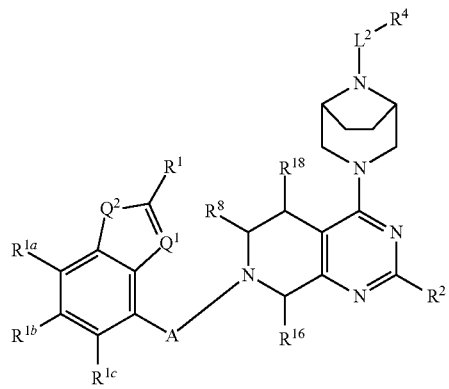

Formula (IIg") wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

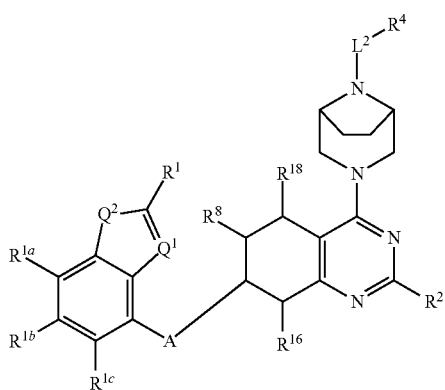

Formula (IIh″) wherein $Q^1$, $Q^2$, $R^1$, $R^{1a}$, $R^{1b}$, $R^{1a}$, A, $R^{16}$, $R^{18}$, $R^8$, $R^2$, $L^2$, and $R^4$ are as described herein, including in any embodiment. In embodiments, the compound has the formula:

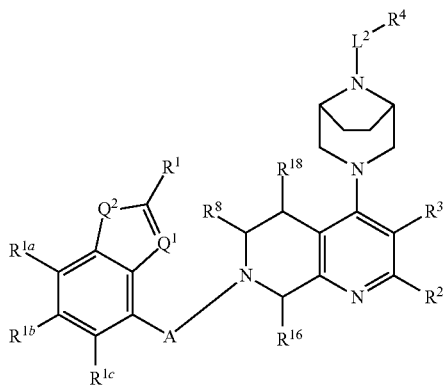

Formula (IIi″) wherein $Q^1$, $Q^2$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

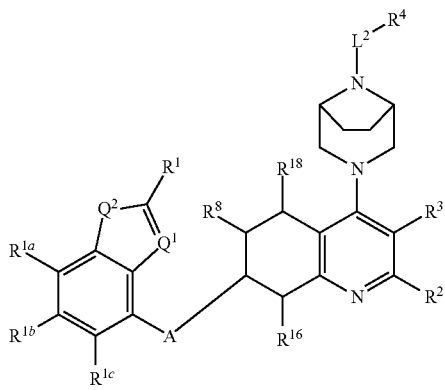

Formula (IIj″) wherein $Q^1$, $Q^2$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

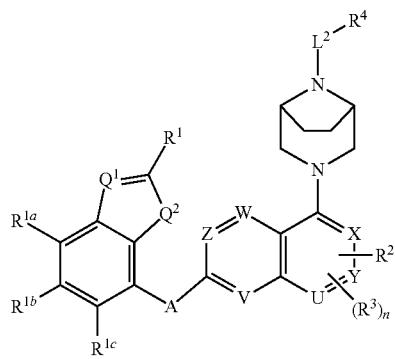

Formula (Ia‴) wherein $Q^1$, $Q^2$, $R^1$, $R^{1a}$, $R^{1b}$, $R^{1c}$, A, V, Z, W, X, Y, U, $R^2$, $R^3$, n, $L^2$, and $R^4$ are as described herein, including in any embodiment. In embodiments, the compound has the formula:

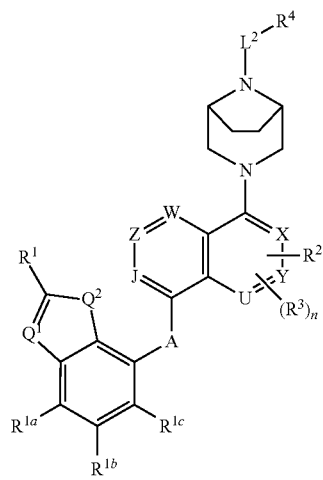

Formula (Ic‴) wherein $Q^1$, $Q^2$, $R^1$, $R^{1a}$, $R^{1b}$, $R^{1c}$, A, J, Z, W, X, Y, U, $R^2$, $R^3$, n, $L^2$, and $R^4$ are as described herein, including in any embodiment. In embodiments, the compound has the formula:

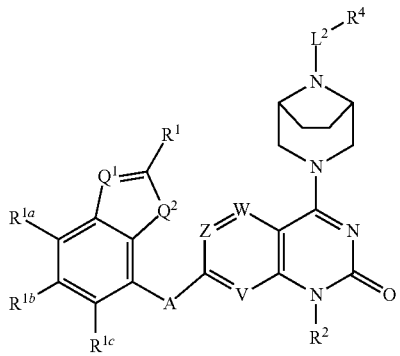

Formula (Ie‴) wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

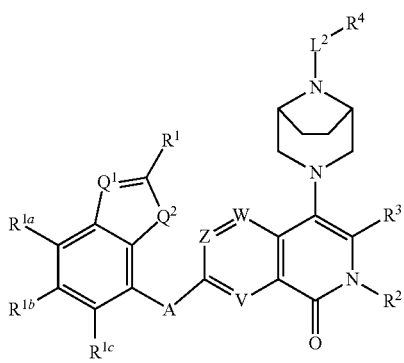

Formula (If''') wherein $Q^1$, $Q^2$, $R^1$, $R^{1a}$, $R^{1b}$, $R^{1c}$, A, V, Z, W, $R^2$, $R^3$, $L^2$, and $R^4$ are as described herein, including in any embodiment.

In embodiments, the compound has the formula:

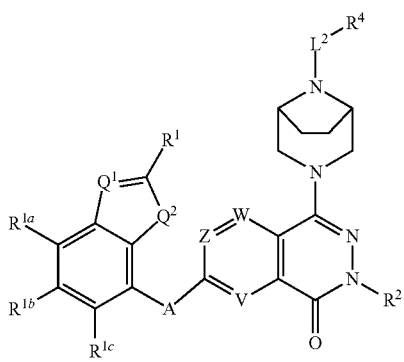

Formula (Ig''') wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula

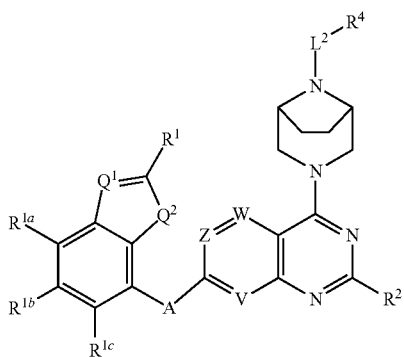

Formula (Ih''') wherein $Q^1$, $Q^2$, $R^1$, $R^{1a}$, $R^{1b}$, $R^{1c}$, A, V, Z, W, $R^2$, $L^2$, and $R^4$ are as described herein, including in any embodiment. In embodiments of formula Ih''', Z is not N. In embodiments, the compound has the formula

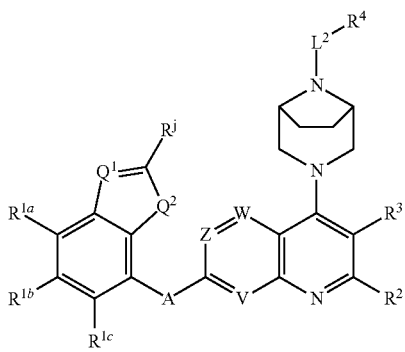

Formula (Ii''') wherein $Q^1$, $Q^2$, $R^1$, $R^{1a}$, $R^{1b}$, $R^{1c}$, A, V, Z, W, $R^2$, $R^3$, $L^2$, and $R^4$ are as described herein, including in any embodiment. In embodiments, the compound has the formula:

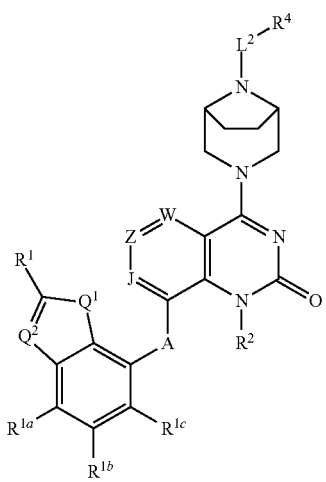

Formula (Ij''') wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

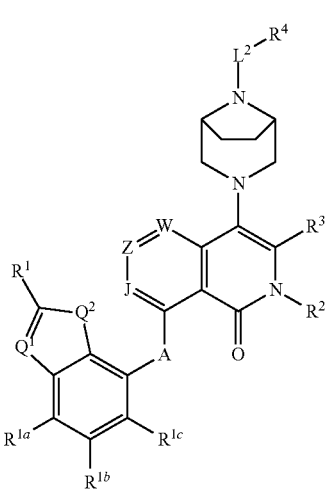

Formula (Ik''') wherein $Q^1$, $Q^2$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula:

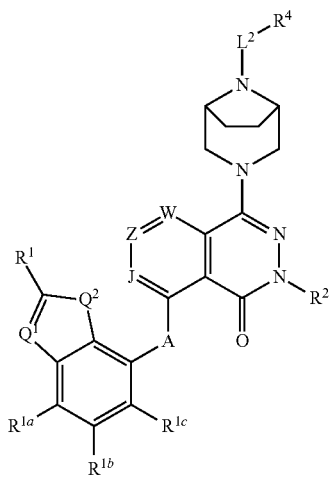

Formula (Im''') wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula:

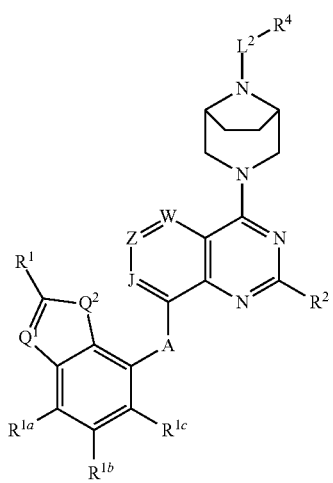

Formula (In''') wherein $Q^1$, $Q^2$, $R^1$, $R^{1a}$, $R^{1b}$, $R^{1c}$, A, J, Z, W, $R^2$, $L^2$, and $R^4$ are as described herein, including in any embodiment. In embodiments, the compound has the formula

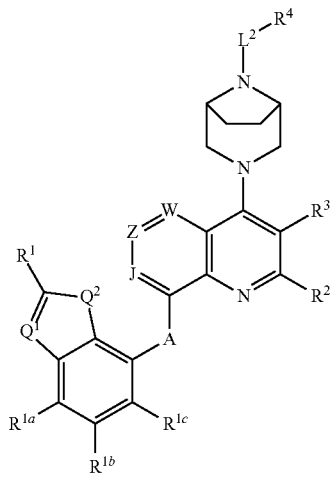

Formula (Io''') wherein $Q^1$, $Q^2$, $R^1$, $R^{1a}$, $R^{1b}$, $R^{1c}$, A, J, Z, W, $R^2$, $R^3$, $L^2$, and $R^4$ are as described herein, including in any embodiment. In embodiments, the compound has the formula:

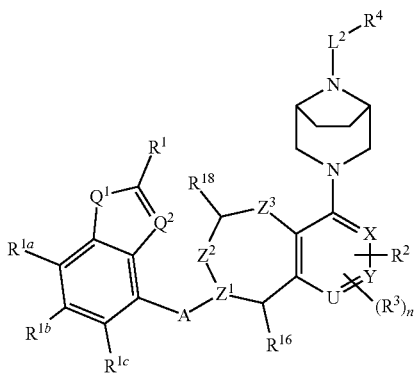

Formula (II''') wherein $Q^1$, $Q^2$, $R^1$, $R^{1a}$, $R^{1b}$, $R^{1c}$, A, $R^{16}$, $R^{18}$, $Z^1$, $Z^2$, $Z^3$, X, Y, U, $R^2$, $R^3$, n, $L^2$, and $R^4$ are as described herein, including in any embodiment. In embodiments, the compound has the formula:

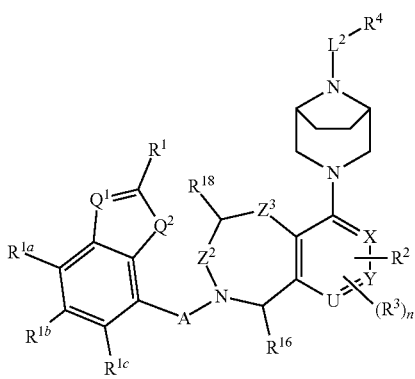

Formula (IIa''') wherein $Q^1$, $Q^2$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

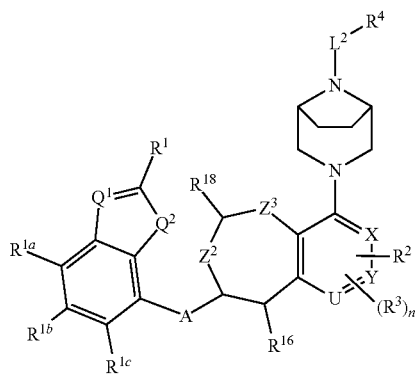

Formula (IIb''') wherein $Q^1$, $Q^2$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

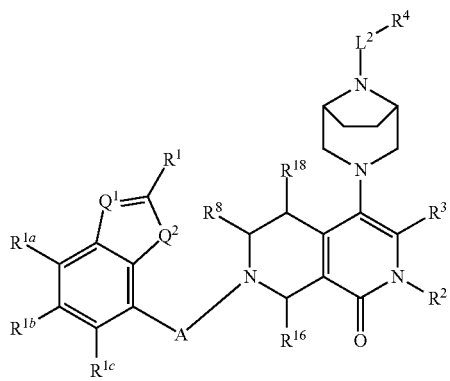

Formula (IIe''') wherein $Q^1$, $Q^2$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

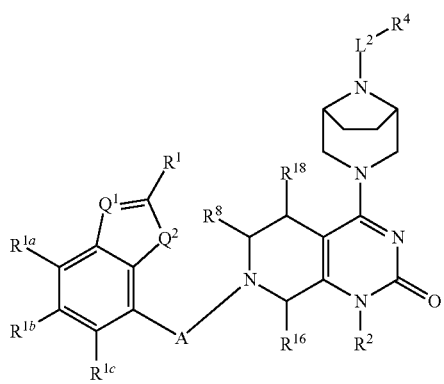

Formula (IIc''') wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

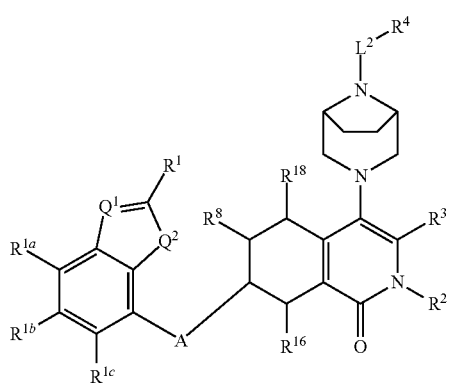

Formula (IIf''') wherein $Q^1$, $Q^2$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

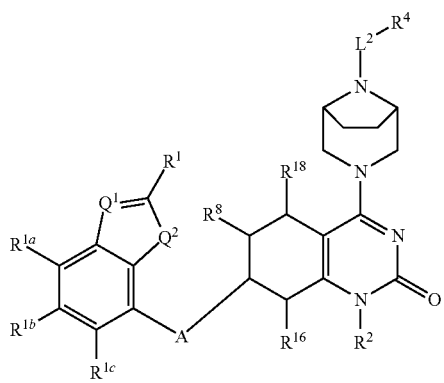

Formula (IId''') wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

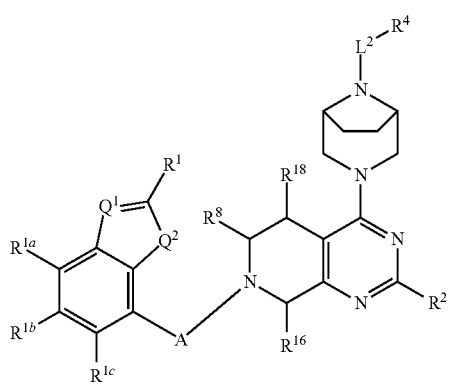

Formula (IIg''') wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

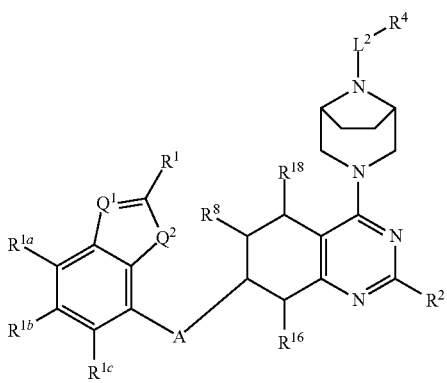

Formula (IIh''') wherein $Q^1$, $Q^2$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

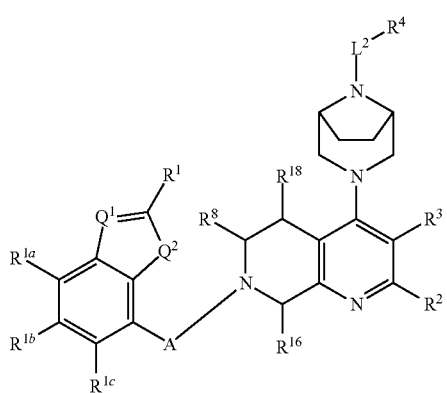

Formula (IIi''') wherein $Q^1$, $Q^2$, $R^1$, $R^{1a}$, $R^{1b}$, $R^{1c}$, A, $R^{16}$, $R^{18}$, $R^3$, $R^2$, $R^3$, $L^2$, and $R^4$ are as described herein, including in any embodiment. In embodiments, the compound has the formula:

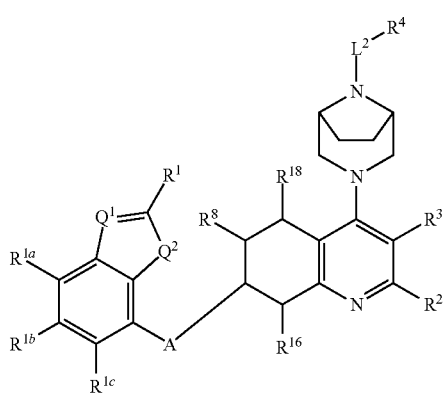

Formula (IIj''') wherein $Q^1$, $Q^2$, $R^1$, $R^{1a}$, $R^{1b}$, $R^{1c}$, A, $R^{16}$, $R^{18}$, $R^3$, $R^2$, $R^3$, $L^2$, and $R^4$ are as described herein, including in any embodiment.

In embodiments, $R^5$ is

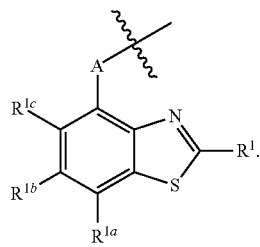

In embodiments, $R^5$ is

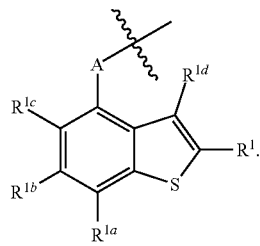

In embodiments, $R^5$ is

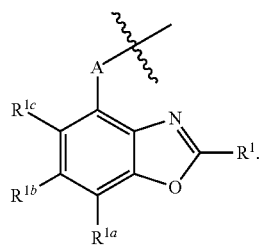

In embodiments, $R^5$ is

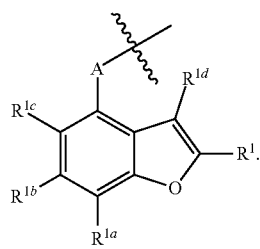

In embodiments, $R^5$ is

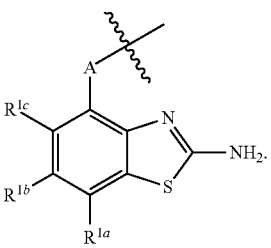

In embodiments, R⁵ is
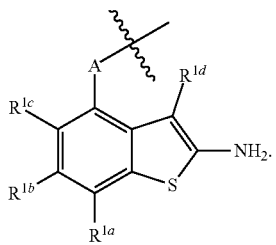
In embodiments, R⁵ is
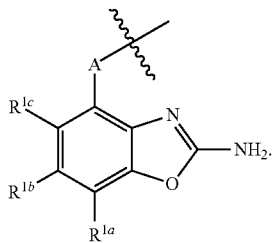
In embodiments, R⁵ is
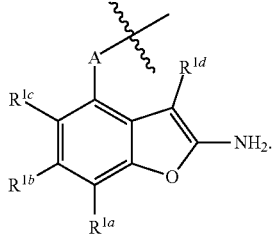
In embodiments, R⁵ is
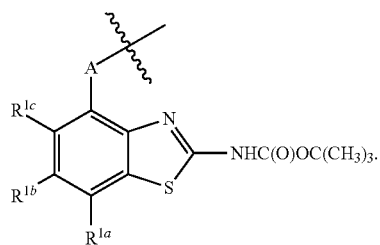
In embodiments, R⁵ is
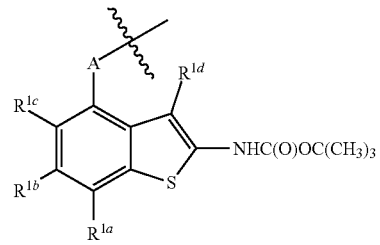
In embodiments, R⁵ is
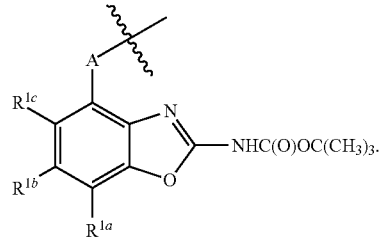
In embodiments, R⁵ is
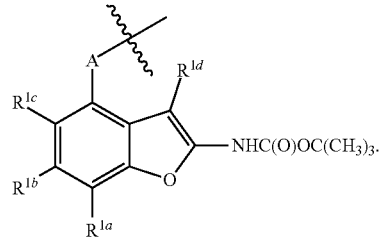
In embodiments, R⁵ is
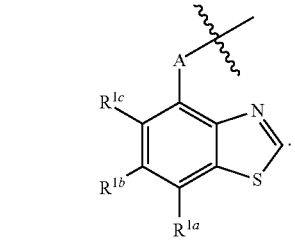
In embodiments, R⁵ is
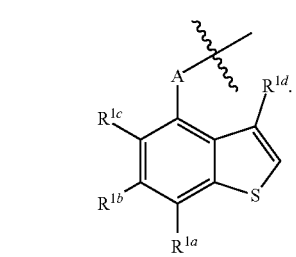

In embodiments, $R^5$ is
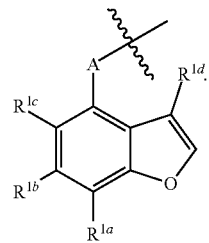
In embodiments, $R^5$ is
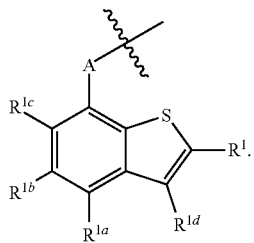
In embodiments, $R^5$ is
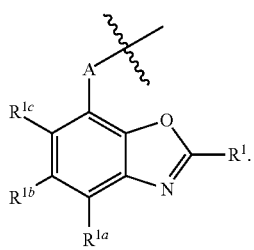
In embodiments, $R^5$ is
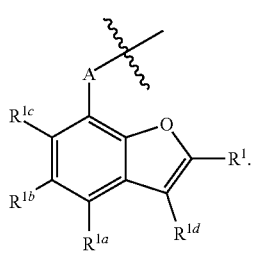
In embodiments, $R^5$ is
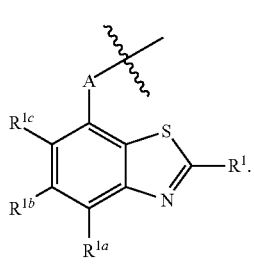
In embodiments, $R^5$ is
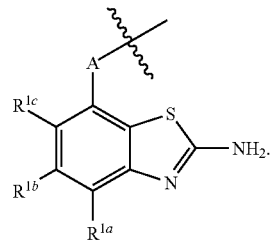
In embodiments, $R^5$ is
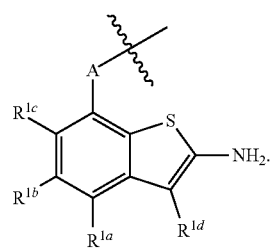
In embodiments, $R^5$ is
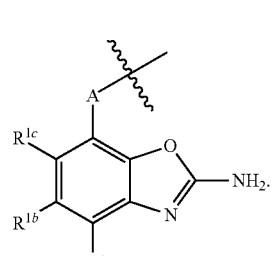
In embodiments, $R^5$ is
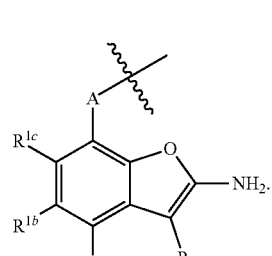
In embodiments, $R^5$ is
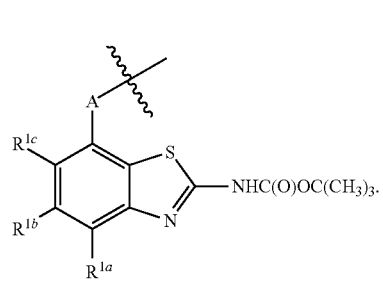

In embodiments, R⁵ is
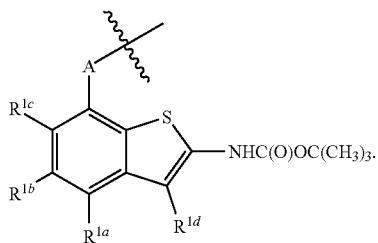
In embodiments, R⁵ is
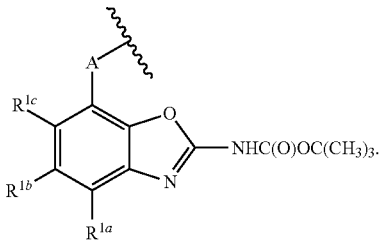
In embodiments, R⁵ is
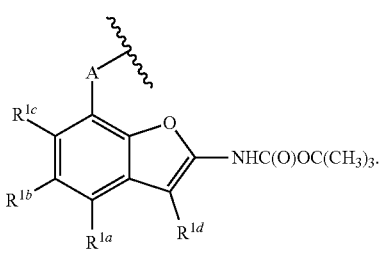
In embodiments, R⁵ is
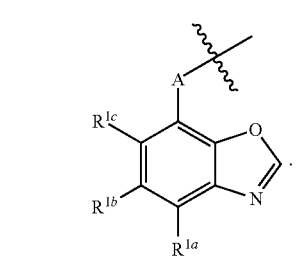
In embodiments, R⁵ is
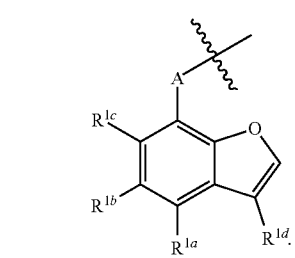
In embodiments, R⁵ is
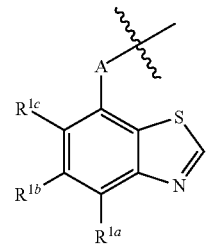
In embodiments, R⁵ is
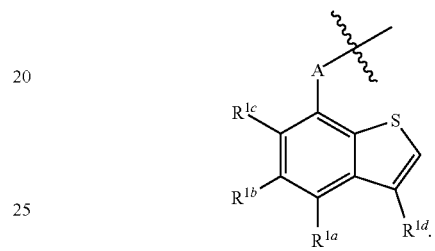
In some embodiments, R⁵ is
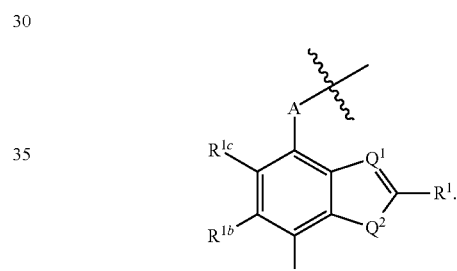
In some embodiments, R⁵ is
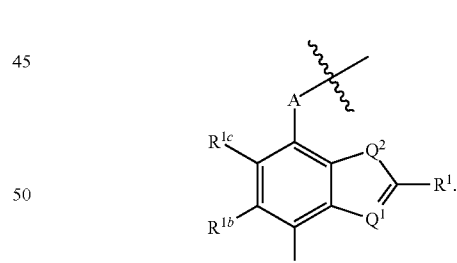
In some embodiments, R⁵ is
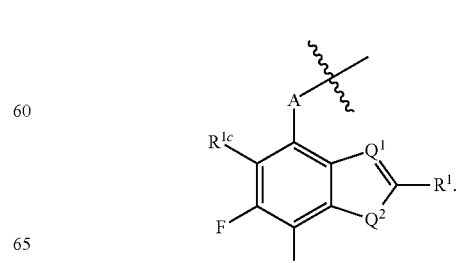

In some embodiments, R⁵ is
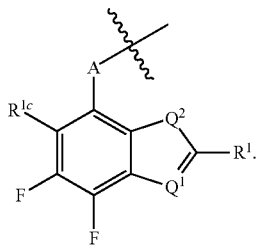
In some embodiments, R⁵ is
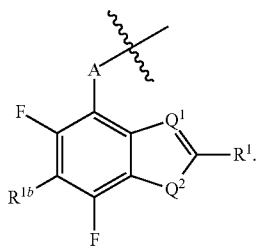
In some embodiments, R⁵ is
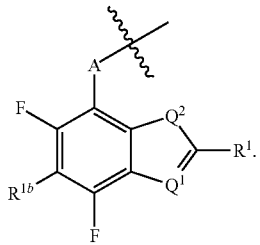
In some embodiments, R⁵ is
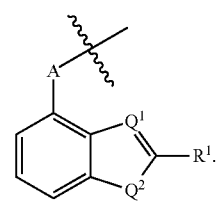
In some embodiments, R⁵ is
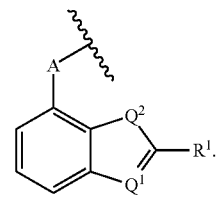
In some embodiments, R⁵ is
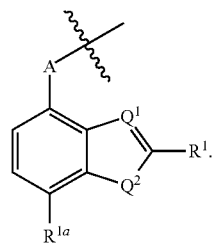
In some embodiments, R⁵ is
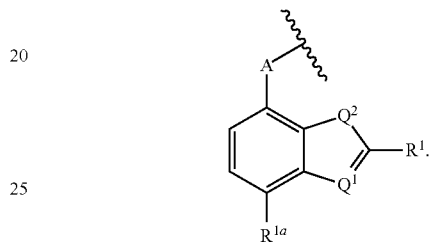
In some embodiments, R⁵ is
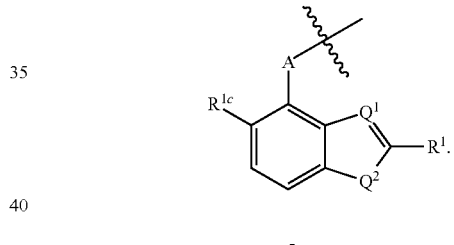
In some embodiments, R⁵ is
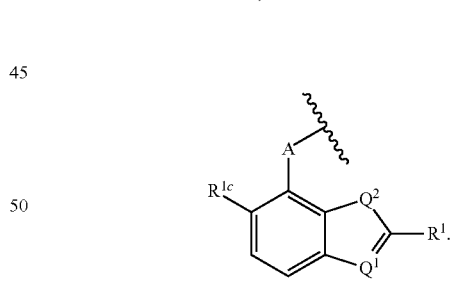
In some embodiments, R⁵ is
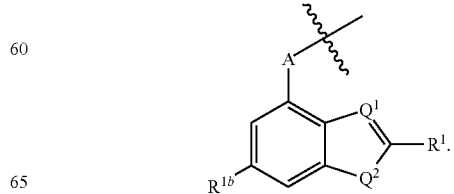

In some embodiments, R⁵ is
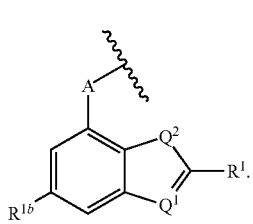
In some embodiments, R⁵ is
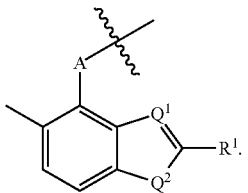
In some embodiments, R⁵ is
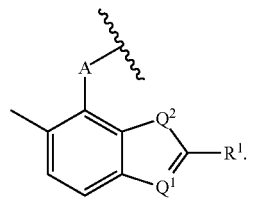
In some embodiments, R⁵ is
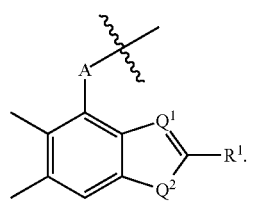
In some embodiments, R⁵ is
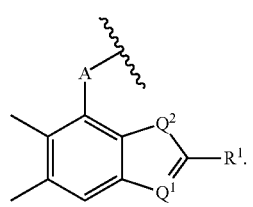
In some embodiments, R⁵ is
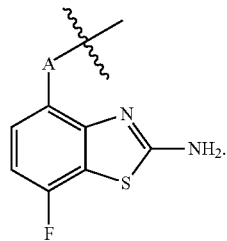
In some embodiments, R⁵ is
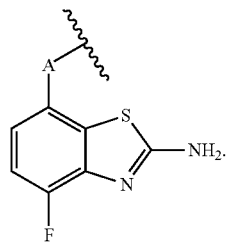
In some embodiments, R⁵ is
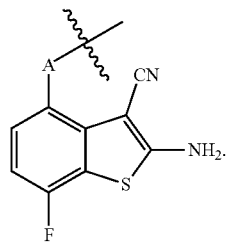
In some embodiments, R⁵ is
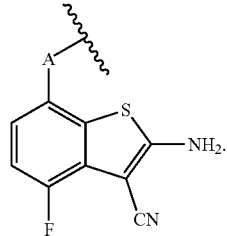
In some embodiments, R⁵ is
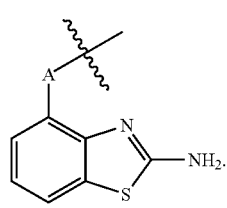

In some embodiments, $R^5$ is
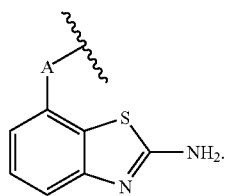
In some embodiments, $R^5$ is
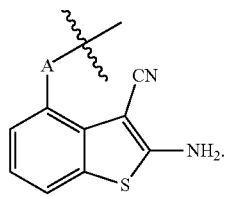
In some embodiments, $R^5$ is
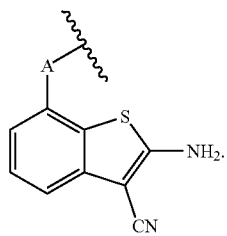
In some embodiments, $R^5$ is
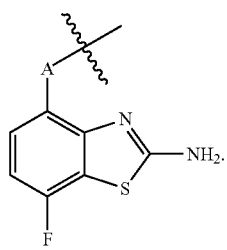
In some embodiments, $R^5$ is
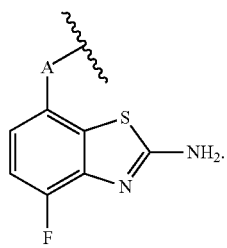
In some embodiments, $R^5$ is
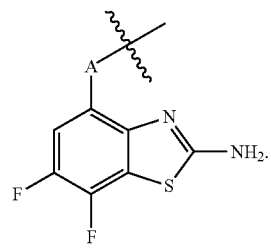
In some embodiments, $R^5$ is
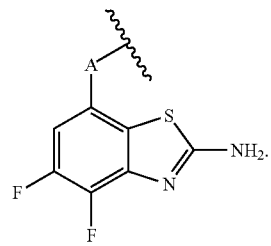
In some embodiments, $R^5$ is
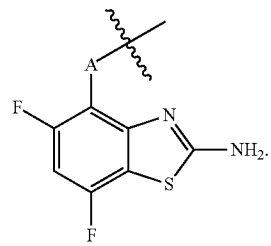
In some embodiments, $R^5$ is
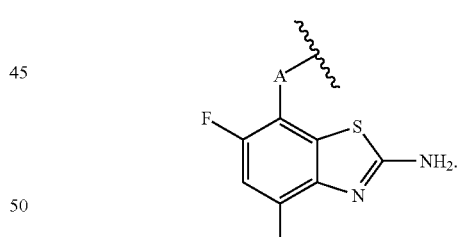
In some embodiments, $R^5$ is
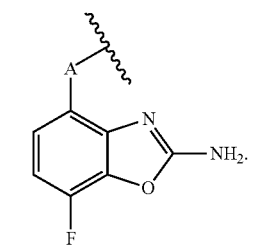

In some embodiments, R⁵ is
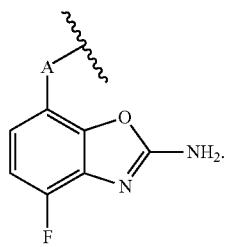
In some embodiments, R⁵ is
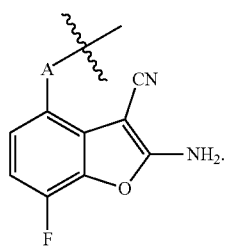
In some embodiments, R⁵ is
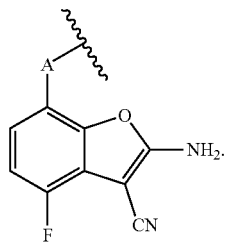
In some embodiments, R⁵ is
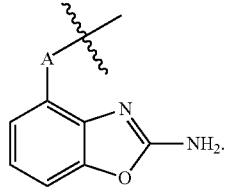
In some embodiments, R⁵ is
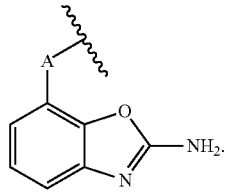
In some embodiments, R⁵ is
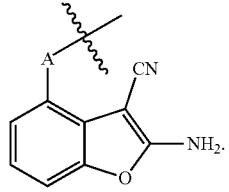
In some embodiments, R⁵ is
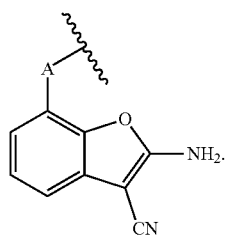
In some embodiments, R⁵ is
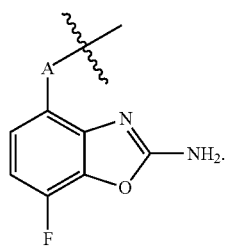
In some embodiments, R⁵ is
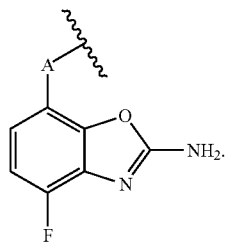
In some embodiments, R⁵ is
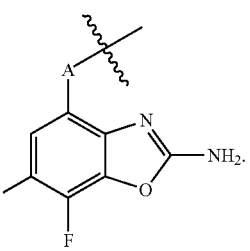

In some embodiments, R⁵ is
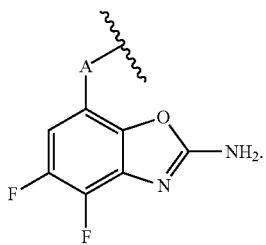
In some embodiments, R⁵ is
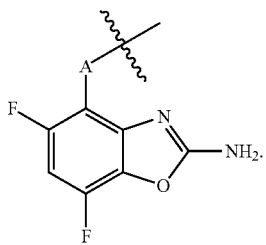
In some embodiments, R⁵ is
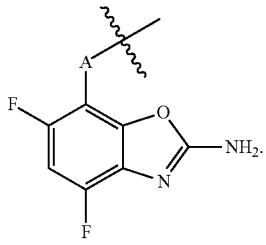
In embodiments, R⁵ is
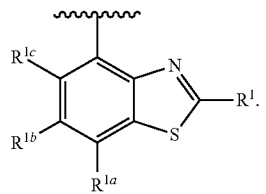
In embodiments, R⁵ is
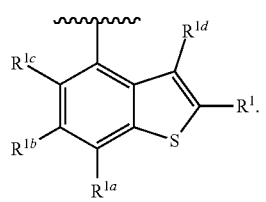
In embodiments, R⁵ is
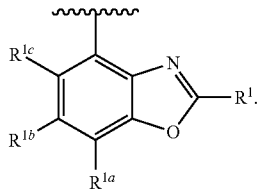
In embodiments, R⁵ is
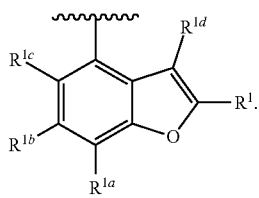
In embodiments, R⁵ is
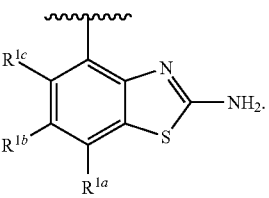
In embodiments, R⁵ is
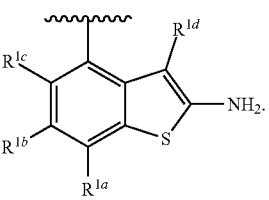
In embodiments, R⁵ is
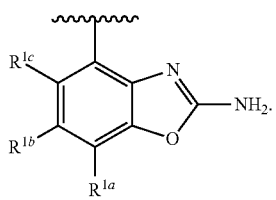
In embodiments, R⁵ is
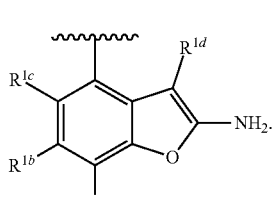

In embodiments, R⁵ is
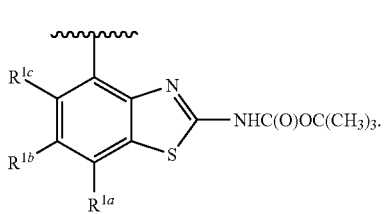
In embodiments, R⁵ is
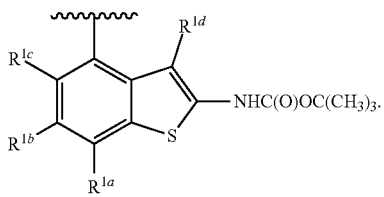
In embodiments, R⁵ is
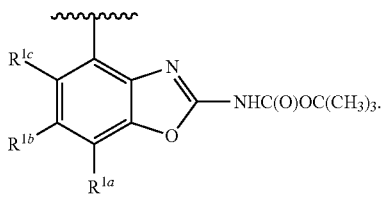
In embodiments, R⁵ is
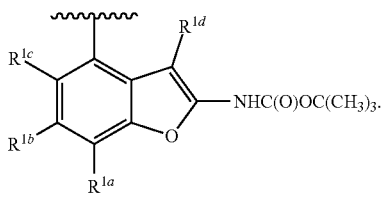
In embodiments, R⁵ is
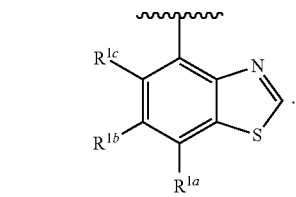
In embodiments, R⁵ is
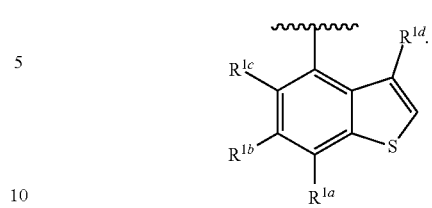
In embodiments, R⁵ is
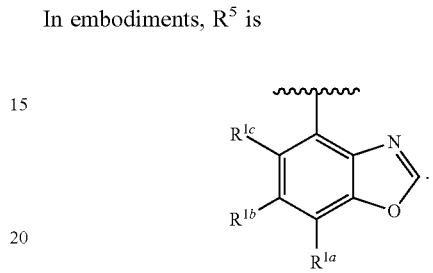
In embodiments, R⁵ is
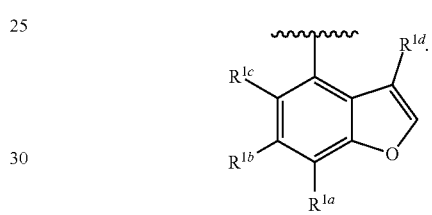
In embodiments, R⁵ is
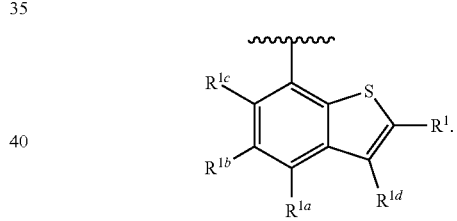
In embodiments, R⁵ is
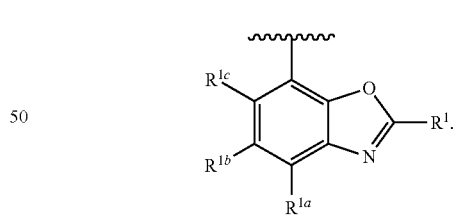
In embodiments, R⁵ is
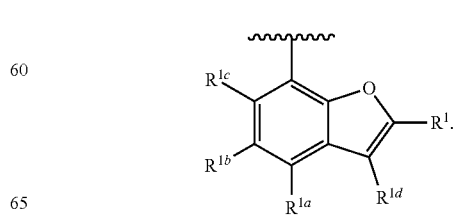

In embodiments, R⁵ is
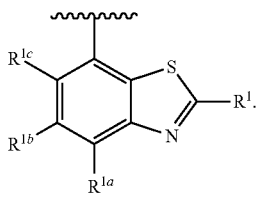
In embodiments, R⁵ is
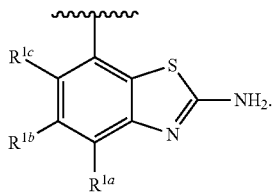
In embodiments, R⁵ is
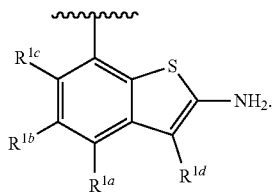
In embodiments, R⁵ is
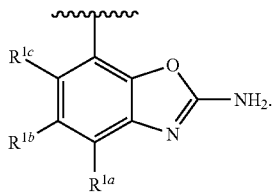
In embodiments, R⁵ is
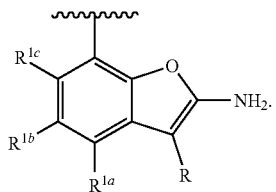
In embodiments, R⁵ is
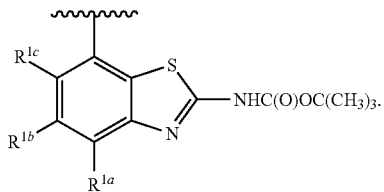
In embodiments, R⁵ is
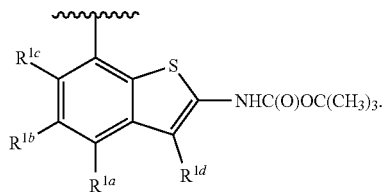
In embodiments, R⁵ is
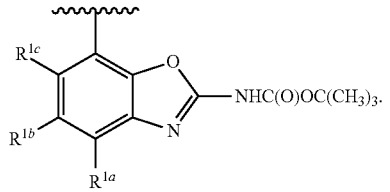
In embodiments, R⁵ is
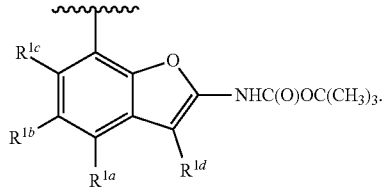
In embodiments, R⁵ is
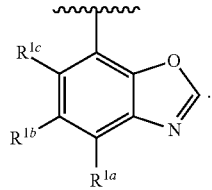
In embodiments, R⁵ is
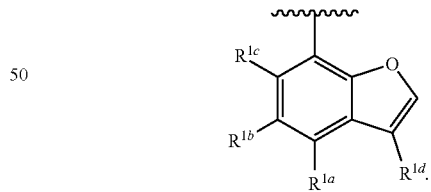
In embodiments, R⁵ is
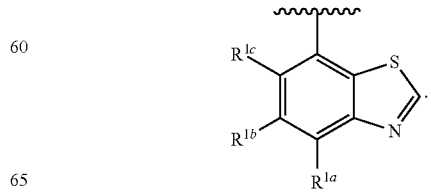

In embodiments, $R^5$ is
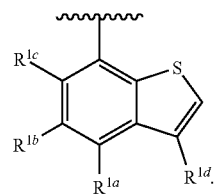
In some embodiments, $R^5$ is
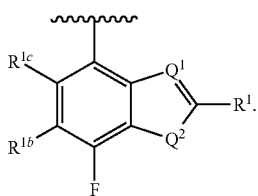
In some embodiments, $R^5$ is
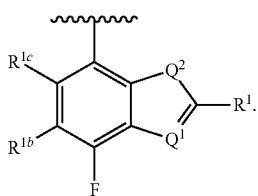
In some embodiments, $R^5$ is
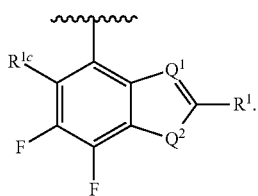
In some embodiments, $R^5$ is
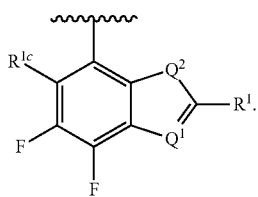
In some embodiments, $R^5$ is
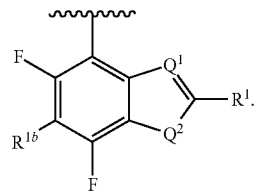
In some embodiments, $R^5$ is
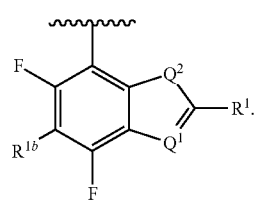
In some embodiments, $R^5$ is
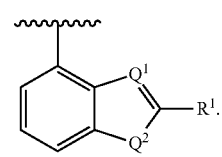
In some embodiments, $R^5$ is
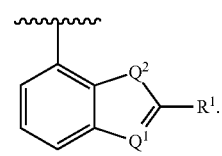
In some embodiments, $R^5$ is
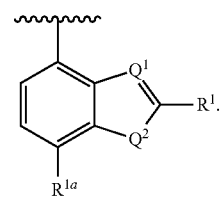
In some embodiments, $R^5$ is
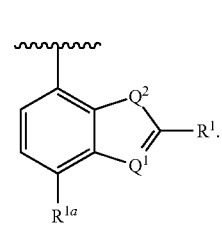

In some embodiments, R⁵ is
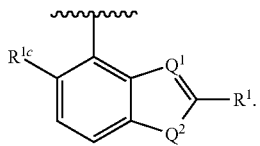
In some embodiments, R⁵ is
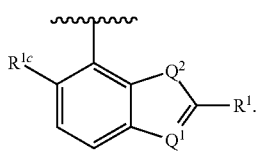
In some embodiments, R⁵ is
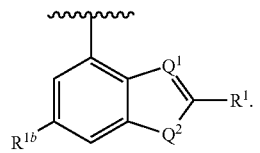
In some embodiments, R⁵ is
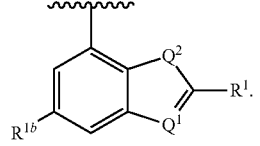
In some embodiments, R⁵ is
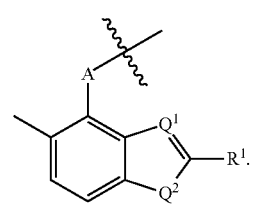
In some embodiments, R⁵ is
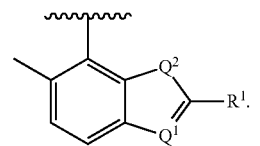
In some embodiments, R⁵ is
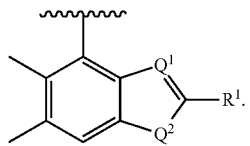
In some embodiments, R⁵ is
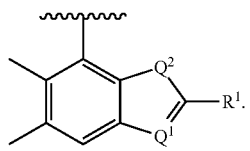
In some embodiments, R⁵ is
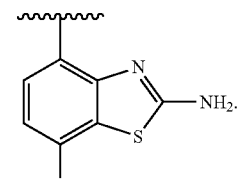
In some embodiments, R⁵ is
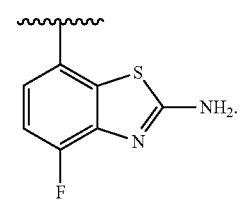
In some embodiments, R⁵ is
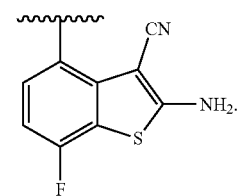 [SMILES: *c1ccc(F)c2sc(N)c(C#N)c12]
In some embodiments, R⁵ is
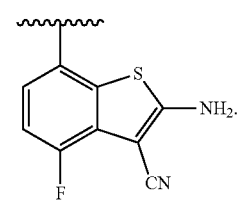 [SMILES: *c1ccc(F)c2c(C#N)c(N)sc12]

In some embodiments, R⁵ is
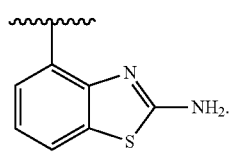
In some embodiments, R⁵ is
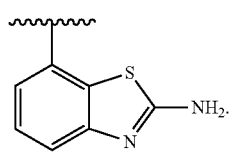
In some embodiments, R⁵ is
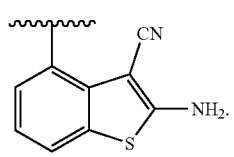
In some embodiments, R⁵ is
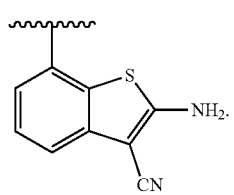 [SMILES: *c1cccc2c(C#N)c(N)sc12]
In some embodiments, R⁵ is
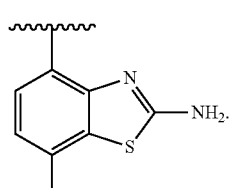
In some embodiments, R⁵ is
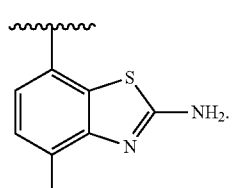
In some embodiments, R⁵ is
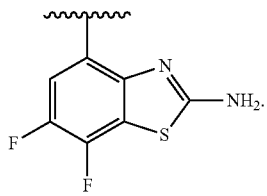 [SMILES: *c1cc(F)c(F)c2sc(N)nc12]
In some embodiments, R⁵ is
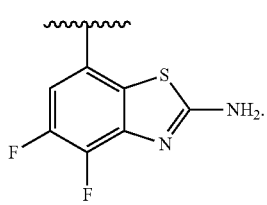 [SMILES: *c1cc(F)c(F)c2nc(N)sc12]
In some embodiments, R⁵ is
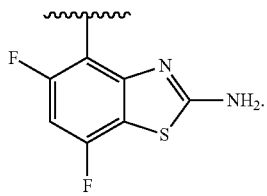 [SMILES: *c1c(F)cc(F)c2sc(N)nc12]
In some embodiments, R⁵ is
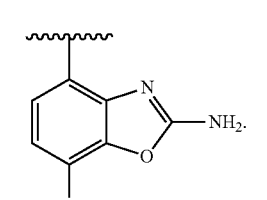
In some embodiments, R⁵ is
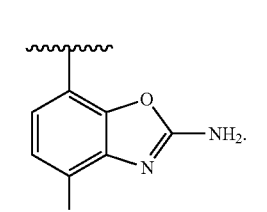

In some embodiments, R⁵ is
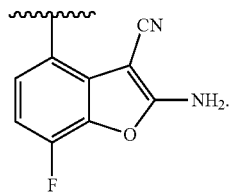 [SMILES: *c1ccc(F)c2oc(N)c(C#N)c12]
In some embodiments, R⁵ is
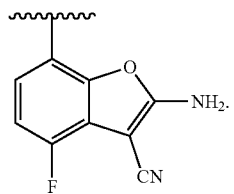 [SMILES: *c1ccc(F)c2c(C#N)c(N)oc12]
In some embodiments, R⁵ is
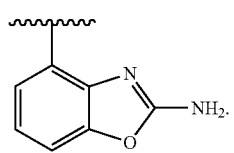 [SMILES: *c1cccc2oc(N)nc12]
In some embodiments, R⁵ is
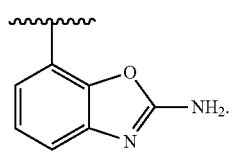 [SMILES: *c1cccc2nc(N)oc12]
In some embodiments, R⁵ is
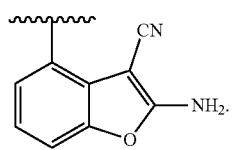 [SMILES: *c1cccc2oc(N)c(C#N)c12]
In some embodiments, R⁵ is
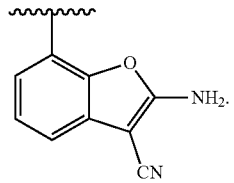 [SMILES: *c1cccc2c(C#N)c(N)oc12]
In some embodiments, R⁵ is
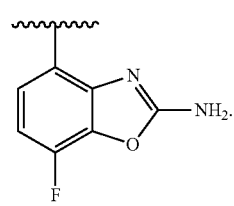
In some embodiments, R⁵ is
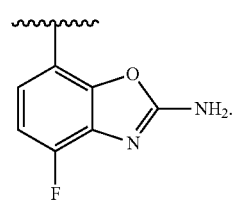 [SMILES: *c1ccc(F)c2nc(N)oc12]
In some embodiments, R⁵ is
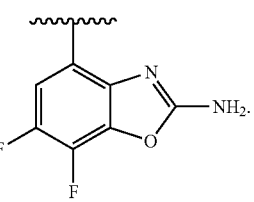
In some embodiments, R⁵ is
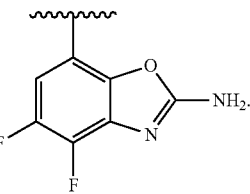
In some embodiments, R⁵ is
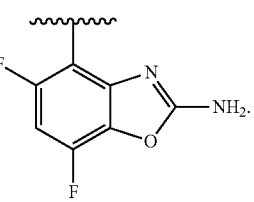

In some embodiments, $R^5$ is

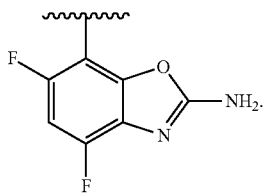

In embodiments, $R^1$ is selected from hydrogen, $C_{1-6}$alkyl, $C_{1-6}$haloalkyl, $C_{2-6}$alkenyl, $C_{2-6}$alkynyl, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —C(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —CH$_2$C(O)N($R^{12}$)($R^{13}$), and —CH$_2$N($R^{14}$)C(O)$R^{15}$, wherein $C_{1-6}$alkyl, $C_{2-6}$alkenyl, and $C_{2-6}$alkynyl are optionally substituted with one, two, or three $R^{20a}$;

In embodiments, $R^1$ is selected from hydrogen and —N($R^{12}$)($R^{13}$).

In embodiments, $R^{1d}$ is independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —O$R^{12}$, —S$R^{12}$, —N($R^{12}$)($R^{13}$), —C(O)O$R^{12}$, —OC(O)N($R^{12}$)($R^{13}$), —N($R^{14}$)C(O)N($R^{12}$)($R^{13}$), —N($R^{14}$)C(O)O$R^{15}$, —N($R^{14}$)S(O)$_2R^{15}$, —C(O)$R^{15}$, —S(O)$R^{15}$, —OC(O)$R^{15}$, —C(O)N($R^{12}$)($R^{13}$), —C(O)C(O)N($R^{12}$)($R^{13}$), —N($R^{14}$)C(O)$R^{15}$, —S(O)$_2R^{15}$, —S(O)$_2$N($R^{12}$)($R^{13}$)—, S(=O)(=NH)N($R^{12}$)($R^{13}$), —CH$_2$C(O)N($R^{12}$)($R^{13}$), —CH$_2$N($R^{14}$)C(O)$R^{15}$, —CH$_2$S(O)$_2R^{15}$, and —CH$_2$S(O)$_2$N($R^{12}$)($R^{13}$), wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$. In embodiments, $R^{1d}$ is independently selected from hydrogen, —CN, $C_{1-6}$alkyl, and $C_{1-6}$haloalkyl, wherein $C_{1-6}$alkyl is optionally substituted with one, two, or three $R^{20a}$;

In some embodiments, A is a bond. In some embodiments, A is O. In some embodiments, A is C($R^{1f}$)($R^{1g}$). In some embodiments, A is CH$_2$.

In embodiments, the compound is selected from

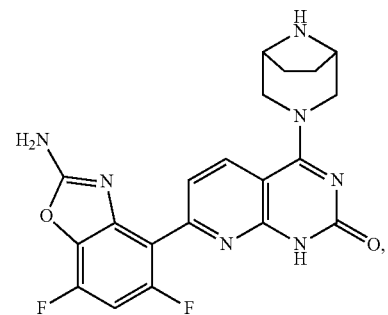

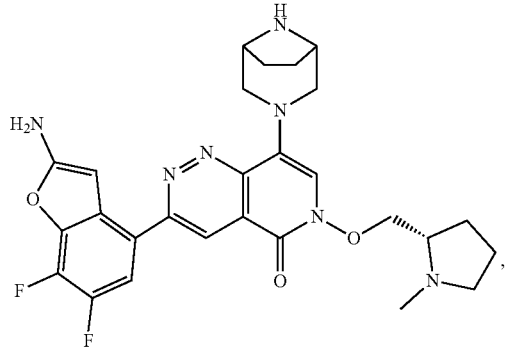

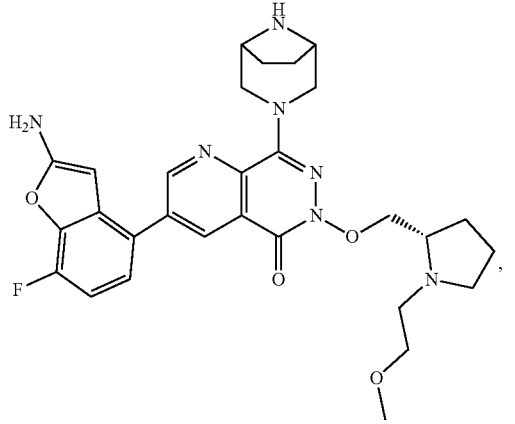

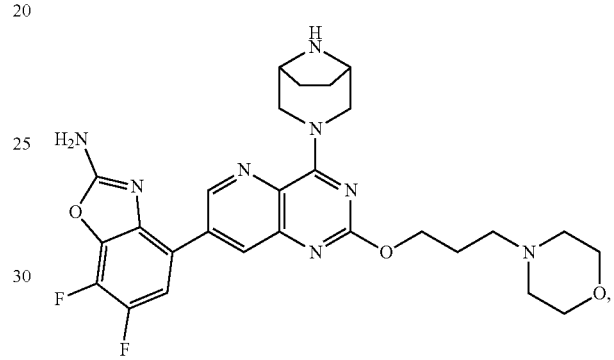

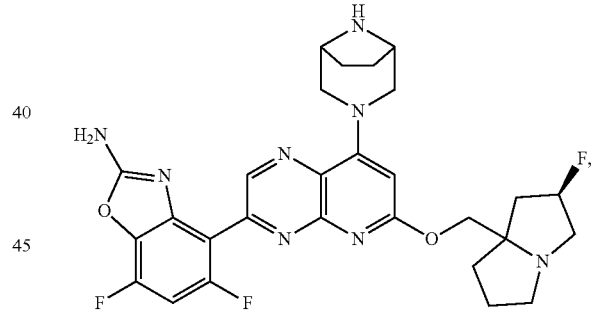

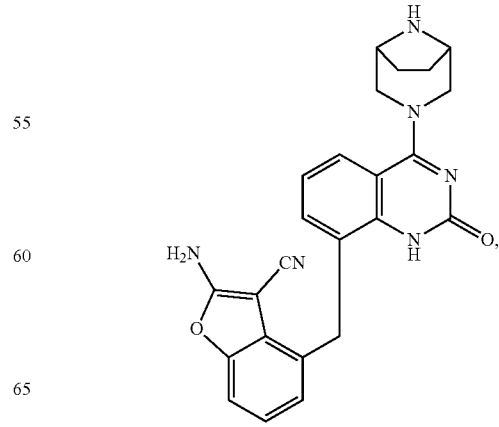

167
-continued
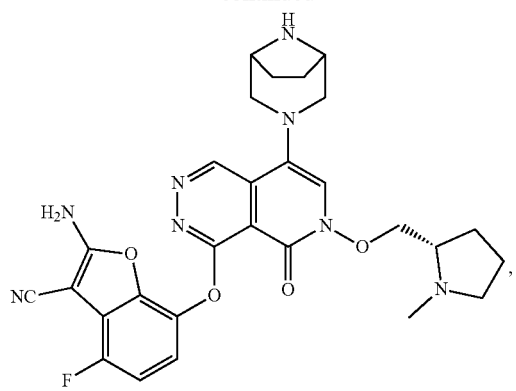
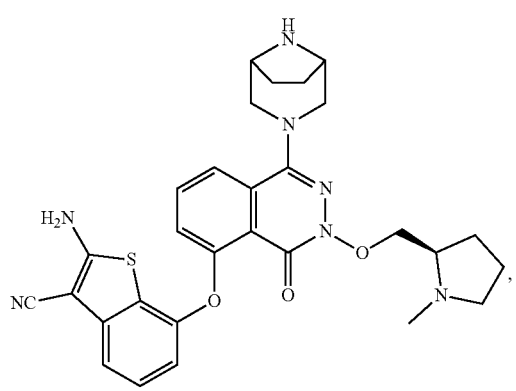
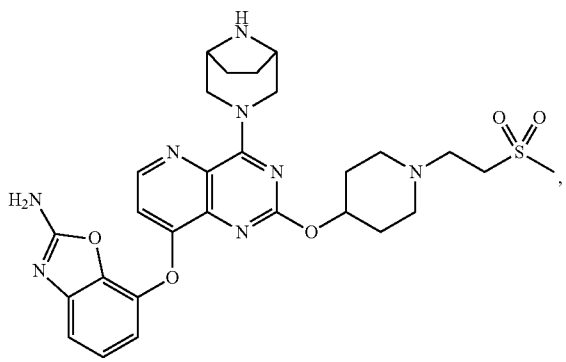
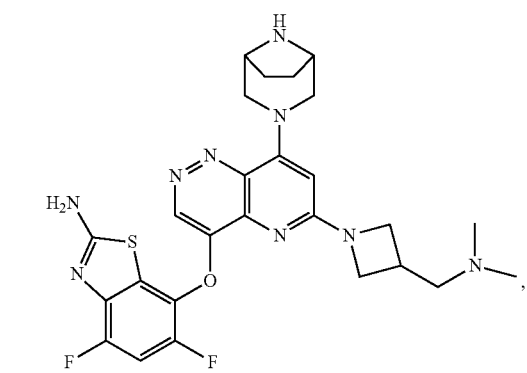
168
-continued
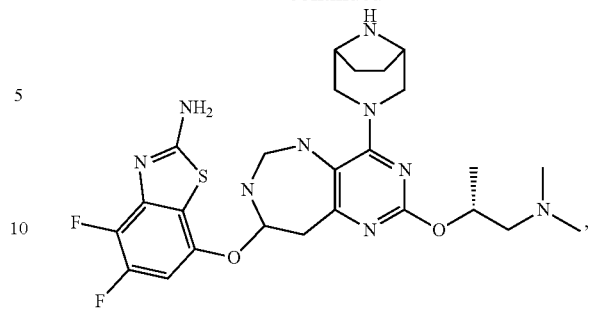
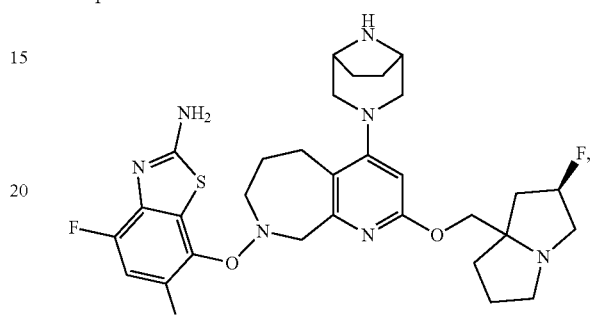
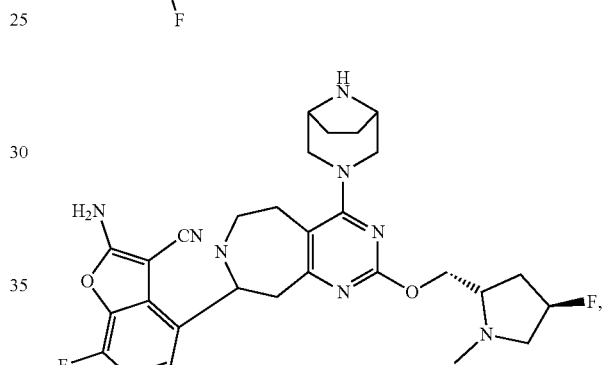
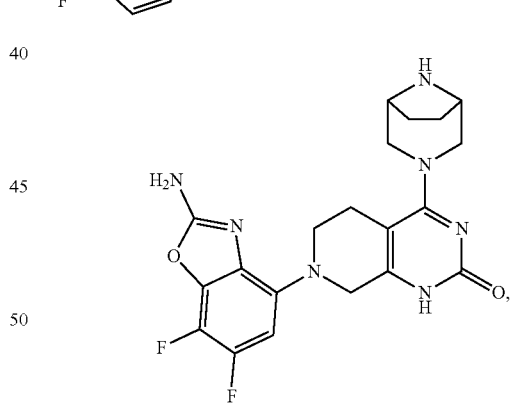
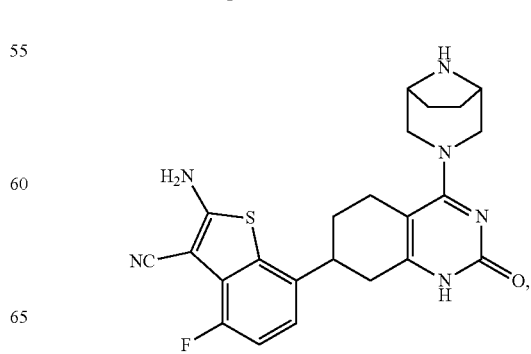

-continued
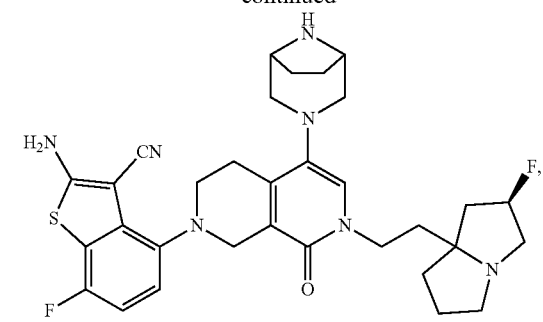
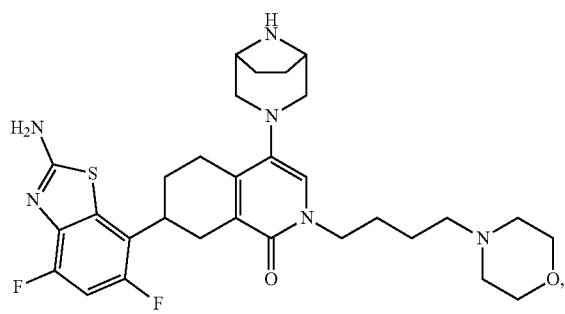
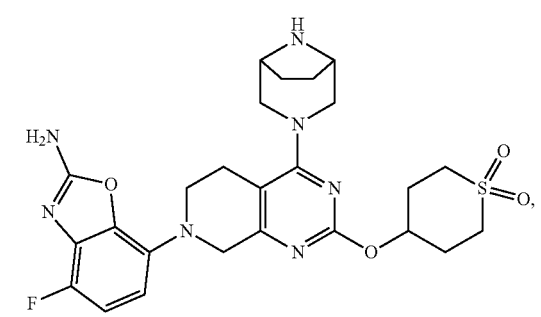
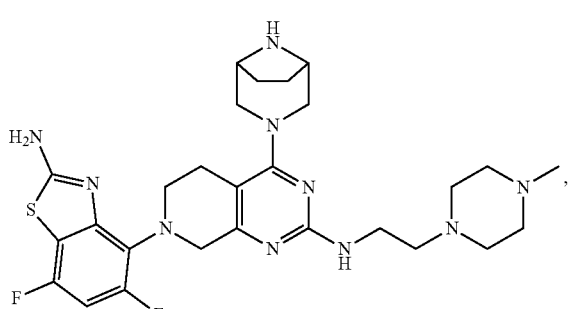
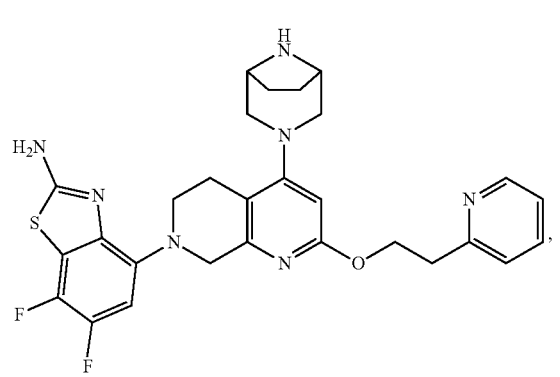
-continued
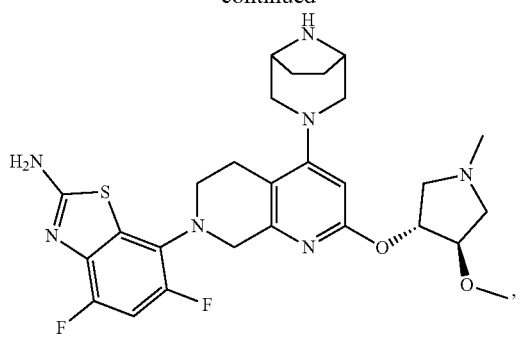
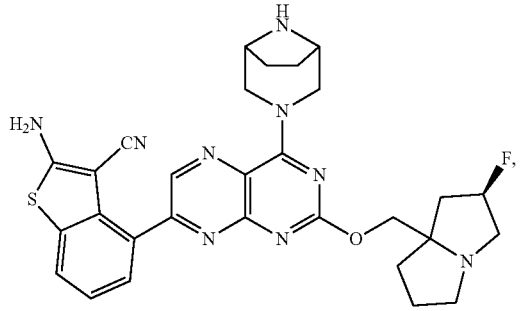
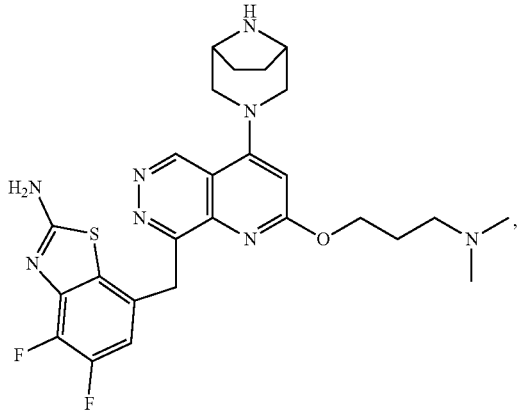
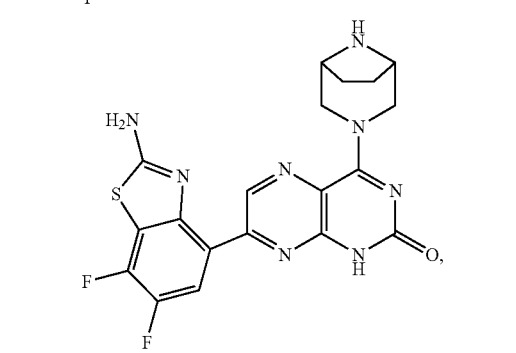
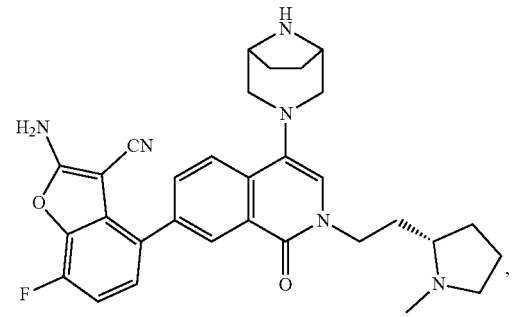

171
-continued
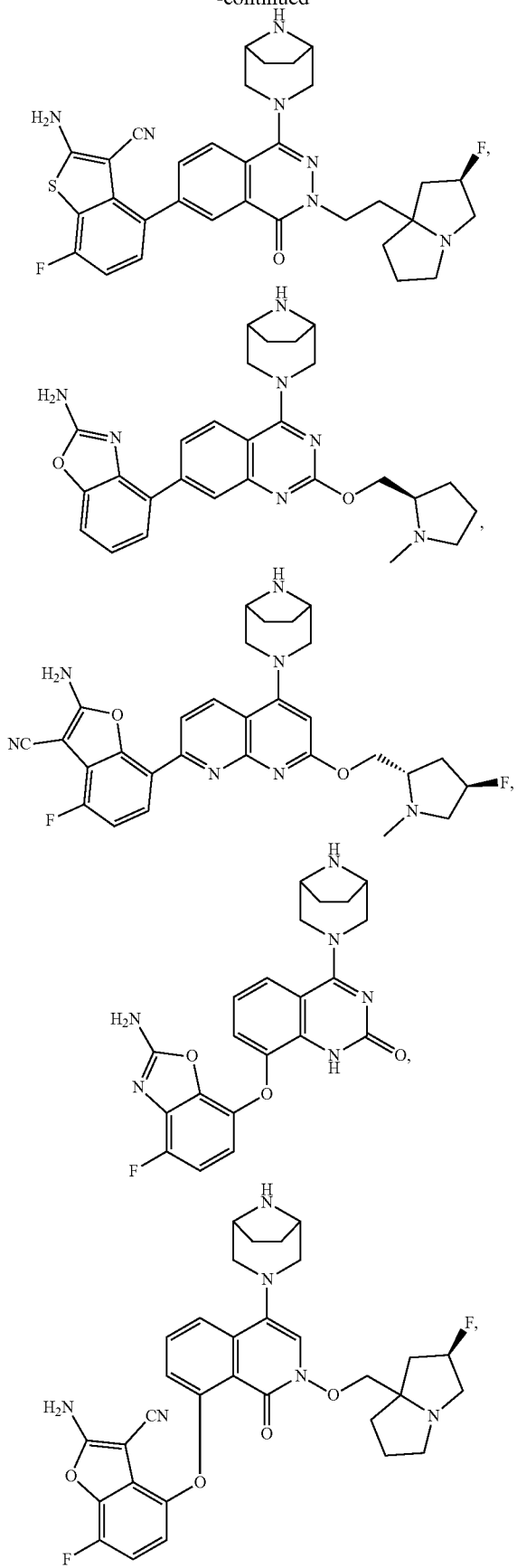
172
-continued
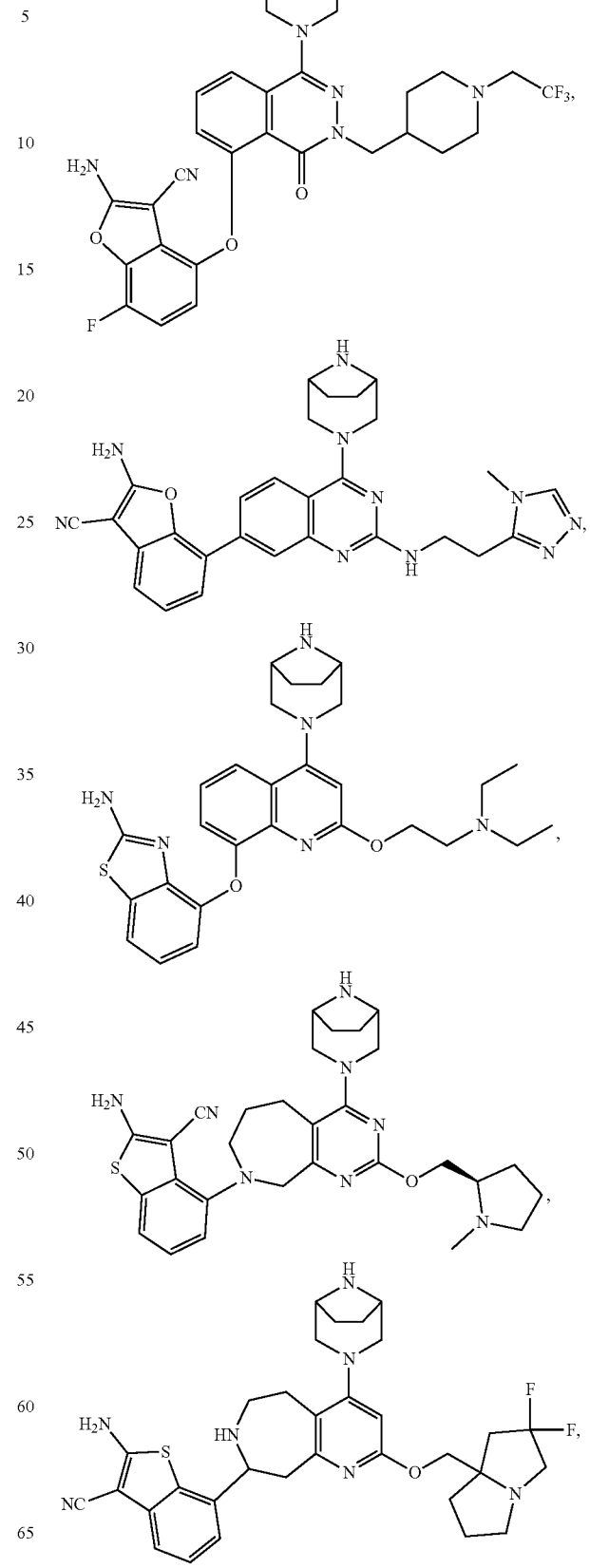

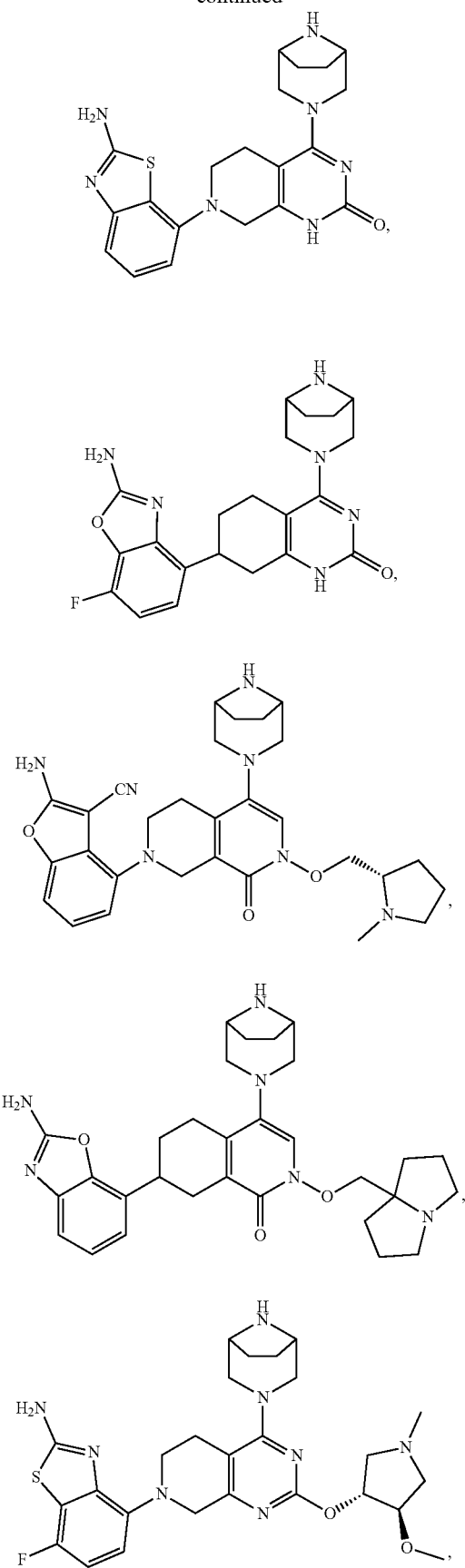
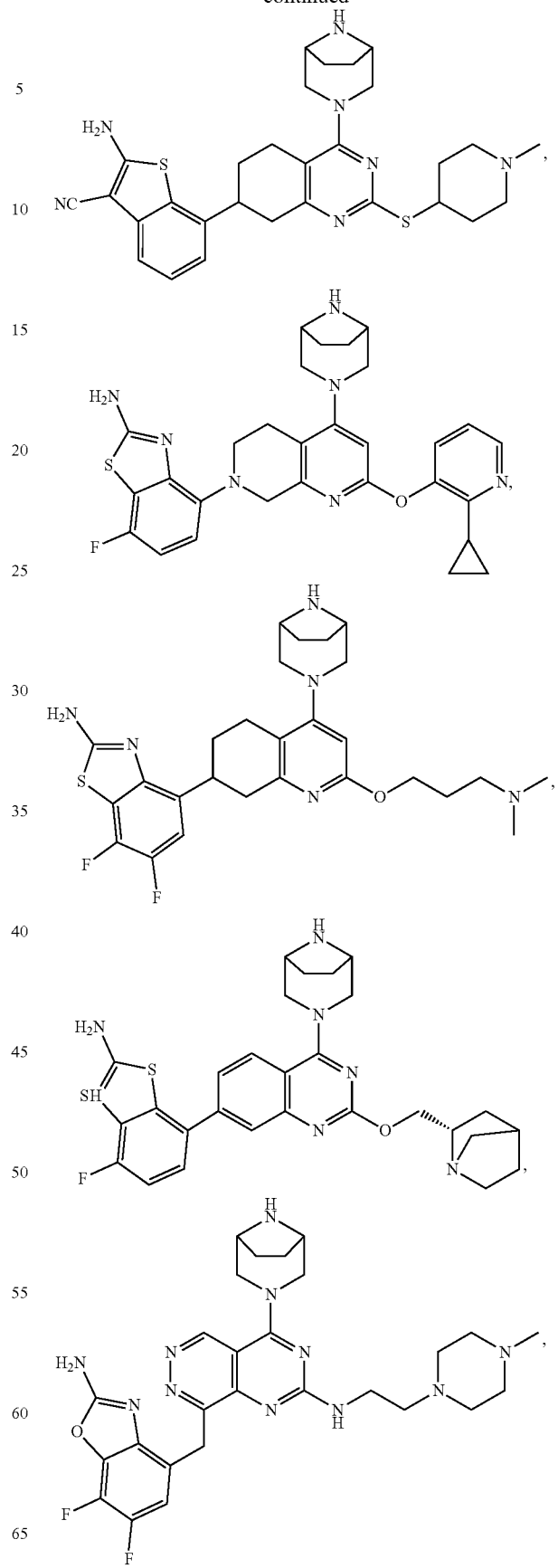

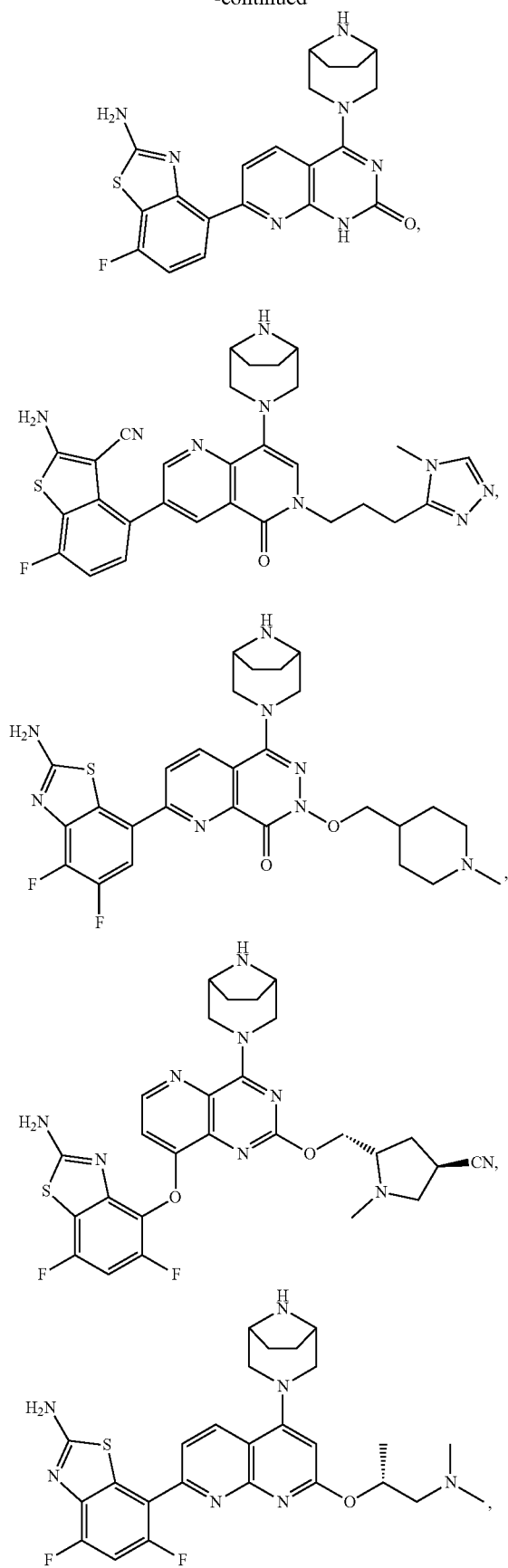
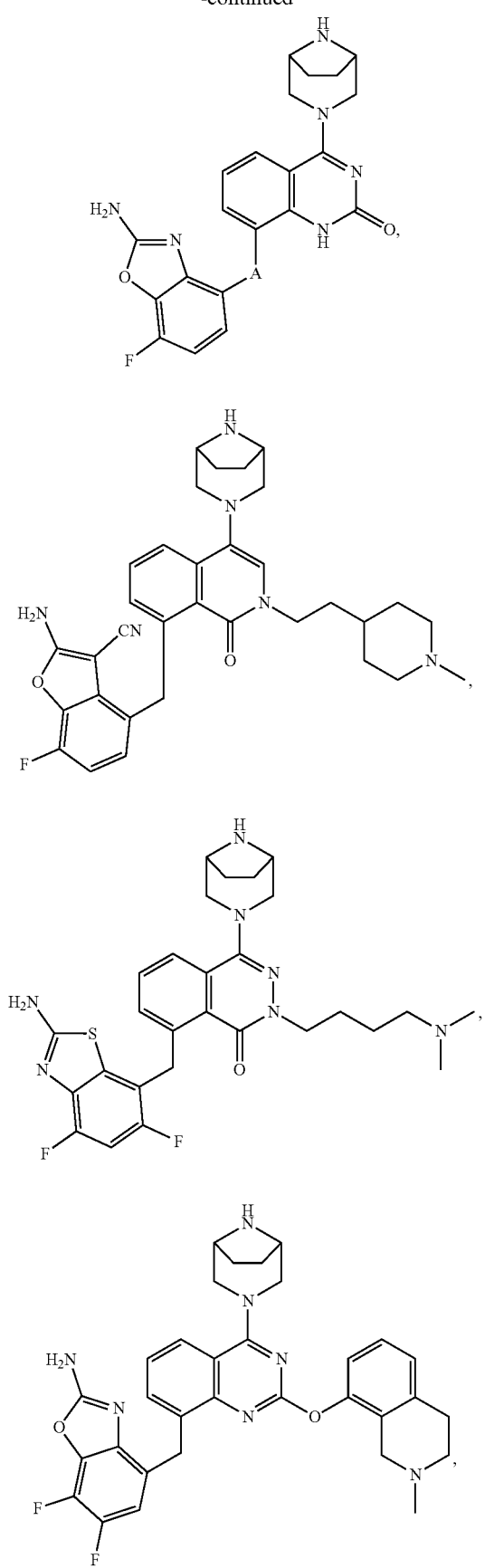

177
-continued
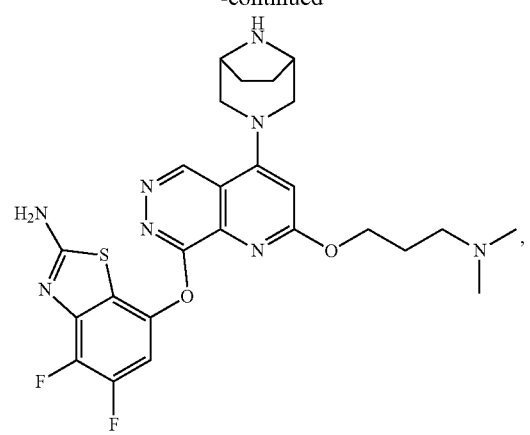
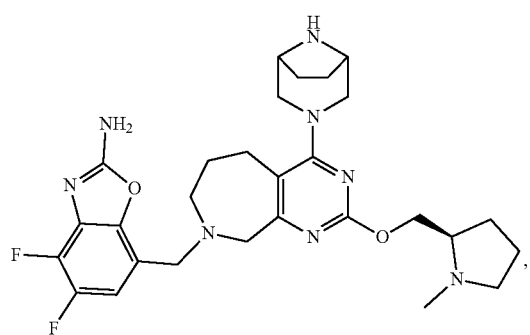
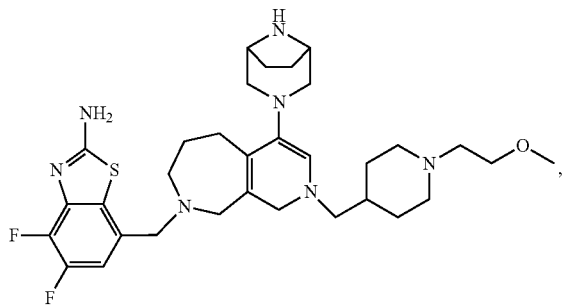
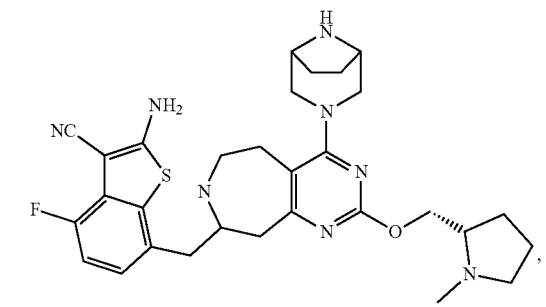
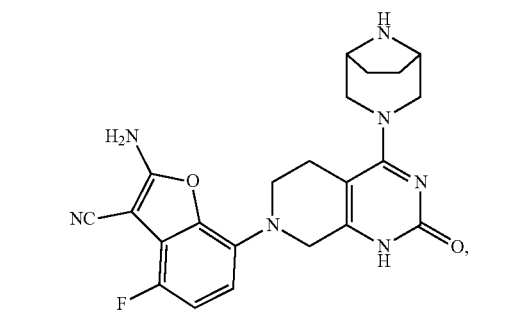
178
-continued
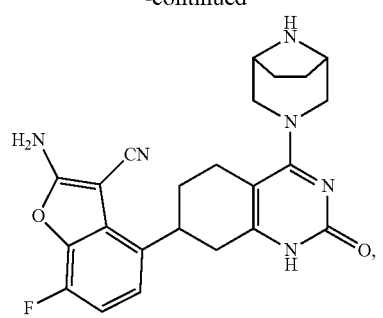
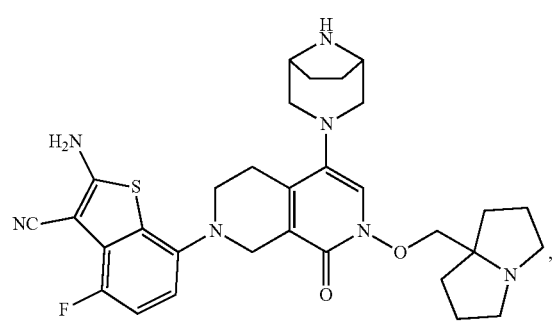
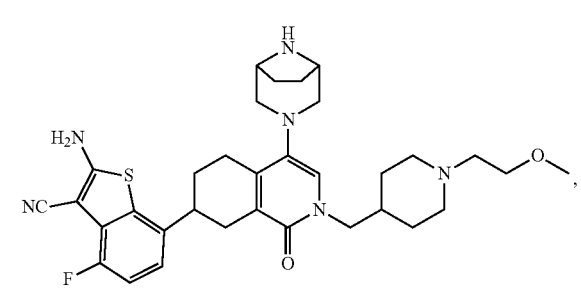
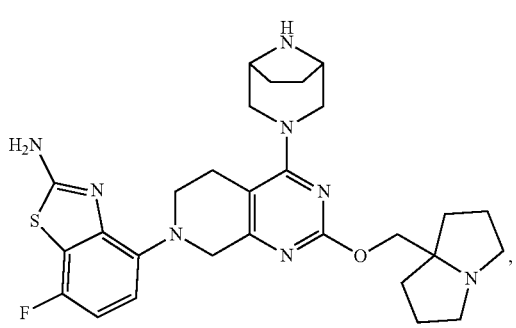
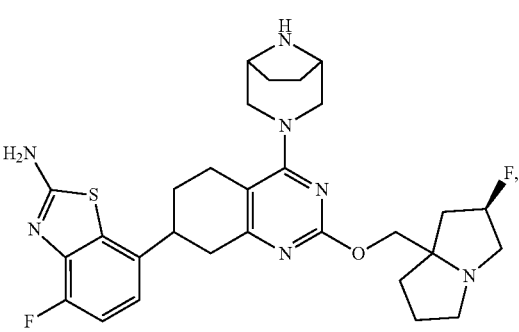

-continued

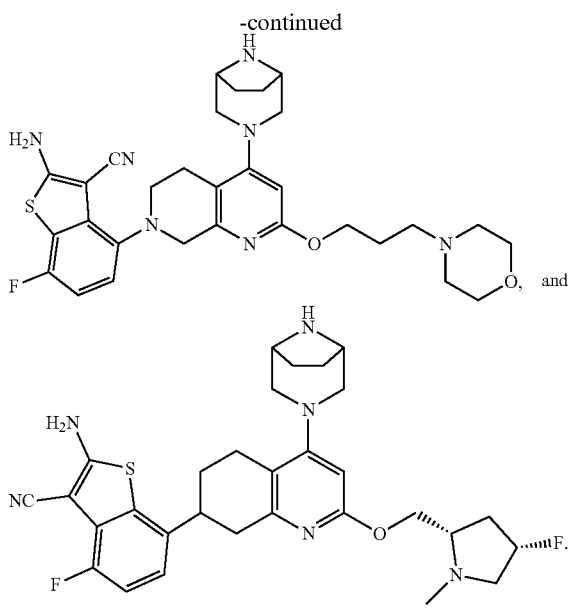

In one aspect, the disclosure provides a compound of Formula (A), or a pharmaceutically acceptable salt or solvate thereof:

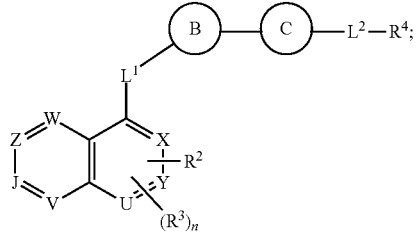

Formula (A)

wherein:

is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, $N(R^{1c})$, or $C(R^{1f})(R^{1g})$;
$Q^1$ is N or $C(R^{1d})$;
$Q^2$ is S or O;
X is C or N;
Y is C, S(O), S(O)$_2$, C(O), or N;
U is C, S(O), S(O)$_2$, C(O), or N;
Z is N or $C(R^8)$;
V and J are independently selected from N, $C(R^5)$, and $C(R^{16})$, wherein one of V and J is $C(R^5)$;
W is N or $C(R^{18})$;
$L^1$ and $L^2$ are independently selected from a bond, $C_1$-$C_6$alkyl, —O—, —N($R^{26}$)—, —C(O)—, —N($R^{26}$)C(O)—, —C(O)N($R^{26}$)—, —S—, —S(O)$_2$—, —S(O)—, —S(O)$_2$N($R^{26}$)—, —S(O)N($R^{26}$)—, —N($R^{26}$)S(O)—, —N($R^{26}$)S(O)$_2$—, —OCON($R^{26}$)—, —N($R^{26}$)C(O)O—, and —N($R^{26}$)C(O)N($R^{26}$)—;
$R^1$ is selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$;
$R^{1a}$, $R^{1b}$, $R^{1c}$, $R^{1d}$, $R^{1e}$, $R^{1f}$, and $R^{1g}$ are each independently selected from hydrogen, halogen, —CN, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1f}$ and $R^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;
$R^2$ is selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20b}$;

each R$^3$ is independently selected from hydrogen, halogen, oxo, C$_1$-C$_6$alkyl, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)$_2$R$^{15}$, and —S(O)$_2$N(R$^{12}$)(R$^{13}$);

R$^4$ is hydrogen, or a group other than an electrophilic moiety capable of forming a covalent bond with the cysteine residue at position 12 of a KRAS protein;

R$^5$ is

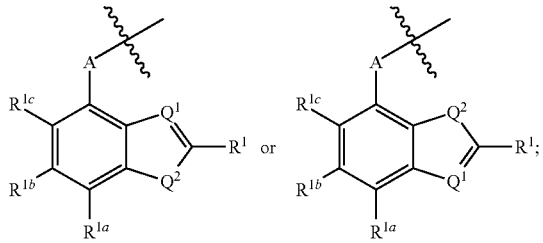

R$^8$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20c}$;

each R$^{10}$ and each R$^{11}$ are independently selected from halogen, oxo, C$_1$-C$_6$alkyl, C$_1$-C$_6$alkyl-CN, C$_1$-C$_6$haloalkyl, —OR$^{12}$, —N(R$^{12}$)(R$^{13}$), —CN, —C(O)OR$^{12}$, —OC(O)N(R$^{12}$)(R$^{13}$), —C(O)R$^{15}$, —S(O)R$^{15}$, and —S(O)$_2$N(R$^{12}$)(R$^{13}$)—;

each R$^{12}$ is independently selected from hydrogen, C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, and —CH$_2$—C$_{1-9}$heteroaryl, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three R$^{20d}$;

each R$^{13}$ is independently selected from hydrogen, C$_{1-6}$alkyl, and C$_{1-6}$haloalkyl; or R$^{12}$ and R$^{13}$, together with the nitrogen to which they are attached, form a C$_{2-9}$heterocycloalkyl ring optionally substituted with one, two, or three R$^{20e}$;

each R$^{14}$ is independently selected from hydrogen, C$_{1-6}$alkyl, and C$_{1-6}$haloalkyl;

each R$^{15}$ is independently selected C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl, wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20f}$;

R$^{16}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20g}$;

R$^{18}$ is selected from hydrogen, halogen, —CN, C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, C$_{1-9}$heteroaryl, —OR$^{12}$, —SR$^{12}$, —N(R$^{12}$)(R$^{13}$), —C(O)OR$^{12}$, —OC(O)N(R$^{12}$)(R$^{13}$), —N(R$^{14}$)C(O)N(R$^{12}$)(R$^{13}$), —N(R$^{14}$)C(O)OR$^{15}$, —N(R$^{14}$)S(O)$_2$R$^{15}$, —C(O)R$^{15}$, —S(O)R$^{15}$, —OC(O)R$^{15}$, —C(O)N(R$^{12}$)(R$^{13}$), —C(O)C(O)N(R$^{12}$)(R$^{13}$), —N(R$^{14}$)C(O)R$^{15}$, —S(O)$_2$R$^{15}$, —S(O)$_2$N(R$^{12}$)(R$^{13}$)—, S(=O)(=NH)N(R$^{12}$)(R$^{13}$), —CH$_2$C(O)N(R$^{12}$)(R$^{13}$), —CH$_2$N(R$^{14}$)C(O)R$^{15}$, —CH$_2$S(O)$_2$R$^{15}$, and —CH$_2$S(O)$_2$N(R$^{12}$)(R$^{13}$), wherein C$_{1-6}$alkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl are optionally substituted with one, two, or three R$^{20h}$;

each R$^{20a}$, R$^{20b}$, R$^{20c}$, R$^{20d}$, R$^{20e}$, R$^{20f}$, R$^{20g}$, R$^{20h}$, and R$^{20i}$, are each independently selected from halogen, oxo, —CN, C$_{1-6}$alkyl, C$_{2-9}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, C$_{1-9}$heteroaryl, —CH$_2$—C$_{1-9}$heteroaryl, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), —OCH$_2$C(O)OR$^{22}$, and —OC(O)R$^{25}$, wherein C$_{1-6}$alkyl, C$_{2-6}$alkenyl, C$_{2-6}$alkynyl, C$_{3-6}$cycloalkyl, —CH$_2$—C$_{3-6}$cycloalkyl, C$_{2-9}$heterocycloalkyl, —CH$_2$—C$_{2-9}$heterocycloalkyl, C$_{6-10}$aryl, —CH$_2$—C$_{6-10}$aryl, —CH$_2$—C$_{1-9}$heteroaryl, and C$_{1-9}$heteroaryl are optionally substituted with one, two, or three groups independently selected from halogen, oxo, —CN, C$_{1-6}$alkyl, C$_{1-6}$haloalkyl, C$_{1-6}$alkoxy, C$_{1-6}$haloalkoxy, —OR$^{21}$, —SR$^{21}$, —N(R$^{22}$)(R$^{23}$), —C(O)OR$^{22}$, —C(O)N(R$^{22}$)(R$^{23}$), —C(O)C(O)N(R$^{22}$)(R$^{23}$), —OC(O)N(R$^{22}$)(R$^{23}$), —N(R$^{24}$)C(O)N(R$^{22}$)(R$^{23}$), —N(R$^{24}$)C(O)OR$^{25}$, —N(R$^{24}$)C(O)R$^{25}$, —N(R$^{24}$)S(O)$_2$R$^{25}$, —C(O)R$^{25}$, —S(O)$_2$R$^{25}$, —S(O)$_2$N(R$^{22}$)(R$^{23}$), and —OC(O)R$^{25}$;

each R$^{21}$ is independently selected from H, C$_{1-6}$alkyl, C$_{1-6}$haloalkyl, C$_{2-6}$alkenyl, C$_{2-6}$alkynyl, C$_{3-6}$cycloalkyl, C$_{2-9}$heterocycloalkyl, C$_{6-10}$aryl, and C$_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

n is 0, 1, or 2; and

----- indicates a single or double bond such that all valences are satisfied.

In another aspect, the disclosure provides a compound of Formula (B), or a pharmaceutically acceptable salt or solvate thereof:

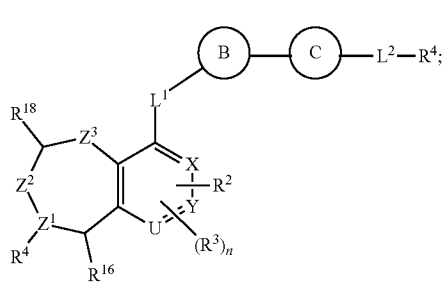

Formula (B)

wherein:

B is absent, a 3-12 membered heterocycloalkyl ring, a 6-10 membered aryl ring, a 5-10 membered heteroaryl ring, or a 3-12 membered cycloalkyl ring, wherein the 3-12 membered heterocycloalkyl ring, 6-10 membered aryl ring, 5-10 membered heteroaryl ring, and 3-12 membered cycloalkyl ring are optionally substituted with one or more $R^{10}$;

C is absent, a 3-12 membered heterocycloalkyl ring, or a 3-12 membered cycloalkyl ring, wherein the 3-12 membered heterocycloalkyl ring and 3-12 membered cycloalkyl ring are optionally substituted with one or more $R^{11}$;

A is a bond, O, S, $N(R^{1c})$, or $C(R^{1f})(R^{1g})$;

$Q^1$ is N or $C(R^{1d})$;

$Q^2$ is S or O;

X is C or N;

Y is C, C(O), or N;

$Z^1$ is N or $C(R^6)$;

$Z^2$ is $N(R^7)$ or $C(R^8)(R^9)$;

$Z^3$ is absent, $N(R^{17})$, or $C(R^{27})(R^{28})$;

U is C, S(O), $S(O)_2$, C(O), or N;

$L^1$ and $L^2$ are independently selected from a bond, $C_1$-$C_6$alkyl, —O—, —$N(R^{26})$—, —C(O)—, —$N(R^{26})$C(O)—, —C(O)N($R^{26}$)—, —S—, —$S(O)_2$—, —S(O)—, —$S(O)_2N(R^{26})$—, —$S(O)N(R^{26})$—, —$N(R^{26})S(O)$—, —$N(R^{26})S(O)_2$—, —OCON($R^{26}$)—, —$N(R^{26})C(O)O$—, and —$N(R^{26})C(O)N(R^{26})$—;

$R^1$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$;

$R^{1a}$, $R^{1b}$, $R^{1c}$, $R^{1d}$, $R^{1e}$, $R^{1f}$, and $R^{1g}$ are each independently selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20a}$; or $R^{1a}$ and $R^{1b}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1b}$ and $R^{1c}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$; or $R^{1f}$ and $R^{1g}$ are joined to form a 4-7 membered heterocycloalkyl ring, a phenyl ring, a 5-6 membered heteroaryl ring, or a 4-7 membered cycloalkyl ring, wherein the 4-7 membered heterocycloalkyl ring, phenyl ring, 5-6 membered heteroaryl ring, or 4-7 membered cycloalkyl ring are optionally substituted with one, two, or three $R^{20a}$;

$R^2$ is selected from halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20b}$;

each $R^3$ is independently selected from hydrogen, halogen, oxo, $C_1$-$C_6$alkyl, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;

$R^4$ is hydrogen, or a group other than an electrophilic moiety capable of forming a covalent bond with the cysteine residue at position 12 of a KRAS protein;

$R^5$ is

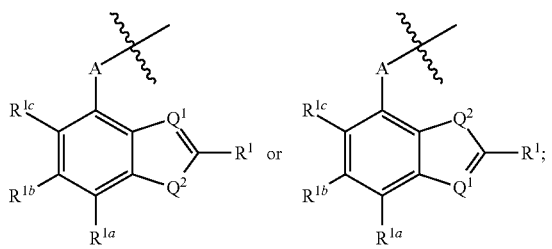

$R^6$ is selected from hydrogen and $C_{1-6}$alkyl;

$R^7$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;

$R^8$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20c}$;

$R^9$ is selected from hydrogen and $C_{1-6}$alkyl;

each $R^{10}$ and each $R^{11}$ are independently selected from halogen, oxo, $C_1$-$C_6$alkyl, $C_1$-$C_6$alkyl-CN, $C_1$-$C_6$haloalkyl, —$OR^{12}$, —$N(R^{12})(R^{13})$, —CN, —$C(O)OR^{12}$, —$OC(O)N(R^{12})(R^{13})$, —$C(O)R^{15}$, —$S(O)_2R^{15}$, and —$S(O)_2N(R^{12})(R^{13})$—;

each $R^{12}$ is independently selected from hydrogen, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, and —$CH_2$—$C_{1-9}$heteroaryl, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl and $C_{1-9}$heteroaryl are optionally substituted with one, two, or three $R^{20d}$;

each $R^{13}$ is independently selected from hydrogen, $C_{1-6}$alkyl, and $C_{1-6}$haloalkyl; or $R^{12}$ and $R^{13}$, together with the nitrogen to which they are attached, form a $C_{2-9}$heterocycloalkyl ring optionally substituted with one, two, or three $R^{20c}$;

each $R^{14}$ is independently selected from hydrogen, $C_{1-6}$alkyl, and $C_{1-6}$haloalkyl;

each $R^{15}$ is independently selected $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20g}$;

$R^{17}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$C(O)OR^{12}$, —$C(O)R^{15}$, —$S(O)R^{15}$, —$C(O)N(R^{12})(R^{13})$, —$C(O)C(O)N(R^{12})(R^{13})$, —$S(O)_2R^{15}$, and —$S(O)_2N(R^{12})(R^{13})$—, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20k}$;

$R^{18}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20h}$;

each $R^{20a}$, $R^{20b}$, $R^{20c}$, $R^{20d}$, $R^{20e}$, $R^{20f}$, $R^{20g}$, $R^{20h}$, $R^{20i}$, $R^{20j}$, and $R^{20k}$ are each independently selected from halogen, oxo, —CN, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, $C_{1-9}$heteroaryl, —$CH_2$—$C_{1-9}$heteroaryl, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, —$OCH_2C(O)OR^{22}$, and —$OC(O)R^{25}$, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, —$CH_2$—$C_{1-9}$heteroaryl, and $C_{1-9}$heteroaryl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, —$OR^{21}$, —$SR^{21}$, —$N(R^{22})(R^{23})$, —$C(O)OR^{22}$, —$C(O)N(R^{22})(R^{23})$, —$C(O)C(O)N(R^{22})(R^{23})$, —$OC(O)N(R^{22})(R^{23})$, —$N(R^{24})C(O)N(R^{22})(R^{23})$, —$N(R^{24})C(O)OR^{25}$, —$N(R^{24})C(O)R^{25}$, —$N(R^{24})S(O)_2R^{25}$, —$C(O)R^{25}$, —$S(O)_2R^{25}$, —$S(O)_2N(R^{22})(R^{23})$, and —$OC(O)R^{25}$;

each $R^{21}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{22}$ is independently selected from H, $C_{1-6}$alkyl, $C_{1-6}$haloalkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{23}$ is independently selected from H and $C_{1-6}$alkyl;

each $R^{24}$ is independently selected from H and $C_{1-6}$alkyl;

each $R^{25}$ is selected from $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl;

each $R^{26}$ is selected from hydrogen, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20i}$;

$R^{27}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, $C_{1-9}$heteroaryl, —$OR^{12}$, —$SR^{12}$, —$N(R^{12})(R^{13})$, —$C(O)OR^{12}$, —$OC(O)N(R^{12})(R^{13})$, —$N(R^{14})C(O)N(R^{12})(R^{13})$, —$N(R^{14})C(O)OR^{15}$, —$N(R^{14})S(O)_2R^{15}$, —$C(O)R^{15}$, —$S(O)R^{15}$, —$OC(O)R^{15}$, —$C(O)N(R^{12})(R^{13})$, —$C(O)C(O)N(R^{12})(R^{13})$, —$N(R^{14})C(O)R^{15}$, —$S(O)_2R^{15}$, —$S(O)_2N(R^{12})(R^{13})$—, $S(=O)(=NH)N(R^{12})(R^{13})$, —$CH_2C(O)N(R^{12})(R^{13})$, —$CH_2N(R^{14})C(O)R^{15}$, —$CH_2S(O)_2R^{15}$, and —$CH_2S(O)_2N(R^{12})(R^{13})$, wherein $C_{1-6}$alkyl, $C_{2-6}$alkenyl, $C_{2-6}$alkynyl, $C_{3-6}$cycloalkyl, $C_{2-9}$heterocycloalkyl, $C_{6-10}$aryl, and $C_{1-9}$heteroaryl are optionally substituted with one, two, or three $R^{20j}$;

$R^{28}$ is selected from hydrogen and $C_{1-6}$alkyl;

n is 0, 1, or 2; and

----- indicates a single or double bond such that all valences are satisfied.

In embodiments, the compound has the formula:

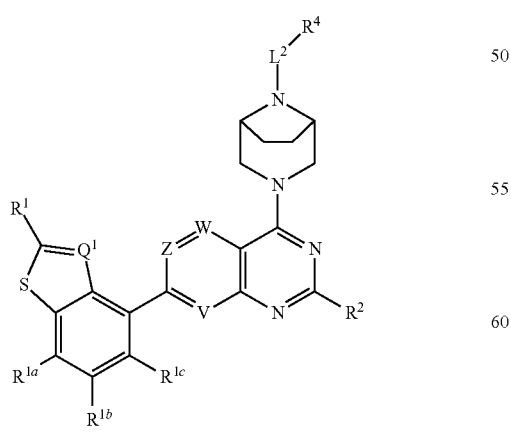

Formula (Iha) wherein $Q^1$, $R^1$, $R^{1a}$, $R^{1b}$, $R^{1c}$, V, Z, W, $R^2$, $L^2$, and $R^4$ are as described herein, including in any embodiment. In embodiments of formula Iha, Z is not N. In embodiments, the compound has the formula:

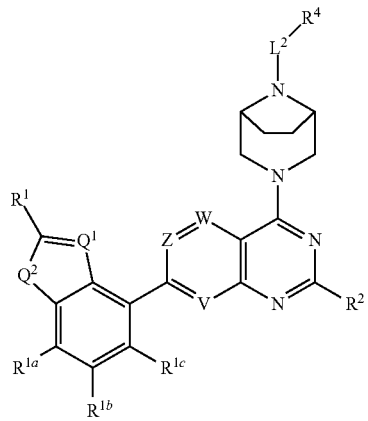

Formula (Ihb) wherein $Q^1$, $Q^2$, $R^1$, $R^{1a}$, $R^{1b}$, $R^{1c}$, V, Z, W, $R^2$, $L^2$, and $R^4$ are as described herein, including in any embodiment. In embodiments of formula Ihb, Z is not N. In embodiments, the compound has the formula:

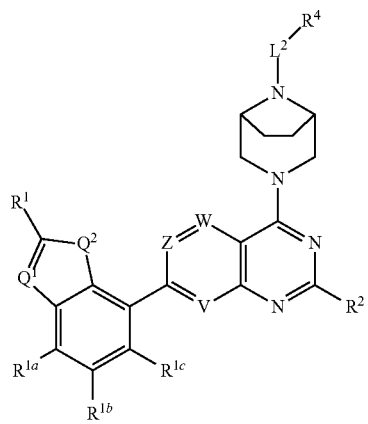

Formula (Ihc) wherein $Q^1$, $Q^2$, $R^1$, $R^{1a}$, $R^{1b}$, $R^{1c}$, V, Z, W, $R^2$, $L^2$, and $R^4$ are as described herein, including in any embodiment. In embodiments of formula Ihc, Z is not N. In embodiments, the compound has the formula:

Formula (Ihd) wherein $Q^1$, $R^1$, $R^{1a}$, $R^{1b}$, $R^{1c}$, V, Z, W, $R^2$, $L^2$, and $R^4$ are as described herein, including in any embodiment. In embodiments of formula Ihd, Z is not N. In embodiments, the compound has the formula:

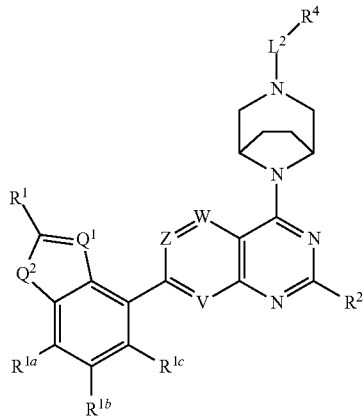

Formula (Ihe) wherein $Q^1$, $Q^2$, $R^1$, $R^{1a}$, $R^{1b}$, $R^{1c}$, V, Z, W, $R^2$, $L^2$, and $R^4$ are as described herein, including in any embodiment. In embodiments of formula Ihe, Z is not N. In embodiments, the compound has the formula:

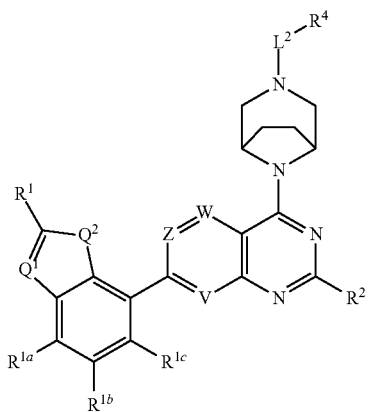

Formula (Ihf) wherein $Q^1$, $Q^2$, $R^1$, $R^{1a}$, $R^{1b}$, $R^{1c}$, V, Z, W, $R^2$, $L^2$, and $R^4$ are as described herein, including in any embodiment. In embodiments of formula Ihf, Z is not N. In embodiments, the compound has the formula:

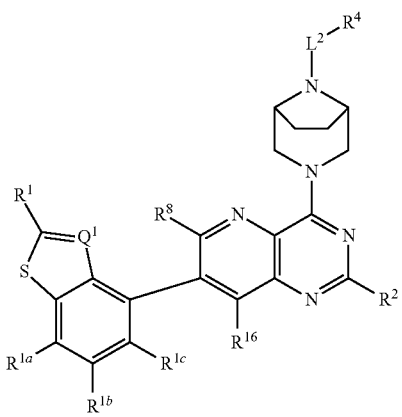

Formula (Iha') wherein $Q^1$, $R^1$, $R^{1a}$, $R^{1b}$, $R^{1c}$, $R^8$, $R^{16}$, $R^2$, $L^2$, and $R^4$ are as described herein, including in any embodiment. In embodiments, the compound has the formula:

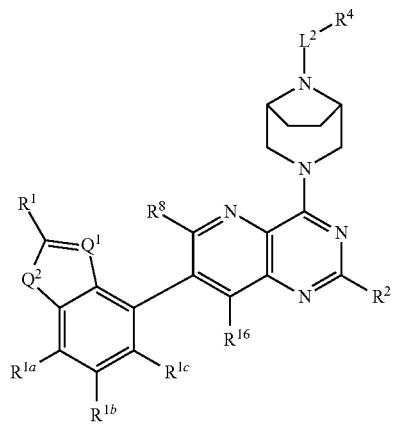

Formula (Ihb') wherein $Q^1$, $Q^2$, $R^1$, $R^{1a}$, $R^{1b}$, $R^{1c}$, $R^8$, $R^{16}$, $R^2$, $L^2$, and $R^4$ are as described herein, including in any embodiment. In embodiments, the compound has the formula:

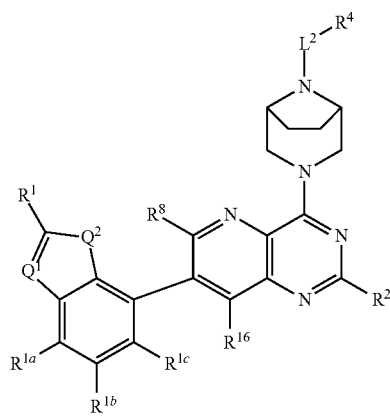

Formula (Ihc') wherein $Q^1$, $Q^2$, $R^1$, $R^{1a}$, $R^{1b}$, $R^{1c}$, $R^8$, $R^{16}$, $R^2$, $L^2$, and $R^4$ are as described herein, including in any embodiment. In embodiments, the compound has the formula:

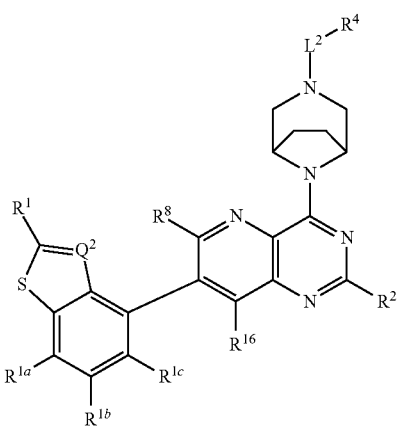

Formula (Ihd') wherein $Q^1$, $R^1$, $R^{1a}$, $R^{1b}$, $R^{1c}$, Re, $R^{16}$, $R^2$, $L^2$, and $R^4$ are as described herein, including in any embodiment. In embodiments, the compound has the formula:

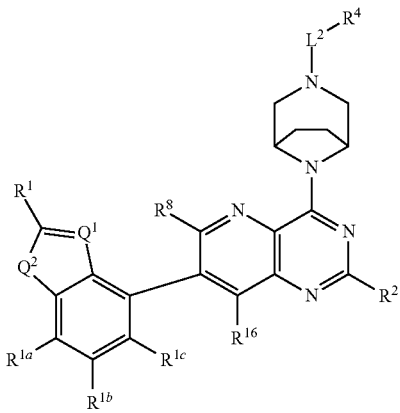

Formula (Ihe') wherein $Q^1$, $Q^2$, $R^1$, $R^{1a}$, $R^{1b}$, $R^{1c}$, $R^8$, $R^{16}$, $R^2$, $L^2$, and $R^4$ are as described herein, including in any embodiment. In embodiments, the compound has the formula:

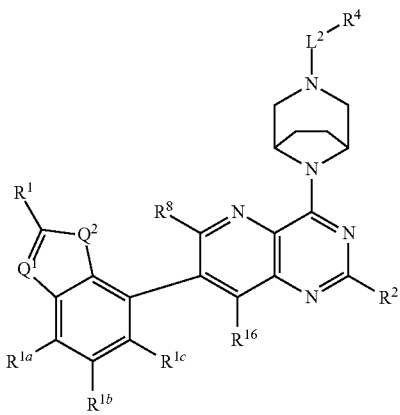

Formula (Ihf') wherein $Q^1$, $Q^2$, $R^1$, $R^{1a}$, $R^{1b}$, $R^{1c}$, $R^8$, $R^{16}$, $R^2$, $L^2$, and $R^4$ are as described herein, including in any embodiment. In embodiments, the compound has the formula:

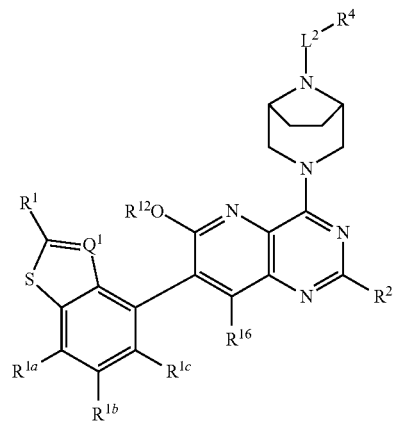

Formula (Iha") wherein $Q^1$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

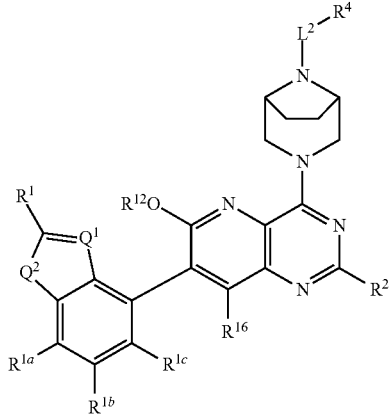

Formula (Ihb") wherein $Q^1$, $Q^2$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

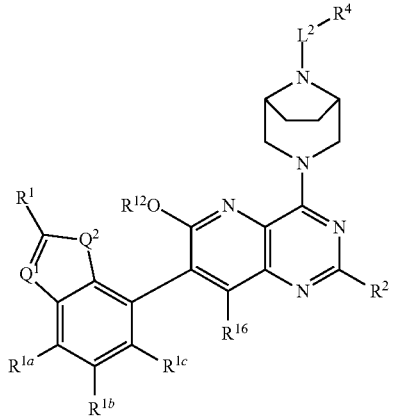

Formula (Ihc") wherein $Q^1$, $Q^2$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

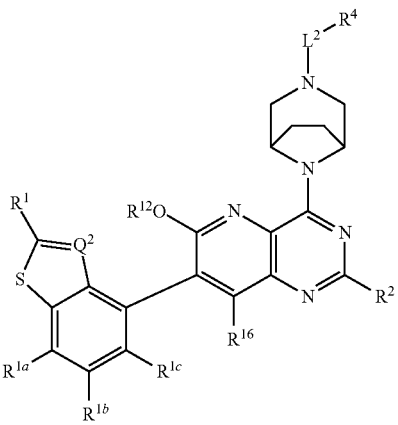

Formula (Ihd″) wherein $Q^1$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

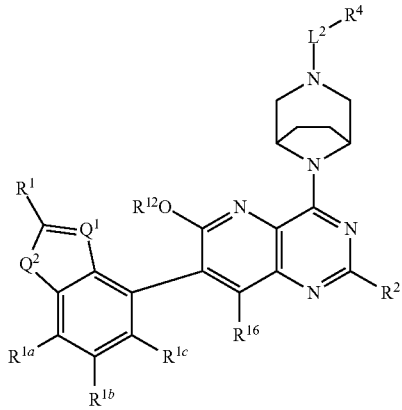

Formula (Ihe″) wherein $Q^1$, $Q^2$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

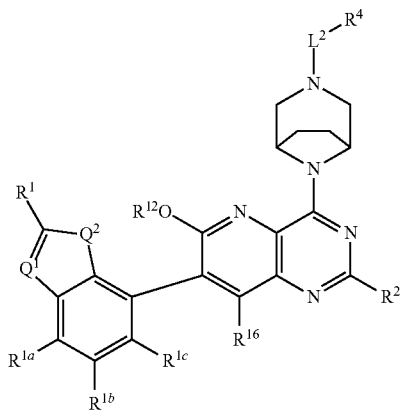

Formula (Ihf″) wherein $Q^1$, $Q^2$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

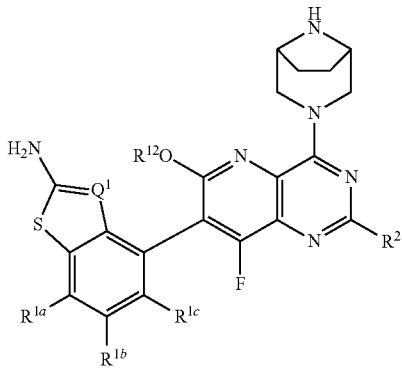

Formula (Iha‴) wherein $Q^1$, $R^{1a}$, $R^{1b}$, $R^{1c}$, $R^{12}$, and $R^2$ are as described herein, including in any embodiment. In embodiments, the compound has the formula:

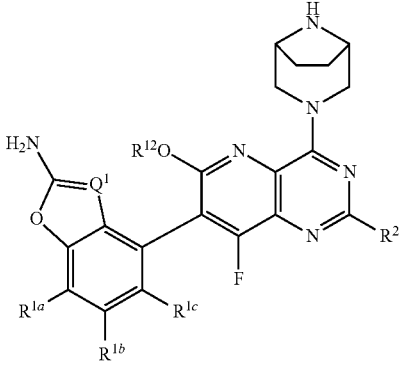

Formula (Ihb‴) wherein $Q^1$, $R^{1a}$, $R^{1b}$, $R^{1c}$, $R^{12}$, and $R^2$ are as described herein, including in any embodiment. In embodiments, the compound has the formula:

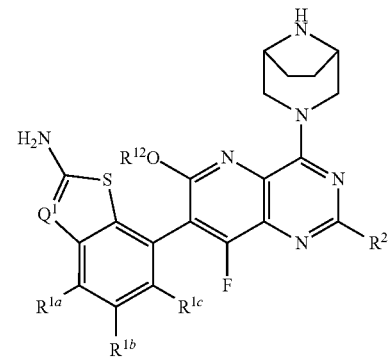

Formula (Ihc‴) wherein $Q^1$, $R^{1a}$, $R^{1b}$, $R^{1c}$, $R^{12}$, and $R^2$ are as described herein, including in any embodiment. In embodiments, the compound has the formula:

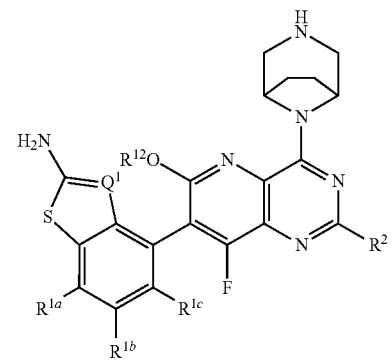

Formula (Ihd‴) wherein $Q^1$, $R^{1a}$, $R^{1b}$, $R^{1c}$, $R^{12}$, and $R^2$ are as described herein, including in any embodiment. In embodiments, the compound has the formula:

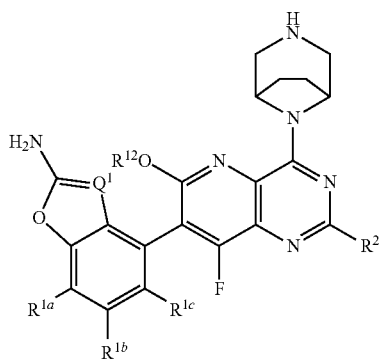

Formula (Ihe''') wherein $Q^1$, $R^{1a}$, $R^{1b}$, $R^{1c}$, $R^{12}$, and $R^2$ are as described herein, including in any embodiment. In embodiments, the compound has the formula:

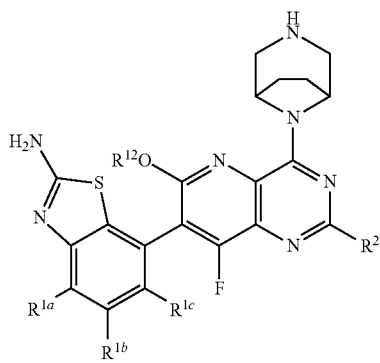

Formula (Ihf''') wherein $Q^1$, $R^{1a}$, $R^{1b}$, $R^{1c}$, $R^{12}$, and $R^2$ are as described herein, including in any embodiment. In embodiments, the compound has the formula:

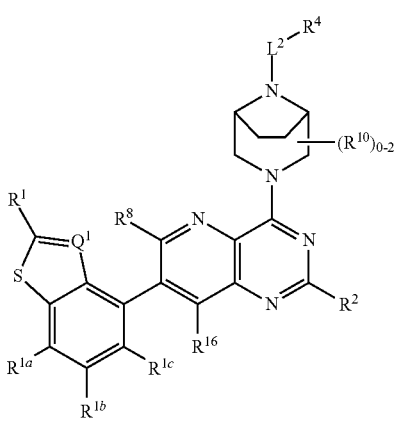

Formula (Ihg) wherein $Q^1$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

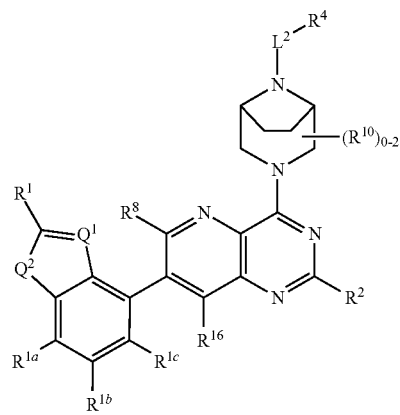

Formula (Ihh) wherein $Q^1$, $Q^2$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

Formula (Ihi) wherein $Q^1$, $Q^2$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

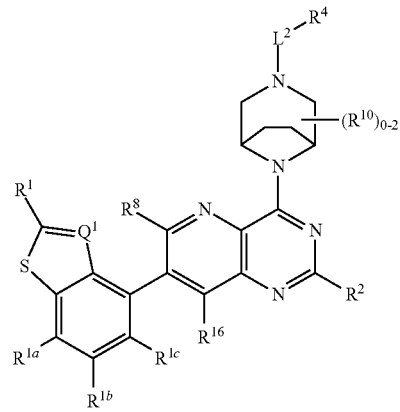

Formula (Ihj) wherein $Q^1$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

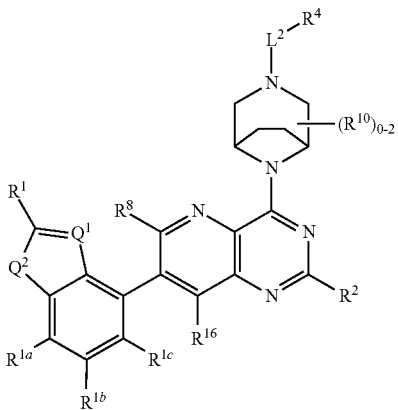

Formula (Ihk) wherein $Q^1$, $Q^2$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

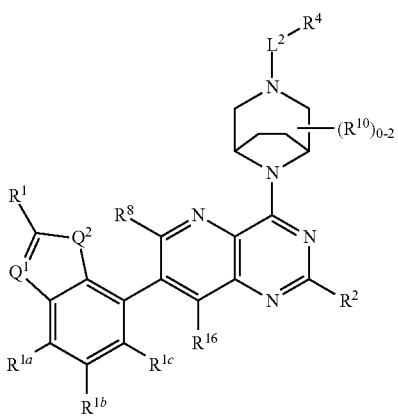

Formula (Ihl) wherein $Q^1$, $Q^2$, $R^1$, $R^{1a}$, $R^{1b}$, $R^{1e}$, $R^8$, $R^{10}$, $R^{16}$, $R^2$, $L^2$, and $R^4$ are as described herein, including in any embodiment. In embodiments, the compound has the formula:

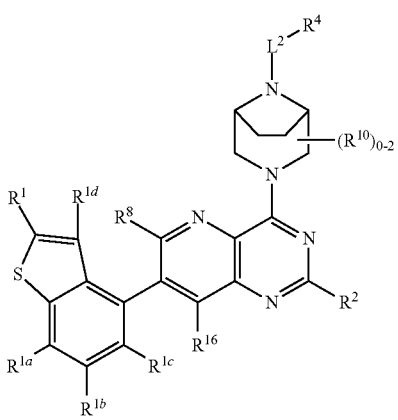

Formula (Ihm) wherein $Q^1$, $R^1$, $R^{1a}$, $R^{1b}$, $R^{1c}$, $R^{14}$, $R^8$, $R^{10}$, $R^{16}$, $R^2$, $L^2$, and $R^4$ are as described herein, including in any embodiment. In embodiments, the compound has the formula:

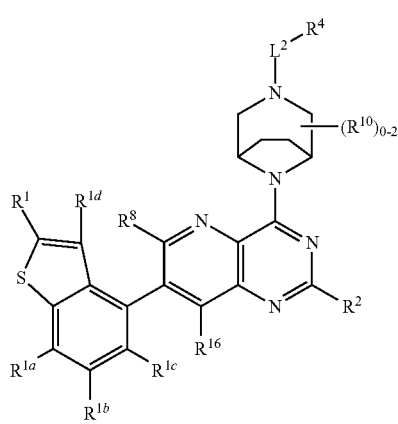

Formula (Ihn) wherein $Q^1$, $R^1$, $R^{1a}$, $R^{1b}$, $R^{1c}$, $R^{14}$, $R^8$, $R^{10}$, $R^{16}$, $R^2$, $L^2$, and $R^4$ are as described herein, including in any embodiment. In embodiments, the compound has the formula:

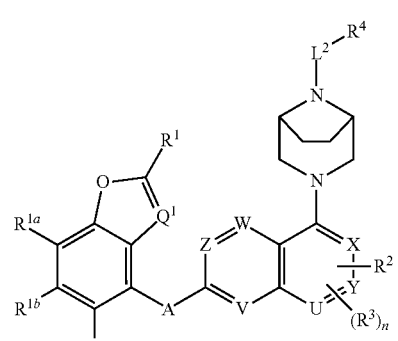

Formula (Ia'1) wherein $Q^1$, $R^1$, $R^{1a}$, $R^{1b}$, $R^{1c}$, A, V, Z, W, X, Y, U, $R^2$, $R^3$, n, $L^2$, and $R^4$ are as described herein, including in any embodiment. In embodiments of formula Ia', Z, X, and U are not all simultaneously N. In embodiments, the compound has the formula:

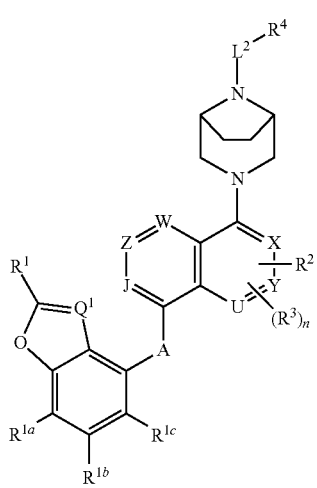

Formula (Ic'1) wherein $Q^1$, $R^1$, $R^{1a}$, $R^{1b}$, $R^{1c}$, A, J, Z, W, X, Y, U, $R^2$, $R^3$, n, $L^2$, and $R^4$ are as described herein, including in any embodiment. In embodiments, the compound has the formula:

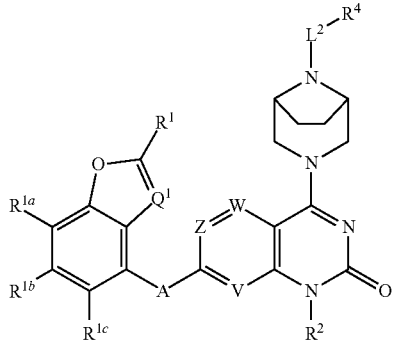

Formula (Ie'1) wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

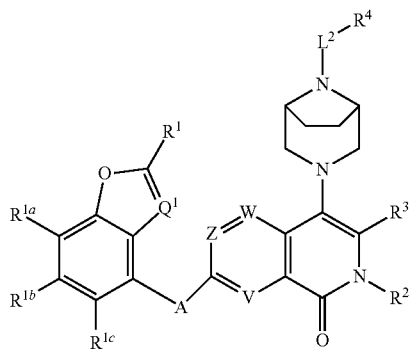

Formula (If'1) wherein $Q^1$, $R^1$, $R^{1a}$, $R^{1b}$, $R^{1c}$, A, V, Z, W, $R^2$, $R^3$, $L^2$, and $R^4$ are as described herein, including in any embodiment. In embodiments, the compound has the formula:

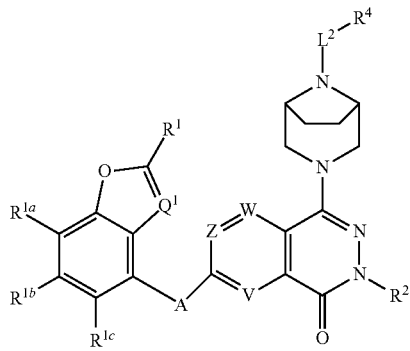

Formula (Ig'1) wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

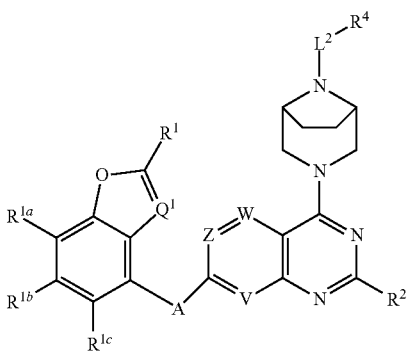

Formula (Ih'1) wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments of formula Ih', Z is not N. In embodiments, the compound has the formula:

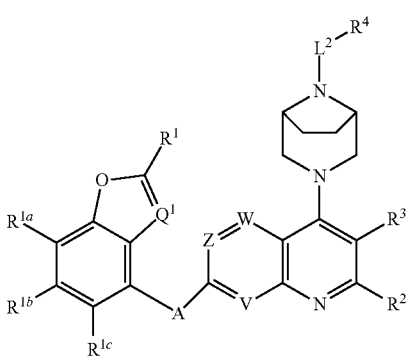

Formula (Ii'1) wherein $Q^1$, $R^1$, $R^{1a}$, $R^{1b}$, $R^{1c}$, A, V, Z, W, $R^2$, $L^2$, and $R^4$ are as described herein, including in any embodiment. In embodiments, the compound has the formula:

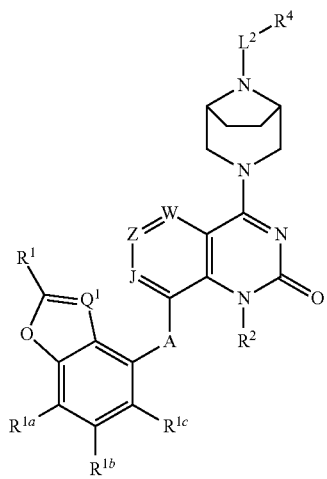

Formula (Ij'1) wherein $Q^1$, $R^1$, $R^{1a}$, $R^{1b}$, $R^1$, A, J, Z, W, $R^2$, $L^2$, and $R^4$ are as described herein, including in any embodiment. In embodiments, the compound has the formula:

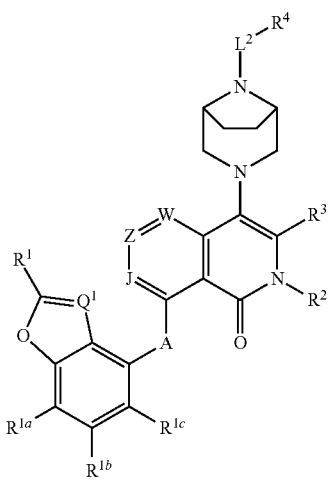

Formula (I'1) wherein Q', R¹, $R^{1a}$, $R^{1b}$, $R^{1c}$, A, J, Z, W, R², R³, L², and R⁴ are as described herein, including in any embodiment. In embodiments, the compound has the formula:

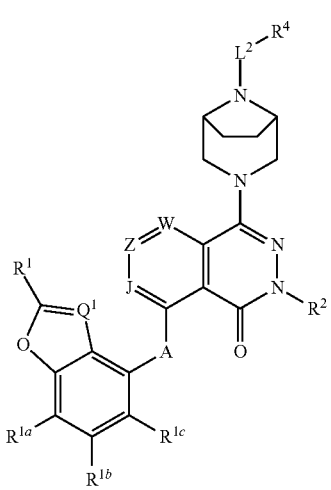

Formula (Im'1) wherein Q¹, R¹, $R^{1a}$, $R^{1b}$, $R^{1c}$, A, J, Z, W, R², L², and R⁴ are as described herein, including in any embodiment. In embodiments, the compound has the formula:

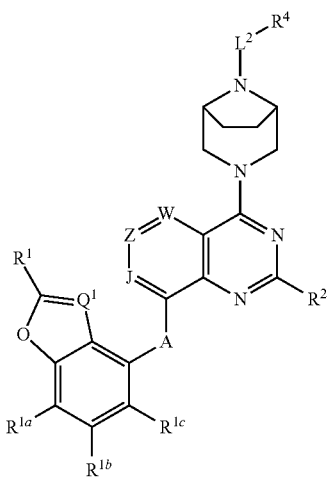

Formula (In'1) wherein Q¹, R¹, $R^{1a}$, $R^{1b}$, $R^{1c}$, A, J, Z, W, R², L², and R⁴ are as described herein, including in any embodiment. In embodiments, the compound has the formula:

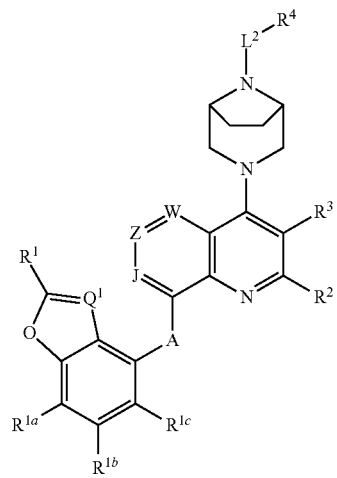

Formula (Io'1) wherein Q¹, R¹, $R^{1a}$, $R^{1b}$, $R^{1c}$, A, J, Z, W, R², R³, L², and R⁴ are as described herein, including in any embodiment. In embodiments, the compound has the formula:

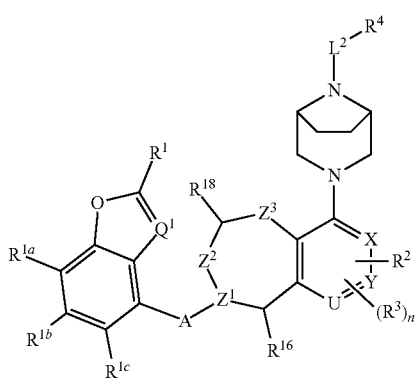

Formula (II'1) wherein Q¹, R¹, $R^{1a}$, $R^{1b}$, $R^{1c}$, A, $R^{16}$, $R^{18}$, Z¹, Z², Z³, X, Y, U, R², R³, n, L², and R⁴ are as described herein, including in any embodiment. In embodiments, the compound has the formula:

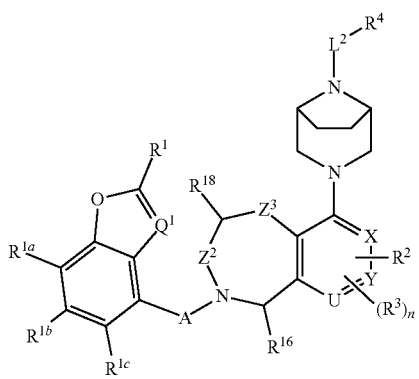

Formula (IIa'1) wherein $Q^1$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

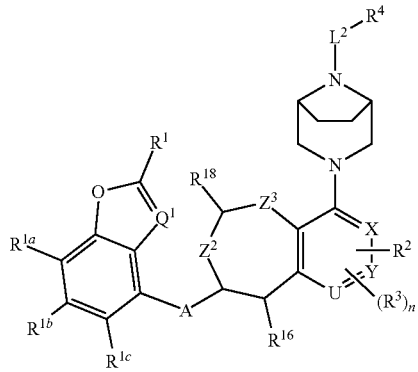

Formula (IIb'1) wherein $Q^1$, $R^1$, $R^{1a}$, $R^{1b}$, $R^{1c}$, A, $R^{16}$, $R^{18}$, $Z^2$, $Z^3$, X, Y, U, $R^2$, $R^3$, n, $L^2$, and $R^4$ are as described herein, including in any embodiment. In embodiments, the compound has the formula:

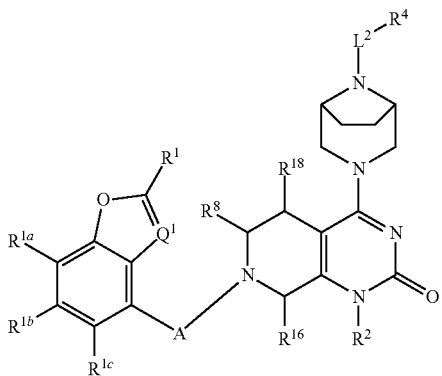

Formula (IIc'1) wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

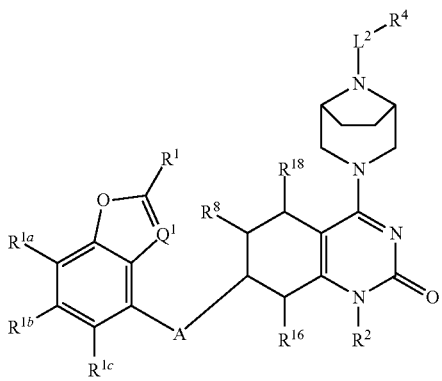

Formula (IId'1) wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

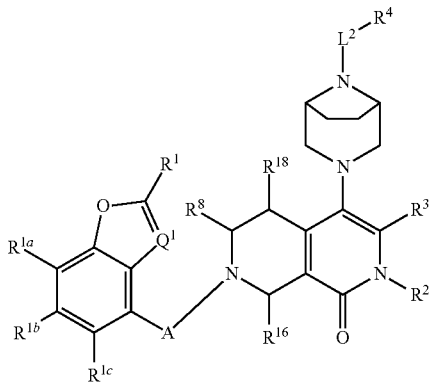

Formula (IIe'1) wherein $Q^1$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

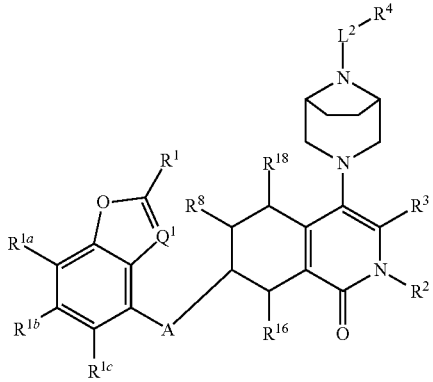

Formula (IIf'1) wherein $Q^1$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment. In embodiments, the compound has the formula:

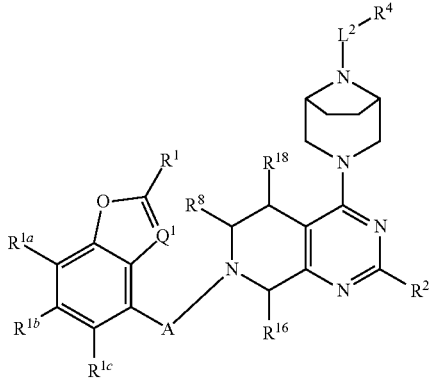

Formula (IIg'1) wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

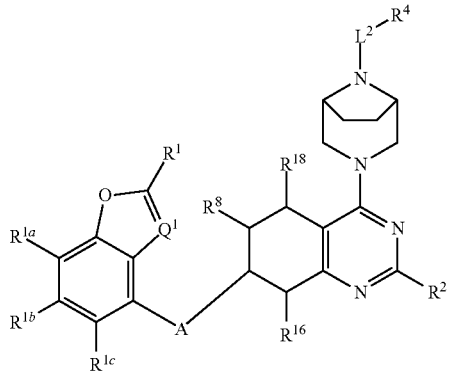

Formula (IIh'1) wherein $Q^1$, $R^1$, $R^{1a}$, $R^{1b}$, $R^{1c}$, A, $R^{16}$, $R^{18}$, $R^8$, $R^2$, $L^2$, and $R^4$ are as described herein, including in any embodiment. In embodiments, the compound has the formula:

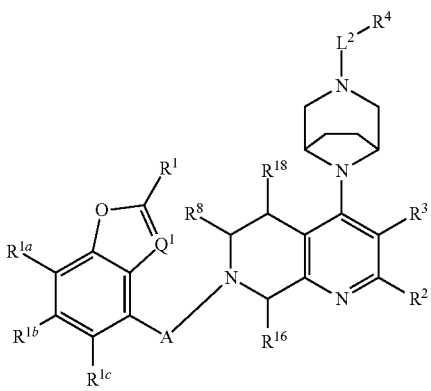

Formula (IIi'1) wherein $Q^1$, $R^1$, $R^{1a}$, $R^{1b}$, $R^{1c}$, A, $R^{16}$, $R^{18}$, $R^8$, $R^2$, $R^3$, $L^2$, and $R^4$ are as described herein, including in any embodiment.

In embodiments, the compound has the formula:

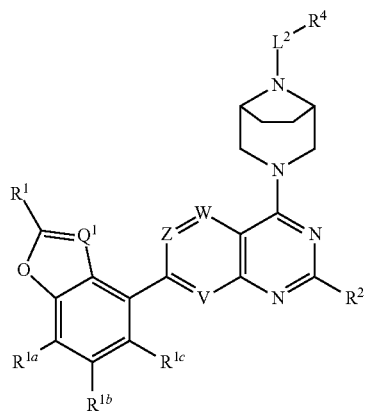

Formula (Iha1) wherein $Q^1$, $R^1$, $R^{1a}$, $R^{1b}$, $R^{1c}$, V, Z, W, $R^2$, $L^2$, and $R^4$ are as described herein, including in any embodiment. In embodiments, the compound has the formula:

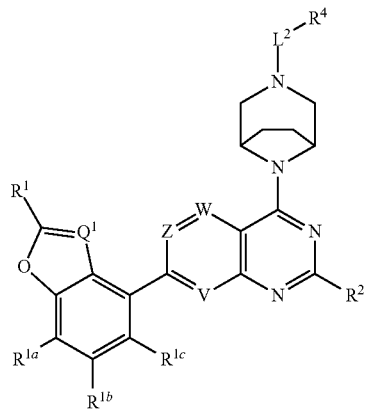

Formula (Ihd1) wherein $Q^1$, $R^1$, $R^{1a}$, $R^{1b}$, $R^{1c}$, V, Z, W, $R^2$, $L^2$, and $R^4$ are as described herein, including in any embodiment. In embodiments of formula Ihf, Z is not N. In embodiments, the compound has the formula:

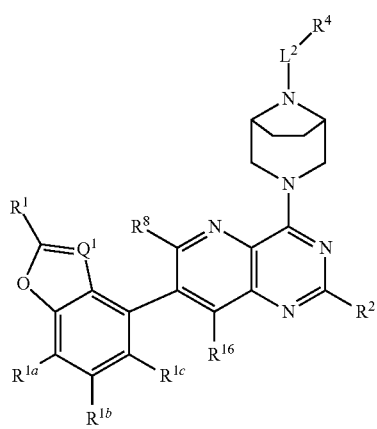

Formula (Iha'1) wherein $Q^1$, $R^1$, $R^{1a}$, $R^{1a}$, $R^{1b}$, $R^8$, $R^{16}$, $R^2$, $L^2$, and $R^4$ are as described herein, including in any embodiment. In embodiments, the compound has the formula:

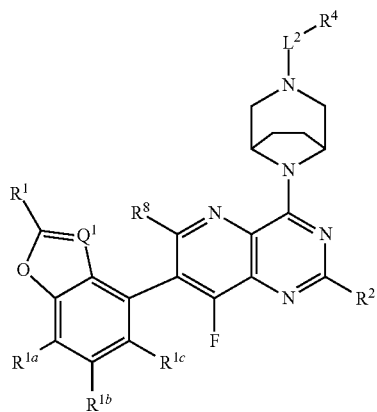

Formula (Ihd'1) wherein $Q^1$, $R^1$, $R^{1a}$, $R^{1b}$, $R^{1c}$, RR, $R^{16}$, $R^2$, $L^2$, and $R^4$ are as described herein, including in any embodiment. In embodiments, the compound has the formula:

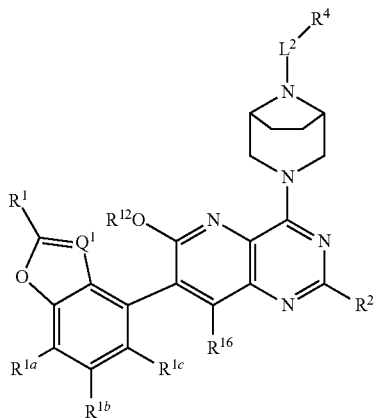

Formula (Iha "1) wherein $Q^1$, $R^1$, $R^{1a}$, $R^{1b}$, $R^{1c}$, $R^{12}$, $R^{16}$, $R^2$, $L^2$, and $R^4$ are as described herein, including in any embodiment. In embodiments, the compound has the formula:

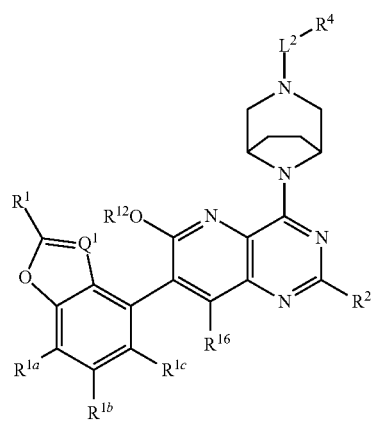

Formula (Ihd" 1) wherein $Q^1$, $R^1$, $R^{1a}$, $R^{14}$, $R^{16}$, $R^{12}$, $R^{16}$, $R^2$, $L^2$, and $R^4$ are as described herein, including in any embodiment. In embodiments, the compound has the formula:

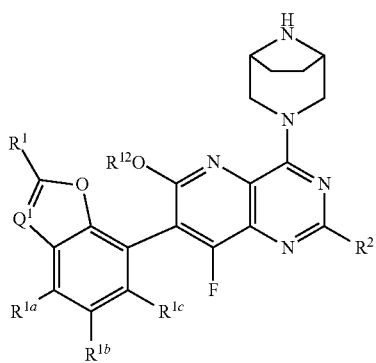

Formula (Ihc'''1) wherein $Q^1$, $R^{1a}$, $R^{1b}$, $R^{1c}$, $R^{12}$, and $R^2$ are as described herein, including in any embodiment. In embodiments, the compound has the formula:

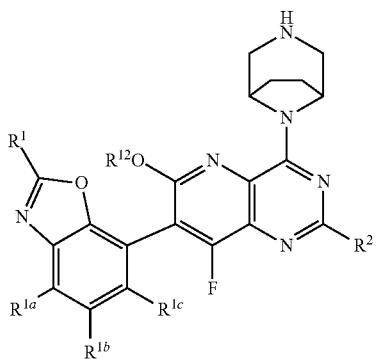

Formula (Ihf'''1) wherein $Q^1$, $R^{14}$, $R^1$, $R^{1e}$, $R^{12}$, and $R^2$ are as described herein, including in any embodiment. In embodiments, the compound has the formula:

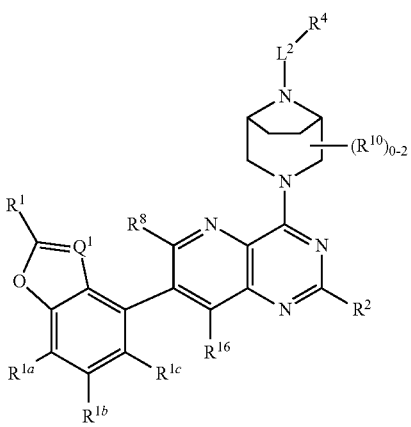

Formula (Ihg1) wherein $Q^1$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

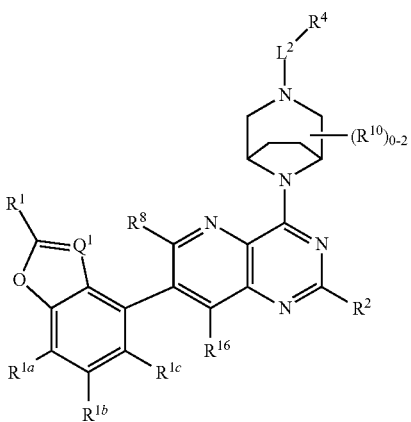

Formula (Ihj1) wherein $Q^1$, $R^1$, $R^{1a}$, $R^{1b}$, $R^{1c}$, $R^8$, $R^{10}$, $R^{16}$, $R^2$, $L^2$, and $R^4$ are as described herein, including in any embodiment. In embodiments, the compound has the formula:

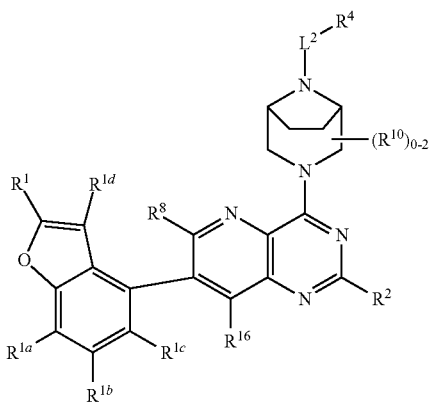

Formula (Ihm1) wherein $Q^1$, $R^1$, $R^{1a}$, $R^{1b}$, $R^{1c}$, $R^{1d}$, $R^8$, $R^{10}$, $R^{16}$, $R^2$, $L^2$, and $R^4$ are as described herein, including in any embodiment. In embodiments, the compound has the formula:

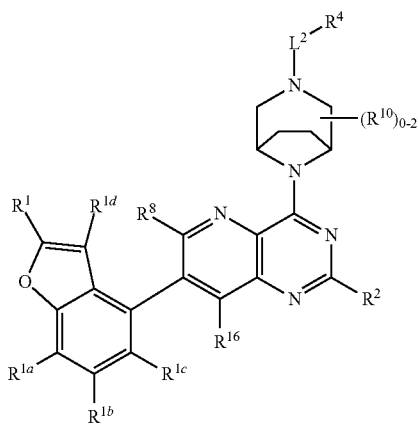

Formula (Ihn1) wherein $Q^1$, $R^1$, $R^{1a}$, $R^{1b}$, $R^{1c}$, $R^{14}$, $R^8$, $R^{10}$, $R^{16}$, $R^2$, $L^2$, and $R^4$ are as described herein, including in any embodiment.

In embodiments, $R^2$ is —O—$CH_2$—$C_{2-9}$heterocycloalkyl optionally substituted with one, two, or three $R^{20d}$ wherein $R^{20d}$ is independently halogen (e.g., F). In embodiments, $R^2$ is —O—$CH_2$—$C_{2-9}$heterocycloalkyl optionally substituted with one, two, or three $R^{20d}$ wherein $R^{20d}$ is independently $C_{1-6}$alkyl (e.g., methyl). In embodiments, $R^2$ is

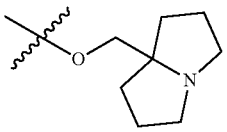

In embodiments, $R^2$ is

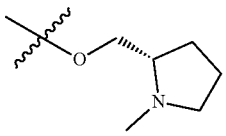

In embodiments, $R^2$ is

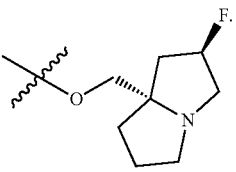 [SMILES: *OC[C@@]12CCCN1C[C@H](F)C2]

In embodiments, $R^2$ is

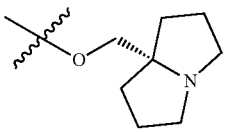

In embodiments, $R^8$ is —$OR^{12}$ wherein $R^{12}$ is independently selected from hydrogen, $C_{1-6}$alkyl, $C_{2-6}$alkenyl, $C_{2-6}$alkynyl, $C_{3-9}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$. In embodiments, $R^{12}$ is independently hydrogen. In embodiments, $R^{12}$ is independently $C_{1-6}$alkyl optionally substituted with one, two, or three $R^{20d}$. In embodiments, $R^{12}$ is independently $C_{2-6}$alkenyl optionally substituted with one, two, or three $R^{20d}$. In embodiments, $R^{12}$ is independently $C_{2-6}$alkynyl optionally substituted with one, two, or three $R^{20d}$. In embodiments, $R^{12}$ is independently $C_{3-6}$cycloalkyl optionally substituted with one, two, or three $R^{20d}$. In embodiments, $R^{12}$ is independently —$CH_2$—$C_{3-6}$cycloalkyl optionally substituted with one, two, or three $R^{20d}$. In embodiments, $R^{12}$ is independently $C_{2-9}$heterocycloalkyl optionally substituted with one, two, or three $R^{20d}$. In embodiments, $R^{12}$ is independently —$CH_2$—$C_{2-9}$heterocycloalkyl optionally substituted with one, two, or three $R^{20d}$. In embodiments, $R^{12}$ is independently $C_{1-6}$alkyl. In embodiments, $R^{12}$ is independently $C_{2-6}$alkenyl. In embodiments, $R^{12}$ is independently $C_{2-6}$alkynyl. In embodiments, $R^{12}$ is independently $C_{3-6}$cycloalkyl. In embodiments, $R^{12}$ is independently —$CH_2$—$C_{3-6}$cycloalkyl. In embodiments, $R^{12}$ is independently $C_{2-9}$heterocycloalkyl. In embodiments, $R^{12}$ is independently —$CH_2$—$C_{2-9}$heterocycloalkyl.

In embodiments, $R^{20d}$ is independently selected from halogen, —CN, and $C_{1-6}$alkyl. In embodiments, $R^{20d}$ is independently halogen (e.g., F). In embodiments, $R^{20d}$ is independently —CN. In embodiments, $R^{20d}$ is independently $C_{1-6}$alkyl. In embodiments, $R^{13}$ is independently $C_{1-6}$alkyl. In embodiments, $R^{13}$ is independently $C_{1-6}$haloalkyl.

In embodiments, $R^8$ is —N($R^{12}$)($R^{13}$) wherein $R^{12}$ is independently selected from hydrogen, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, $C_{6-10}$aryl, —CH$_2$—$C_{6-10}$aryl, and $C_{1-9}$heteroaryl are optionally substituted with one, two, or three $R^{20d}$; and $R^{13}$ is independently selected from hydrogen, $C_{1-6}$alkyl, and $C_{1-6}$haloalkyl. In embodiments, $R^8$ is —NH($R^{12}$).

In embodiments, $R^{12}$ is independently hydrogen. In embodiments, $R^{12}$ is independently $C_{1-6}$alkyl optionally substituted with one, two, or three $R^{20d}$. In embodiments, $R^{12}$ is independently $C_{2-6}$alkenyl optionally substituted with one, two, or three $R^{20d}$. In embodiments, $R^{12}$ is independently $C_{2-6}$alkynyl optionally substituted with one, two, or three $R^{20d}$. In embodiments, $R^{12}$ is independently $C_{3-6}$cycloalkyl optionally substituted with one, two, or three $R^{20d}$. In embodiments, $R^{12}$ is independently —CH$_2$—$C_{3-6}$cycloalkyl optionally substituted with one, two, or three $R^{20d}$. In embodiments, $R^{12}$ is independently $C_{2-9}$heterocycloalkyl optionally substituted with one, two, or three $R^{20d}$. In embodiments, $R^{12}$ is independently —CH$_2$—$C_{2-9}$heterocycloalkyl optionally substituted with one, two, or three $R^{20d}$. In embodiments, $R^{12}$ is independently $C_{1-6}$alkyl. In embodiments, $R^{12}$ is independently $C_{2-6}$alkenyl. In embodiments, $R^{12}$ is independently $C_{2-6}$alkynyl. In embodiments, $R^{12}$ is independently $C_{3-6}$cycloalkyl. In embodiments, $R^{12}$ is independently —CH$_2$—$C_{3-6}$cycloalkyl. In embodiments, $R^{12}$ is independently $C_{2-9}$heterocycloalkyl. In embodiments, $R^{12}$ is independently —CH$_2$—$C_{2-9}$heterocycloalkyl.

In embodiments, $R^{20d}$ is independently selected from halogen, —CN, and $C_{1-6}$alkyl. In embodiments, $R^{20d}$ is independently halogen (e.g., F). In embodiments, $R^{20d}$ is independently —CN. In embodiments, $R^{20d}$ is independently $C_{1-6}$alkyl. In embodiments, $R^{20d}$ is independently $C_{1-6}$alkyl optionally substituted with one, two, or three groups independently selected from halogen, oxo, —CN, $C_{1-6}$alkyl, and $C_{1-6}$haloalkyl.

In embodiments, $R^{13}$ is independently hydrogen. In embodiments, $R^{13}$ is independently $C_{1-6}$alkyl. In embodiments, $R^{13}$ is independently $C_{1-6}$haloalkyl.

In embodiments, $R^8$ is hydrogen. In embodiments, $R^8$ is halogen. In embodiments, $R^8$ is —CN. In embodiments, $R^8$ is independently hydrogen. In embodiments, $R^8$ is independently $C_{1-6}$alkyl optionally substituted with one, two, or three $R^{20c}$. In embodiments, $R^8$ is independently $C_{2-6}$alkenyl optionally substituted with one, two, or three $R^{20c}$. In embodiments, $R^8$ is independently $C_{2-6}$alkynyl optionally substituted with one, two, or three $R^{20c}$. In embodiments, $R^8$ is independently $C_{3-6}$cycloalkyl optionally substituted with one, two, or three $R^{20c}$. In embodiments, $R^8$ is independently —CH$_2$—$C_{3-6}$cycloalkyl optionally substituted with one, two, or three $R^{20c}$. In embodiments, $R^8$ is independently $C_{2-9}$heterocycloalkyl optionally substituted with one, two, or three $R^{20c}$. In embodiments, $R^8$ is independently —CH$_2$—$C_{2-9}$heterocycloalkyl optionally substituted with one, two, or three $R^{20c}$. In embodiments, $R^8$ is independently $C_{1-6}$alkyl. In embodiments, $R^8$ is independently $C_{2-6}$alkenyl. In embodiments, $R^8$ is independently $C_{2-6}$alkynyl. In embodiments, $R^8$ is independently $C_{3-6}$cycloalkyl. In embodiments, $R^8$ is independently —CH$_2$—$C_{3-6}$cycloalkyl. In embodiments, $R^8$ is independently $C_{2-9}$heterocycloalkyl. In embodiments, $R^8$ is independently —CH$_2$—$C_{2-9}$heterocycloalkyl.

In embodiments, $R^{20c}$ is independently selected from halogen, —CN, and $C_{1-6}$alkyl. In embodiments, $R^{20c}$ is independently halogen (e.g., F). In embodiments, $R^{20c}$ is independently —CN. In embodiments, $R^{20c}$ is independently $C_{1-6}$alkyl.

In embodiments, $R^{20c}$ is independently selected from $C_{2-6}$alkenyl. In embodiments, $R^{20c}$ is independently $C_{2-6}$alkynyl. In embodiments, $R^{20c}$ is independently $C_{3-6}$cycloalkyl. In embodiments, $R^{20c}$ is independently —CH$_2$—$C_{3-6}$cycloalkyl. In embodiments, $R^{20c}$ is independently $C_{2-9}$heterocycloalkyl. In embodiments, $R^{20c}$ is independently —CH$_2$—$C_{2-9}$heterocycloalkyl. In embodiments, $R^{20c}$ is independently $C_{6-10}$aryl. In embodiments, $R^{20c}$ is independently —CH$_2$—$C_{6-10}$aryl. In embodiments, $R^{20c}$ is independently $C_{1-9}$heteroaryl.

In embodiments, $R^{20c}$ is independently $C_{1-6}$alkyl optionally substituted with one, two, or three groups independently selected from halogen, oxo, —CN, $C_{1-6}$alkyl, and $C_{1-6}$haloalkyl. In embodiments, $R^{20c}$ is independently selected from $C_{2-6}$alkenyl optionally substituted with one, two, or three groups independently selected from halogen, oxo, —CN, $C_{1-6}$alkyl, and $C_{1-6}$haloalkyl. In embodiments, $R^{20c}$ is independently $C_{2-6}$alkynyl optionally substituted with one, two, or three groups independently selected from halogen, oxo, —CN, $C_{1-6}$alkyl, and $C_{1-6}$haloalkyl. In embodiments, $R^{20c}$ is independently $C_{3-6}$cycloalkyl optionally substituted with one, two, or three groups independently selected from halogen, oxo, —CN, $C_{1-6}$alkyl, and $C_{1-6}$haloalkyl. In embodiments, $R^{20c}$ is independently —CH$_2$—$C_{3-6}$cycloalkyl optionally substituted with one, two, or three groups independently selected from halogen, oxo, —CN, $C_{1-6}$alkyl, and $C_{1-6}$haloalkyl. In embodiments, $R^{20c}$ is independently $C_{2-9}$heterocycloalkyl optionally substituted with one, two, or three groups independently selected from halogen, oxo, —CN, $C_{1-6}$alkyl, and $C_{1-6}$haloalkyl. In embodiments, $R^{20c}$ is independently —CH$_2$—$C_{2-9}$heterocycloalkyl optionally substituted with one, two, or three groups independently selected from halogen, oxo, —CN, $C_{1-6}$alkyl, and $C_{1-6}$haloalkyl. In embodiments, $R^{20c}$ is independently $C_{6-10}$aryl optionally substituted with one, two, or three groups independently selected from halogen, oxo, —CN, $C_{1-6}$alkyl, and $C_{1-6}$haloalkyl. In embodiments, $R^{20c}$ is independently —CH$_2$—$C_{6-10}$aryl optionally substituted with one, two, or three groups independently selected from halogen, oxo, —CN, $C_{1-6}$alkyl, and $C_{1-6}$haloalkyl. In embodiments, $R^{20c}$ is independently $C_{1-9}$heteroaryl optionally substituted with one, two, or three groups independently selected from halogen, oxo, —CN, $C_{1-6}$alkyl, and $C_{1-6}$haloalkyl.

In embodiments, $R^{1a}$, $R^{1b}$, $R^{1c}$ are independently selected from hydrogen and halogen. In embodiments, $R^{1a}$ is halogen and $R^{1b}$ and $R^{1c}$ are hydrogen. In embodiments, $R^{1b}$ is halogen and $R^{1a}$ and $R^{1c}$ are hydrogen. In embodiments, $R^{1c}$ is halogen and $R^{1b}$ and $R^{1a}$ are hydrogen. In embodiments, $R^{1a}$ is hydrogen and $R^{1b}$ and $R^{1c}$ are independently halogen. In embodiments, $R^{1b}$ is hydrogen and $R^{1a}$ and $R^{1c}$ are independently halogen. In embodiments, $R^{1c}$ is hydrogen and $R^{1b}$ and $R^{1a}$ are independently halogen. In embodiments, $R^{1a}$ is F. In embodiments, $R^{1a}$ is Cl. In embodiments, $R^{1b}$ is F. In embodiments, $R^{1b}$ is Cl. In embodiments, $R^{1c}$ is F. In embodiments, $R^{1c}$ is Cl.

In embodiments, $Q^1$ is $C(R^{1d})$.

In embodiments, Rid is independently hydrogen. In embodiments, $R^{1d}$ is independently $C_{1-6}$alkyl optionally substituted with one, two, or three $R^{20a}$. In embodiments, $R^{1d}$ is independently $C_{2-6}$alkenyl optionally substituted with one, two, or three $R^{20a}$. In embodiments, $R^{1d}$ is independently $C_{2-6}$alkynyl optionally substituted with one, two, or three $R^{20a}$. In embodiments, $R^{1d}$ is independently $C_{3-6}$cycloalkyl (e.g., cyclopropyl) optionally substituted with one, two, or three $R^{20a}$. In embodiments, $R^{1d}$ is independently $C_{2-9}$heterocycloalkyl optionally substituted with one, two, or three $R^{20a}$. In embodiments, $R^{1d}$ is independently $C_{1-6}$alkyl. In embodiments, $R^{1d}$ is independently $C_{2-6}$alkenyl. In embodiments, $R^{1d}$ is independently $C_{2-6}$alkynyl. In embodiments, $R^{1d}$ is independently $C_{3-6}$cycloalkyl. In embodiments, $R^{1d}$ is independently —$CH_2$—$C_{3-6}$cycloalkyl. In embodiments, $R^{1d}$ is independently $C_{2-9}$heterocycloalkyl. In embodiments, $R^{12}$ is independently —$CH_2$—$C_{2-9}$heterocycloalkyl. In embodiments, $R^{1d}$ is independently —CN.

In embodiments, $R^{20a}$ is independently halogen. In embodiments, $R^{20a}$ is independently —CN. In embodiments, $R^{20a}$ is independently $C_{1-6}$alkyl. In embodiments, $R^{20a}$ is independently $C_{2-6}$alkenyl. In embodiments, $R^{20a}$ is independently $C_{2-6}$alkynyl. In embodiments, $R^{20a}$ is independently $C_{3-6}$cycloalkyl. In embodiments, $R^{20a}$ is independently —$CH_2$—$C_{3-6}$cycloalkyl (e.g., cyclopropyl). In embodiments, $R^{20a}$ is independently $C_{2-9}$heterocycloalkyl. In embodiments, $R^{20a}$ is independently —$CH_2$—$C_{2-9}$heterocycloalkyl. In embodiments, $R^{20a}$ is independently $C_{6-10}$aryl. In embodiments, $R^{20a}$ is independently —$CH_2$—$C_{6-10}$aryl. In embodiments, $R^{20a}$ is independently $C_{1-9}$heteroaryl.

In embodiments, $R^{16}$ is selected from hydrogen, halogen, —CN, $C_{1-6}$alkyl, $C_{2-6}$alkenyl, $C_{2-6}$alkynyl, $C_{3-6}$cycloalkyl, $C_{2-9}$heterocycloalkyl, —$OR^{12}$, —$N(R^{12})(R^{13})$, wherein $C_{1-6}$alkyl, $C_{2-6}$alkenyl, $C_{2-6}$alkynyl, $C_{3-6}$cycloalkyl, and $C_{2-9}$heterocycloalkyl are optionally substituted with one, two, or three $R^{20g}$. In embodiments, $R^{16}$ is hydrogen. In embodiments, $R^{16}$ is halogen. In embodiments, $R^{16}$ is —CN. In embodiments, $R^{16}$ is $C_{1-6}$alkyl. In embodiments, $R^{16}$ is $C_{2-6}$alkenyl. In embodiments, $R^{16}$ is $C_{2-6}$alkynyl. In embodiments, $R^{16}$ is $C_{3-6}$cycloalkyl. In embodiments, $R^{16}$ is $C_{2-9}$heterocycloalkyl. In embodiments, $R^{16}$ is —$OR^{12}$. In embodiments, $R^{16}$ is —$N(R^{12})(R^{13})$. In embodiments, $R^{16}$ is $C_{1-6}$alkyl optionally substituted with one, two, or three $R^{20g}$. In embodiments, $R^{16}$ is $C_{2-6}$alkenyl optionally substituted with one, two, or three $R^{20g}$. In embodiments, $R^{16}$ is $C_{2-6}$alkynyl optionally substituted with one, two, or three $R^{20g}$. In embodiments, $R^{16}$ is $C_{3-6}$cycloalkyl optionally substituted with one, two, or three $R^{20g}$. In embodiments, $R^{16}$ is $C_{2-9}$heterocycloalkyl optionally substituted with one, two, or three $R^{20g}$.

In embodiments, $R^{20g}$ is independently selected from halogen, —CN, and $C_{1-6}$alkyl. In embodiments, $R^{20g}$ is independently halogen (e.g., F). In embodiments, $R^{20g}$ is independently —CN. In embodiments, $R^{20g}$ is independently $C_{1-6}$alkyl.

In embodiments, $R^{20g}$ is independently selected from $C_{2-6}$alkenyl. In embodiments, $R^{20g}$ is independently $C_{2-6}$alkynyl. In embodiments, $R^{20g}$ is independently $C_{3-6}$cycloalkyl. In embodiments, $R^{20g}$ is independently —$CH_2$—$C_{3-6}$cycloalkyl. In embodiments, $R^{20g}$ is independently $C_{2-9}$heterocycloalkyl. In embodiments, $R^{20g}$ is independently —$CH_2$—$C_{2-9}$heterocycloalkyl. In embodiments, $R^{20g}$ is independently $C_{6-10}$aryl. In embodiments, $R^{20g}$ is independently —$CH_2$—$C_{6-10}$aryl. In embodiments, $R^{20g}$ is independently $C_{1-9}$heteroaryl.

In embodiments, $R^{20g}$ is independently $C_{1-6}$alkyl optionally substituted with one, two, or three groups independently selected from halogen, oxo, —CN, $C_{1-6}$alkyl, and $C_{1-6}$haloalkyl. In embodiments, $R^{20g}$ is independently selected from $C_{2-6}$alkenyl optionally substituted with one, two, or three groups independently selected from halogen, oxo, —CN, $C_{1-6}$alkyl, and $C_{1-6}$haloalkyl. In embodiments, $R^{20g}$ is independently $C_{2-6}$alkynyl optionally substituted with one, two, or three groups independently selected from halogen, oxo, —CN, $C_{1-6}$alkyl, and $C_{1-6}$haloalkyl. In embodiments, $R^{20g}$ is independently $C_{3-6}$cycloalkyl optionally substituted with one, two, or three groups independently selected from halogen, oxo, —CN, $C_{1-6}$alkyl, and $C_{1-6}$haloalkyl. In embodiments, $R^{20g}$ is independently —$CH_2$—$C_{3-6}$cycloalkyl optionally substituted with one, two, or three groups independently selected from halogen, oxo, —CN, $C_{1-6}$alkyl, and $C_{1-6}$haloalkyl. In embodiments, $R^{20g}$ is independently $C_{2-9}$heterocycloalkyl optionally substituted with one, two, or three groups independently selected from halogen, oxo, —CN, $C_{1-6}$alkyl, and $C_{1-6}$haloalkyl. In embodiments, $R^{20g}$ is independently —$CH_2$—$C_{2-9}$heterocycloalkyl optionally substituted with one, two, or three groups independently selected from halogen, oxo, —CN, $C_{1-6}$alkyl, and $C_{1-6}$haloalkyl. In embodiments, $R^{20g}$ is independently $C_{6-10}$aryl optionally substituted with one, two, or three groups independently selected from halogen, oxo, —CN, $C_{1-6}$alkyl, and $C_{1-6}$haloalkyl. In embodiments, $R^{20g}$ is independently —$CH_2$—$C_{6-10}$aryl optionally substituted with one, two, or three groups independently selected from halogen, oxo, —CN, $C_{1-6}$alkyl, and $C_{1-6}$haloalkyl. In embodiments, $R^{20g}$ is independently $C_{1-9}$heteroaryl optionally substituted with one, two, or three groups independently selected from halogen, oxo, —CN, $C_{1-6}$alkyl, and $C_{1-6}$haloalkyl.

In embodiments, $R^{16}$ is —$OR^{12}$. In embodiments, $R^{16}$ is —$OR^{12}$ wherein $R^{12}$ is independently selected from hydrogen, $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, —$CH_2$—$C_{3-6}$cycloalkyl, $C_{2-9}$heterocycloalkyl, —$CH_2$—$C_{2-9}$heterocycloalkyl, $C_{6-10}$aryl, —$CH_2$—$C_{6-10}$aryl, and $C_{1-9}$heteroaryl are optionally substituted with one, two, or three $R^{20d}$. In embodiments, $R^{12}$ is independently hydrogen. In embodiments, $R^{12}$ is independently $C_{1-6}$alkyl optionally substituted with one, two, or three $R^{20d}$. In embodiments, $R^{12}$ is independently $C_{2-6}$alkenyl optionally substituted with one, two, or three $R^{20d}$. In embodiments, $R^{12}$ is independently $C_{2-6}$alkynyl optionally substituted with one, two, or three $R^{20d}$. In embodiments, $R^{12}$ is independently $C_{3-6}$cycloalkyl optionally substituted with one, two, or three $R^{20d}$. In embodiments, $R^{12}$ is independently —$CH_2$—$C_{3-6}$cycloalkyl optionally substituted with one, two, or three $R^{20d}$. In embodiments, $R^{12}$ is independently $C_{2-9}$heterocycloalkyl optionally substituted with one, two, or three $R^{20d}$. In embodiments, $R^{12}$ is independently —$CH_2$—$C_{2-9}$heterocycloalkyl optionally substituted with one, two, or three $R^{20d}$. In embodiments, $R^{12}$ is independently $C_{1-6}$alkyl. In embodiments, $R^{12}$ is independently $C_{2-6}$alkenyl. In embodiments, $R^{12}$ is independently $C_{2-6}$alkynyl. In embodiments, $R^{12}$ is independently $C_{3-6}$cycloalkyl. In embodiments, $R^{12}$ is independently —$CH_2$—$C_{3-6}$cycloalkyl. In embodiments, $R^{12}$ is independently $C_{2-9}$heterocycloalkyl. In embodiments, $R^{12}$ is independently —$CH_2$—$C_{2-9}$heterocycloalkyl.

In embodiments, $R^{20d}$ is independently selected from halogen, —CN, and $C_{1-6}$alkyl. In embodiments, $R^{20d}$ is independently halogen (e.g., F). In embodiments, $R^{20d}$ is independently —CN. In embodiments, $R^{20d}$ is independently $C_{1-6}$alkyl. In embodiments, $R^{13}$ is independently $C_{1-6}$alkyl. In embodiments, $R^{13}$ is independently $C_{1-6}$haloalkyl.

In embodiments, $R^{16}$ is —N($R^{12}$)($R^{13}$). In embodiments, $R^{16}$ is —N($R^{12}$)($R^{13}$) wherein $R^{12}$ is independently selected from hydrogen, $C_{1-6}$alkyl, $C_{2-6}$alkenyl, $C_{2-6}$alkynyl, $C_{3-6}$cycloalkyl, —CH$_2$—C$_{3-6}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, and $C_{1-9}$heteroaryl, wherein $C_{1-6}$alkyl, $C_{2-6}$alkenyl, $C_{2-6}$alkynyl, $C_{3-6}$cycloalkyl, —CH$_2$—C$_{3-6}$cycloalkyl, $C_{2-9}$heterocycloalkyl, —CH$_2$—C$_{2-9}$heterocycloalkyl, $C_{6-10}$aryl, —CH$_2$—C$_{6-10}$aryl, and $C_{1-9}$heteroaryl are optionally substituted with one, two, or three $R^{20d}$; and $R^{13}$ is independently selected from hydrogen, $C_{1-6}$alkyl, and $C_{1-6}$haloalkyl. In embodiments, $R^8$ is —NH($R^{12}$).

In embodiments, $R^{12}$ is independently hydrogen. In embodiments, $R^{12}$ is independently $C_{1-6}$alkyl optionally substituted with one, two, or three $R^{20d}$. In embodiments, $R^{12}$ is independently $C_{2-6}$alkenyl optionally substituted with one, two, or three $R^{20d}$. In embodiments, $R^{12}$ is independently $C_{2-6}$alkynyl optionally substituted with one, two, or three $R^{20d}$. In embodiments, $R^{12}$ is independently $C_{3-6}$cycloalkyl optionally substituted with one, two, or three $R^{20d}$. In embodiments, $R^{12}$ is independently —CH$_2$—C$_{3-6}$cycloalkyl optionally substituted with one, two, or three $R^{20d}$. In embodiments, $R^{12}$ is independently $C_{2-9}$heterocycloalkyl optionally substituted with one, two, or three $R^{20d}$. In embodiments, $R^{12}$ is independently —CH$_2$—C$_{2-9}$heterocycloalkyl optionally substituted with one, two, or three $R^{20d}$. In embodiments, $R^{12}$ is independently $C_{1-6}$alkyl. In embodiments, $R^{12}$ is independently $C_{2-6}$alkenyl. In embodiments, $R^{12}$ is independently $C_{2-6}$alkynyl. In embodiments, $R^{12}$ is independently $C_{3-6}$cycloalkyl. In embodiments, $R^{12}$ is independently —CH$_2$—C$_{3-6}$cycloalkyl. In embodiments, $R^{12}$ is independently $C_{2-9}$heterocycloalkyl. In embodiments, $R^{12}$ is independently —CH$_2$—C$_{2-9}$heterocycloalkyl.

In embodiments, $R^{20d}$ is independently selected from halogen, —CN, and $C_{1-6}$alkyl. In embodiments, $R^{20d}$ is independently halogen (e.g., F). In embodiments, $R^{20d}$ is independently —CN. In embodiments, $R^{20d}$ is independently $C_{1-6}$alkyl. In embodiments, $R^{20d}$ is independently $C_{1-6}$alkyl optionally substituted with one, two, or three groups independently selected from halogen, oxo, —CN, $C_{1-6}$alkyl, and $C_{1-6}$haloalkyl.

In embodiments, $R^{13}$ is independently hydrogen. In embodiments, $R^{13}$ is independently $C_{1-6}$alkyl. In embodiments, $R^{13}$ is independently $C_{1-6}$haloalkyl.

In some embodiments, the compound is selected from

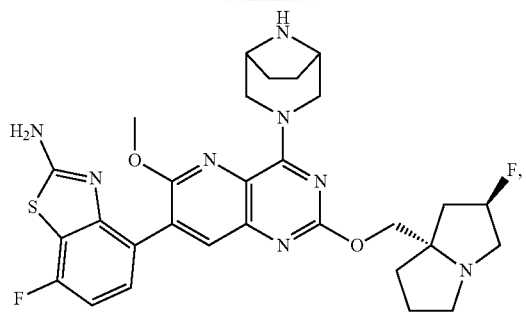

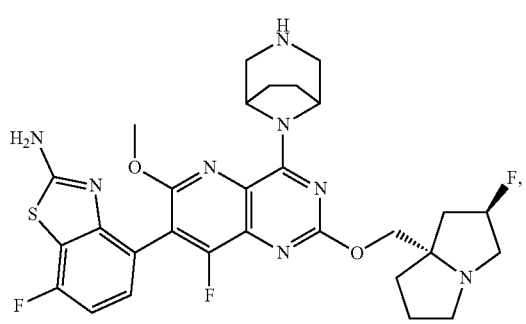

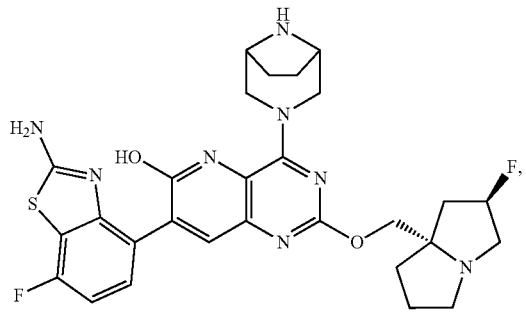

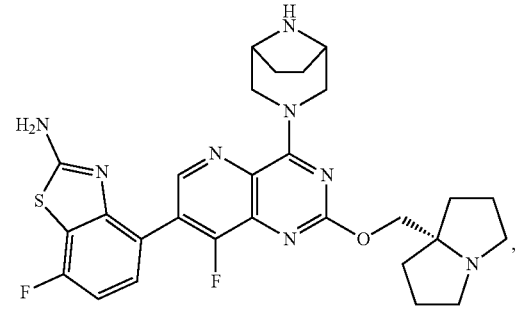

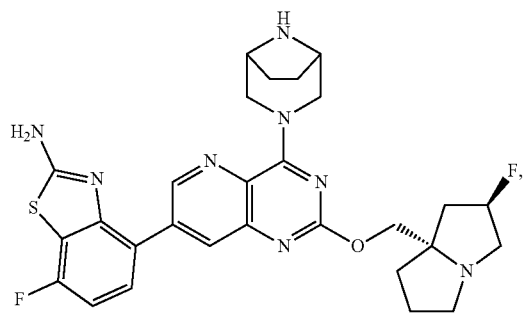

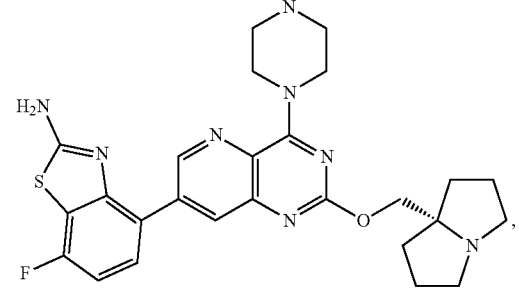

-continued
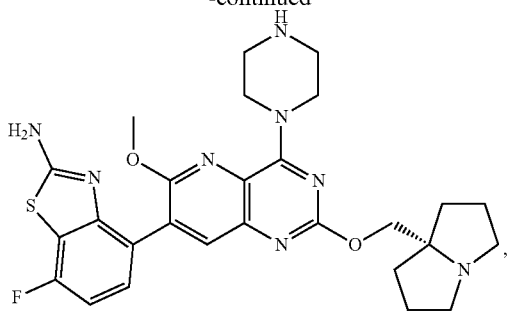
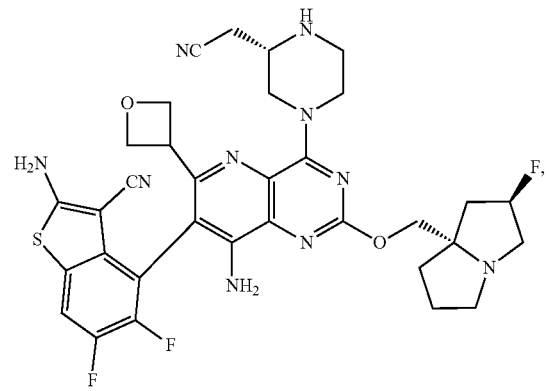
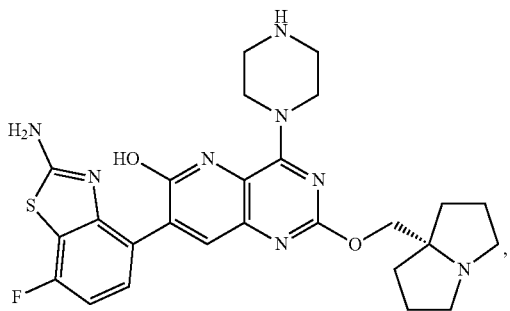
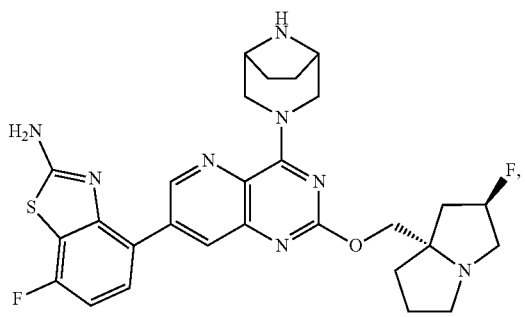
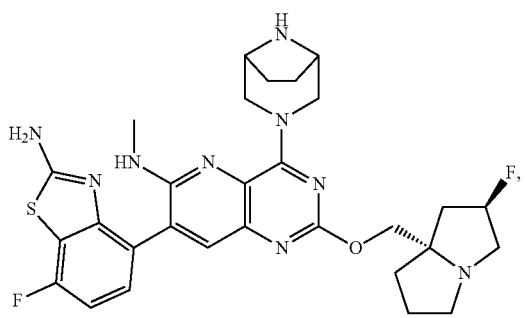
-continued
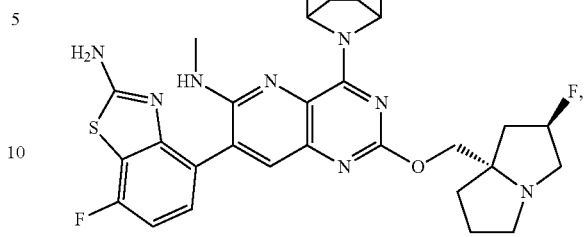
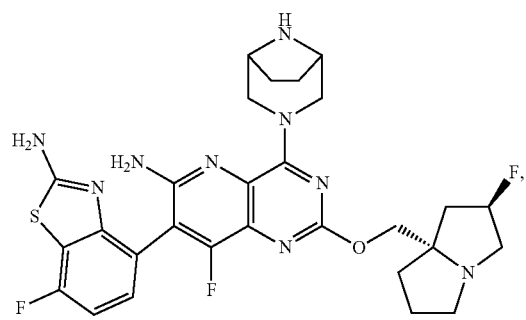
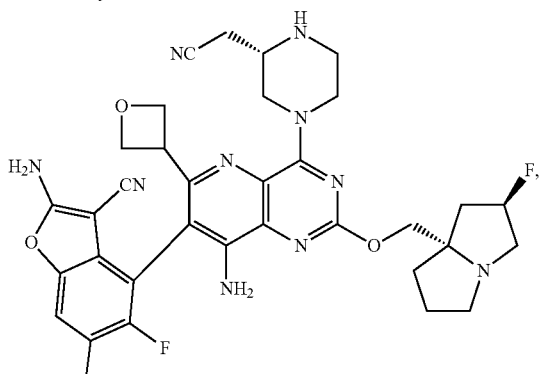
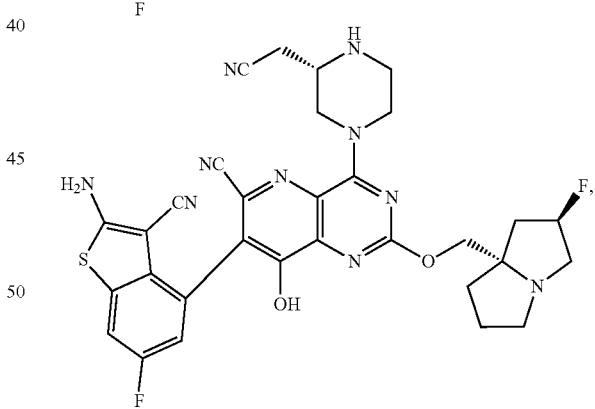
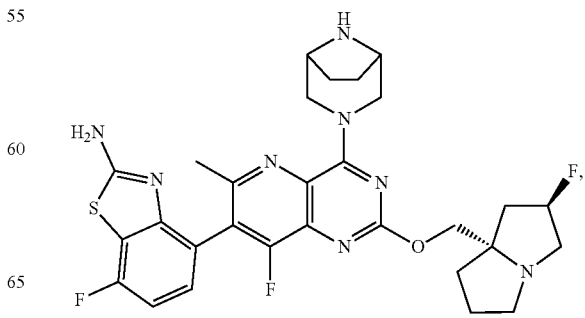

219
-continued
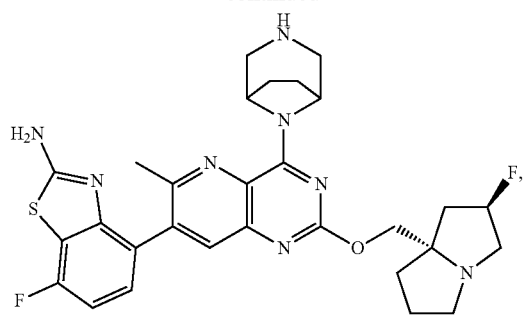
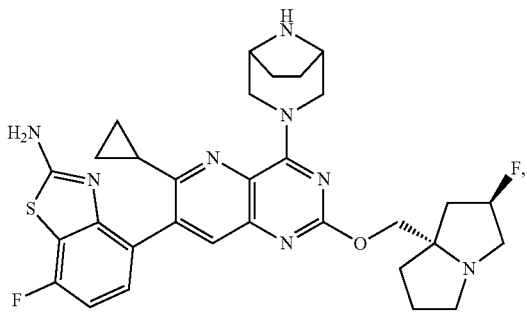
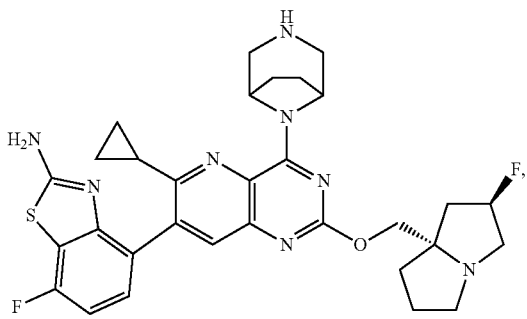
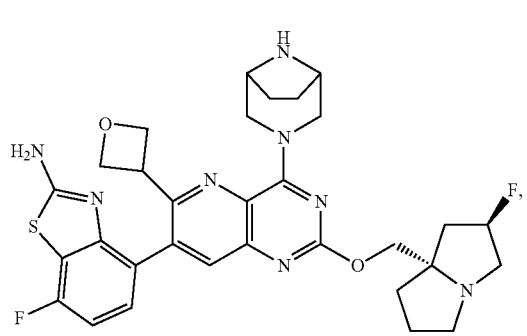
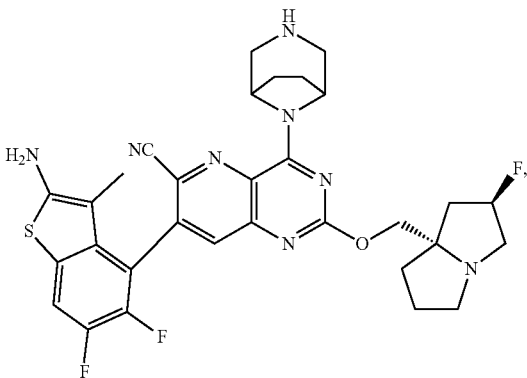
220
-continued
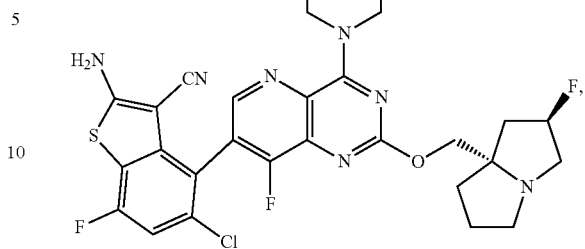
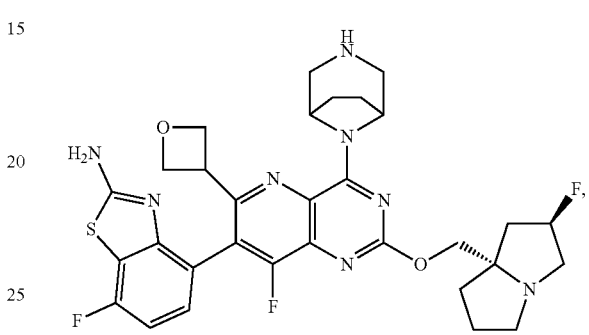
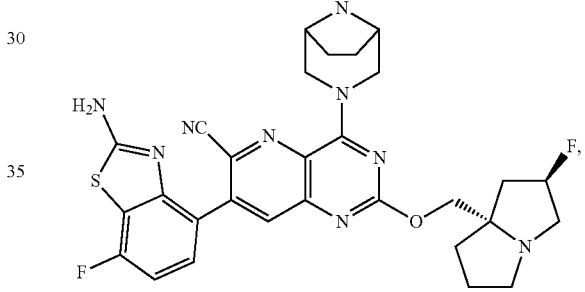
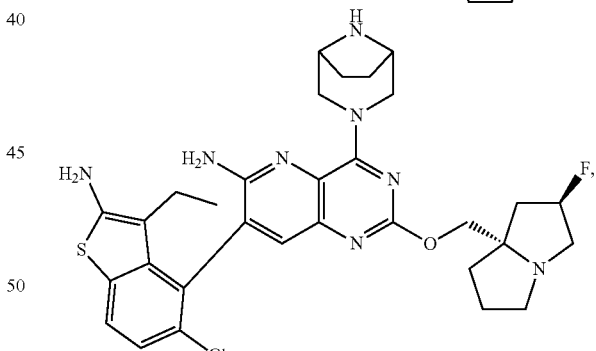
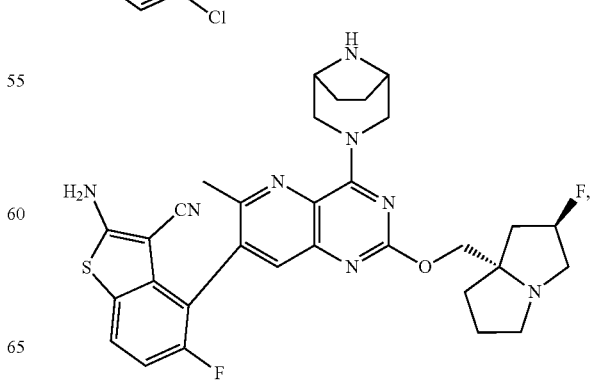

221
-continued
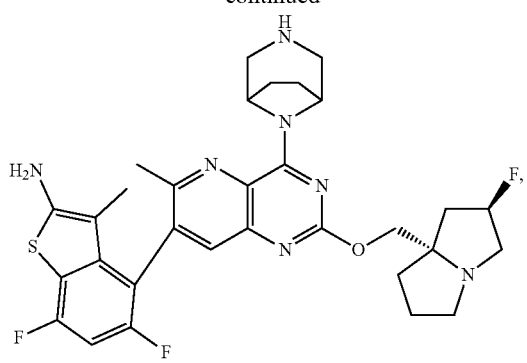
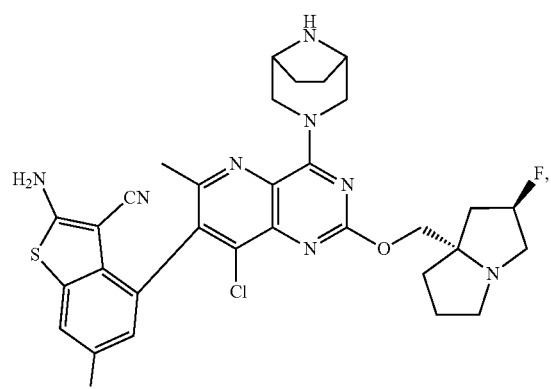
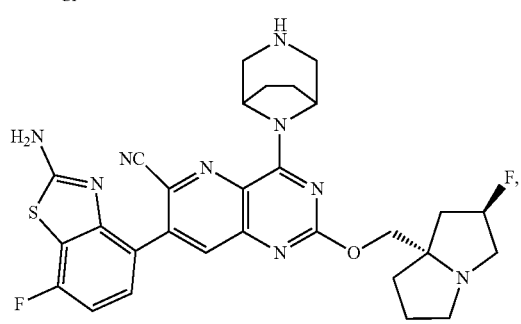
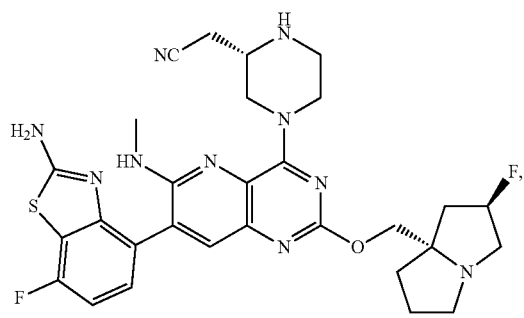
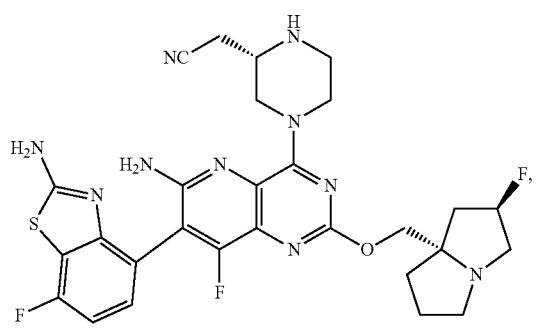
222
-continued
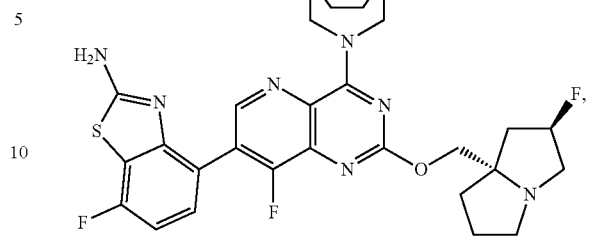
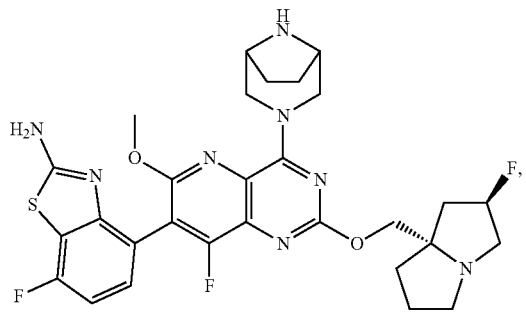
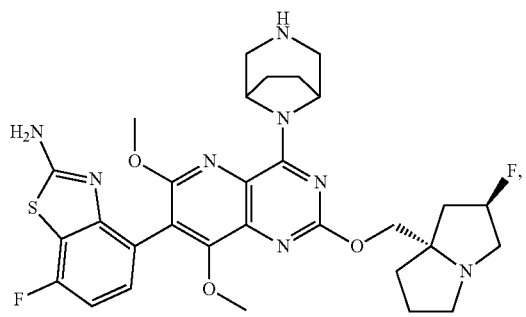
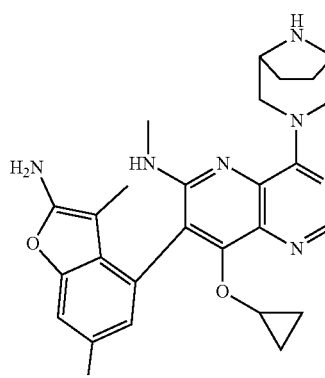
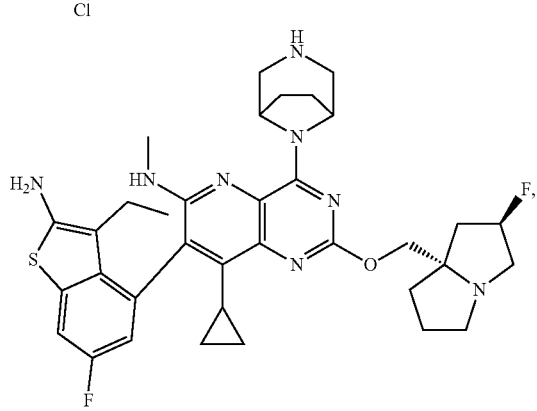

-continued
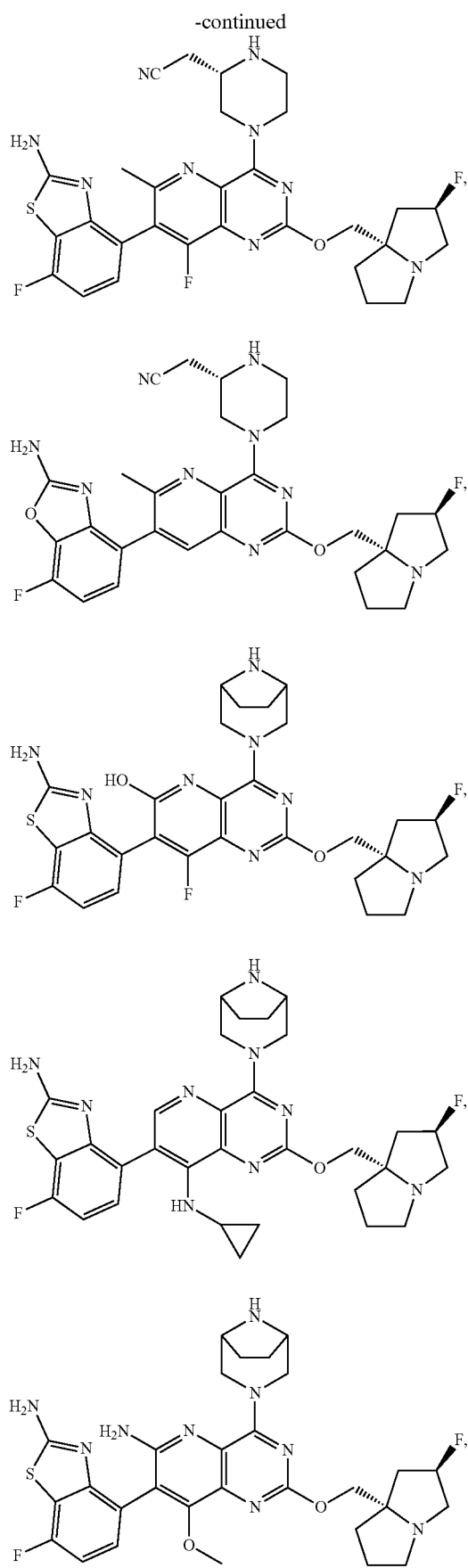
-continued
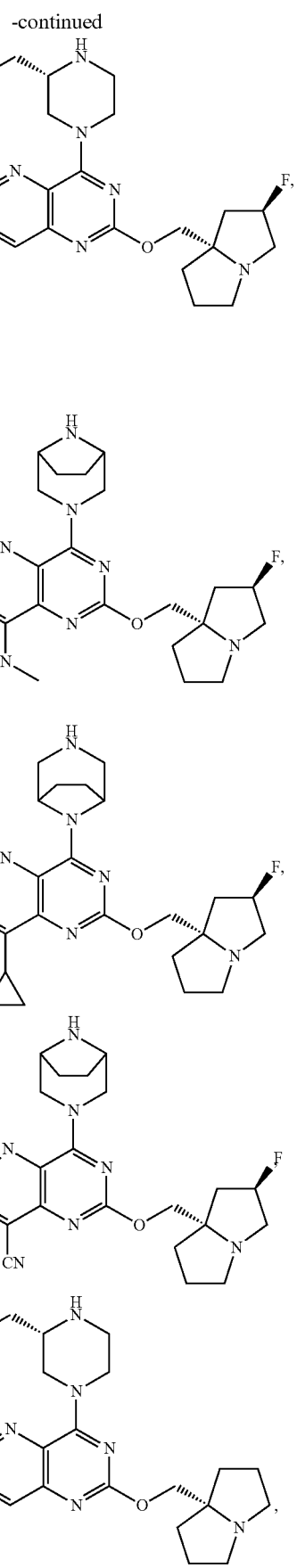

-continued
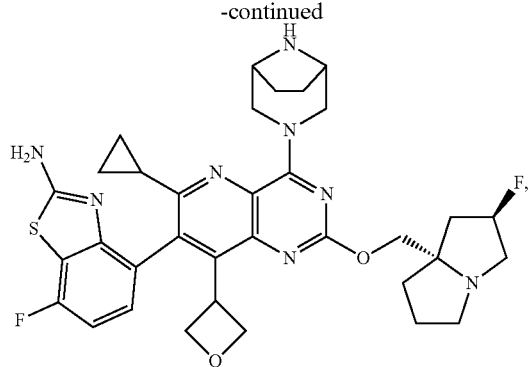
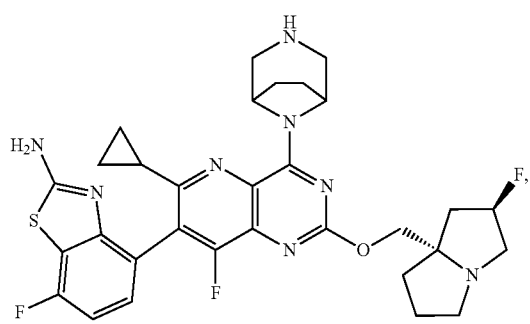
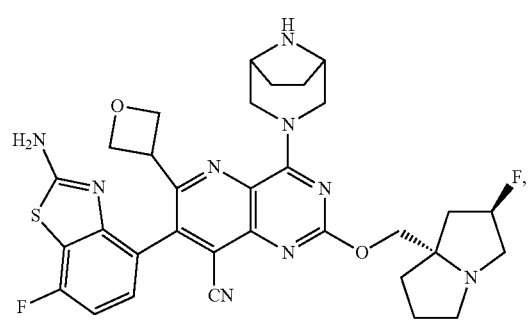
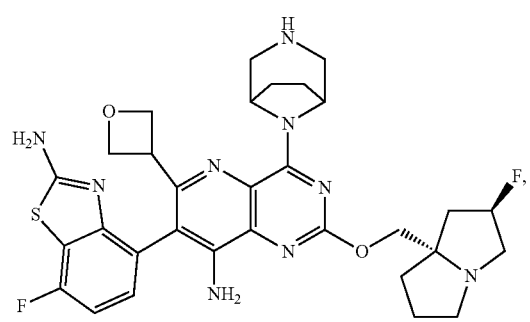
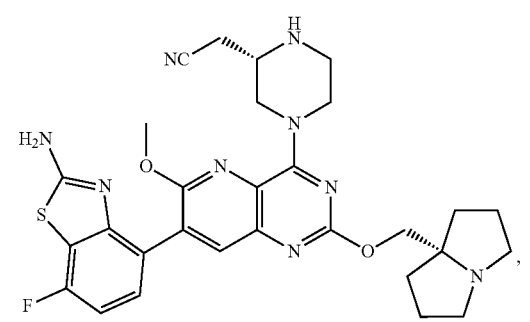
-continued
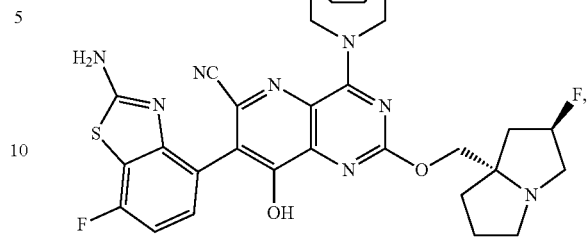
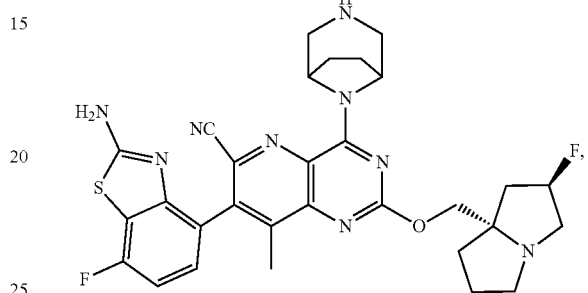
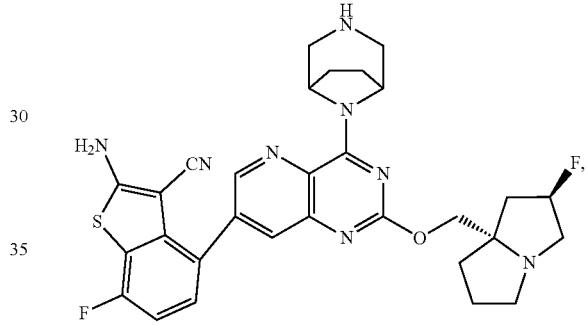
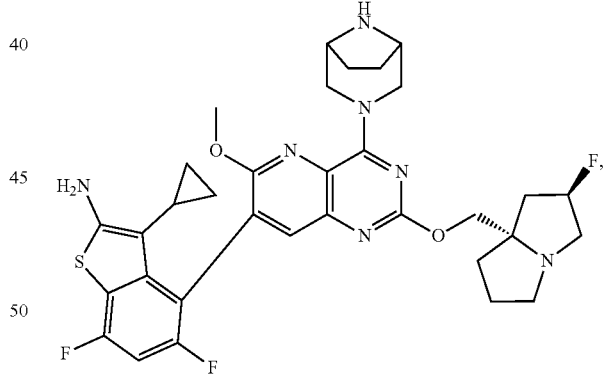
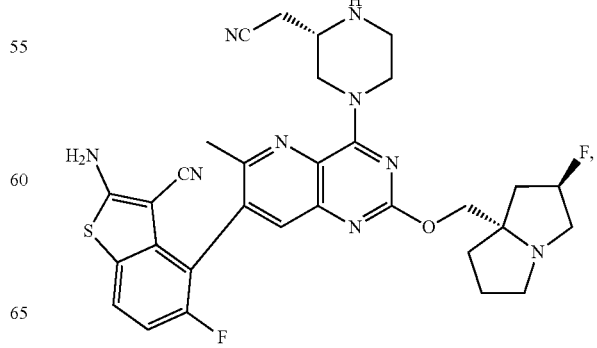

-continued
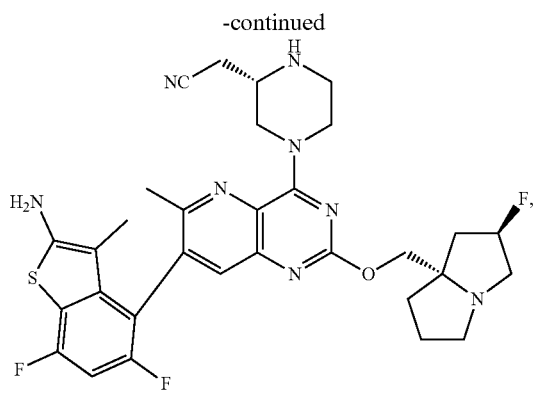
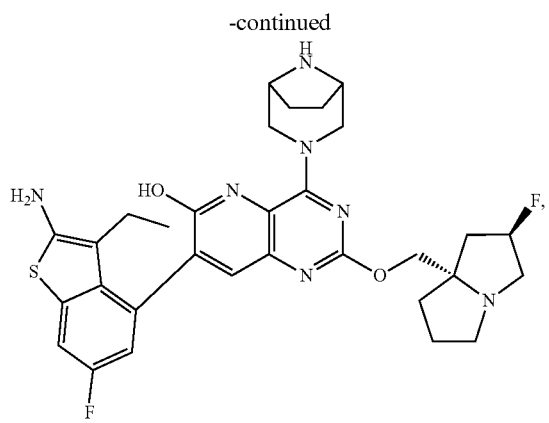
-continued
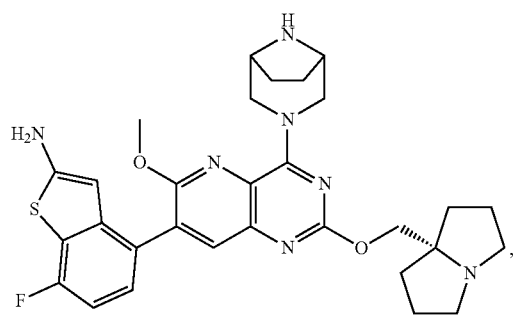
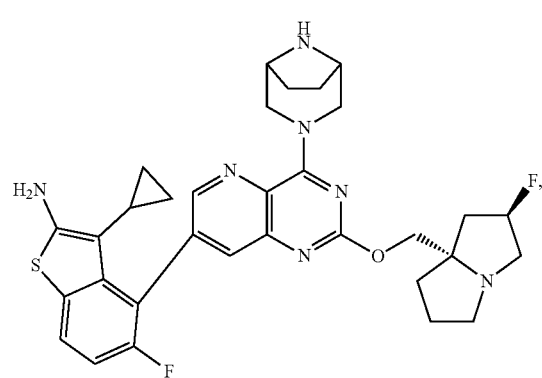
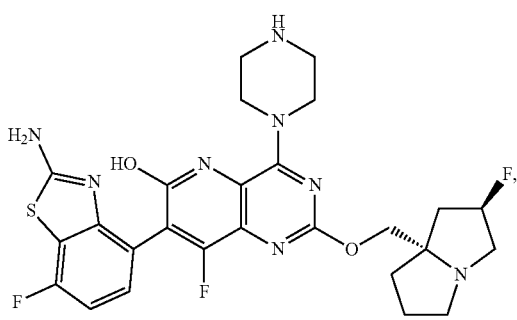
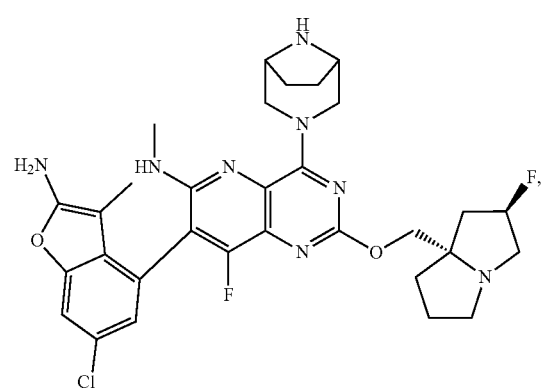
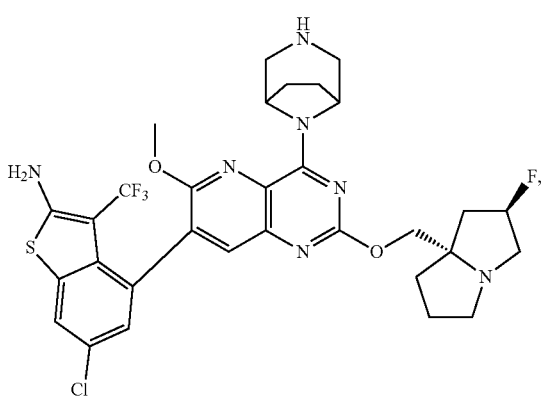
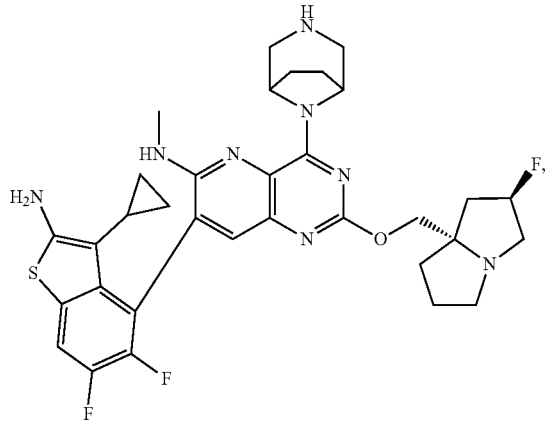

229
-continued
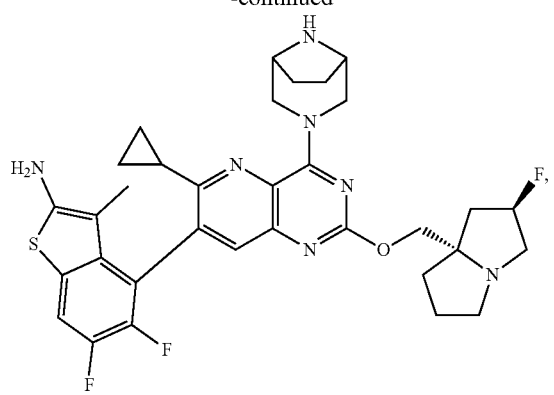
230
-continued
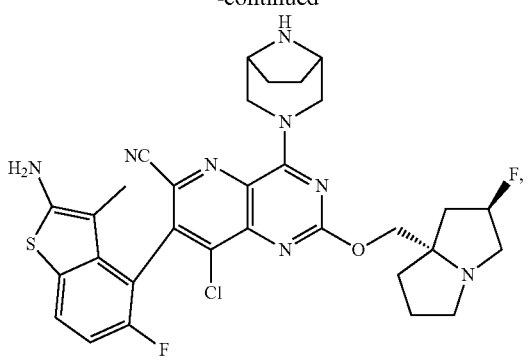
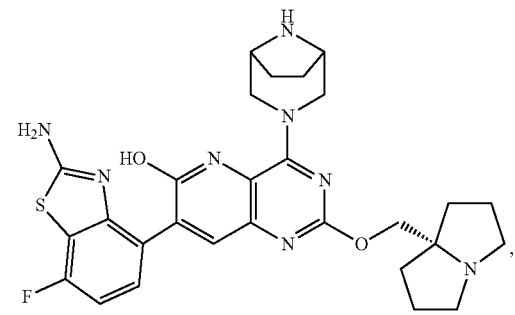
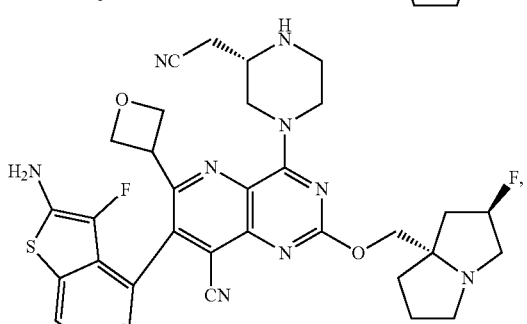
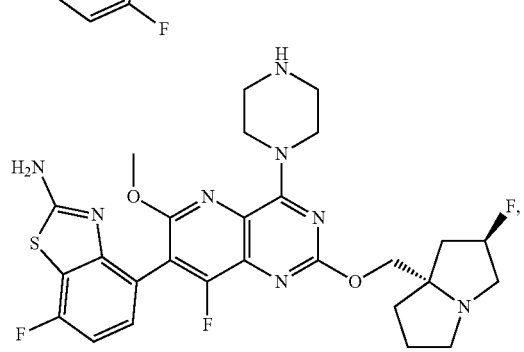
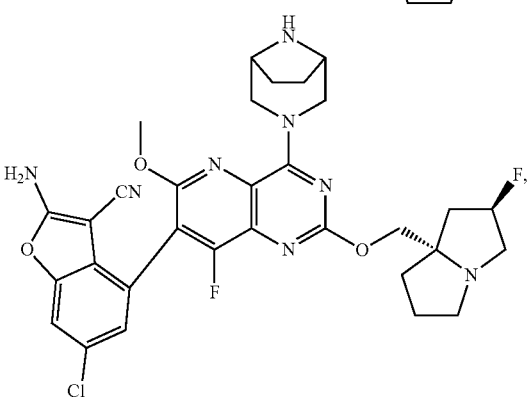

231
-continued
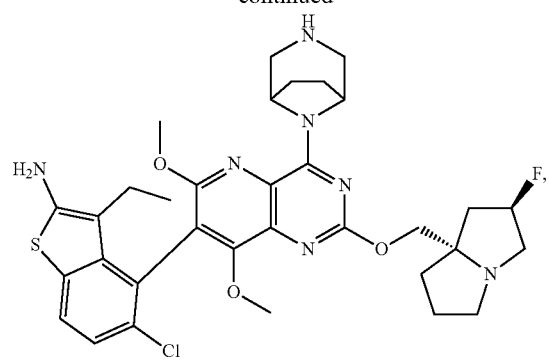
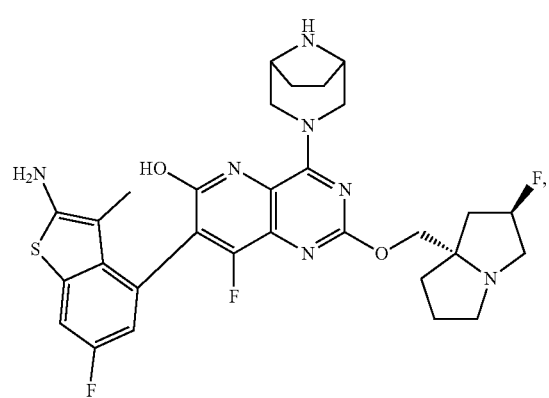
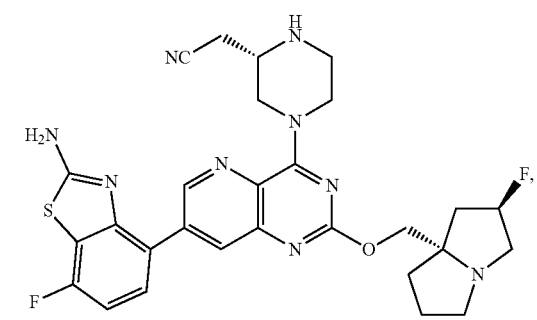
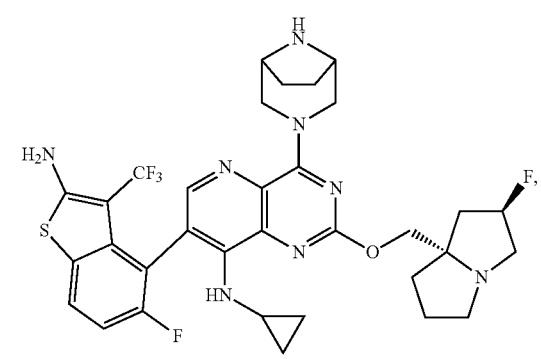
232
-continued
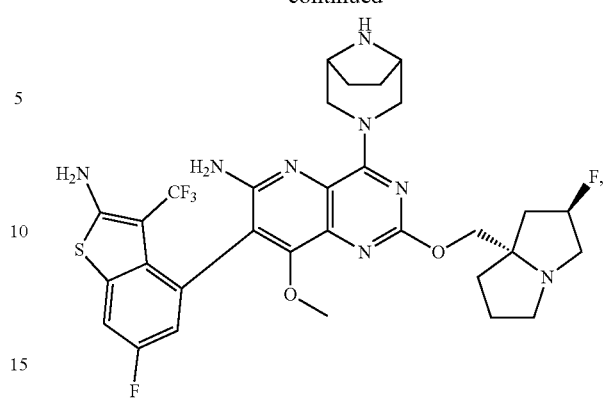
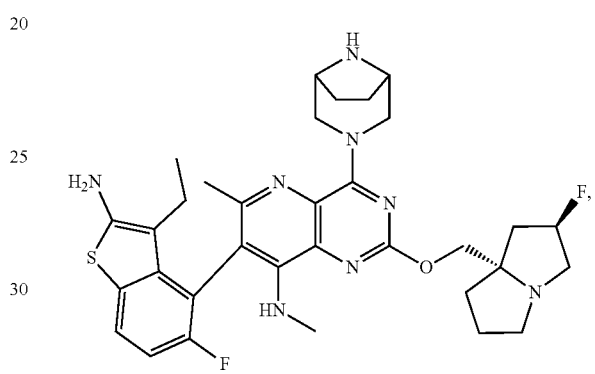
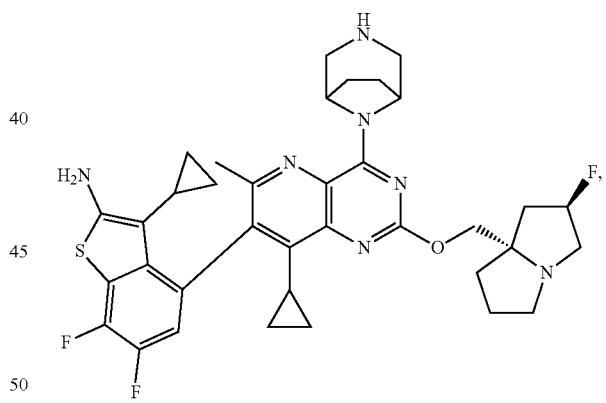
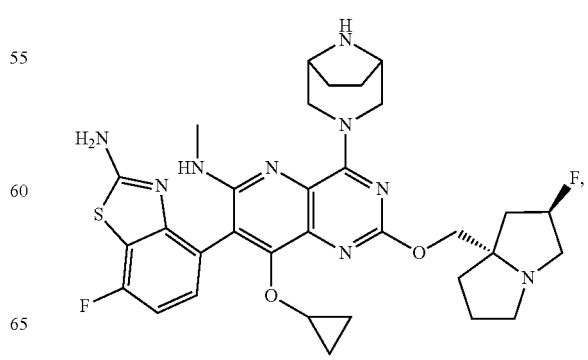

-continued
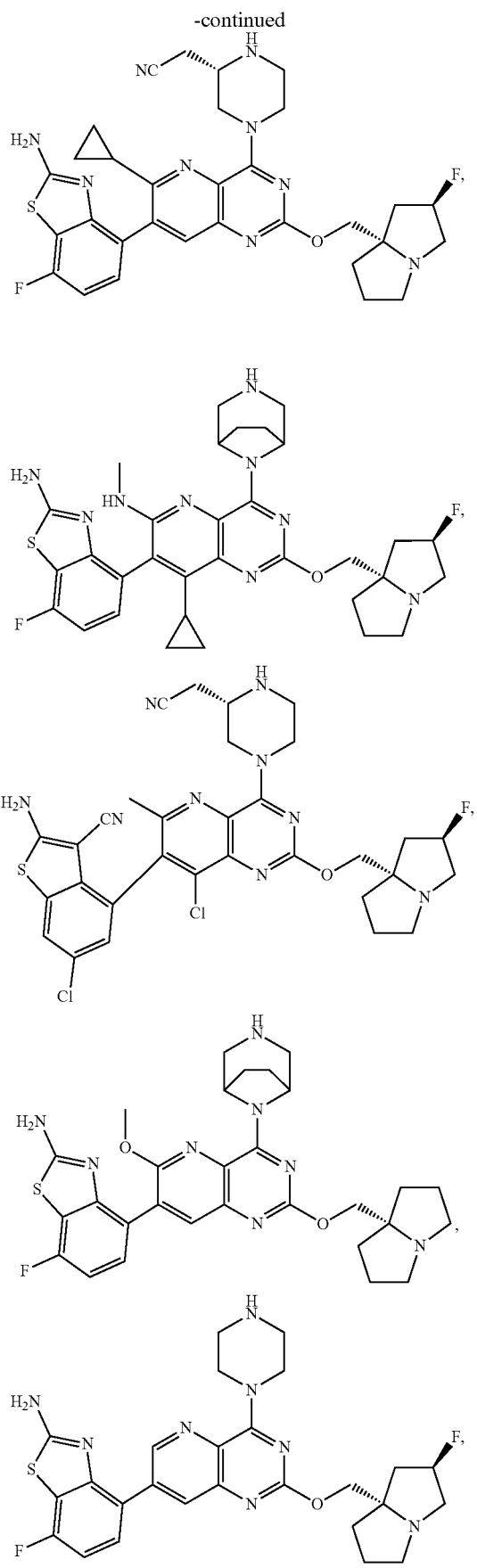
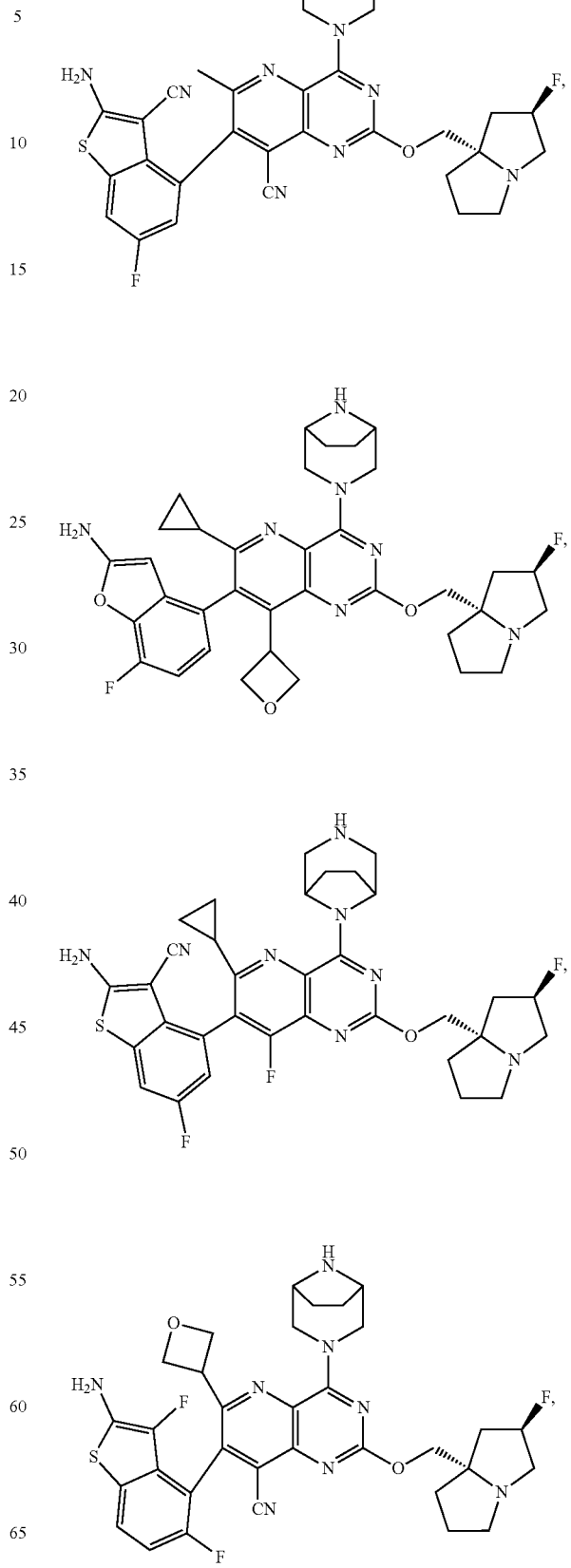

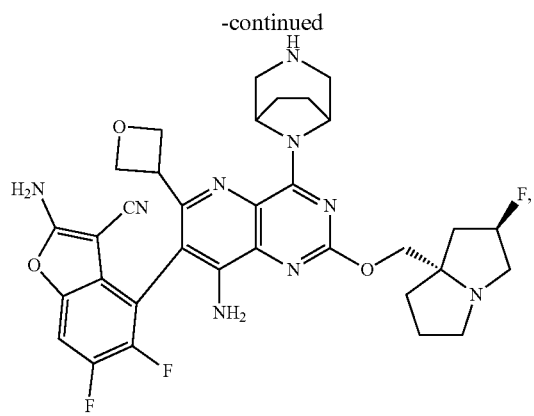
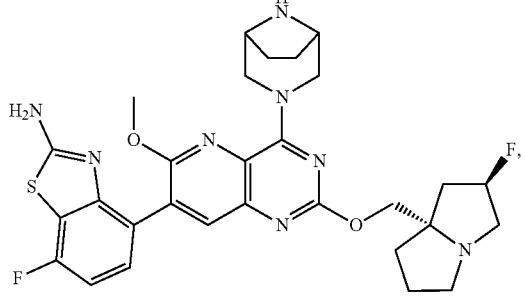
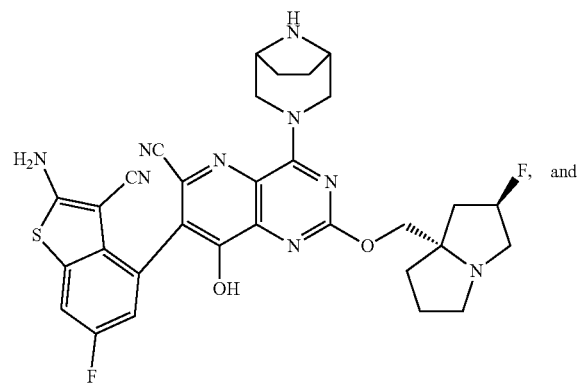
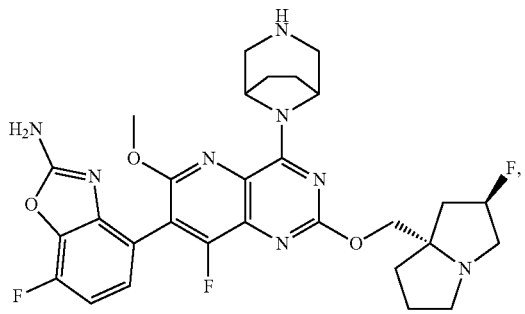
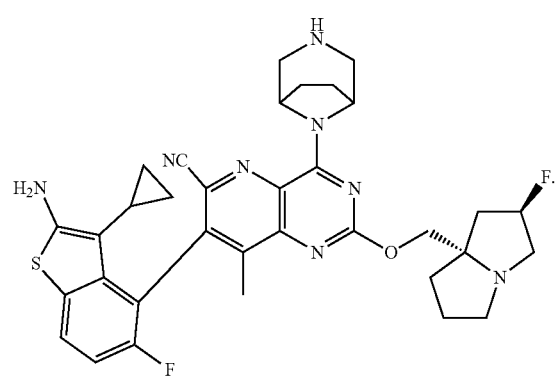
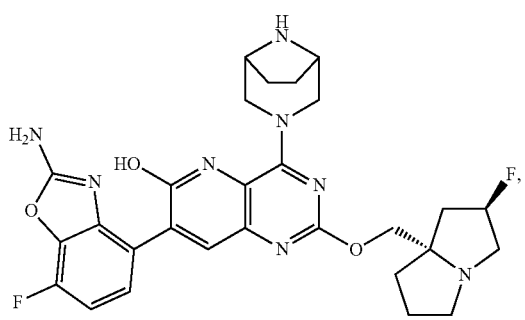
In some embodiments, the compound is selected from
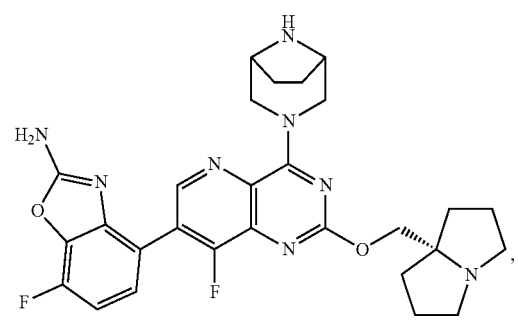
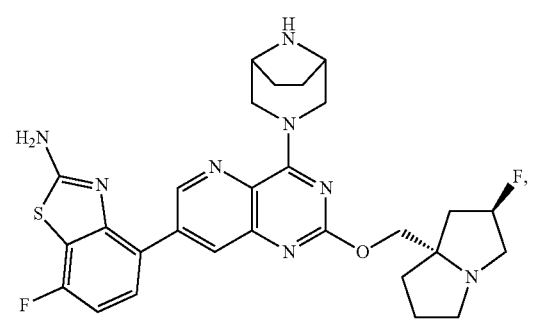
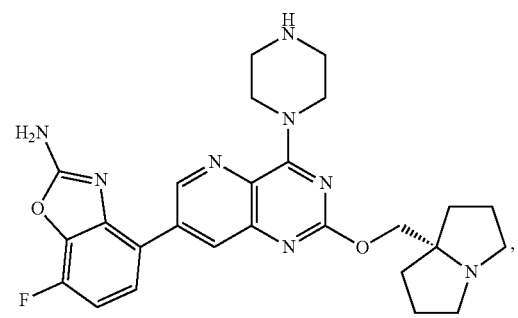

237
-continued
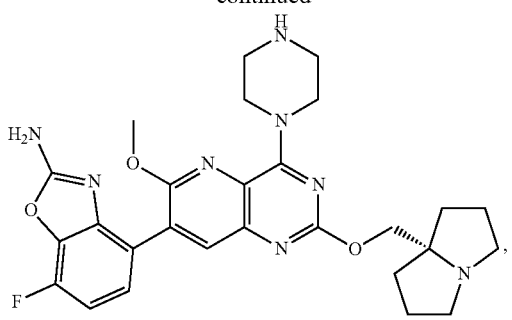,
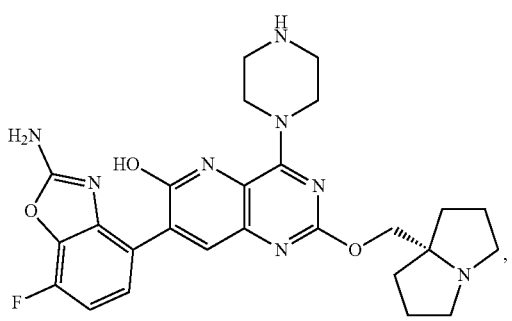,
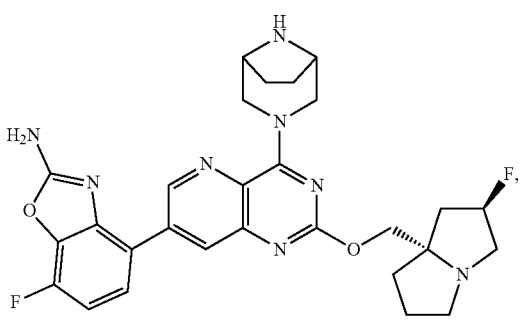
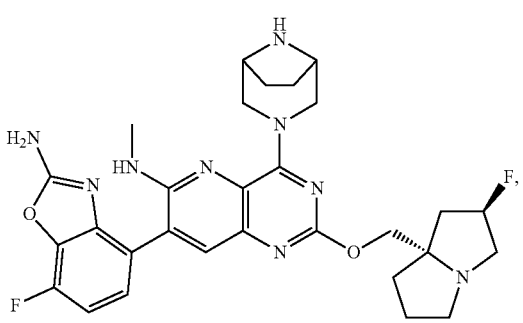
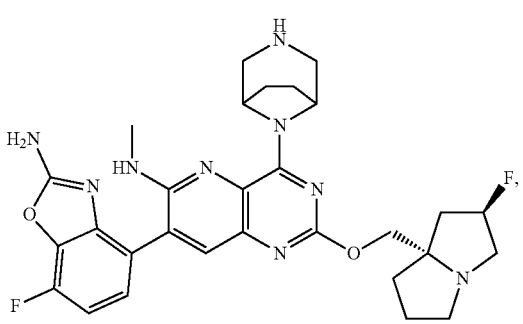
238
-continued
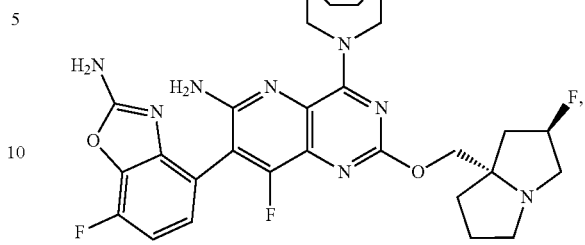,
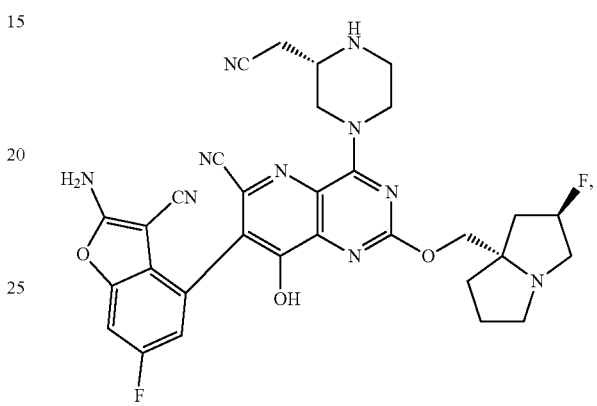
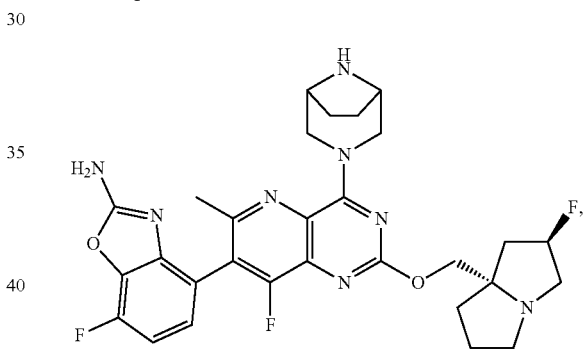
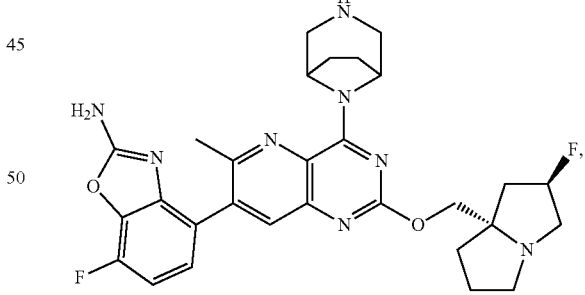
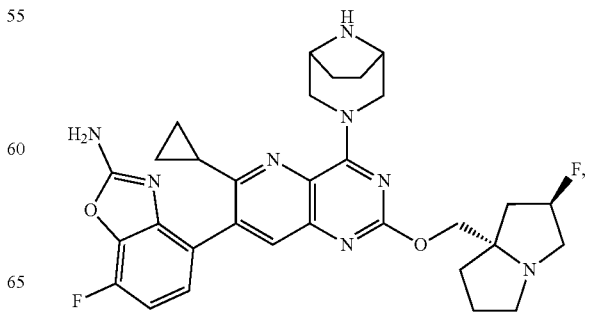

239
-continued
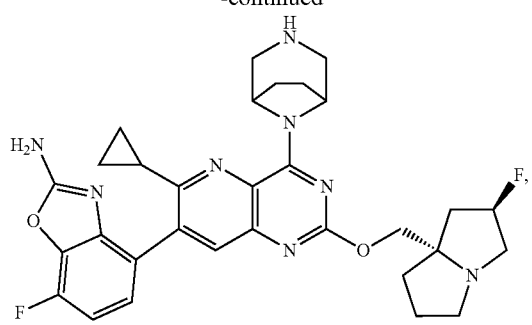
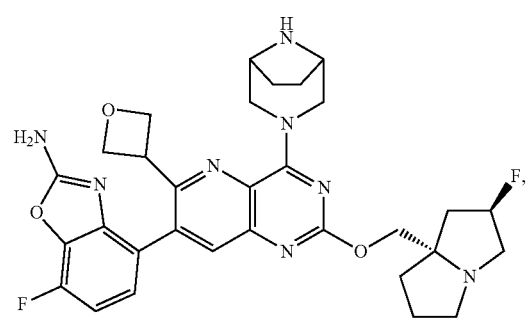
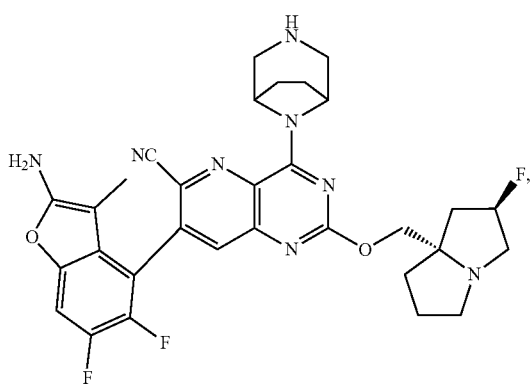
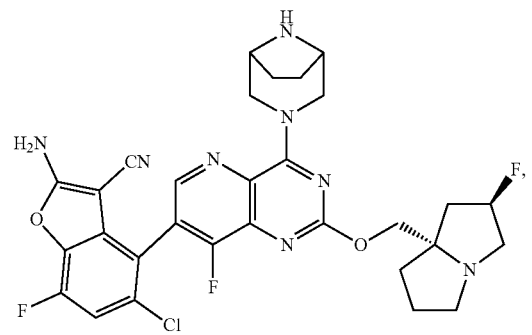
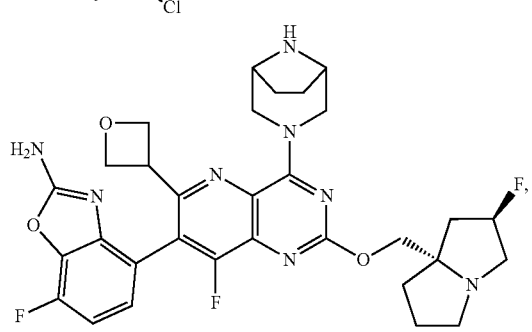
240
-continued
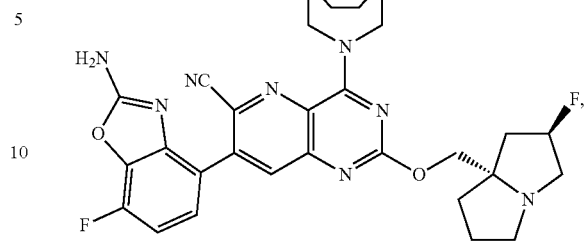
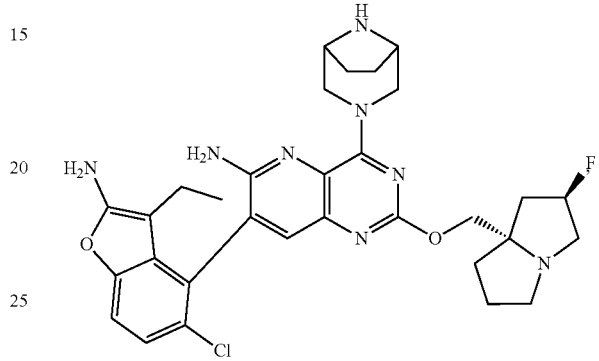
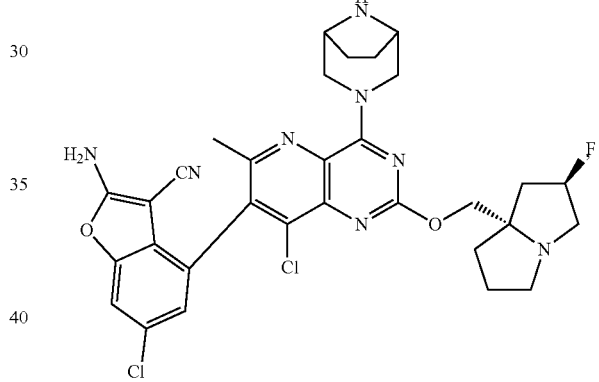
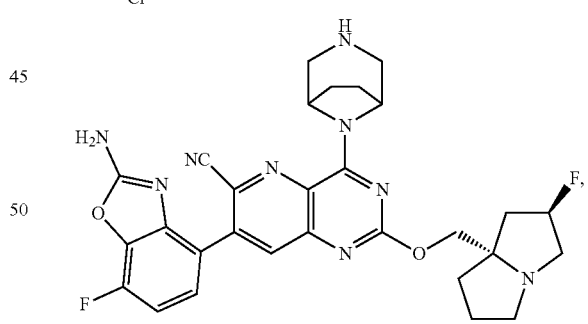
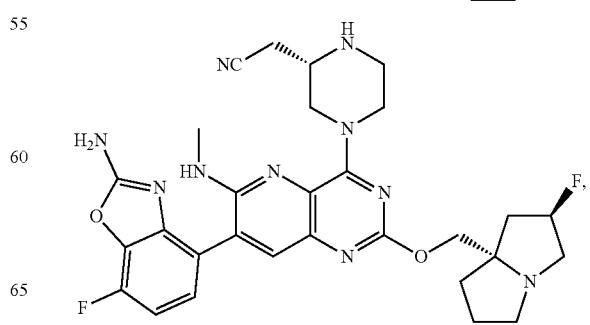

241
-continued
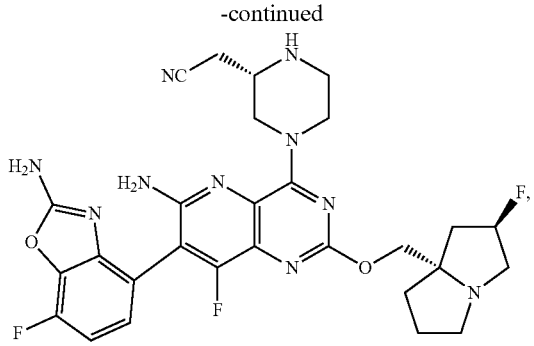
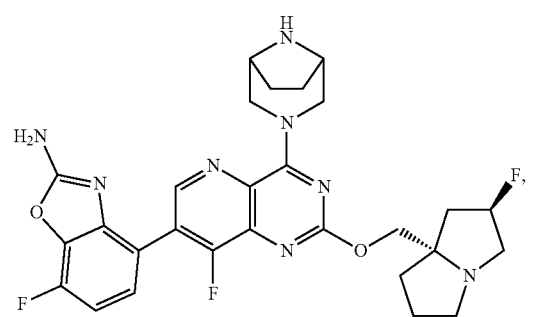
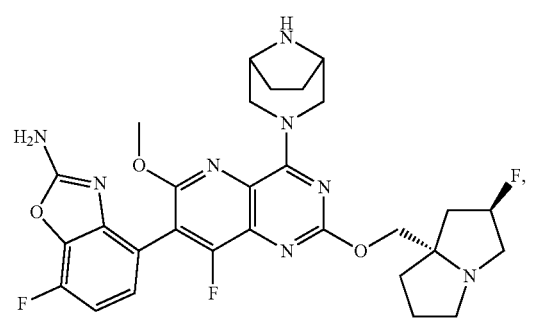
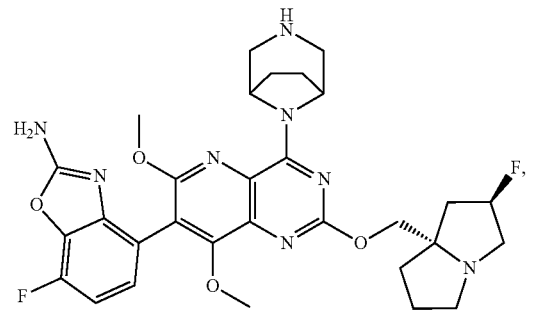
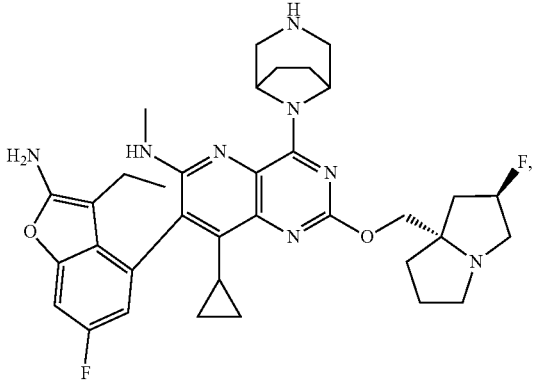
242
-continued
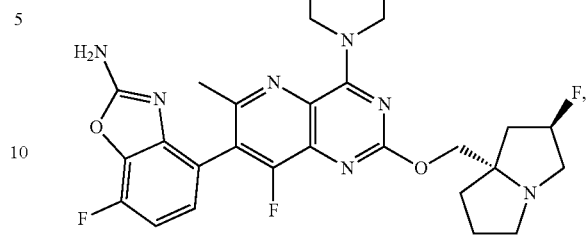
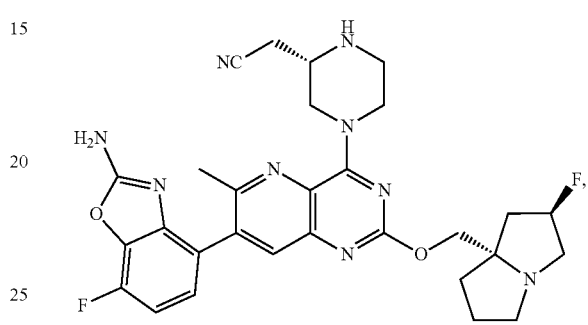
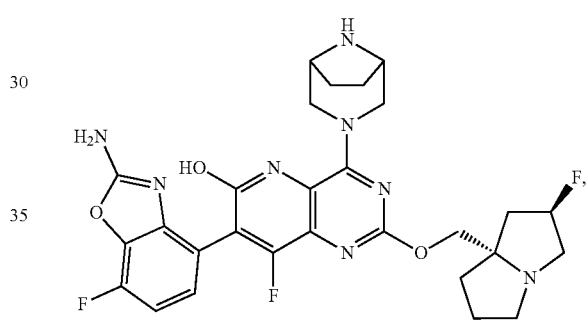
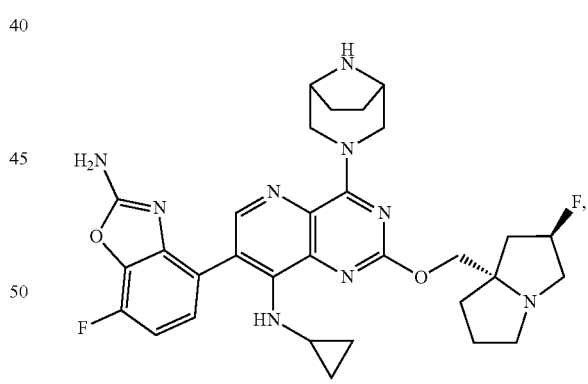
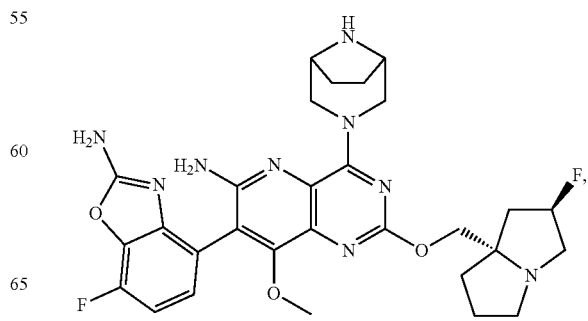

243
-continued
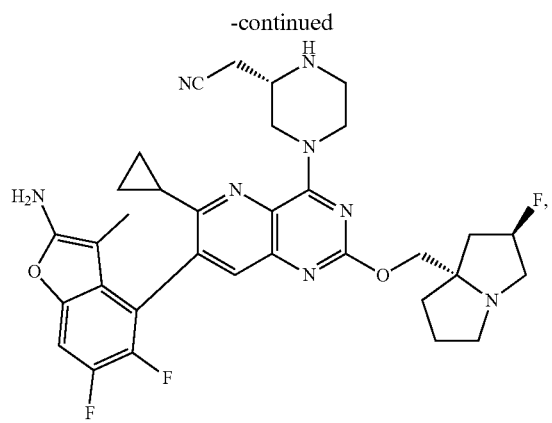
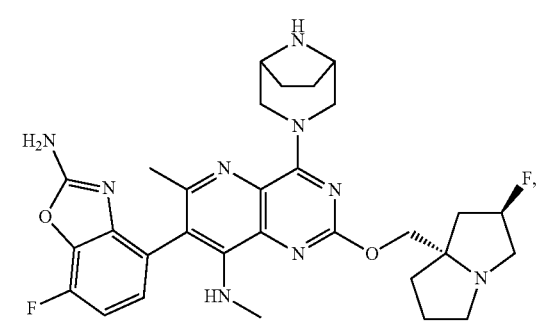
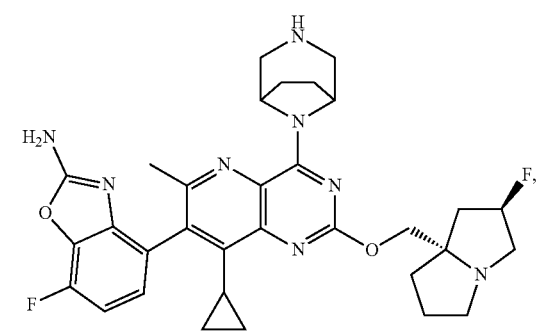
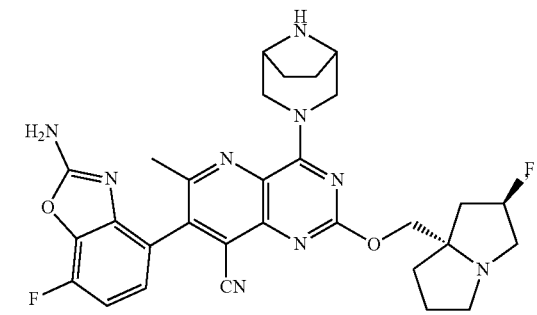
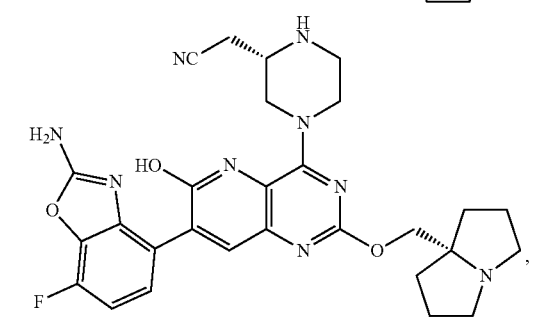
244
-continued
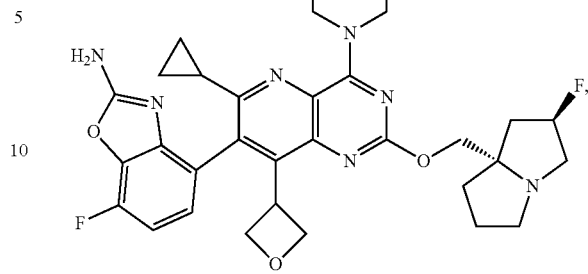
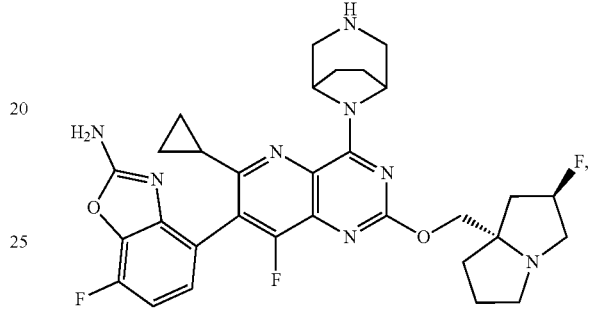
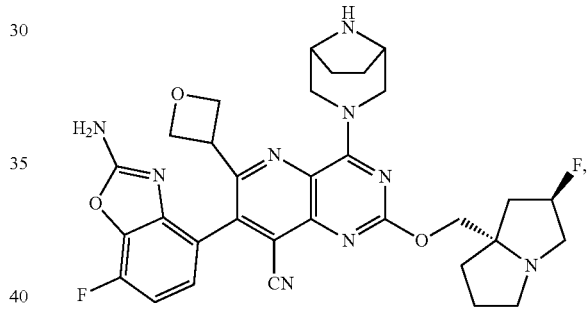
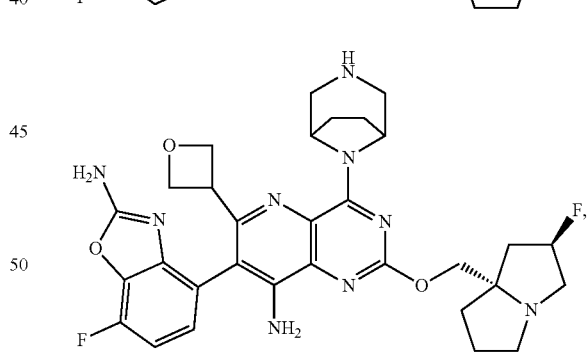
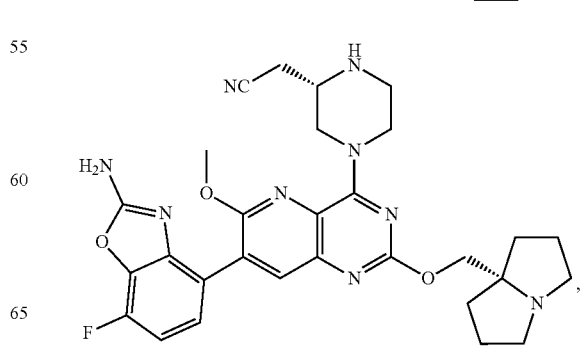

245
-continued
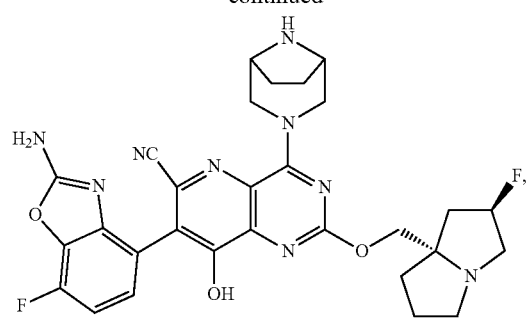
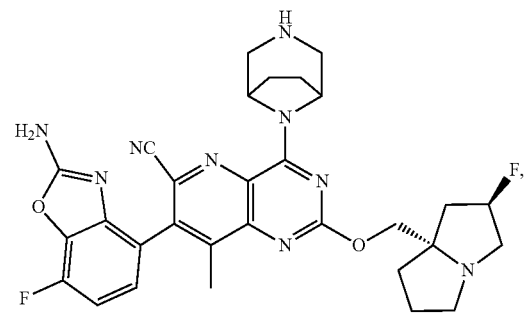
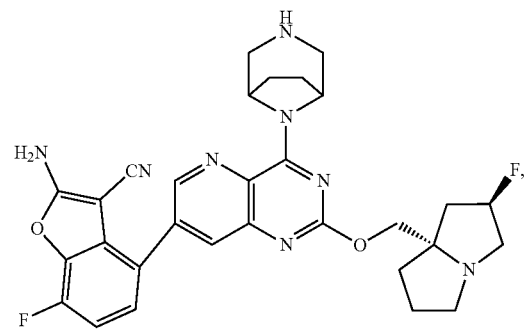
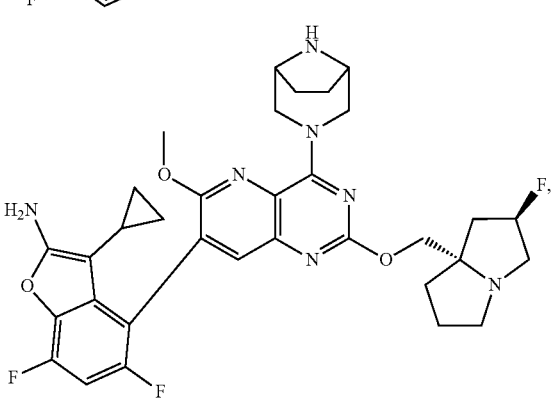
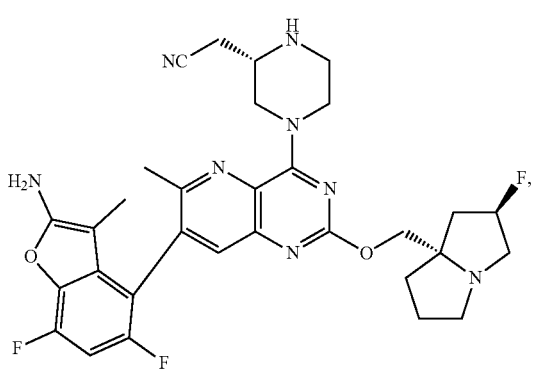
246
-continued
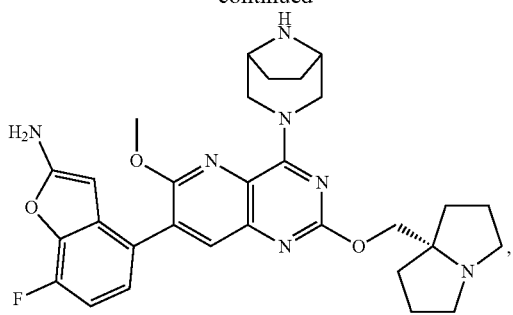
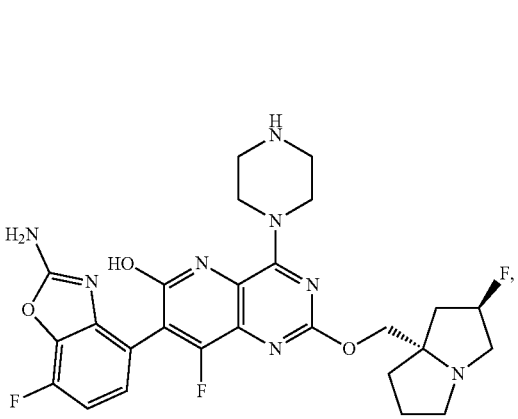
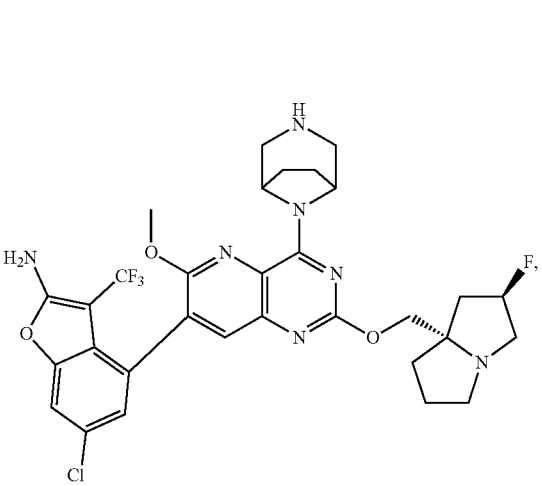
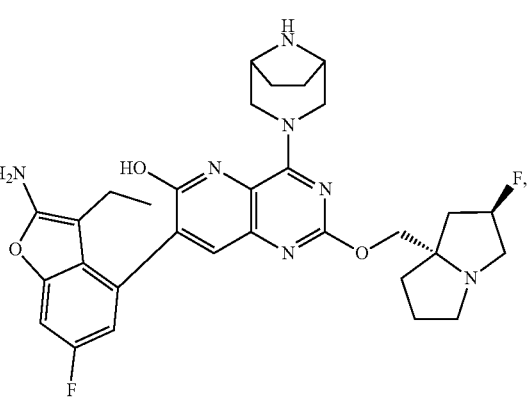

-continued
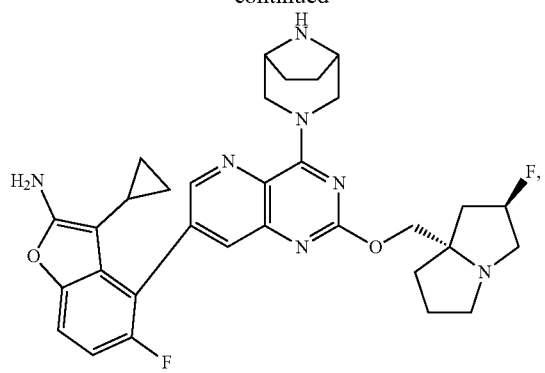
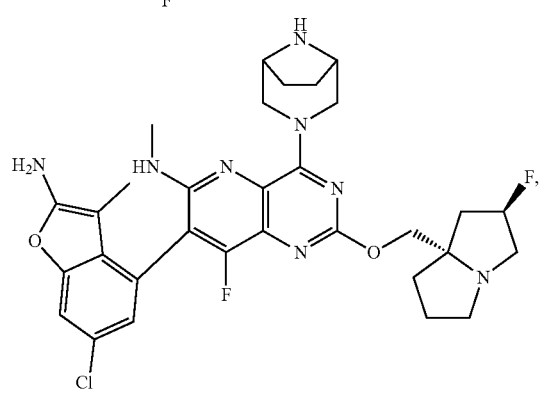
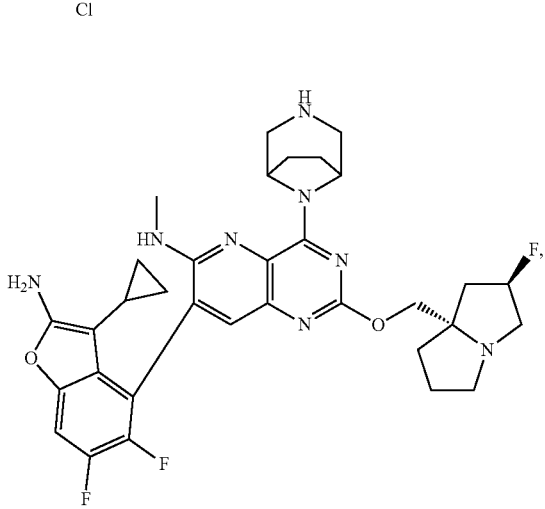
-continued
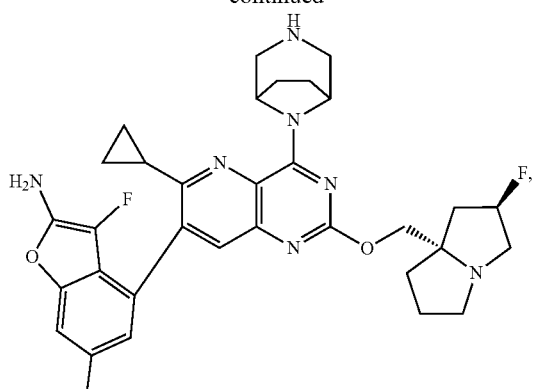
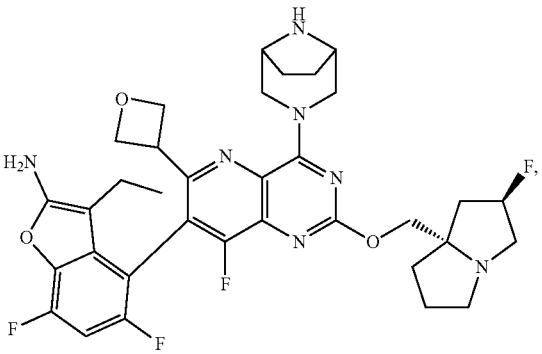
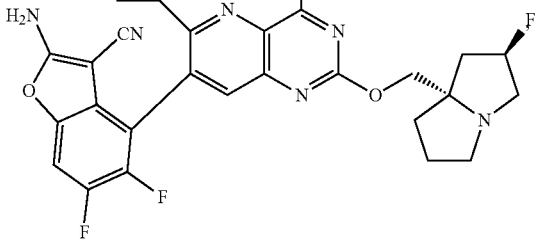

249
-continued
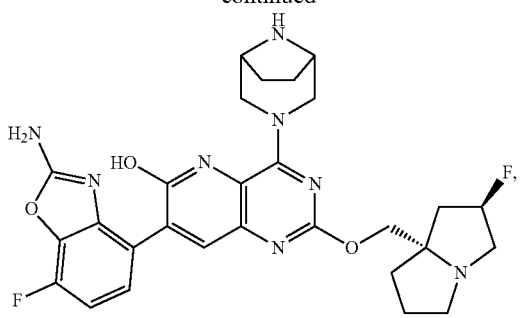
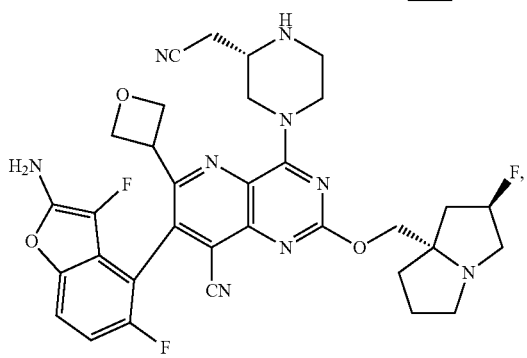
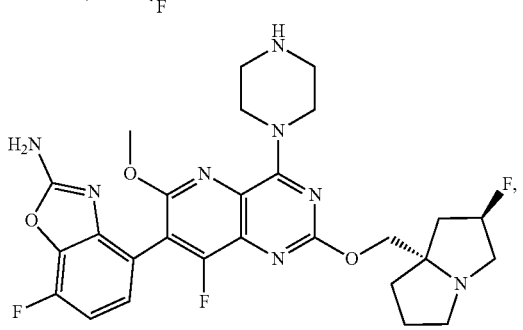
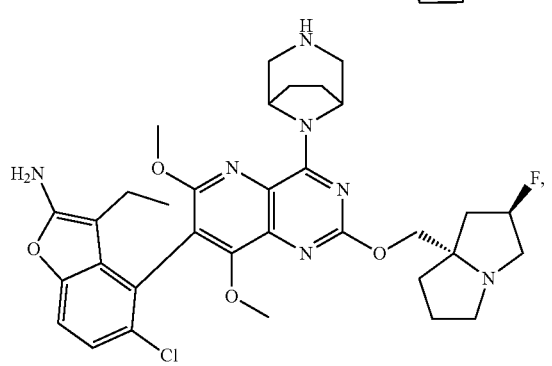
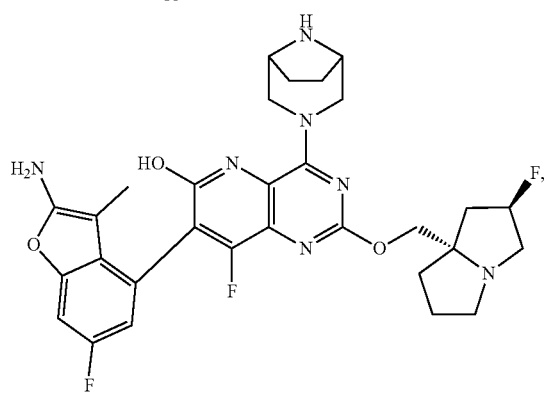
250
-continued
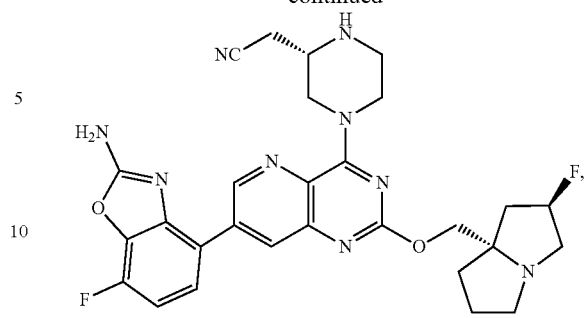
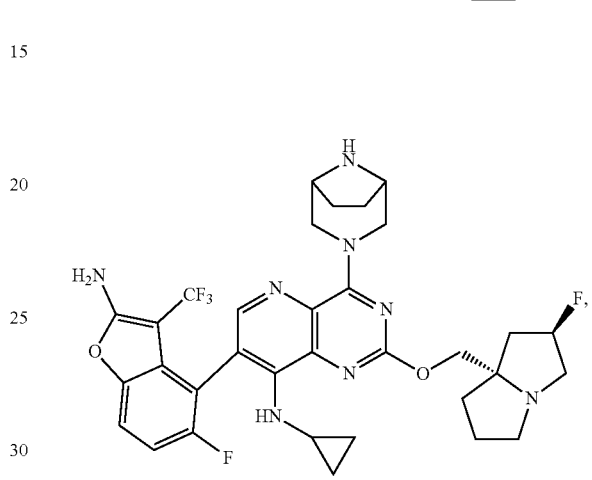
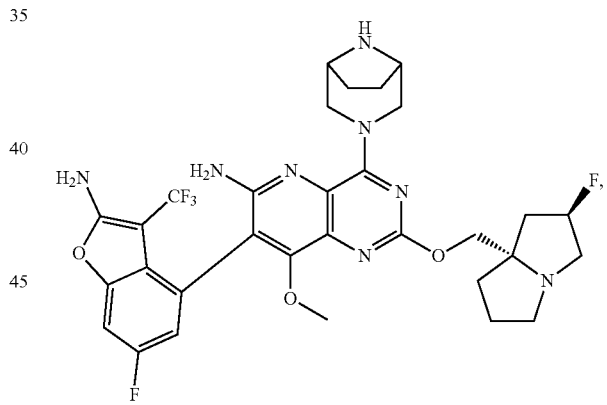
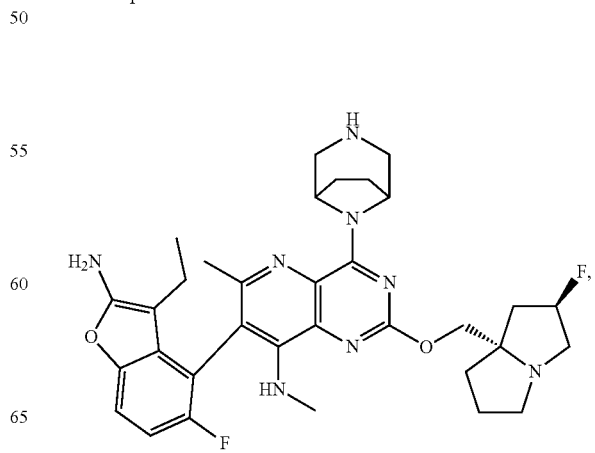

251
-continued
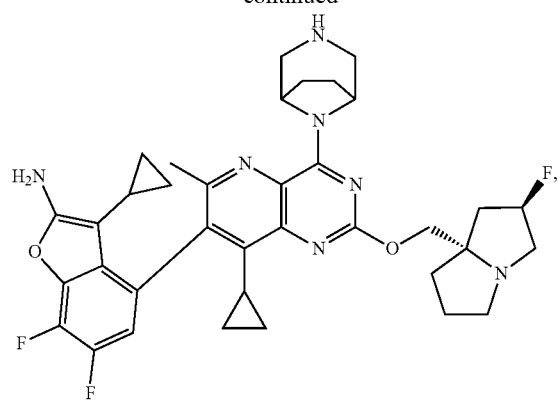
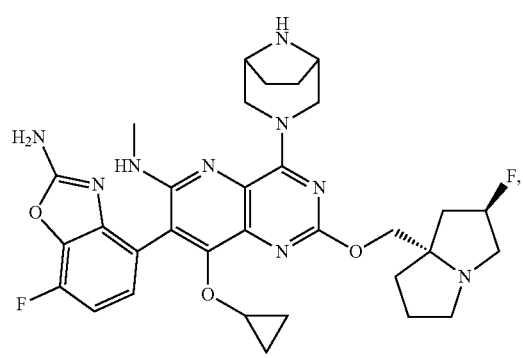
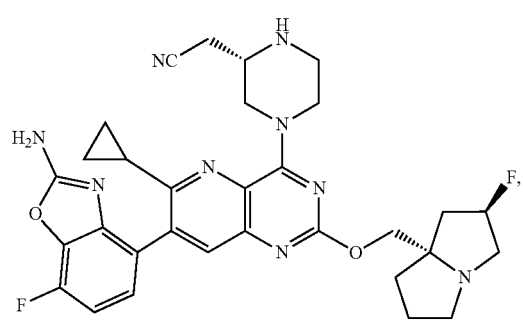
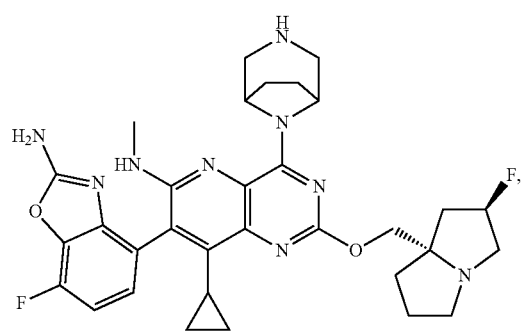
252
-continued
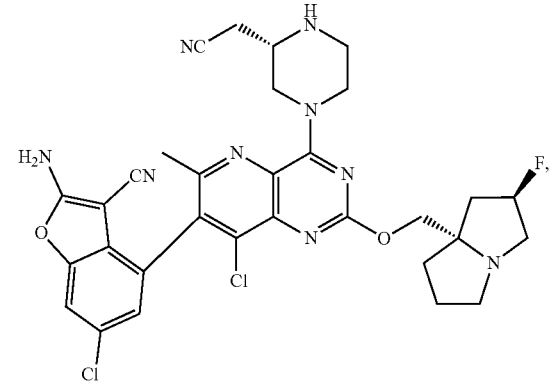
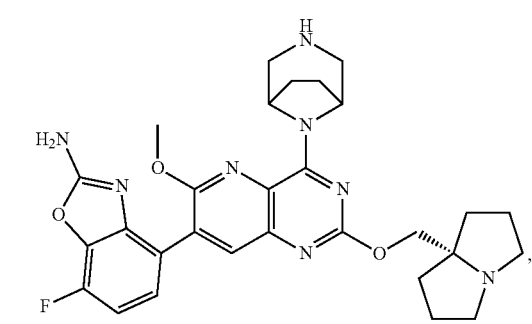
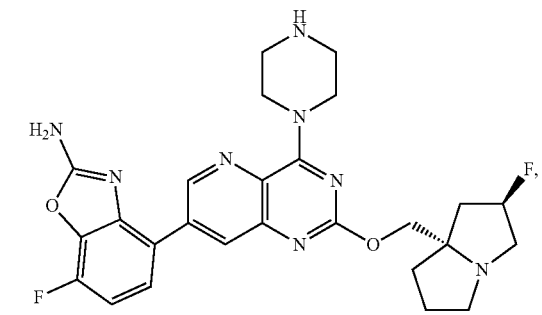
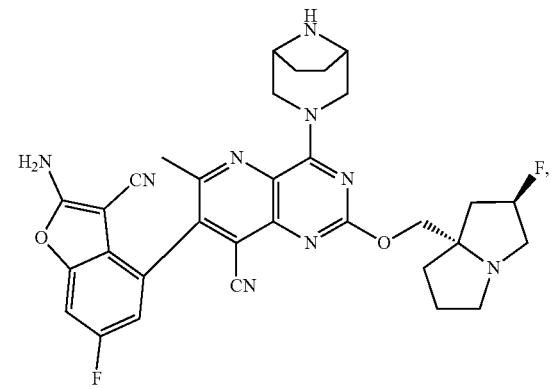

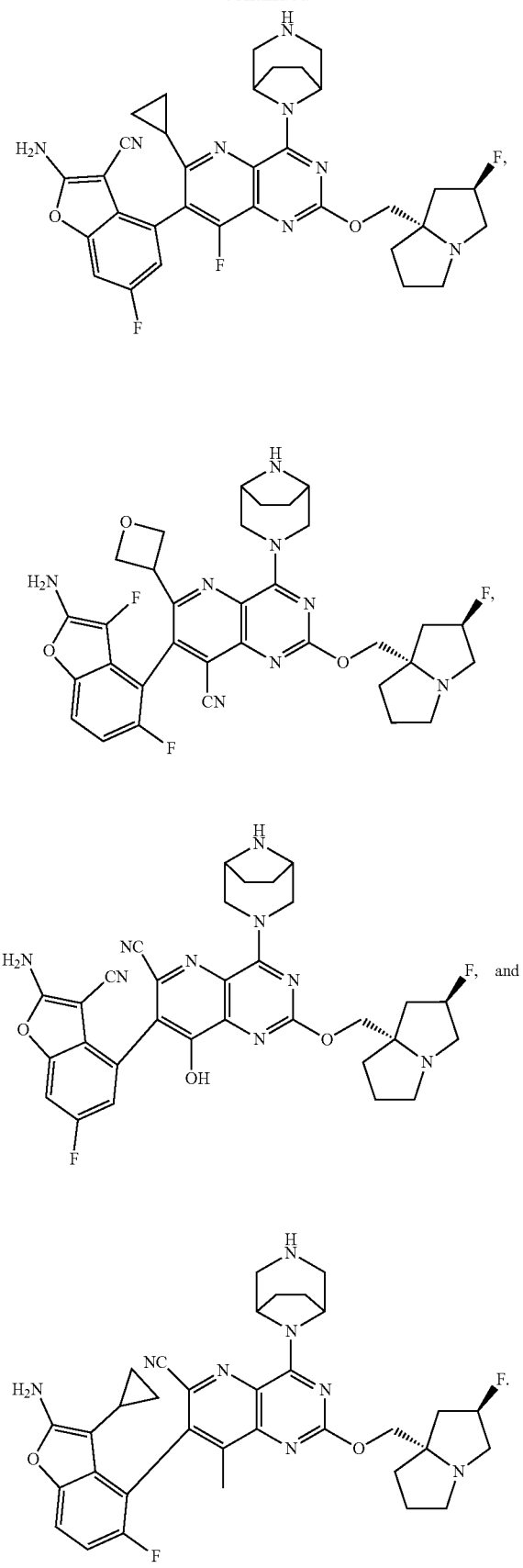
In some embodiments, the compound is selected from
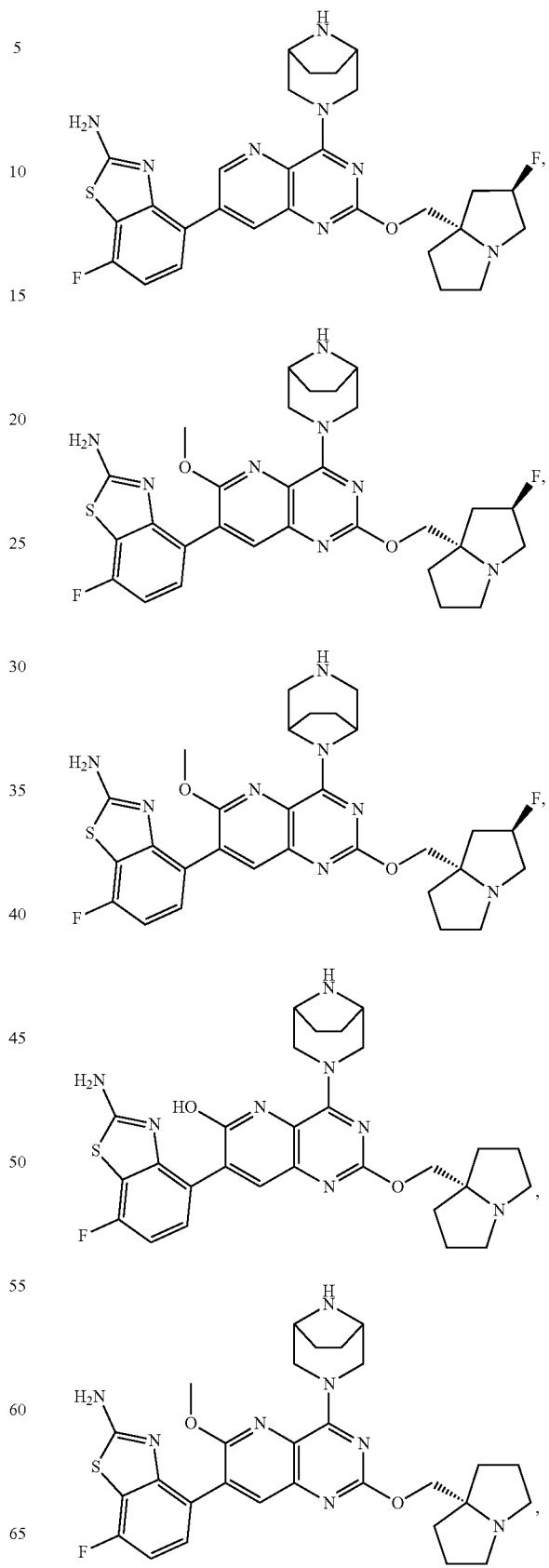

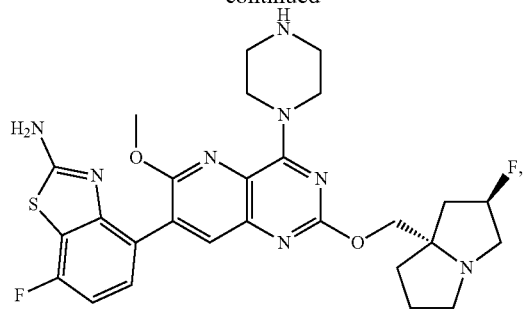

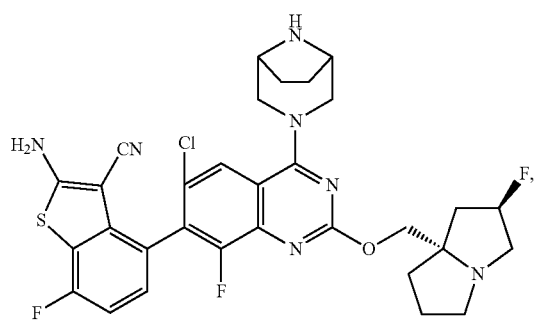

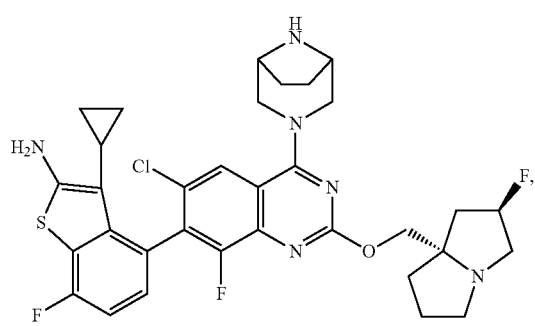

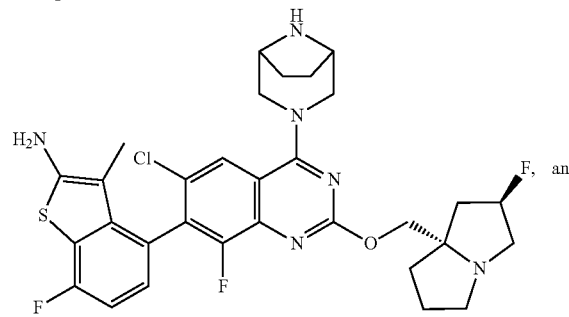

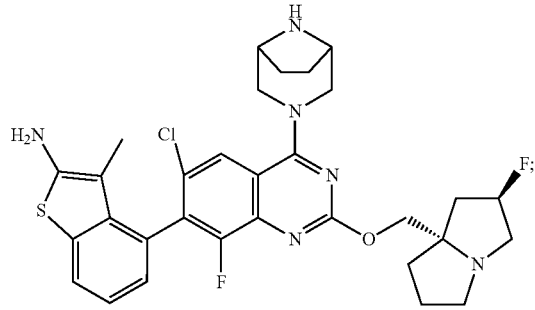

In some embodiments is a compound of Formula (I) having the structure of Formula (Ig), or a pharmaceutically acceptable salt or solvate thereof.

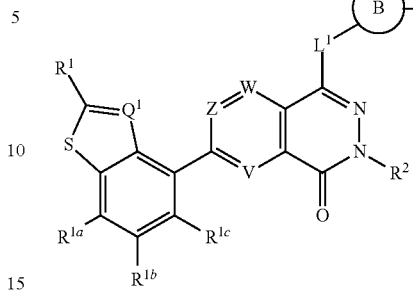

Formula (Ig)

In some embodiments is a compound of Formula (I) having the structure of Formula (Ih), or a pharmaceutically acceptable salt or solvate thereof.

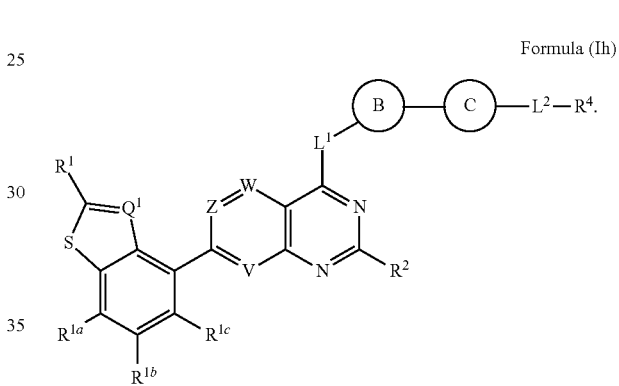

Formula (Ih)

In some embodiments is a compound of Formula (I) having the structure of Formula (Ii), or a pharmaceutically acceptable salt or solvate thereof.

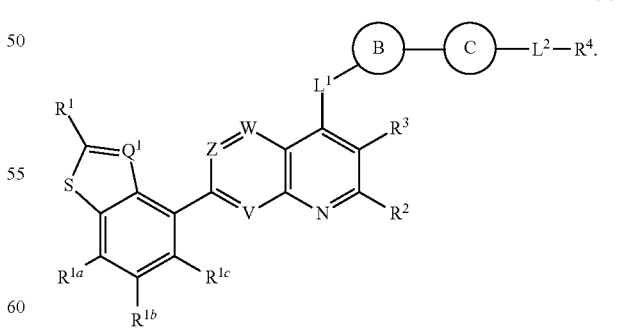

Formula (Ii)

In some embodiments is a compound of Formula (I) having the structure of Formula (Ij), or a pharmaceutically acceptable salt or solvate thereof:

Formula (Ij)

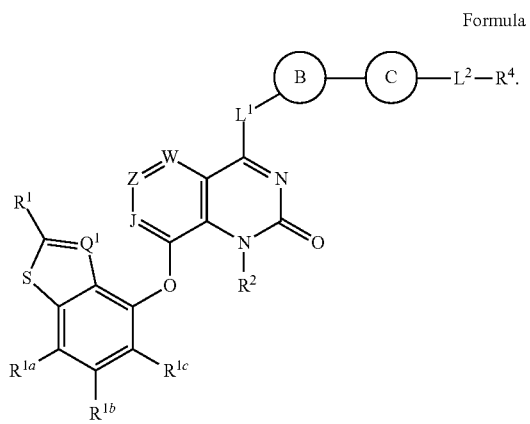

In some embodiments is a compound of Formula (I) having the structure of Formula (Ik), or a pharmaceutically acceptable salt or solvate thereof:

Formula (Ik)

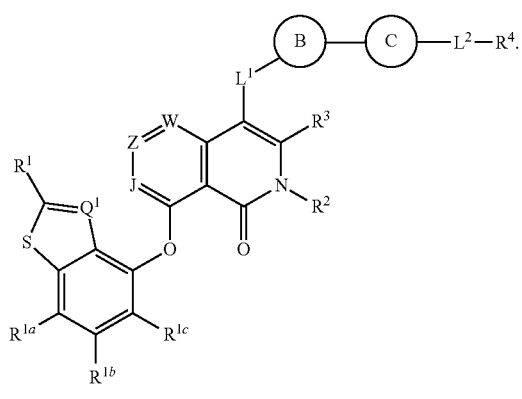

In some embodiments is a compound of Formula (I) having the structure of Formula (Im), or a pharmaceutically acceptable salt or solvate thereof.

Formula (Im)

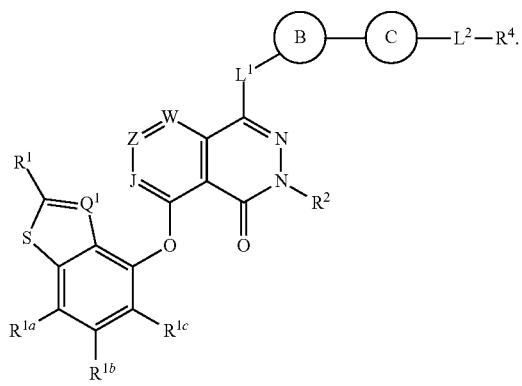

In some embodiments is a compound of Formula (I) having the structure of Formula (In), or a pharmaceutically acceptable salt or solvate thereof.

Formula (In)

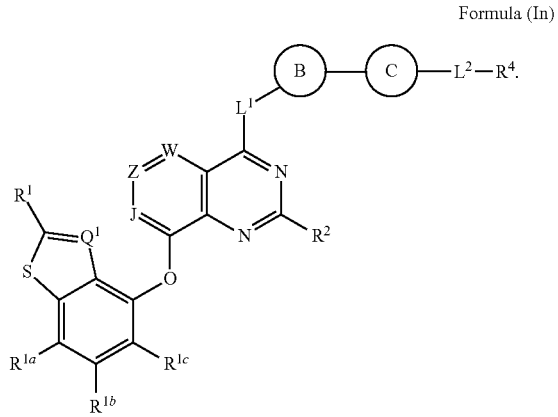

In some embodiments is a compound of Formula (I) having the structure of Formula (Io), or a pharmaceutically acceptable salt or solvate thereof:

Formula (Io)

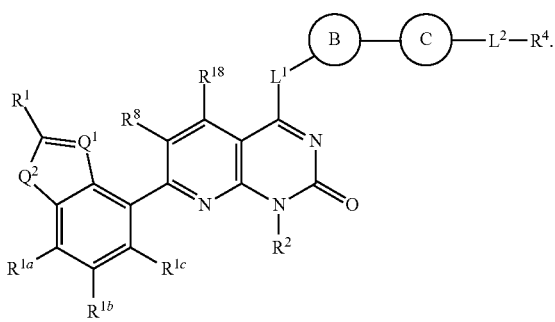

In some embodiments is a compound of Formula (I) having the structure of Formula (Ie2), or a pharmaceutically acceptable salt or solvate thereof:

Formula (Ie2)

In some embodiments is a compound of Formula (I) having the structure of Formula (IIg1), or a pharmaceutically acceptable salt or solvate thereof:

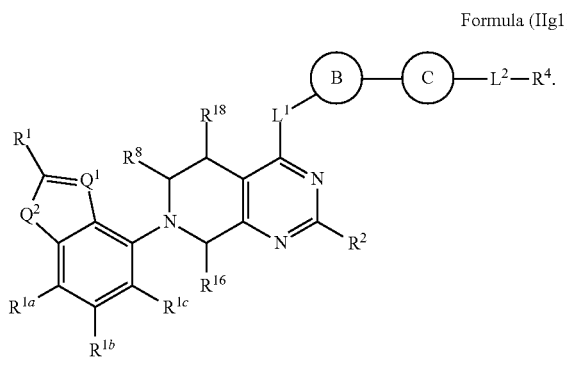

Formula (IIg1)

In some embodiments is a compound of Formula (I) having the structure of Formula (IIi1), or a pharmaceutically acceptable salt or solvate thereof:

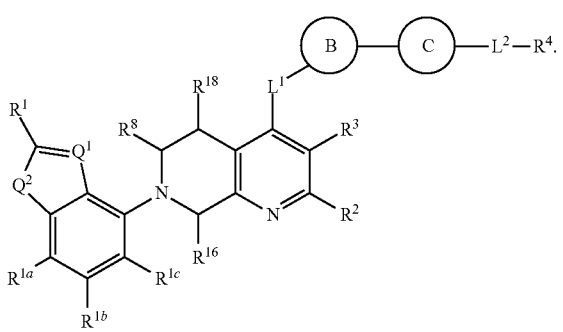

Formula (IIi1)

In some embodiments is a compound of Formula (I) having the structure of Formula (Ic3), or a pharmaceutically acceptable salt or solvate thereof:

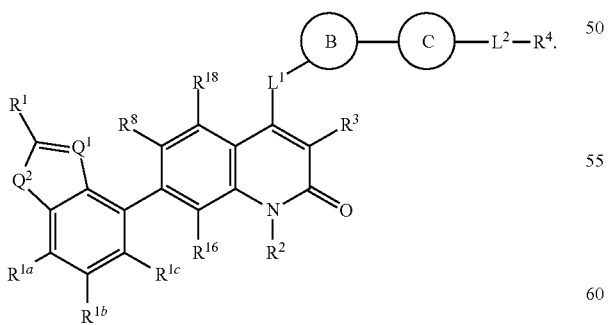

Formula (Ie3)

In some embodiments is a compound of Formula (I) having the structure of Formula (Ic4), or a pharmaceutically acceptable salt or solvate thereof:

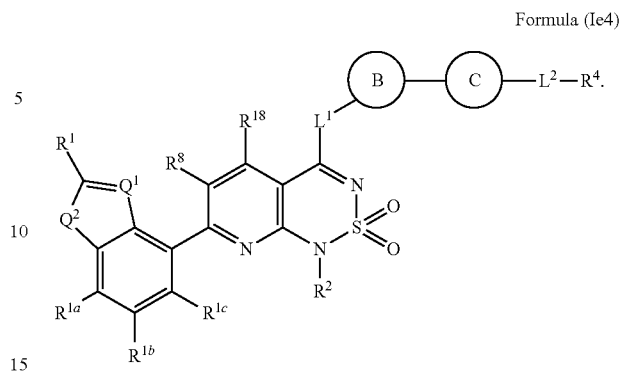

Formula (Ie4)

In some embodiments is a compound of Formula (I) having the structure of Formula (Ie5), or a pharmaceutically acceptable salt or solvate thereof:

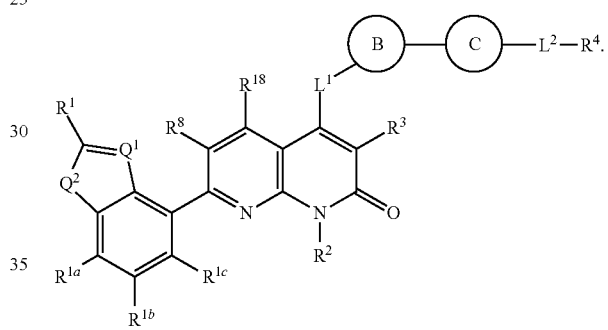

Formula (Ie5)

In some embodiments is a compound of Formula (II) having the structure of Formula (IIh1), or a pharmaceutically acceptable salt or solvate thereof:

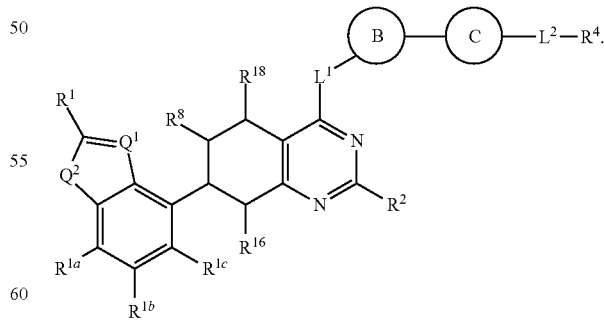

Formula (IIh1)

In some embodiments is a compound of Formula (II) having the structure of Formula (IIc1), or a pharmaceutically acceptable salt or solvate thereof:

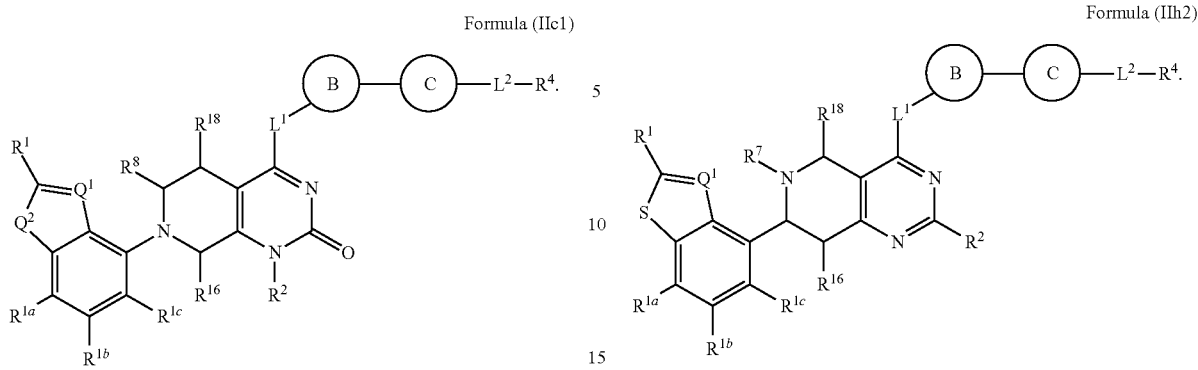

In some embodiments is a compound of Formula (II) having the structure of Formula (III), or a pharmaceutically acceptable salt or solvate thereof:

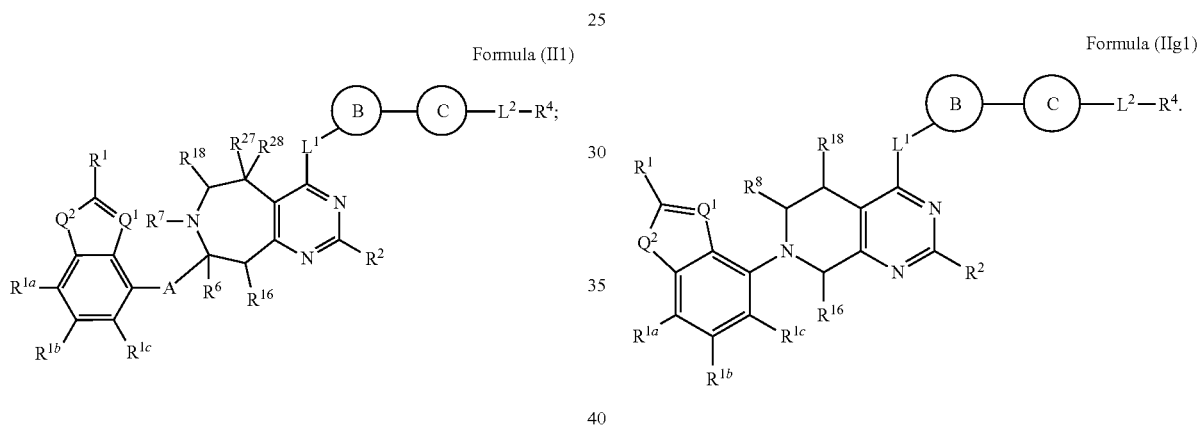

In some embodiments is a compound of Formula (II) having the structure of Formula (112), or a pharmaceutically acceptable salt or solvate thereof:

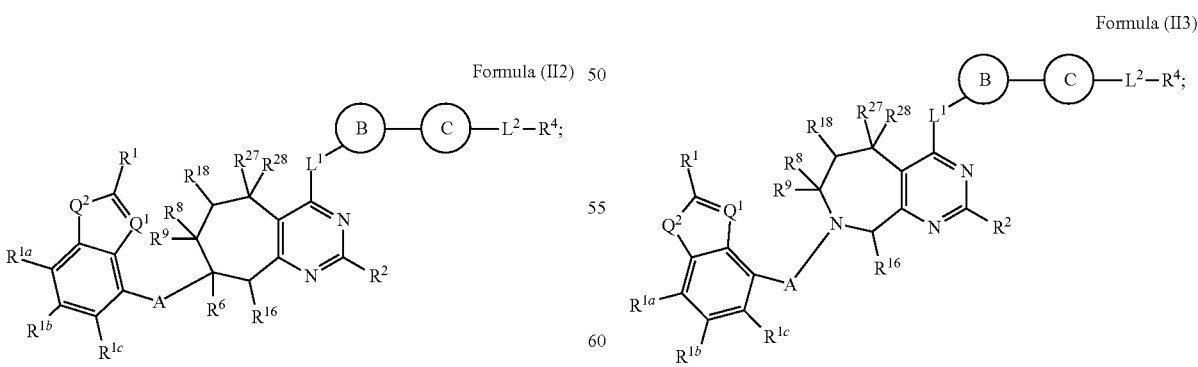

In some embodiments is a compound of Formula (II) having the structure of Formula (IIh2), or a pharmaceutically acceptable salt or solvate thereof:

In some embodiments is a compound of Formula (II) having the structure of Formula (IIg1), or a pharmaceutically acceptable salt or solvate thereof:

In some embodiments is a compound of Formula (II) having the structure of Formula (II3), or a pharmaceutically acceptable salt or solvate thereof:

In some embodiments is a compound of Formula (I) having the structure of Formula (Ih2), or a pharmaceutically acceptable salt or solvate thereof:

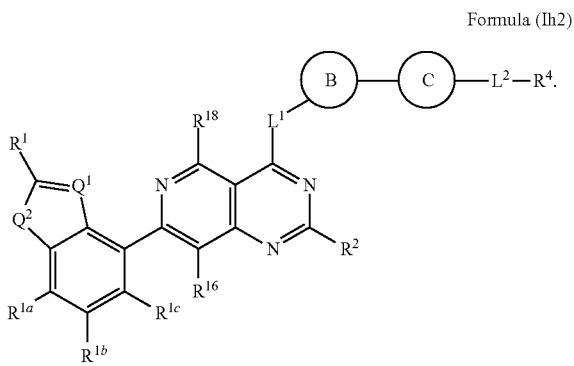

Formula (Ih2)

The compounds described herein (e.g., Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2)) may be in the form of a prodrug, pharmaceutically acceptable salt, or solvate of the compound (e.g., Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2)).

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i.e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999)(all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. In some embodiments, the following synthetic methods may be utilized.

General Synthetic Method 1

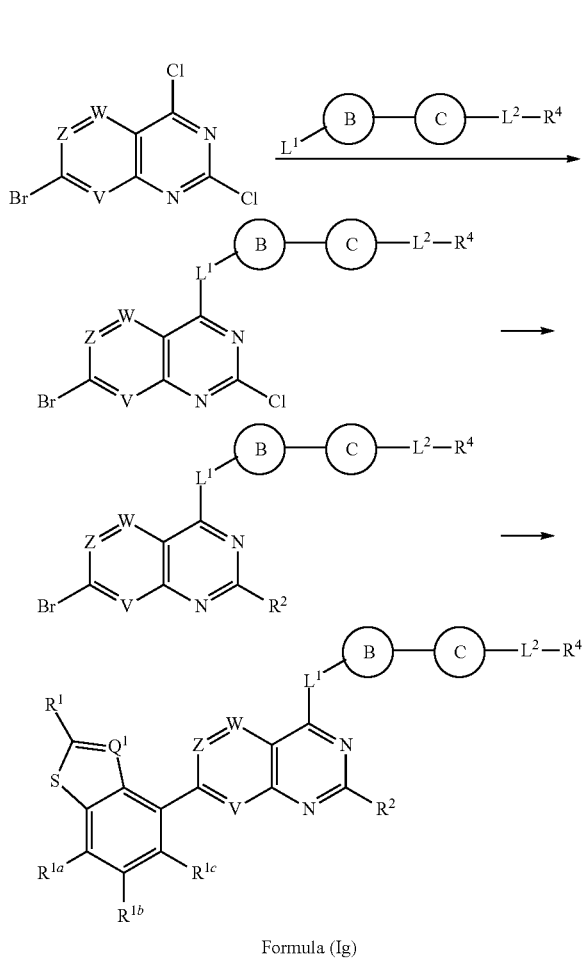

Formula (Ig)

General Synthetic Method 2

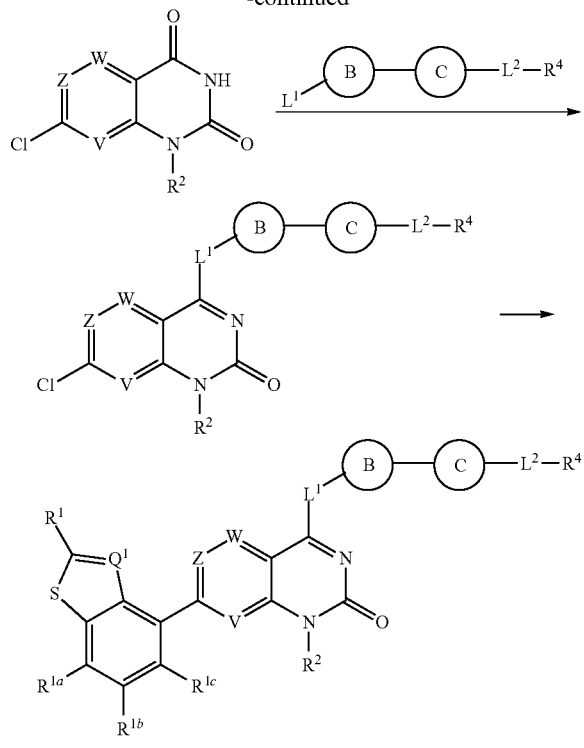

Formula (Ie)

In some embodiments, the compounds of the present invention exhibit one or more functional characteristics disclosed herein. For example, a subject compound binds to a Ras protein, Kras protein or a mutant form thereof. In some embodiments, a subject compound binds specifically and also inhibits a Ras protein, Kras protein or a mutant form thereof. In some embodiments, a subject compound selectively inhibits a Kras mutant relative to a wildtype Kras. In some embodiment, a subject compound selectively inhibits KrasG12D and/or KrasG12V relative to wildtype Kras. In some embodiments, the IC50 of a subject compound (including those shown in Table 1) for a Kras mutant (e.g., including G12D) is less than about less than about 5 uM, less than about 1 uM, less than about 50n nM, less than about 10 nM, less than about 1 nM, less than about 0.5 nM, less than about 100 pM, or less than about 50 pM, as measured in an in vitro assay known in the art or exemplified herein.

In some embodiments, a subject compound of the present disclosure is capable of reducing Ras signaling output. Such reduction can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, and (v) reduction (e.g., inhibition) of cell growth of Ras-driven tumor cells (e.g., those derived from a tumor cell line disclosed herein). In some cases, the reduction in Ras signaling output can be evidenced by two, three, four or all of (i)-(v) above.

It shall be understood that different aspects of the invention can be appreciated individually, collectively, or in combination with each other. Various aspects of the invention described herein may be applied to any of the particular applications disclosed herein. The compositions of matter including compounds of any formulae disclosed herein in the composition section of the present disclosure may be utilized in the method section including methods of use and production disclosed herein, or vice versa.

Methods

In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is a solid tumor or a hematological cancer. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof, wherein the cancer is a solid tumor or a hematological cancer. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is a solid tumor. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof, wherein the cancer is a solid tumor. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is selected from prostate cancer, brain cancer, colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is a hematological cancer. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof, wherein the cancer is a hematological cancer. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof, wherein the cancer is a hematological cancer selected from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, and pre-leukemia. In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL). In some embodiments is a method of treating cancer in a subject in need thereof, comprising administering to the subject a therapeutically effective amount of a compound Formula (I), (Ia), (Ib), (Ic), (Id), (Ie), (If), (Ig), (Ih), (Ii), (Ij), (Ik), (Im), (In), (Io), (Ip), (II), (IIa), (IIb), (IIc), (IId), (IIe), (IIf), (IIg), (IIh), (IIi), (IIj), (Ia'), (Ib'), (Ic'), (Id'), (Ie'), (If'), (Ig'), (Ih'), (Ii'), (Ij'), (Ik'), (Im'), (In'), (Io'), (II'), (IIa'), (IIb'), (IIc'), (IId'), (IIe'), (IIf'), (IIg'), (IIh'), (IIi'), (IIj'), (Ia"), (Ib"), (Ic"), (Id"), (Ie"), (If"), (Ig"), (Ih"), (Ii"), (Ij"), (Ik"), (Im"), (In"), (Io"), (II"), (IIa"), (IIb"), (IIc"), (IId"), (IIe"), (IIf"), (IIg"), (IIh"), (IIi"), (IIj"), (Ia'''), (Ib'''), (Ic'''), (Id'''), (Ie'''), (If'''), (Ig'''), (Ih'''), (Ii'''), (Ij'''), (Ik'''), (Im'''), (In'''), (Io'''), (II'''), (IIa'''), (IIb'''), (IIc'''), (IId'''), (IIe'''), (IIf'''), (IIg'''), (IIh'''), (IIi'''), (IIj'''), (Iha), (Ihb), (Ihc), (Ihd), (Ihe), (Ihf), (Iha'), (Ihb'), (Ihc'), (Ihd'), (Ihe'), (Ihf'), (Iha"), (Ihb"), (Ihc"), (Ihd"), (Ihe"), (Ihf"), (Iha'''), (Ihb'''), (Ihc'''), (Ihd'''), (Ihe'''), (Ihf'''), (Ihg), (Ihh), (Ihi), (Ihj), (Ihk), (Ihl), (Ihm), (Ihn), (Ia'1), (Ic'1), (Ie'1), (If'1), (Ig'1), (Ih'1), (Ii'1), (Ij'1), (Ik'1), (Im'1), (In'1), (Io'1), (II'1), (IIa'1), (IIb'1), (IIc'1), (IId'1), (IIe'1), (IIf'1), (IIg'1), (IIh'1), (IIi'1), (Iha1), (Ihd1), (Iha'1), (Ihd'1), (Iha"1), (Ihd"1), (Ihc'''1), (Ihf'''1), (Ihg1), (Ihj1), (Ihm1), (Ihn1), (Ie2), (Ie3), (Ie4), (Ie5), (IIg1), (IIi1), (IIh1), (IIc1), (II1), (II2), (IIh2), (IIg1), (II3), or (Ih2), or a pharmaceutically acceptable salt or solvate thereof, wherein the cancer is one or more cancers selected from the group consisting of chronic lymphocytic leukemia (CLL), acute myeloid leukemia (AML), T-cell acute lymphoblastic leukemia (T-ALL), B cell acute lymphoblastic leukemia (B-ALL), and/or acute lymphoblastic leukemia (ALL).

Any of the treatment methods disclosed herein can be administered alone or in combination or in conjunction with another therapy or another agent. By "combination" it is meant to include (a) formulating a subject composition containing a subject compound together with another agent, and (b) using the subject composition separate from the another agent as an overall treatment regimen. By "conjunction" it is meant that the another therapy or agent is administered either simultaneously, concurrently or sequentially with a subject composition comprising a compound disclosed herein, with no specific time limits, wherein such conjunctive administration provides a therapeutic effect.

In some embodiment, a subject treatment method is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, and combinations thereof.

In one embodiment, a subject treatment method is combined with a chemotherapeutic agent.

Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzamab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). Additional chemotherapeutic agents contemplated for use in combination include busulfan (Myleran®), busulfan injection (Busulfex®), cladribine (Leustatin®), cyclophosphamide (Cytoxan® or Neosar®), cytarabine, cytosine arabinoside (Cytosar-U®), cytarabine liposome injection (DepoCyt®), daunorubicin hydrochloride (Cerubidine®), daunorubicin citrate liposome injection (DaunoXome®), dexamethasone, doxorubicin hydrochloride (Adriamycin®, Rubex®), etoposide (Vepesid®), fludarabine phosphate (Fludara®), hydroxyurea (Hydrea®), Idarubicin (Idamycin®), mitoxantrone (Novantrone®), Gemtuzumab Ozogamicin (Mylotarg®), anastrozole (Arimidex®), bicalutamide (Casodex®), bleomycin sulfate (Blenoxane®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), dacarbazine (DTIC-Dome®), dactinomycin (Actinomycin D, Cosmegan), dexamethasone, docetaxel (Taxotere®), 5-fluorouracil (Adrucil®, Efudex®), flutamide (Eulexin®), tezacitibine, Gemcitabine (difluorodeoxycitidine), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Anti-cancer agents of particular interest for combinations with a compound of the present invention include: anthracyclines; alkylating agents; antimetabolites; drugs that inhibit either the calcium dependent phosphatase calcineurin or the p70S6 kinase FK506) or inhibit the p70S6 kinase; mTOR inhibitors; immunomodulators; anthracyclines; vinca alkaloids; proteosome inhibitors; GITR agonists; protein tyrosine phosphatase inhibitors; a CDK4 kinase inhibitor; a BTK inhibitor; a MKN kinase inhibitor; a DGK kinase inhibitor; or an oncolytic virus.

Exemplary antimetabolites include, without limitation, pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), azacitidine (Vidaza®), decitabine and gemcitabine (Gemzar®). Preferred antimetabolites include, cytarabine, clofarabine and fludarabine.

Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, RevimmuneTM), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

In an aspect, compositions provided herein can be administered in combination with radiotherapy such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L1, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, P 5-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1 BB antibody. In some embodiments, the checkpoint immune blockade agents are selected from the group consisting of anti-PD-L$^1$ antibodies (alezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., C9B7W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldeskeukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some embodiments, any of the compounds herein that is capable of binding a Ras protein (e.g., KRAS) to modulate activity of such Ras protein may be administered in combination or in conjunction with one or more pharmacologically active agents comprising (1) an inhibitor of MEK (e.g., MEK1, MEK2) or of mutants thereof (e.g., trametinib, cobimetinib, binimetinib, selumetinib, refametinib); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a; SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-7112, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor (e.g., 6-(4-amino-4-methylpiperidin-1-yl)-3-(2,3-dichlorophenyl) pyrazin-2-amine), as well as SHIP1 inhibitors; (27) an inhibitor of SRC(e.g., dasatinib); (28) an inhibitor of JAK (e.g., tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib), (31) a ROS1 inhibitor (e.g., entrectinib), (32) an inhibitor of FLT3, HDAC, VEGFR, PDGFR, LCK, Bcr-Abl or AKT or (33) an inhibitor of KrasG12C mutant (e.g., including but not limited to AMG510, MRTX849, and any covalent inhibitors binding to the cysteine residue 12 of Kras, the structures of these compounds are publically known)(e.g., an inhibitor of Ras G12C as described in US20180334454, US20190144444, US20150239900, U.S. Pat. No. 10,246, 424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety), (34) a SHC inhibitor (e.g., PP2, AID371185), (35) a GAB inhibitor (e.g., GAB-0001), (36) a GRB inhibitor, (37) a PI-3 kinase inhibitor (e.g., Idelalisib, Copanlisib, Duvelisib, Alpelisib, Taselisib, Perifosine, Buparlisib, Umbralisib, NVP-BEZ235-AN), (38) a MARPK inhibitor, (39)CDK4/6 (e.g., palbociclib, ribociclib, abemaciclib), or (40) MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197), or (41) an inhibitor of SHP pathway including SHP2 inhibitor (e.g., 6-(4-amino-4-methylpiperidin-1-yl)-3-(2,3-dichlorophenyl) pyrazin-2-amine, RMC-4630, TNO155

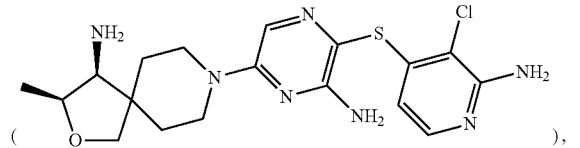
JAB-3068

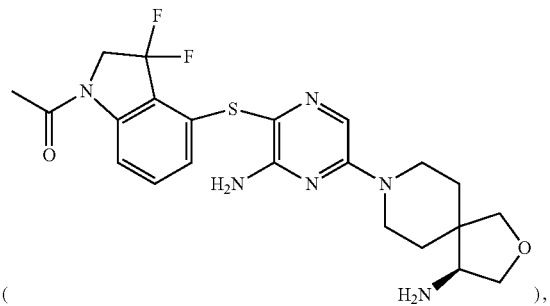
IACS-13909/BBP-398

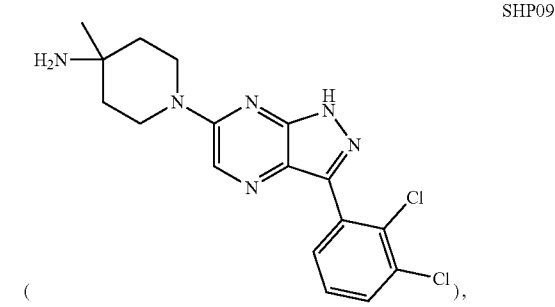
SHP099

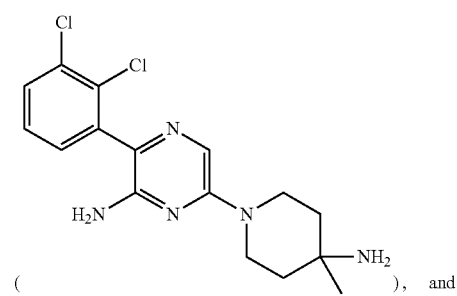
ERAS-601
and

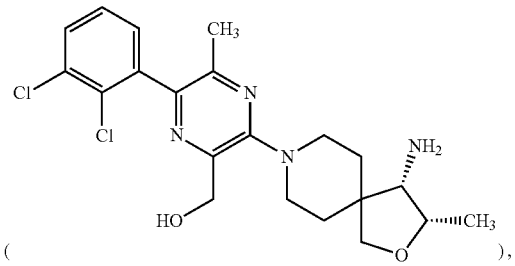
RMC-4550 as well as SHP1 inhibitors. In some embodiments, any of the compounds herein that is capable of binding a Ras protein (e.g., Kras) to modulate activity of such Ras protein may be administered in combination or in conjunction with one or more checkpoint immune blockade agents (e.g., anti-PD-1 and/or anti-PD-L1 antibody, anti-CLTA-4 antibody). In some embodiments, any of the compounds herein that is capable of binding a Ras protein (e.g., KRAS) to modulate activity of such Ras protein may be administered in combination or in conjunction with one or more pharmacologically active agents comprising an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHIP1, SHIP2, SHP2, SRC, JAK, PARP, BTK, FLT3, HDAC, VEGFR, PDGFR, LCK, Bcr-Abl, AKT, KrasG12C mutant, and ROS1. Where desired, the additional agent can be an inhibitor against one or more targets selected from the group of: MEK, epidermal growth factor receptor (EGFR), FGFR1, FGFR2, FGFR3, mitotic kinase, topoisomerase, ALK, c-MET, ErbB2, AXL, NTRK1, RET, A-Raf, B-Raf, C-Raf, ERK, MDM2, mTOR, BET, IGF1/2, IGF1-R, CDK9, SHP2, SRC, JAK, PARP, BTK, FLT3, HDAC, VEGFR, PDGFR, LCK, Bcr-Abl, AKT, KrasG12C mutant, and ROS1. In some embodiments, any of the compounds herein that is capable of binding a Ras protein (e.g., KRAS, mutant Ras protein) to modulate activity of such Ras protein (e.g., mutant Ras protein such as G12D mutant KRas protein) may be administered in combination or in conjunction with one or more additional pharmacologically active agents comprising an inhibitor of SOS(e.g., SOS1, SOS2) or of mutants thereof. In embodiments, the additional pharmacologically active agent administered in combination or in conjunction with a compound described herein (e.g., compound capable of binding a Ras protein) is an inhibitor of SOS(e.g., SOS1, SOS2). In embodiments, the additional pharmacologically active agent administered in combination or in conjunction with a compound (e.g., compound capable of binding a Ras protein) described herein is an inhibitor of SOS(e.g., SOS1, SOS2). In embodiments, the additional pharmacologically active agent administered in combination or in conjunction with a compound (e.g., compound capable of binding a Ras protein) described herein is an inhibitor of SOS(e.g., SOS1, SOS2) selected from RMC-5845, BI-3406 (

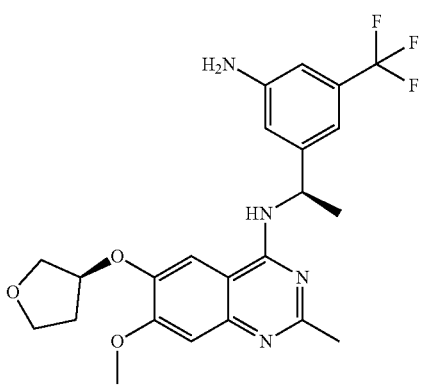 [SMILES: COc1cc2nc(C)nc(N[C@H](C)c3cc(N)cc(C(F)(F)F)c3)c2cc1O[C@H]1CCOC1]

), BI-1701963, and BAY 293 (

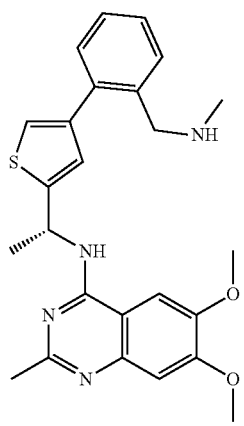

). In embodiments, the additional pharmacologically active agent administered in combination or in conjunction with a compound described herein (e.g., compound capable of binding a Ras protein) is an inhibitor of SOS(e.g., SOS1, SOS2) described in WO2021092115, WO2018172250, WO2019201848, WO2019122129, WO2018115380, WO2021127429, WO2020180768, or WO2020180770, all of which are herein incorporated by reference in their entirety for all purposes.

In combination therapy, a compound provided herein and other anti-cancer agent(s) may be administered either simultaneously, concurrently or sequentially with no specific time limits, wherein such administration provides therapeutically effective levels of the two compounds in the body of the patient.

In some embodiments, the compound of the present disclosure and the other anti-cancer agent(s) are generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

An antibiotic can be administered to a subject as part of a therapeutic regime. An antibiotic can be administered at a therapeutically effective dose. An antibiotic can kill or inhibit growth of bacteria. An antibiotic can be a broad spectrum antibiotic that can target a wide range of bacteria. Broad spectrum antibiotics, either a $3^{rd}$ or $4^{th}$ generation, can be cephalosporin or a quinolone. An antibiotic can also be a narrow spectrum antibiotic that can target specific types of bacteria. An antibiotic can target a bacterial cell wall such as penicillins and cephalosporins. An antibiotic can target a cellular membrane such as polymyxins. An antibiotic can interfere with essential bacterial enzymes such as antibiotics: rifamycins, lipiarmycins, quinolones, and sulfonamides. An antibiotic can also be a protein synthesis inhibitor such as macrolides, lincosamides, and tetracyclines. An antibiotic can also be a cyclic lipopeptide such as daptomycin, glycylcyclines such as tigecycline, oxazolidiones such as linezolid, and lipiarmycins such as fidaxomicin. In some cases, an antibiotic can be $1^{st}$ generation, $2^{nd}$ generation, $3^{rd}$ generation, $4^{th}$ generation, or $5^{th}$ generation. A first-generation antibiotic can have a narrow spectrum. Examples of $1^{st}$ generation antibiotics can be penicillins (Penicillin G or Penicillin V), Cephalosporins (Cephazolin, Cephalothin, Cephapirin, Cephalethin, Cephradin, or Cephadroxin). In some cases, an antibiotic can be $2^{nd}$ generation. $2^{nd}$ generation antibiotics can be a penicillin (Amoxicillin or Ampicillin), Cephalosporin (Cefuroxime, Cephamandole, Cephoxitin, Cephaclor, Cephrozil, Loracarbef). In some cases, an antibiotic can be $3^{rd}$ generation. A $3^{rd}$ generation antibiotic can be penicillin (carbenicillin and ticarcillin) or cephalosporin (Cephixime, Cephtriaxone, Cephotaxime, Cephtizoxime, and Cephtazidime). An antibiotic can also be a $4^{th}$ generation antibiotic. A $4^{th}$ generation antibiotic can be Cephipime. An antibiotic can also be $5^{th}$ generation. $5^{th}$ generation antibiotics can be Cephtaroline or Cephtobiprole.

In some cases, an anti-viral agent may be administered as part of a treatment regime. In some cases, a herpes virus prophylaxis can be administered to a subject as part of a treatment regime. A herpes virus prophylaxis can be valacyclovir (Valtrex). Valtrex can be used orally to prevent the occurrence of herpes virus infections in subjects with positive HSV serology. It can be supplied in 500 mg tablets. Valacyclovir can be administered at a therapeutically effective amount.

In some cases, a treatment regime may be dosed according to a body weight of a subject. In subjects who are determined obese (BMI >35) a practical weight may need to be utilized. BMI is calculated by: BMI=weight (kg)/[height (m)]$^2$.

Body weight may be calculated for men as 50 kg+2.3* (number of inches over 60 inches) or for women 45.5 kg+2.3 (number of inches over 60 inches). An adjusted body weight may be calculated for subjects who are more than 20% of their ideal body weight. An adjusted body weight may be the sum of an ideal body weight+(0.4×(Actual body weight-ideal body weight)). In some cases, a body surface area may be utilized to calculate a dosage. A body surface area (BSA) may be calculated by: BSA (m2)=√Height (cm)*Weight (kg)/3600.

In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, thereby modulating the activity of the Ras protein. In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein said modulating comprises inhibiting the Ras protein activity. In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the Ras protein is a K-Ras protein. In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the Ras protein is a G12D or G12V mutant K-Ras. In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the Ras protein is a G12D mutant K-Ras. In some embodiments is a method of modulating activity of a Ras protein, comprising contacting a Ras protein with an effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein the Ras protein is a G12V mutant K-Ras.

In some embodiments, provided is a method of reducing Ras signaling output in a cell by contacting the cell with a compound of the present disclosure. A reduction in Ras signalling can be evidenced by one or more members of the following: (i) an increase in steady state level of GDP-bound Ras protein; (ii) a reduction of phosphorylated AKTs473, (iii) a reduction of phosphorylated ERKT202/y204, (iv) a reduction of phosphorylated S6S235/236, and (v) reduction (e.g., inhibition) of cell growth of Ras-driven tumor cells (e.g., those derived from a tumor cell line). In some cases, the reduction in Ras signaling output can be evidenced by two, three, four or all of (i)-(v) above. In some embodiments, the reduction any one or more of (i)-(v) can be 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, or more as compared to control untreated with a subject compound. A reduction in cell growth can be demonstrated with the use of tumor cells or cell lines. A tumor cell line can be derived from a tumor in one or more tissues, e.g., pancreas, lung, ovary, biliary tract, intestine (e.g., small intestine, large intestine (i.e. colon)), endometrium, stomach, hematopoietic tissue (e.g., lymphoid tissue), etc. Examples of the tumor cell line with a K-Ras mutation may include, but are not limited to, A549 (e.g., K-Ras G12S), AGS(e.g., K-Ras G12D), ASPC1 (e.g., K-Ras G12D), Calu-6 (e.g., K-Ras $Q^{61}K$), CFPAC-1 (e.g., K-Ras G12V), CL40 (e.g., K-Ras G12D), COLO678 (e.g., K-Ras G12D), COR-L23 (e.g., K-Ras G12V), DAN-G (e.g., K-Ras G12V), GP2D (e.g., K-Ras G12D), GSU (e.g., K-Ras G12F), HCT116 (e.g., K-Ras G13D), HECIA (e.g., K-Ras G12D), HEC1B (e.g., K-Ras G12F), HEC50B (e.g., K-Ras G12F), HEYA8 (e.g., K-Ras G12D or G13D), HPAC(e.g., K-Ras G12D), HPAFII (e.g., K-Ras G12D), HUCCT1 (e.g., K-Ras G12D), KARPAS620 (e.g., K-Ras G13D), KOPN8 (e.g., K-Ras G13D), KP-3 (e.g., K-Ras G12V), KP-4 (e.g., K-Ras G12D), L3.3 (e.g., K-Ras G12D), LoVo (e.g., K-Ras G13D), LS180 (e.g., K-Ras G12D), LS513 (e.g., K-Ras G12D), MCAS(e.g., K-Ras G12D), NB4 (e.g., K-Ras A18D), NCI-H1355 (e.g., K-Ras G13C), NCI-H1573 (e.g., K-Ras G12A), NCI-H1944 (e.g., K-Ras G13D), NCI-H2009 (e.g., K-Ras G12A), NCI-H441 (e.g., K-Ras G12V), NCI-H747 (e.g., K-Ras G13D), NOMO-1 (e.g., K-Ras G12D), OV7 (e.g., K-Ras G12D), PANC0203 (e.g., K-Ras G12D), PANC0403 (e.g., K-Ras G12D), PANC0504 (e.g., K-Ras G12D), PANC0813 (e.g., K-Ras G12D), PANC1 (e.g., K-Ras G12D), Panc-10.05 (e.g., K-Ras G12D), PaTu-8902 (e.g., K-Ras G12V), PK1 (e.g., K-Ras G12D), PK45H (e.g., K-Ras G12D), PK59 (e.g., K-Ras G12D), SK-CO-1 (e.g., K-Ras G12V), SKLU1 (e.g., K-Ras G12D), SKM-1 (e.g., K-Ras K117N), SNUI (e.g., K-Ras G12D), SNU1033 (e.g., K-Ras G12D), SNU1197 (e.g., K-Ras G12D), SNU407 (e.g., K-Ras G12D), SNU410 (e.g., K-Ras G12D), SNU601 (e.g., K-Ras G12D), SNU61 (e.g., K-Ras G12D), SNU8 (e.g., K-Ras G12D), SNU869 (e.g., K-Ras G12D), SNU-$C_2A$ (e.g., K-Ras G12D), SU.86.86 (e.g., K-Ras G12D), SUIT2 (e.g., K-Ras G12D), SW1990 (e.g., K-Ras G12D), SW403 (e.g., K-Ras G12V), SW480 (e.g., K-Ras G12V), SW620 (e.g., K-Ras G12V), SW948 (e.g., K-Ras $Q^{61}L$), T3M10 (e.g., K-Ras G12D), TCC-PAN2 (e.g., K-Ras G12R), TGBC11TKB (e.g., K-Ras G12D), and MIA Pa-Ca (e.g., MIA Pa-Ca 2 (e.g., K-Ras G12C)).

In some embodiments is a Ras protein bound by a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, wherein activity of said Ras protein is reduced as compared to a Ras protein unbound to said compound.

Pharmaceutical Compositions and Methods of Administration

The compounds of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, described herein are administered to subjects in a biologically compatible form suitable for administration to treat or prevent diseases, disorders or conditions. Administration of the compounds described herein can be in any pharmacological form including a therapeutically effective amount of a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof, alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient(s)(or carrier(s)) is acceptable or suitable if the excipient is compatible with the other ingredients of the composition and not deleterious to the recipient (i.e., the subject) of the composition.

In some embodiments is a pharmaceutical composition comprising a pharmaceutically acceptable excipient and a compound of Formula (I), (Ia), (Ib), (Ic), (Id), (Ie), (If), (Ig), (Ih), (Ii), (Ij), (Ik), (Im), (In), (Io), (II), (IIa), (IIb), (IIc), (IId), (IIe), (IIf), (IIg), (IIh), (IIi), or (IIj), or a pharmaceutically acceptable salt or solvate thereof. In some embodiments is a pharmaceutical composition comprising a pharmaceutically acceptable excipient and a compound of Formula (I), or a pharmaceutically acceptable salt or solvate thereof. In some embodiments is a pharmaceutical composition comprising a pharmaceutically acceptable excipient and a compound of Formula (I'), or a pharmaceutically acceptable salt or solvate thereof. In some embodiments is a pharmaceutical composition comprising a pharmaceutically acceptable excipient and a compound of Formula (Ia), or a pharmaceutically acceptable salt or solvate thereof. In some embodiments is a pharmaceutical composition comprising a pharmaceutically acceptable excipient and a compound of Formula (Ib), or a pharmaceutically acceptable salt or solvate thereof. In some embodiments is a pharmaceutical composition comprising a pharmaceutically acceptable excipient and a compound of Formula (Ic), or a pharmaceutically acceptable salt or solvate thereof. In some embodiments is a pharmaceutical composition comprising a pharmaceutically acceptable excipient and a compound of Formula (Id), or a pharmaceutically acceptable salt or solvate thereof. In some embodiments is a pharmaceutical composition comprising a pharmaceutically acceptable excipient and a compound of Formula (Ie), or a pharmaceutically acceptable salt or solvate thereof. In some embodiments is a pharmaceutical composition comprising a pharmaceutically acceptable excipient and a compound of Formula (If), or a pharmaceutically acceptable salt or solvate thereof. In some embodiments is a pharmaceutical composition comprising a pharmaceutically acceptable excipient and a compound of Formula (Ig), or a pharmaceutically acceptable salt or solvate thereof. In some embodiments is a pharmaceutical composition comprising a pharmaceutically acceptable excipient and a compound of Formula (Ih), or a pharmaceutically acceptable salt or solvate thereof. In some embodiments is a pharmaceutical composition comprising a pharmaceutically acceptable excipient and a compound of Formula (Ij), or a pharmaceutically acceptable salt or solvate thereof. In some embodiments is a pharmaceutical composition comprising a pharmaceutically acceptable excipient and a compound of Formula (Ii), or a pharmaceutically acceptable salt or solvate thereof. In some embodiments is a pharmaceutical composition comprising a pharmaceutically acceptable excipient and a compound of Formula (Ij), or a pharmaceutically acceptable salt or solvate thereof. In some embodiments is a pharmaceutical composition comprising a pharmaceutically acceptable excipient and a compound of Formula (Ik), or a pharmaceutically acceptable salt or solvate thereof. In some embodiments is a pharmaceutical composition comprising a pharmaceutically acceptable excipient and a compound of Formula (Im), or a pharmaceutically acceptable salt or solvate thereof. In some embodiments is a pharmaceutical composition comprising a pharmaceutically acceptable excipient and a compound of Formula (II), or a pharmaceutically acceptable salt or solvate thereof. In some embodiments is a pharmaceutical composition comprising a pharmaceutically acceptable excipient and a compound of Formula (IIa), or a pharmaceutically acceptable salt or solvate thereof. In some embodiments is a pharmaceutical composition comprising a pharmaceutically acceptable excipient and a compound of Formula (IIb), or a pharmaceutically acceptable salt or solvate thereof. In some embodiments is a pharmaceutical composition comprising a pharmaceutically acceptable excipient and a compound of Formula (IIc), or a pharmaceutically acceptable salt or solvate thereof. In some embodiments is a pharmaceutical composition comprising a pharmaceutically acceptable excipient and a compound of Formula (IId), or a pharmaceutically acceptable salt or solvate thereof. In some embodiments is a pharmaceutical composition comprising a pharmaceutically acceptable excipient and a compound of Formula (IIe), or a pharmaceutically acceptable salt or solvate thereof. In some embodiments is a pharmaceutical composition comprising a pharmaceutically acceptable excipient and a compound of Formula (IIf), or a pharmaceutically acceptable salt or solvate thereof. In some embodiments is a pharmaceutical composition comprising a pharmaceutically acceptable excipient and a compound of Formula (IIg), or a pharmaceutically acceptable salt or solvate thereof. In some embodiments is a pharmaceutical composition comprising a pharmaceutically acceptable excipient and a compound of Formula (IIh), or a pharmaceutically acceptable salt or solvate thereof. In some embodiments is a pharmaceutical composition comprising a pharmaceutically acceptable excipient and a compound of Formula (Ii), or a pharmaceutically acceptable salt or solvate thereof. In some embodiments is a pharmaceutical composition comprising a pharmaceutically acceptable excipient and a compound of Formula (IIj), or a pharmaceutically acceptable salt or solvate thereof.

In some embodiments of the methods described herein, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments of the methods described herein, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

EXAMPLES

The following examples are provided for illustrative purposes only and not to limit the scope of the claims provided herein.

As used herein, the following abbreviations, unless otherwise indicated, shall be understood to have the following meanings:

| | |
|---|---|
| ACN or MeCN | acetonitrile |
| AcOH | acetic acid |
| Ac | acetyl |
| BINAP | 2,2'-bis(diphenylphosphino)-1,1'-binaphthalene |
| Bn | benzyl |
| BOC or Boc | tert-butyl carbamate |
| i-Bu | iso-butyl |
| t-Bu | tert-butyl |
| DCM | dichloromethane ($CH_2Cl_2$) |
| DIBAL-H | diisobutylaluminum hydride |
| DIPEA or DIEA | diisopropylethylamine |
| DMAP | 4-(N,N-dimethylamino)pyridine |
| DME | 1,2-dimethoxyethane |
| DMF | N,N-dimethylformamide |
| DMA | N,N-dimethylacetamide |
| DMSO | dimethylsulfoxide |
| Dppf or dppf | 1,1'-bis(diphenylphosphino)ferrocene |
| EDC or EDCI | N-(3-dimethylaminopropyl)-N'-ethylcarbodiimide hydrochloride |
| eq | equivalent(s) |
| Et | ethyl |
| $Et_2O$ | diethyl ether |
| EtOH | ethanol |
| EtOAc | ethyl acetate |
| HPLC | high performance liquid chromatography |
| KHMDS | potassium bis(trimethylsilyl)amide |
| NaHMDS | sodium bis(trimethylsilyl)amide |
| LIHMDS | lithium bis(trimethylsilyl)amide |
| LAH | lithium aluminum anhydride |
| LCMS | liquid chromatography mass spectrometry |
| Me | methyl |
| MeOH | methanol |
| MS | mass spectroscopy |
| Ms | mesyl |
| NMR | nuclear magnetic resonance |
| Ph | phenyl |
| iPr/i-Pr | iso-propyl |
| RP-HPLC | reverse-phase high-pressure liquid chromatography |
| rt | room temperature |
| TBS | tert-butyldimethylsilyl |
| TEA | triethylamine |
| TFA | trifluoroacetic acid |
| THF | tetrahydrofuran |
| TLC | thin layer chromatography |
| TMS | trimethylsilyl |
| TsOH/p-TsOH | p-toluenesulfonic acid. |

EXAMPLE 1: Synthesis of 4-(6-chloro-8-fluoro-2-(((S)-1-methylpyrrolidin-2-yl)methoxy)-4-(piperazin-1-yl)quinazolin-7-yl)benzo[d]thiazol-2-amine (1)

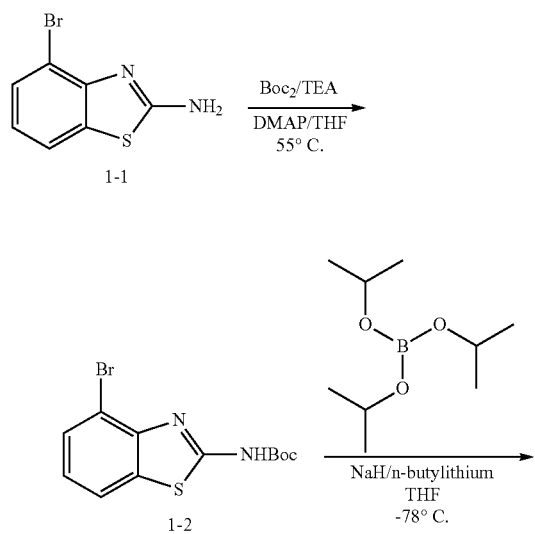

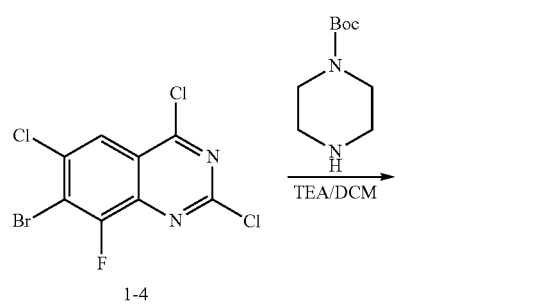

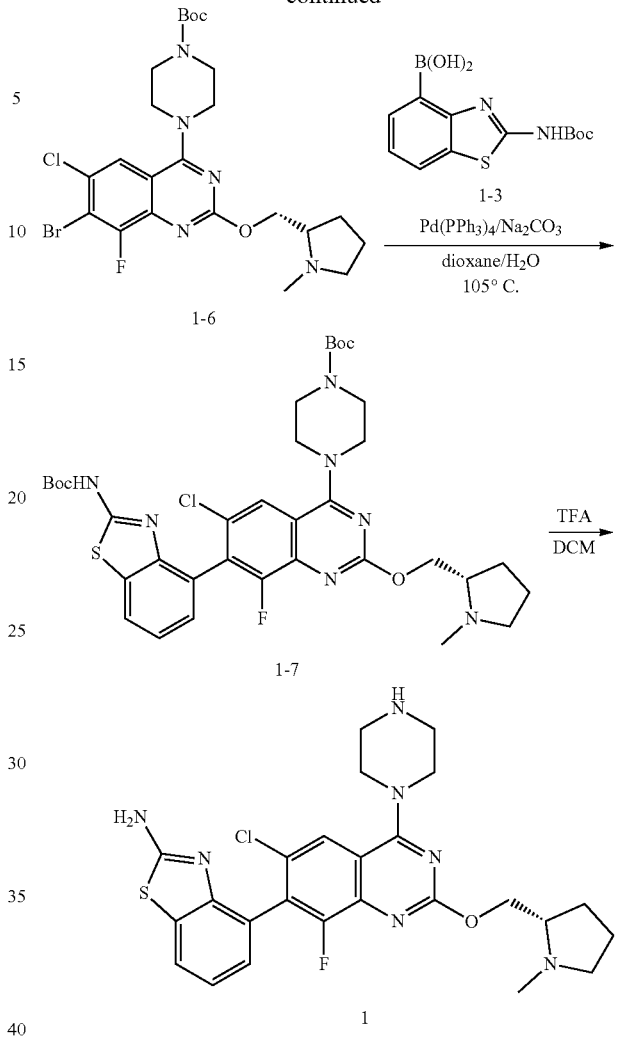

To a solution of 4-bromobenzo[d]thiazol-2-amine (2 g, 8.81 mmol, 1 eq) in THF (20 mL) was added Boc$_2$O (2.88 g, 13.21 mmol, 1.5 eq), TEA (2.66 g, 26.43 mmol, 3 eq) and DMAP (107 mg, 0.88 mmol, 0.1 eq). The resulting solution was stirred at 55° C. overnight. The mixture was partitioned between ethyl acetate and water. The organic layer was concentrated and the residue was purified on a silica gel column to afford tert-butyl (4-bromobenzo[d]thiazol-2-yl) carbamate (1-2)(1.7 g). ESI-MS m/z: 327.99 [M+H]$^+$.

To a solution of tert-butyl (4-bromobenzo[d]thiazol-2-yl) carbamate (1-2) (1.7 g, 5.18 mmol) in THF (30 mL) at 0° C. under argon was added NaH (60 mass % in paraffin oil, 310 mg, 1.5 eq) in portions. The resulting mixture was stirred for 10 min, and then was cooled to −78° C. To this mixture, n-butyllithium (2.5 M in hexanes, 3.1 mL, 1.5 eq) was added dropwise. The resulting mixture was stirred at −78° C. for 25 min. Triisopropyl borate (4.25 mL, 3 eq) was added dropwise. The resulting mixture was stirred at −78° C. for 25 min. The reaction mixture was allowed to warm to room temperature, quenched with saturated aqueous NH$_4$Cl and extracted with ethyl acetate. The combined organic layer was washed with water and brine. The organic layer was concentrated and the residue was purified on a silica gel column to afford (2-((tert-butoxycarbonyl)amino)benzo[d] thiazol-4-yl)boronic acid (1-3)(714 mg). ESI-MS m/z: 294.08 [M+H]$^+$.

To a solution of 7-bromo-2,4,6-trichloro-8-fluoroquinazoline (1-4)(5 g, 15.3 mmol, 1 eq) in dichloromethane (100 mL) at 0° C., were added TEA (4.63 g, 45.9 mmol, 3 eq) and tert-butyl piperazine-1-carboxylate (2.84 g, 15.3 mmol, 1 eq). The resulting solution was stirred at 0° C. for 1 h. The mixture was partitioned between dichloromethane and water. The organic layer was concentrated and the residue was purified on a silica gel column eluting with ethyl acetate/petroleum (1:4) to afford tert-butyl 4-(7-bromo-2,6-dichloro-8-fluoroquinazolin-4-yl)piperazine-1-carboxylate (1-5)(6.5 g). ESI-MS m/z: 478.00 [M+H]$^+$.

To a solution of tert-butyl 4-(7-bromo-2,6-dichloro-8-fluoroquinazolin-4-yl)piperazine-1-carboxylate (1-5)(1.6 g, 3.32 mmol) in DMSO (20 mL) was added KF (1.54 g, 26.56 mmol, 8 eq) and (S)—(1-methylpyrrolidin-2-yl) methanol (764 mg, 6.64 mmol, 2 eq). The resulting mixture was stirred at 120° C. under argon for 3 h. The mixture was partitioned between ethyl acetate and water. The organic layer was concentrated. The residue was purified on a silica gel column to afford tert-butyl(S)—4-(7-bromo-6-chloro-8-fluoro-2-((1-methylpyrrolidin-2-yl)methoxy) quinazolin-4-yl)piperazine-1-carboxylate (1-6)(960 mg). ESI-MS m/z: 557.12 [M+H]$^+$.

To a solution of tert-butyl(S)—4-(7-bromo-6-chloro-8-fluoro-2-((1-methylpyrrolidin-2-yl)methoxy) quinazolin-4-yl)piperazine-1-carboxylate (1-6)(100 mg, 0.58 mmol) in 1,4-dioxane (8 mL) and water (2 mL) were added (2-((tert-butoxycarbonyl)amino)benzo[d]thiazol-4-yl)boronic acid (1-3)(514 mg, 2.93 mmol, 1 eq), tetrakis(triphenylphosphine) palladium (20 mg, 0.018 mmol) and Na$_2$CO$_3$ (57 mg, 0.54 mmol) and the resulting mixture was stirred at 100° C. under argon overnight. The mixture was partitioned between ethyl acetate and water. The organic layer was concentrated. The residue was purified on a silica gel column to afford tert-butyl 4-(7-(2-((tert-butoxycarbonyl)amino)benzo[d]thiazol-4-yl)-6-chloro-8-fluoro-2-(((S)-1-methylpyrrolidin-2-yl)methoxy) quinazolin-4-yl)piperazine-1-carboxylate (1-7) (85 mg). ESI-MS m/z: 727.27 [M+H]$^+$.

To a solution of tert-butyl 4-(7-(2-((tert-butoxycarbonyl)amino)benzo[d]thiazol-4-yl)-6-chloro-8-fluoro-2-(((S)—1-methylpyrrolidin-2-yl)methoxy) quinazolin-4-yl)piperazine-1-carboxylate (1-7)(85 mg) in DCM (6 mL) was added TFA (2 mL) and the resulting solution was stirred at room temperature for 30 min. The reaction mixture was concentrated. The residue was dissolved in ethyl acetate and basified with aqueous NaHCO$_3$ solution to adjust the pH to ~8. The mixture was partitioned between ethyl acetate and water. The organic layer was concentrated. The residue was purified on a silica gel column to afford 4-(6-chloro-8-fluoro-2-(((S)-1-methylpyrrolidin-2-yl)methoxy)-4-(piperazin-1-yl)quinazolin-7-yl)benzo[d]thiazol-2-amine (Compound 1)(8 mg). ESI-MS m/z: 528.4 [M+H]$^+$. $^1$H NMR (400 MHZ, CD$_3$OD): δ 8.00 (s, 1H), 7.77-7.75 (dd, J=6.8, 2.4 Hz, 1H), 7.24-7.22 (m, 2H), 4.77-4.72 (m, 1H), 4.19-4.17 (m, 4H), 3.97-3.95 (m, 1H), 3.76-3.73 (m, 1H), 3.53-3.50 (m, 4H), 3.37 (s, 1H), 3.30-3.27 (m, 1H), 3.11 (s, 3H), 2.44-2.43 (m, 1H), 2.23-2.20 (m, 1H), 2.15-2.10 (m, 2H).

Compounds 2-12 shown in Table 1 below were synthesized in a similar manner as described for Compound 1 above.

TABLE 1

| Compound | Structure | Name | [M + H]$^+$ |
|---|---|---|---|
| 2 | 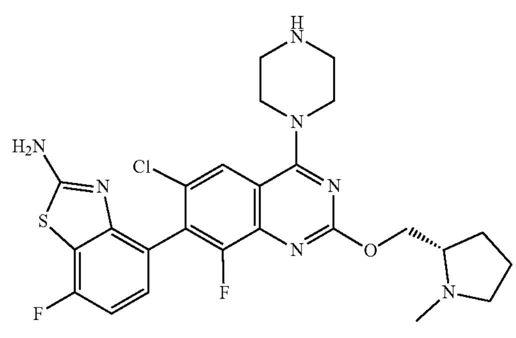 [SMILES: CN1CCC[C@H]1COc1nc(N2CCNCC2)c2cc(Cl)c(-c3ccc(F)c4sc(N)nc34)c(F)c2n1] | 4-(6-chloro-8-fluoro-2-(((S)-1-methylpyrrolidin-2-yl)methoxy)-4-(piperazin-1-yl)quinazolin-7-yl)-7-fluorobenzo[d]thiazol-2-amine | 546.1 |
| 3 | 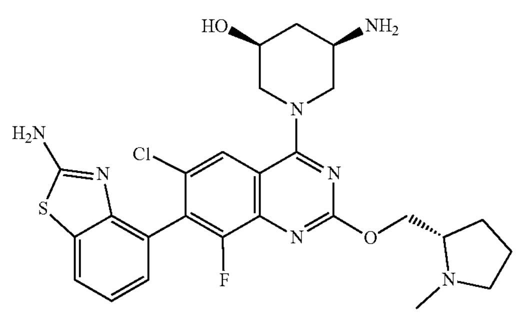 [SMILES: CN1CCC[C@H]1COc1nc(N2C[C@H](N)C[C@H](O)C2)c2cc(Cl)c(-c3cccc4sc(N)nc34)c(F)c2n1] | (3S,5R)-5-amino-1-(7-(2-aminobenzo[d]thiazol-4-yl)-6-chloro-8-fluoro-2-(((S)-1-methylpyrrolidin-2-yl)methoxy)quinazolin-4-yl)piperidin-3-ol | 558.6 |

TABLE 1-continued

| Compound | Structure | Name | [M + H]+ |
|---|---|---|---|
| 4 | 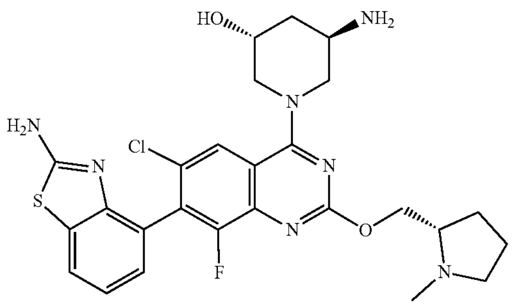 [SMILES: CN1CCC[C@H]1COc1nc(N2C[C@H](N)C[C@@H](O)C2)c2cc(Cl)c(-c3cccc4sc(N)nc34)c(F)c2n1] | (3R,5R)-5-amino-1-(7-(2-aminobenzo[d]thiazol-4-yl)-6-chloro-8-fluoro-2-(((S)-1-methylpyrrolidin-2-yl)methoxy)quinazolin-4-yl)piperidin-3-ol | 558.6 |
| 5 | 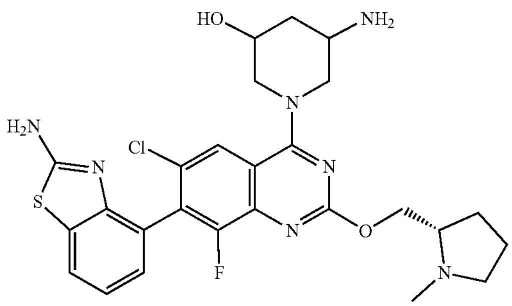 [SMILES: CN1CCC[C@H]1COc1nc(N2CC(N)CC(O)C2)c2cc(Cl)c(-c3cccc4sc(N)nc34)c(F)c2n1] | 5-amino-1-(7-(2-aminobenzo[d]thiazol-4-yl)-6-chloro-8-fluoro-2-(((S)-1-methylpyrrolidin-2-yl)methoxy)quinazolin-4-yl)piperidin-3-ol | 558.6 |
| 6 | 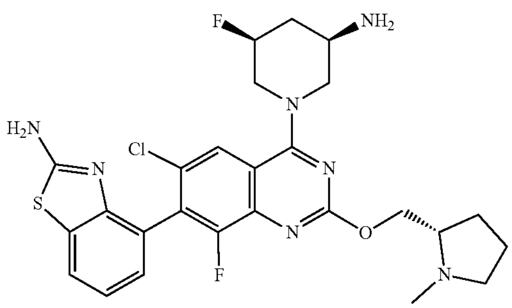 [SMILES: CN1CCC[C@H]1COc1nc(N2C[C@H](N)C[C@H](F)C2)c2cc(Cl)c(-c3cccc4sc(N)nc34)c(F)c2n1] | 4-(4-((3R,5S)-3-amino-5-fluoropiperidin-1-yl)-6-chloro-8-fluoro-2-(((S)-1-methylpyrrolidin-2-yl)methoxy)quinazolin-7-yl)benzo[d]thiazol-2-amine | 560.7 |
| 7 | 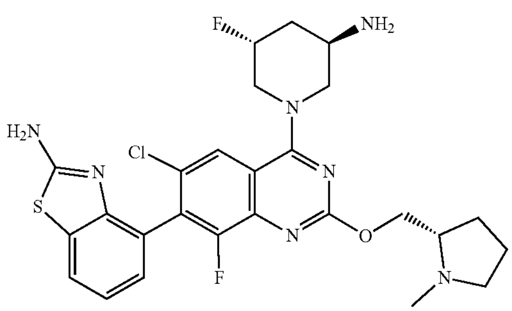 [SMILES: CN1CCC[C@H]1COc1nc(N2C[C@H](N)C[C@@H](F)C2)c2cc(Cl)c(-c3cccc4sc(N)nc34)c(F)c2n1] | 4-(4-((3R,5R)-3-amino-5-fluoropiperidin-1-yl)-6-chloro-8-fluoro-2-(((S)-1-methylpyrrolidin-2-yl)methoxy)quinazolin-7-yl)benzo[d]thiazol-2-amine | 560.6 |
| 8 | 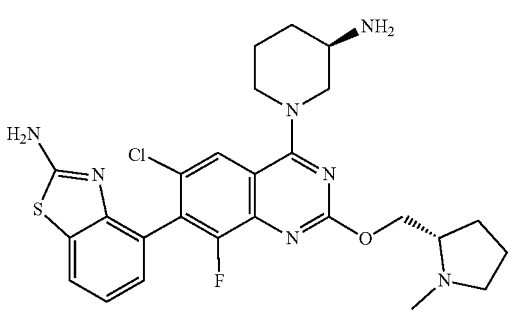 [SMILES: CN1CCC[C@H]1COc1nc(N2CCC[C@@H](N)C2)c2cc(Cl)c(-c3cccc4sc(N)nc34)c(F)c2n1] | 4-(4-((R)-3-aminopiperidin-1-yl)-6-chloro-8-fluoro-2-(((S)-1-methylpyrrolidin-2-yl)methoxy)quinazolin-7-yl)benzo[d]thiazol-2-amine | 542.4 |

TABLE 1-continued

| Compound | Structure | Name | [M + H]+ |
|---|---|---|---|
| 9 | 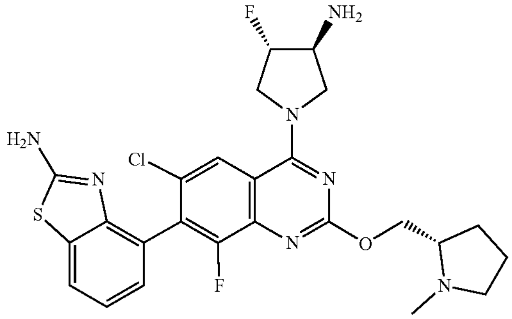 [SMILES: CN1CCC[C@H]1COc1nc(N2C[C@H](N)[C@@H](F)C2)c2cc(Cl)c(-c3cccc4sc(N)nc34)c(F)c2n1] | 4-(4-((3S,4S)-3-amino-4-fluoropyrrolidin-1-yl)-6-chloro-8-fluoro-2-(((S)-1-methylpyrrolidin-2-yl)methoxy)quinazolin-7-yl)benzo[d]thiazol-2-amine | 546.5 |
| 10 | 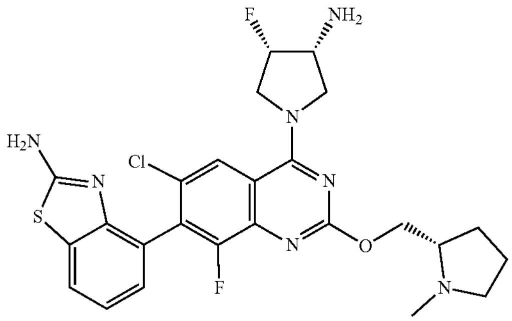 [SMILES: CN1CCC[C@H]1COc1nc(N2C[C@@H](N)[C@@H](F)C2)c2cc(Cl)c(-c3cccc4sc(N)nc34)c(F)c2n1] | 4-(4-((3R,4S)-3-amino-4-fluoropyrrolidin-1-yl)-6-chloro-8-fluoro-2-(((S)-1-methylpyrrolidin-2-yl)methoxy)quinazolin-7-yl)benzo[d]thiazol-2-amine | 546.2 |
| 11 | 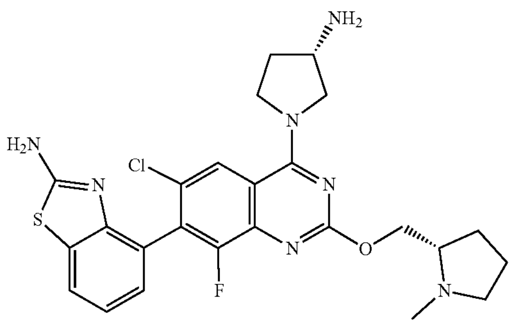 [SMILES: CN1CCC[C@H]1COc1nc(N2CC[C@H](N)C2)c2cc(Cl)c(-c3cccc4sc(N)nc34)c(F)c2n1] | 4-(4-((S)-3-aminopyrrolidin-1-yl)-6-chloro-8-fluoro-2-(((S)-1-methylpyrrolidin-2-yl)methoxy)quinazolin-7-yl)benzo[d]thiazol-2-amine | 528.2 |
| 12 | 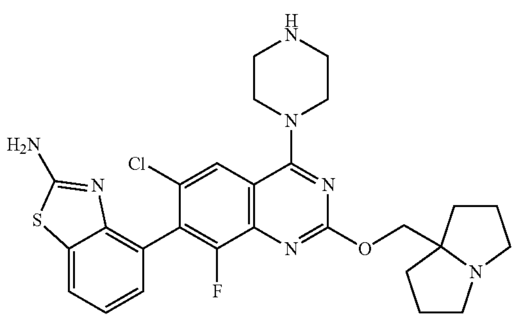 [SMILES: Nc1nc2c(-c3c(Cl)cc4c(N5CCNCC5)nc(OCC56CCCN5CCC6)nc4c3F)cccc2s1] | 4-(6-chloro-8-fluoro-4-(piperazin-1-yl)-2-((tetrahydro-1H-pyrrolizin-7a(5H)-yl)methoxy)quinazolin-7-yl)benzo[d]thiazol-2-amine | 554.5 |
| 13 | 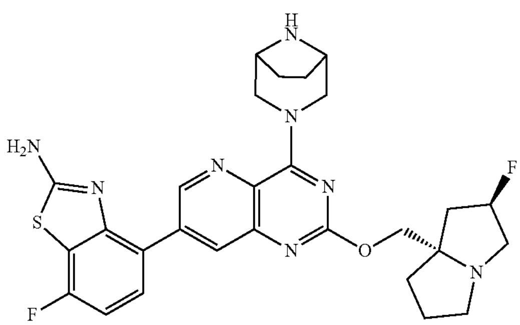 | 4-(4-(3,8-diazabicyclo[3.2.1]octan-3-yl)-2-(((2R,7aS)-2-fluorotetrahydro-1H-pyrrolizin-7a(5H)-yl)methoxy)pyrido[3,2-d]pyrimidin-7-yl)-7-fluorobenzo[d]thiazol-2-amine | 565.2 |

TABLE 1-continued

| Compound | Structure | Name | [M + H]+ |
|---|---|---|---|
| 14 | 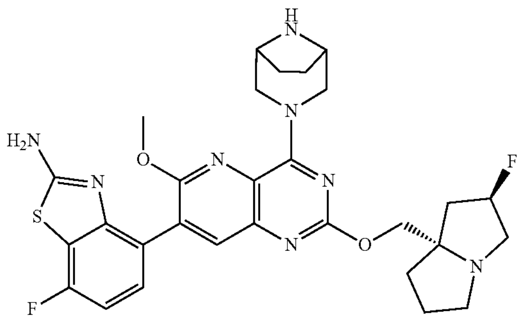 | 4-(4-(3,8-diazabicyclo[3.2.1]octan-3-yl)-2-(((2R,7aS)-2-fluorotetrahydro-1H-pyrrolizin-7a(5H)-yl)methoxy)-6-methoxypyrido[3,2-d]pyrimidin-7-yl)-7-fluorobenzo[d]thiazol-2-amine | 595.4 |
| 15 | 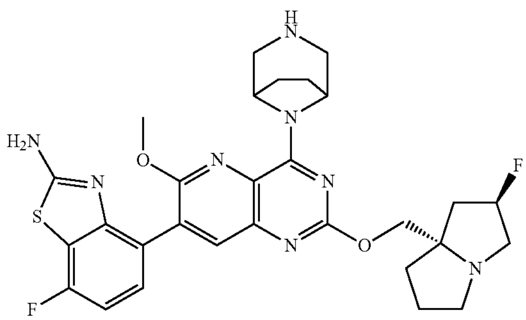 [SMILES: COc1nc2c(N3C4CCC3CNC4)nc(OC[C@@]34CCCN3C[C@H](F)C4)nc2cc1-c1ccc(F)c2sc(N)nc12] | 4-(4-(3,8-diazabicyclo[3.2.1]octan-8-yl)-2-(((2R,7aS)-2-fluorotetrahydro-1H-pyrrolizin-7a(5H)-yl)methoxy)-6-methoxypyrido[3,2-d]pyrimidin-7-yl)-7-fluorobenzo[d]thiazol-2-amine | 595.4 |
| 16 | 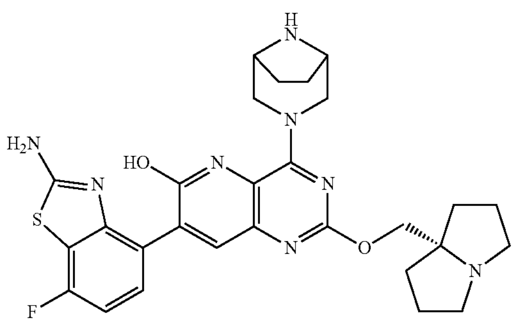 | 7-(2-amino-7-fluorobenzo[d]thiazol-4-yl)-4-(3,8-diazabicyclo[3.2.1]octan-3-yl)-2-((tetrahydro-1H-pyrrolizin-7a(5H)-yl)methoxy)pyrido[3,2-d]pyrimidin-6-ol | 563.3 |
| 17 | 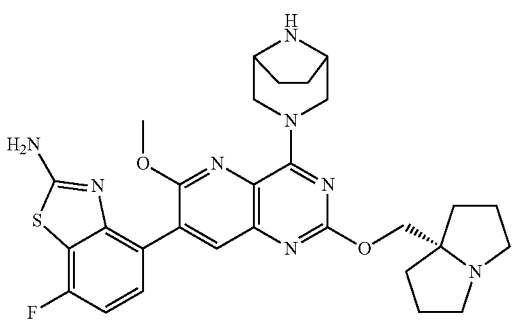 | 4-(4-(3,8-diazabicyclo[3.2.1]octan-3-yl)-6-methoxy-2-((tetrahydro-1H-pyrrolizin-7a(5H)-yl)methoxy)pyrido[3,2-d]pyrimidin-7-yl)-7-fluorobenzo[d]thiazol-2-amine | 577.4 |
| 18 | 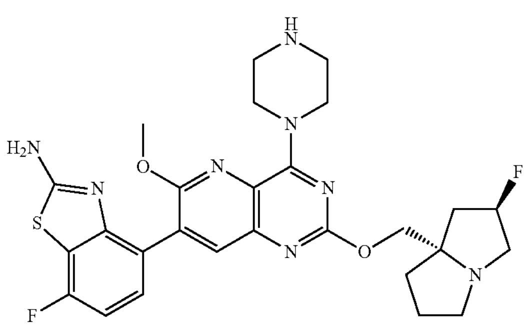 [SMILES: COc1nc2c(N3CCNCC3)nc(OC[C@@]34CCCN3C[C@H](F)C4)nc2cc1-c1ccc(F)c2sc(N)nc12] | 7-fluoro-4-(2-(((2R,7aS)-2-fluorotetrahydro-1H-pyrrolizin-7a(5H)-yl)methoxy)-6-methoxy-4-(piperazin-1-yl)pyrido[3,2-d]pyrimidin-7-yl)benzo[d]thiazol-2-amine | 551.4 |

TABLE 1-continued

| Compound | Name | [M + H]+ |
|---|---|---|
| 19 | 4-(4-((1R,5S)-3,8-diazabicyclo[3.2.1]octan-3-yl)-6-chloro-8-fluoro-2-(((2R,7aS)-2-fluorotetrahydro-1H-pyrrolizin-7a(5H)-yl)methoxy)quinazolin-7-yl)-2-amino-7-fluorobenzo[b]thiophene-3-carbonitrile | 640.3 |
| 20 | 4-(4-((1R,5S)-3,8-diazabicyclo[3.2.1]octan-3-yl)-6-chloro-8-fluoro-2-(((2R,7aS)-2-fluorotetrahydro-1H-pyrrolizin-7a(5H)-yl)methoxy)quinazolin-7-yl)-3-cyclopropyl-7-fluorobenzo[b]thiophen-2-amine | 655.5 |
| 21 | 4-(4-((1R,5S)-3,8-diazabicyclo[3.2.1]octan-3-yl)-6-chloro-8-fluoro-2-(((2R,7aS)-2-fluorotetrahydro-1H-pyrrolizin-7a(5H)-yl)methoxy)quinazolin-7-yl)-7-fluoro-3-methylbenzo[b]thiophen-2-amine | 629.5 |
| 22 | 4-(4-((1R,5S)-3,8-diazabicyclo[3.2.1]octan-3-yl)-6-chloro-8-fluoro-2-(((2R,7aS)-2-fluorotetrahydro-1H-pyrrolizin-7a(5H)-yl)methoxy)quinazolin-7-yl)-3-methylbenzo[b]thiophen-2-amine | 611.6 |

EXAMPLE 2: Ras Sequence

Human K-Ras4b (SEQ ID NO. 1):

```
  1 MTEYKLVVVG AGGVGKSALT IQLIQNHFVD EYDPTIEDSY RKQVVIDGET

51 CLLDILDTAG QEEYSAMRDQ YMRTGEGFLC VFAINNTKSF EDIHHYREQI

101 KRVKDSEDVP MVLVGNKCDL PSRTVDTKQA QDLARSYGIP FIETSAKTRQ

151 GVDDAFYTLV REIRKHKEKM SKDGKKKKKK SKTKCVIM
```

EXAMPLE 3: Protein Expression

DNA expression constructs encoding one or more protein sequences of interest (e.g., Kras fragments thereof, mutant variants thereof, etc.) and its corresponding DNA sequences are optimized for expression in E. coli and synthesized by, for example, the GeneArt Technology at Life Technologies. In some cases, the protein sequences of interest are fused with a tag (e.g., glutathione S-transferase (GST), histidine (His), or any other affinity tags) to facilitate recombinant expression and purification of the protein of interest. Such tag can be cleaved subsequent to purification. Alternatively, such tag may remain intact to the protein of interest and may not interfere with activities (e.g., target binding and/or phosphorylation) of the protein of interest A resulting expression construct is additionally encoded with (i) att-site sequences at the 5' and 3' ends for subcloning into various destination vectors using, for example, the Gateway Technology, as well as (ii) a Tobacco Etch Virus (TEV) protease site for proteolytic cleavage of one or more tag sequences. The applied destination vectors can be a pET vector series from Novagen (e.g., with ampicillin resistance gene), which provides an N-terminal fusion of a GST-tag to the integrated gene of interest and/or a pET vector series (e.g., with ampicillin resistance gene), which provides a N-terminal fusion of a HIS-tag to the integrated gene. To generate the final expression vectors, the expression construct of the protein of interest is cloned into any of the applied destination ventors. The expression vectors are transformed into E. coli strain, e.g., BL21 (DE3). Cultivation of the transformed strains for expression is performed in 10 L and 1 L fermenter. The cultures are grown, for example, in Terrific Broth media (MP Biomedicals, Kat. #1 13045032) with 200 ug/mL ampicillin at a temperature of 37° C. to a density of 0.6 (OD600), shifted to a temperature of ~27° C. (for K-Ras expression vectors) induced for expression with 100 mM IPTG, and further cultivated for 24 hours. After cultivation, the transformed E. coli cells are harvested by centrifugation and the resulting pellet is suspended in a lysis buffer, as provided below, and lysed by passing three-times through a high pressure device. The lysate is centrifuged (49000 g, 45 min, 4° C.) and the supernatant is used for further purification.

EXAMPLE 4: Ras Protein Purification

A Ras (e.g., K-Ras wildtype or a mutant such as K-Ras G12D, K-Ras G12V or K-RasG12C) construct or a variant thereof is tagged with GST. E. coli culture from a 10 L fermenter is lysed in lysis buffer (50 mM Tris HCl 7.5, 500 mM NaCl, 1 mM DTT, 0.5% CHAPS, Complete Protease Inhibitor Cocktail-(Roche)). As a first chromatography step, the centrifuged lysate is incubated with 50 mL Glutathione Agarose 4B (Macherey-Nagel; 745500.100) in a spinner flask (16 h, 100). The Glutathione Agarose 4B loaded with protein is transferred to a chromatography column connected to a chromatography system, e.g., an Akta chromatography system. The column is washed with wash buffer (50 mM Tris HCl 7.5, 500 mM NaCl, 1 mM DTT) and the bound protein is eluted with elution buffer (50 mM Tris HCl 7.5, 500 mM NaCl, 1 mM DTT, 15 mM Glutathione). The main fractions of the elution peak (monitored by OD280) is pooled. For further purification by size-exclusion chromatography, the above eluate volume is applied to a column Superdex 200 HR prep grade (GE Healthcare) and the resulting peak fractions of the eluted fusion protein is collected. Native mass spectrometry analyses of the final purified protein construct can be performed to assess its homogeneous load with GDP.

EXAMPLE 5: Ras-SOS Interaction Assay

The ability of any compound of the present disclosure to inhibit a Ras protein signalling can be assessed in vitro. For example, the equilibrium interaction of human SOS1 (hSOS1) with human K-Ras mutant (e.g., hK-Ras G12C mutant, or hK-RasG12C) can be assessed as a proxy or an indication for a subject compound's ability to inhibit Kras or a mutant Kras protein. Detection of such interaction is achieved by measuring homogenous time-resolved fluorescence resonance energy transfer (HTRF) from (i) a fluorescence resonance energy transfer (FRET) donor (e.g., anti-GST-Europium) that is bound to GST-tagged K-RasG12C to (ii) a FRET acceptor (e.g., anti-6His-XL665) bound to a His-tagged hSOS1.

The assay buffer can contain 5 mM HEPES pH 7.4 (Applichem), 150 mM NaCl (Sigma), 10 mM EDTA (Promega), 1 mM DTT (Thermofisher), 0.05% BSA Fraction V, pH 7.0, (ICN Biomedicals), 0.0025% (v/v) Igepal (Sigma) and 100 mM KF (FLUKA).

Concentrations of protein batches used for the Ras-SOS interaction assay can be optimized to be within the linear range of the HTRF signal. A Ras working solution is prepared in assay buffer containing typically 10 nM of the protein construct (e.g., GST-tagged hK-RasG12C) and 2 nM of the FRET donor (e.g., antiGST-Eu (K) from Cisbio, France). A SOS1 working solution is prepared in assay buffer containing typically 20 nM of the protein construct (e.g., His-hSOS1) and 10 nM of the FRET acceptor (e.g., anti-6His-XL665 from Cisbio, France). An inhibitor control solution is prepared in assay buffer containing 10 nM of the FRET acceptor without the SOS construct.

A fixed volume of a 100-fold concentrated solution of the test compound in DMSO is transferred into a black microtiter test plate (384 or 1536, Greiner Bio-One, Germany). For this, either a Hummingbird liquid handler (Digilab, MA, USA) or an Echo acoustic system (Labcyte, CA, USA) can be used.

All steps of the assay can be performed at 20° C. A volume of 2.5 milliliter (mL) of the Ras working solution is added to all wells of the test plate using a Multidrop dispenser (Thermo Labsystems). After 2 min preincubation, 2.5 mL of the SOS1 working solution is added to all wells except for those wells at the side of the test plate that were subsequently filled with 2.5 mL of the inhibitor control solution. After a 60 min incubation, the fluorescence is measured with a Pherastar (BMG, Germany) using the HTRF module (excitation 337 nm, emission 1: 620 nm, emission 2: 665 nm). The ratiometric data (e.g., emission 2 divided by emission 1) is normalized using the controls (DMSO=0% inhibition; inhibition control wells with inhibitor control solution=100% inhibition). Compounds are tested in multiplicates (e.g., duplicates, triplicates, etc.) at various concentrations from e.g., ~20 uM to 5 nM. IC50 values can be calculated by 4-Parameter fitting using a commercial software package (Genedata Screener, Switzerland). The resulting IC50 value can be a measurement against a given Ras protein (e.g., a Kras-mutant such as G12D or any others disclosed herein or known in the art) by disrupting its interaction with SOS(e.g., binding) with a compound exemplified in Table 1.

EXAMPLE 6: GTPase Activity Assay

The ability of any compound of the present disclosure to inhibit a Ras protein signalling can be demonstrated by a reduced GTPase activity. This assay can be also used to assess a selective inhibition of a mutant Ras protein relative to a wildtype, or relative to a different mutant Ras protein. For instance, the assay can be used to establish a subject compound's ability to selectively inhibit Kras G12D relative to wildtype, Kras G12V relative to wildtype, or KrasG12D relative KrasG12V. In particular, intrinsic and GTPase-activating protein (GAP)-stimulated GTPase activity for K-Ras construct or a mutant thereof can be measured using EnzCheck phosphate assay system (Life Technologies). For example K-Ras WT, K-Ras D154Q mutant, K-Ras G12D mutant, and K-Ras G12D/D154Q mutant proteins (2.5 mg/ml) in buffer (20 mmol/L Tris, pH 8.0, 50 mM NaCl) is loaded with GTP at room temperature for 2 hours by exposing to exchange buffer containing EDTA. Proteins are buffer exchanged to assay buffer (30 mM Tris, pH 7.5, 1 mM DTT) and the concentration is adjusted to 2 mg/ml. GTP loading is verified by back extraction of nucleotide using 6M urea and evaluation of nucleotide peaks by HPLC using an ion-exchange column. The assay is performed in a clear 384-well plate (Costar) by combining GTP-loaded K-Ras proteins (50 mM final) with 2-amino-6-mercapto-7-methyl-purine ribonucleoside (MESG) (200 mM final), and purine nucleotide phosphorylase (5 U/ml final). GTP hydrolysis is initiated by the addition of MgCl2 at a working concentration of 40 mM. For GAP stimulation, Ras p21 protein activator 1 (P120GAP) can be included at 50 mM. Absorbance at 360 nm can be measured every 8 to 15 s for 1,000 s at 20° C. Samples are tested with or without a subject compound disclosed herein including compounds exemplified in Table 1 to assess each compound's ability to inhibit signaling of a given Ras protein (e.g., a given mutant Kras) of interest.

EXAMPLE 7: Nucleotide Exchange Assay

The ability of a compound of the present disclosure to inhibit a Ras protein signaling can be demonstrated by a reduced nucleotide exchange activity. This assay can be also used to assess a selective inhibition of a mutant Ras protein relative to a wildtype, or relative to a different mutant Ras protein. For example, 250 nM or 500 nM GDP-loaded K-Ras proteins (e.g., wildtype or a mutant thereof including those mentioned in Example 6), each was incubated with different concentrations of compounds (for example ~60 µM, ~20 µM, ~6.7 µM, ~2.2 µM, ~0.7 µM, ~0.2 µM subject compound). A control reaction without subject compound was also included. SOS1 (catalytic domain) protein was added to the K-Ras protein solution. The nucleotide exchange reaction was initiated by adding fluorescent labelled GDP (Guanosine 5'-Diphosphate, BODIPY™ FL 2'-(or-3')—O—(N-(2-Aminoethyl) Urethane) to a final concentration of 0.36 µM. Fluorescence was measured every 30 s for 70 minutes at 490 nm/515 nm (excitation/emission) in a M1000Pro plate reader (Tecan). Data is exported and analyzed to calculate an IC50 using GraphPad Prism (GraphPad Software). Samples were tested with or without a subject compound disclosed herein including compounds exemplified in Table 1 to assess each compound's ability to inhibit K-Ras signaling or its IC50 against a given Ras protein (e.g., a given mutant K-Ras) of interest. IC50 data for compounds exemplified herein is presented in Table 2 below.

TABLE 2

| Compound | IC50 against mutant Kras | IC50 against wildtype Kras | Compound | IC50 against mutant Kras | IC50 against wildtype Kras |
|---|---|---|---|---|---|
| 1 | ++++ | +++ | 2 | ++++ | ++++ |
| 3 | ++++ | +++ | 4 | ++++ | ++ |
| 5 | ++++ | +++ | 6 | +++ | ++ |
| 7 | +++ | ++ | 8 | ++++ | +++ |
| 9 | NT | NT | 10 | +++ | +++ |
| 11 | ++++ | +++ | 12 | ++++ | +++ |
| 13 | ++++ | ++ | 14 | ++++ | +++ |
| 15 | ++++ | ++ | 16 | ++++ | ++ |
| 17 | ++++ | +++ | 18 | +++ | ++ |
| 19 | ++++ | ++++ | 20 | ++++ | +++ |
| 21 | ++++ | ++++ | 22 | ++++ | ++++ | where '++++' means IC50 at or less than about 0.5 µM;
where '+++' means IC50 between about 500 nM and less than about 5 µM;
where '++' means IC50 at or greater than 5 µM;
'NT' means not tested.

EXAMPLE 8: Ras Cellular Assay

The ability of any compound of the present disclosure to inhibit a Ras protein signalling can be demonstrated by inhibiting growth of a given Kras mutant cells. For example, this assay can be also used to assess a selective growth inhibition of a mutant Ras protein relative to a wildtype, or relative to a different mutant Ras protein.

a. Growth of cells with K-Ras G12C mutation

MIA PaCa-2 (ATCC CRL-1420) and NCI-H1792 (ATCC CRL-5895) cell lines comprise a G12C mutation and can be used to assess Ras cellular signaling in vitro, e.g., in response to a subject inhibitor compounds of the present disclosure. This cellular assay can also be used to discern selective inhibition of a subject compounds against certain types of Kras mutants, e.g., more potent inhibition against KrasG12D relative to KrasG12C mutant, by using MIA PaCa-2 (G12C driven tumor cell line) as a comparison. MIA PaCa-2 culture medium is prepared with DMEM/Ham's F12 (e.g., with stable Glutamine, 10% FCS, and 2.5% Horse Serum. NCI-H1792 culture medium is prepared with RPMI 1640 (e.g., with stable Glutamine) and 10% FCS.

On a first day (e.g., Day 1), Softagar (Select Agar, Invitrogen, 3% in ddH$_2$O autoclaved) is boiled and tempered at 48° C. Appropriate culture medium (i.e., medium) is tempered to 37° C. Agar (3%) is diluted 1:5 in medium (=0.6%) and 50 ml/well plated into 96 well plates (Corning, #3904), then incubated at room temperature for agar solidification. A 3% agar is diluted to 0.25% in medium (1:12 dilution) and tempered at 42° C. Cells are trypsinized, counted, and tempered at 37° C. The cells (e.g., MIA PaCa-2 at about 125-150 cells, NCI-H1792 at about 1000 cells) are resuspended in 100 mL 0.25% Agar and plated, followed by incubation at room temperature for agar solidification. The wells are overlaid with 50 mL of the medium. Sister wells in a separate plate are plated for time zero determination. All plates are incubated overnight at 37° C. and 5% $CO_2$.

On a second day (e.g., Day 2), time zero values are measured. A 40 mL volume of Cell Titer 96 Aqueous Solution (Promega) is added to each well and incubated in the dark at 37° C. and 5% $CO_2$. Absorption can be measured at 490 nm and reference wavelength 660 nm. DMSO-prediluted test compounds are added to wells of interest, e.g., with HP Dispenser, to one or more desired concentrations (e.g., a final DMSO concentration of 0.3%).

On a third day (e.g., Day 10), absorption by wells treated with the test compounds and control wells are measured with, for example, Cell Titer 96 AQueous and analyzed in comparison to the time zero measurements. The IC50 values are determined using the four parameter fit. The resulting IC50 value is a measurement of the ability of the compounds herein to reduce cell growth of Ras-driven cells (e.g., tumor cell lines) in vitro and/or in vivo.

b. Growth of Cells with K-Ras G12D Mutation

ASPC-1 (ATCC CRL-1682), Panc-10.05 (ATCC CRL-2547), A427 cell lines comprise a G12D mutation and can be used to assess Ras cellular signaling in vitro, e.g., in response to the compounds herein. ASPC-1 culture medium is prepared with RPMI-1640 and 10% heat-inactivated FBS. Panc-10.05 culture medium is prepared with RPMI-1640, 10 Units/ml human recombinant insulin, and 10% FBS. A427 cell culture is prepared with RPMI-1640 and 10% heat-inactivated FBS. A CellTiter-Glo (CTG) luminescent based assay (Promega) is used to assess growth of the cells, as a measurement of the ability of the compounds herein to inhibit Ras signaling in the cells. The cells (e.g., 800-1,200 per well) are seeded in their respective culture medium in standard tissue culture-treated 96-well format plates (Corning Costar #3903) or ultra-low attachment surface 96-well format plates (Corning Costar #3474). The day after plating, cells are treated with a dilution series (e.g., a 9 point 3-fold dilution series) of the compounds herein (e.g., approximately 100 μl final volume per well). Cell viability can be monitored (e.g., approximately 5 days later) according to the manufacturer's recommended instructions, where the CellTiter-Glo reagent is added (e.g., approximately 50 μl), vigorously mixed, covered, and placed on a plate shaker (e.g., approximately for 20 min) to ensure sufficient cell lysis prior to assessment of luminescent signal.

EXAMPLE 9: In Vivo Ras Inhibition

The in vivo reduction in Ras signaling output by a compound of the present disclosure is determined in a mouse tumor xenograft model.

a. Xenograft with K-Ras G12C Mutation

In an example, tumor xenografts are established by administration of tumor cells with K-Ras G12C mutation (e.g., MIA PaCa-2 cells) into mice, e.g., injection of the tumor cells into the right flanks of female BomTacNMRI-Foxn1nu mice with an age between 6 to 8 weeks.

In case of the subcutaneous (s.c.) MIA PaCa-2 xenograft mouse models, MIA PaCa-2 cells are grown in cell culture flasks in appropriate medium. Cultures are incubated at 37° C. and 5% $CO_2$ in a humidified atmosphere, with medium change or subcultivation performed 2-3 times a week. For injection, the cultured tumor cells are mixed with PBS including 5% FCS and Matrigel in a 1:1 ratio. About 1×10E7 cells in a volume of 100 μL is injected s.c. in each mouse to establish tumors. Mice are randomized into treatment groups of 7-10 mice, once tumors reach a desirable size (e.g., between about 86 to about 170 mm³, or between about 115 to about 170 mm³). Treatment with a subject compound disclosed herein or controls (e.g., vehicle control) may start on the day of randomization and can be continued until end of the study (e.g., 22 days). The test samples are administered intragastrically using a gavage needle at an application volume of 10 mL/kg in a volume of 10 mL/kg per mouse daily twice with a 6 h difference. In some cases, the test compounds are dissolved in 0.5% DMSO (or 0.5% and 0.5% Natrosol) in sterile PBS.

Mice are housed under standardized conditions at 21.5±1.5° C. and 55±10% humidity. Standardized irradiated diet and autoclaved tap water is provided ad libitum. In some cases, tags (e.g., ear tags, microchips implanted subcutaneously under isoflurane anesthesia) are used to identify each mouse. The tumor diameter is measured two or three times a week with a caliper. The volume of each tumor (in mm³) is calculated according to the formula "tumor volume= (π*length*width2)/6." To monitor side effects of treatment, mice are inspected daily for abnormalities and body weight is determined, e.g., daily. Animals are sacrificed at the end of the study. Animals with necrotic tumors or tumor sizes exceeding 1500 mm³ are sacrificed early during the study for ethical reasons.

b. Xenograft with K-Ras G12D Mutation

In another example, tumor xenografts are established by administration of tumor cells with K-Ras G12D mutation (e.g., ASPC-1 or Panc-10.05 cells) into mice.

Female 6- to 8-week-old athymic BALB/c nude (NCr) nu/nu mice are used for xenografts. The tumor cells (e.g., approximately 5×10⁶) are harvested on the day of use and injected in growth-factor-reduced Matrigel/PBS(e.g., 50% final concentration in 100 μl). One flank is inoculated subcutaneously per mouse. Mice are monitored daily, weighed twice weekly, and caliper measurements begin when tumors become visible. For efficacy studies, animals are randomly assigned to treatment groups by an algorithm that assigns animals to groups to achieve best case distributions of mean tumor size with lowest possible standard deviation. Tumor volume can be calculated by measuring two perpendicular diameters using the following formula: (L×w²)/2 in which L and w refer to the length and width tumor diameter, respectively. Percent tumor volume change can be calculated using the following formula: ($V_{final}$−$V_{initial}$)/$V_{initial}$×100. Percent of tumor growth inhibition (% TGI) can be calculated using the following formula: % TGI=100×(1−(average $V_{final}$−$V_{initial}$ of treatment group)/ (average $V_{final}$−$V_{initial}$ of control group). When tumors reach a threshold average size (e.g., approximately 200-400 mm³). mice are randomized into 3-10 mice per group and are treated with vehicle (e.g., 100% Labrasol®) or a subject compound disclosed herein using, for example, a daily schedule by oral gavage. Results can be expressed as mean and standard deviation of the mean.

```
                              SEQUENCE LISTING

Sequence total quantity: 1
SEQ ID NO: 1              moltype = AA    length = 188
FEATURE                   Location/Qualifiers
source                    1..188
                          mol_type = protein
                          organism = Homo sapiens
SEQUENCE: 1
MTEYKLVVVG AGGVGKSALT IQLIQNHFVD EYDPTIEDSY RKQVVIDGET CLLDILDTAG    60
QEEYSAMRDQ YMRTGEGFLC VFAINNTKSF EDIHHYREQI KRVKDSEDVP MVLVGNKCDL   120
PSRTVDTKQA QDLARSYGIP FIETSAKTRQ GVDDAFYTLV REIRKHKEKM SKDGKKKKKK   180
SKTKCVIM                                                            188
```

What is claimed is:

1. A compound of the formula:

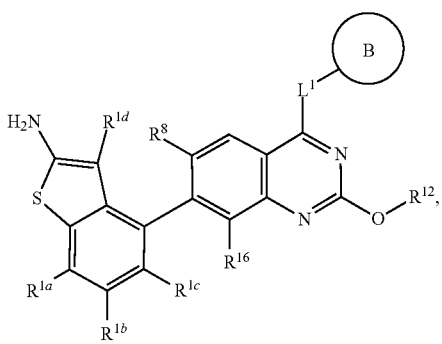

or a pharmaceutically acceptable salt or solvate thereof, wherein:

is a 3-12 membered heterocycloalkyl ring optionally substituted with one or more $R^{10}$;

$L^1$ is selected from a bond, $C_{1-6}$alkyl, —O—, —N($R^{26}$)—, and —C(O)—;

$R^{1a}$, $R^{1b}$, $R^{1c}$, and $R^{1d}$ are each independently selected from hydrogen, halogen, —CN, and $C_{1-6}$alkyl;

$R^8$ is selected from hydrogen, halogen, and $C_{1-6}$alkyl, wherein $C_{1-6}$alkyl is optionally substituted with one, two, or three $R^{20c}$;

each $R^{10}$ is independently selected from halogen, oxo, $C_{1-6}$alkyl, $C_{1-6}$haloalkyl, —CN, and —C(O)$R^{15}$;

$R^{12}$ is selected from $C_{3-6}$cycloalkyl, —CH$_2$—$C_{3-6}$cycloalkyl, $C_{2-9}$heterocycloalkyl, and —CH$_2$—$C_{2-9}$heterocycloalkyl, wherein $C_{3-6}$cycloalkyl, —CH$_2$—$C_{3-6}$cycloalkyl, $C_{2-9}$heterocycloalkyl, and —CH$_2$—$C_{2-9}$heterocycloalkyl are optionally substituted with one, two, or three $R^{20d}$;

each $R^{15}$ is independently selected from $C_{3-6}$cycloalkyl, $C_{2-9}$heterocycloalkyl, $C_{6-10}$aryl, and $C_{1-9}$heteroaryl, wherein $C_{3-6}$cycloalkyl, $C_{2-9}$heterocycloalkyl, $C_{6-10}$aryl, and $C_{1-9}$heteroaryl are optionally substituted with one, two, or three $R^{20f}$;

$R^{16}$ is selected from hydrogen, halogen, and $C_{1-6}$alkyl, wherein $C_{1-6}$alkyl is optionally substituted with one, two, or three $R^{20g}$;

each $R^{20c}$, $R^{20d}$, $R^{20f}$, $R^{20g}$, and $R^{20i}$ is independently selected from halogen, —CN, $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, —CH$_2$—$C_{2-9}$heterocycloalkyl, and —OR$^{21}$, wherein $C_{1-6}$alkyl, $C_{2-6}$alkenyl, $C_{2-6}$alkynyl, $C_{3-6}$cycloalkyl, —CH$_2$—$C_{3-6}$cycloalkyl, $C_{2-9}$heterocycloalkyl, and —CH$_2$—$C_{2-9}$heterocycloalkyl are optionally substituted with one, two, or three groups independently selected from halogen, oxo, —CN, $C_{1-6}$alkyl, $C_{1-6}$haloalkyl, $C_{1-6}$alkoxy, $C_{1-6}$haloalkoxy, and —OR$^{21}$;

each $R^{21}$ is independently selected from hydrogen, $C_{1-6}$alkyl, and $C_{1-6}$haloalkyl; and each $R^{26}$ is selected from hydrogen, $C_{1-6}$alkyl, $C_{2-6}$alkenyl, $C_{2-6}$alkynyl, and $C_{3-6}$cycloalkyl, wherein $C_{1-6}$alkyl, $C_{2-6}$alkenyl, $C_{2-6}$alkynyl, and $C_{3-6}$cycloalkyl are optionally substituted with one, two, or three $R^{20i}$.

2. The compound of claim 1, or a pharmaceutically acceptable salt or solvate thereof, wherein $R^{1a}$, $R^{1b}$, and $R^{1c}$ are each independently selected from hydrogen and halogen.

3. The compound of claim 2, or a pharmaceutically acceptable salt or solvate thereof, wherein $R^{1d}$ is —CN.

4. The compound of claim 1, or a pharmaceutically acceptable salt or solvate thereof, wherein $L^1$ is a bond.

5. The compound of claim 1, or a pharmaceutically acceptable salt or solvate thereof, wherein $L^1$ is —O—.

6. The compound of claim 1, or a pharmaceutically acceptable salt or solvate thereof, wherein $L^1$ is —N($R^{26}$)—.

7. The compound of claim 1, or a pharmaceutically acceptable salt or solvate thereof, wherein $R^{12}$ is —CH$_2$—$C_{2-9}$heterocycloalkyl optionally substituted with one, two, or three $R^{20d}$.

8. The compound of claim 1, or a pharmaceutically acceptable salt or solvate thereof, wherein -OR$^{12}$ is selected from

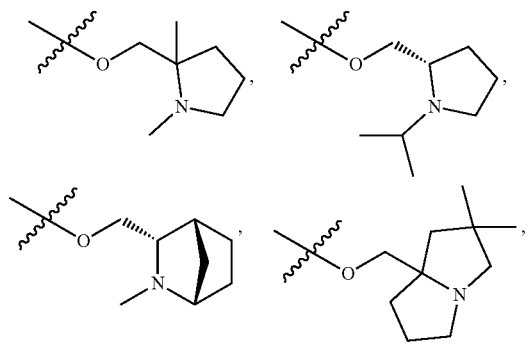

-continued

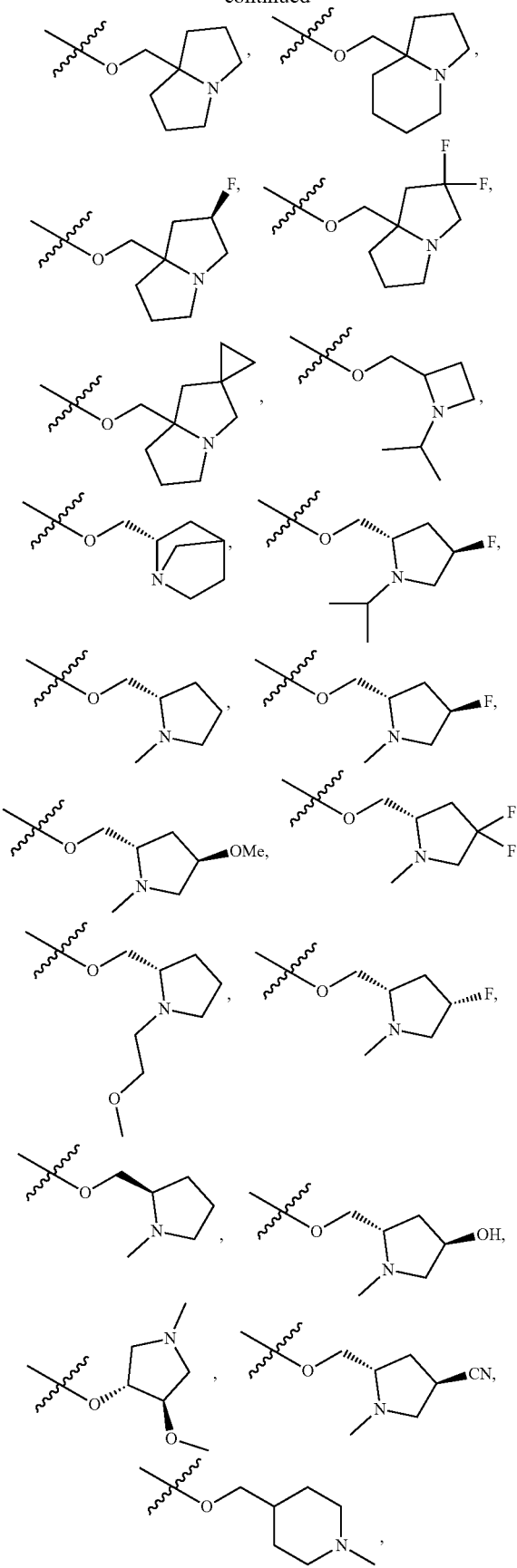

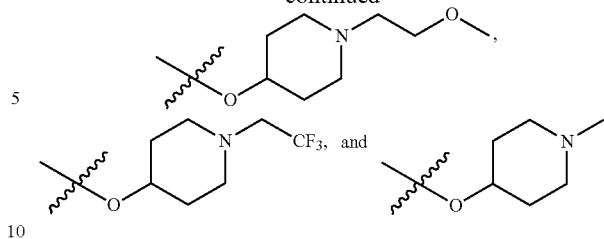

9. The compound of claim 1, or a pharmaceutically acceptable salt or solvate thereof, wherein -OR$^{12}$ is

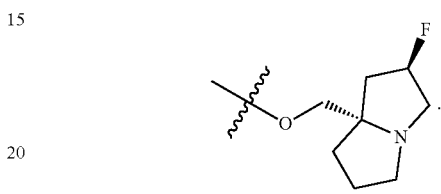

10. The compound of claim 1, or a pharmaceutically acceptable salt or solvate thereof, wherein R$^8$ is selected from halogen and C$_{1-6}$alkyl, wherein C$_{1-6}$alkyl is optionally substituted with one, two, or three halogen.

11. The compound of claim 1, or a pharmaceutically acceptable salt or solvate thereof, wherein R$^8$ is halogen.

12. The compound of claim 1, or a pharmaceutically acceptable salt or solvate thereof, wherein R$^{16}$ is halogen.

13. The compound of claim 3, or a pharmaceutically acceptable salt or solvate thereof, wherein -OR$^{12}$ is

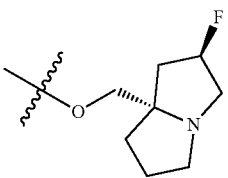 [SMILES: *OC[C@@]12CCCN1C[C@H](F)C2]

R$^8$ is selected from halogen and C$_{1-6}$alkyl, wherein C$_{1-6}$alkyl is optionally substituted with one, two, or three halogen; and R$^{16}$ is halogen.

14. The compound of claim 9, or a pharmaceutically acceptable salt or solvate thereof, wherein R$^{1a}$ is fluoro; R$^{1b}$ and R$^{1c}$ are each hydrogen; R$^{1d}$ is —CN; R$^8$ is selected from chloro and —CF$_3$; and R$^{16}$ is fluoro.

15. A pharmaceutical composition comprising a compound of claim 1, or a pharmaceutically acceptable salt or solvate thereof, and a pharmaceutically acceptable excipient.

16. A method of treating cancer in a subject comprising a Ras mutant protein, comprising administering to the subject a therapeutically effective amount of the compound of claim 1, or a pharmaceutically acceptable salt or solvate thereof.

17. The method of claim 16, wherein the cancer is a solid tumor.

18. The method of claim 16, wherein the cancer is a hematological cancer.

19. The method of claim 16, further comprising administering an additional agent.

20. A method of modulating activity of a Ras protein, comprising contacting a Ras protein with an effective amount of a compound of claim 1, or a pharmaceutically acceptable salt or solvate thereof, thereby modulating the activity of the Ras protein.

\* \* \* \* \*